US005726306A

United States Patent [19]

Yukimasa et al.

[11] Patent Number: 5,726,306
[45] Date of Patent: Mar. 10, 1998

[54] 4,1-BENZOXAZEPIN DERIVATIVES AND THEIR USE

[75] Inventors: Hidefumi Yukimasa, Nara; Ryuichi Tozawa, Osaka; Masakuni Kori, Hyogo; Kazuaki Kitano, Osaka; Yasuo Sugiyama, Hyogo, all of Japan

[73] Assignee: Takeda Chemical Industries, Ltd., Osaka, Japan

[21] Appl. No.: 338,163

[22] Filed: Nov. 9, 1994

Related U.S. Application Data

[63] Continuation-in-part of Ser. No. 195,131, Feb. 9, 1994, abandoned, which is a continuation of Ser. No. 49,455, Apr. 20, 1993, abandoned.

[30] Foreign Application Priority Data

| Apr. 20, 1992 | [JP] | Japan | 4-099541 |
| Dec. 21, 1992 | [JP] | Japan | 4-339947 |
| Oct. 7, 1994 | [JP] | Japan | 6-244136 |

[51] Int. Cl.$^6$ ............................................. C07D 267/14
[52] U.S. Cl. ............................................................. 540/490
[58] Field of Search ................................................ 540/490

[56] References Cited

FOREIGN PATENT DOCUMENTS

| 0 567 026 | 10/1993 | European Pat. Off. |
| 0 645 378 | 3/1995 | European Pat. Off. |
| 95 21834 | 8/1995 | WIPO |

OTHER PUBLICATIONS

Feszt et al., "Influence of Some Benzodiazepines on Serum Lipids Levels in Hyperlipidaemic Rabbits" Agressologie, vol. 18, No. 5, (1977) pp. 265–267.

Horak et al., "Effects of Benzodizepine Derivatives on Triton WR–1339–Induced Hyperlipidemia in Rats", Atherosclerosis, vol. 24, (1976) pp. 81–97.

Takeda Chen. Ind., Chemical Abstracts, vol. 97, entry 127667 (1982).

Masuoka et al, Chemical Abstracts, vol. 106, entry 102252 (1986).

*Primary Examiner*—John M. Ford
*Attorney, Agent, or Firm*—Foley & Lardner

[57] ABSTRACT

N-containing, condensed heterocyclic compounds and salts thereof are disclosed which are useful for inhibiting squalene synthetase and fungal growth, and which are useful for treating or preventing hyperlipidemia. Also disclosed is a method for producing these compounds.

11 Claims, No Drawings

4,1-BENZOXAZEPIN DERIVATIVES AND THEIR USE

This application is a Continuation-In-Part of U.S. Ser. No. 08/195,131 filed Feb. 9, 1994, now abandoned which is a Continuation of U.S. Ser. No. 08/049,455, filed Apr. 20, 1993, abandoned.

FIELD OF THE INVENTION

This invention relates to N-containing, condensed heterocyclic compounds or salts which are useful for inhibiting squalene synthetase and fungal growth, and which are useful for treating or preventing hyperlipidemia, and the production thereof.

BACKGROUND OF THE INVENTION

Hypercholesteremia, high blood pressure and smoking are known as three major, dangerous factors causing ischemic diseases. Adequate control of cholesterol concentration in blood is remarkably important for the prophylaxis or therapy of, not only ischemic diseases, but also coronary sclerosis.

Abnormal elevations of lipid levels in the serum or the plasma are called hyperlipidemia or hyperlipemia. There are various lipids, such as cholesterol (cholesteryl ester and free cholesterol), phospholipids (lecithin, sphingomyelin and so on), triglyceride, free fatty acids and other sterols in the serum or the plasma. Especially cholesterol and triglyceride are clinically important among them.

Therefore, it is important to control blood lipid levels within normal range for the treatment and the prevention of various diseases related to atherosclerosis, such as coronary heart disease and cerebral infarction. Hypertriglyceridemia is also related to the development of pancreatitis.

As pharmaceutical compositions for lowering cholesterol in blood, attention has been drawn to those for controlling the biosynthesis of cholesterol, besides those of inhibiting its absorption by binding bile acid including, among others, cholestyramine, colestipol (disclosed in, for example, U.S. Pat. No. 4,027,009), and those of suppressing the intestinal absorption of cholesterol by inhibiting acyl coenzyme A cholesterol acyl transferase (ACAT) including melinamide (disclosed in French Patent No.1476569). As pharmaceutical preparations for controlling the biosynthesis of cholesterol, lovastatin (disclosed in U.S. Pat. No. 4,231, 938), simvastatin (disclosed in U.S. Pat. No. 4,444,784), pravastatin (U.S. Pat. No. 4,346,227), etc., which are capable of inhibiting especially 3-hydroxy-3-methyl glutaryl coenzyme (HMG-CoA) reductase, are provided for medicinal use. However, when HMG-COA reductase is inhibited, not only the biosynthesis of cholesterol but the biosynthesis of some other components such ubiquinone, dolichol and heme A, which are necessary for the living body, is also inhibited, so that occurrences of undesirable side effects to be caused thereby are feared.

Squalene synthetase is the enzyme involved in the committed step of the de novo cholesterol biosynthetic pathway. This enzyme catalyzes the reductive dimerization of two molecules of farnesyl pyrophosphate to form squalene.

On the other hand, the compounds expected as inhibitors of cholesterol biosynthesis by inhibiting squalene synthetase are disclosed in JPA H1(1989)-213288, JPA H2(1990)-101088, JPA H2(1990)-235820, JPA H2(1990)-235821, JPA H3(1991)-20226, JPA H3(1991)68591, JPA H3(1991)-48288, U.S. Pat. No. 5,019,390, Journal of Medicinal Chemistry, 51 (10), p.1869–1871 (1988), U.S. Pat. No. 5,135,935 and WO 9215579.

Also, the compounds expected as inhibitors of fungal growth by inhibiting squalene synthetase are disclosed in JPA H4 (1992)-279589, EP 475706-A, EP 494622-A and EP 503520-A.

Among 4,1-benzoxazepine derivatives, in 4,1-benzoxazepin-2-one derivatives in which 2-position is substituted with a ketone group, those in which one of the hydrogen atoms at 3-position is replaced with a different substituent, are disclosed in JPA S57(1982)345765 and Chem. Pharm. Bull., 34, 140 (1986).

Ubiquinone, dolichol and heme A have been known as being synthesized from farnesyl pyrophosphate along the cholesterol biosynthesis pathway. Therefore, for avoiding occurrence of side effects due to loss of these substances, it is desirable to inhibit enzymes subsequent to farnesyl pyrophosphate, especially squalene synthetase, in the cholesterol biosynthetic pathway.

In addition, fabric acid derivatives, such as clofibrate (British patent No. 860303) and phenofibrate (Germany patent No. 2250327), are on the market as hypotriglyceridemic agents. But, caution is claimed against the combination therapy of fibrates with statins because of the heightened risk of myopathy and rhabdomyolysis.

Hyperlipidemia or hyperlipoproteinemia is classified by WHO as follows:

Type I: Hyperchyromicronemia

Type IIa: Hyper low density lipoproteinemia (Hypercholesterolemia)

Type IIb: Mixed-type hyperlipidemia which shows increases in low density lipoprotein and very low density lipoprotein Type III: Abnormal β-lipoproteinemia which shows the presence of β-very low density lipoprotein Type IV: Hyper very low density lipoproteinemia (Hypertriglyceridemia)

Type V: Mixed-type hyperlipemia which shows increases in very low density lipoprotein and chyromicron

SUMMARY OF THE INVENTION

Through intensive investigations from the above viewpoint, the present inventors found that certain N-containing, condensed heterocyclic compounds exhibit excellent squalene synthetase inhibitory action, antifungal action, and hypotriglyceridemic action, thereby resulting in the present invention.

More specifically, the present invention is to provide a pharmaceutical composition which comprises the compound represented by the formula (Ir)

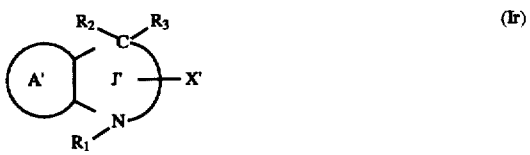

wherein $R_I$ is hydrogen or an optionally substituted hydrocarbon group; $R_2$ and $R_3$ independently is hydrogen, an optionally substituted alkyl group, an optionally substituted phenyl group or an optionally substituted aromatic heterocyclic ring group; X' is a substituent comprising an optionally esterified carboxyl group, an optionally substituted carbamoyl group, an optionally substituted hydroxyl group, an optionally substituted amino group or an optionally substituted heterocyclic radical having a protonizable hydrogen; Ring A' is an optionally substituted benzene ring or an optionally substituted aromatic heterocyclic ring; Ring J' is a 7- to 8-membered heterocyclic ring containing at most three ring constituting hetero atoms; the Ring J' optionally having, besides $R_1$, $R_2$, $R_3$ and X', a further substituent, or a pharmaceutically acceptable salt thereof.

A further embodiment relates to the composition mentioned above, wherein the compound is represented by the formula (Ir'):

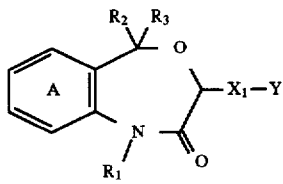

wherein $R_1$ is hydrogen or an optionally substituted hydrocarbon group; $R_2$ and $R_3$ independently is hydrogen, an optionally substituted alkyl group, an optionally substituted phenyl group or an optionally substituted aromatic heterocyclic ring group; $X_1$ is a bond or a divalent atomic chain; Y is an optionally esterified carboxyl group, an optionally substituted carbamoyl group, an optionally substituted hydroxyl group, an optionally substituted amino group or an optionally substituted heterocyclic radical having protonizable hydrogen; Ring A is an optionally substituted benzene ring, or a pharmaceutically acceptable salt thereof.

The compounds described above and in the following subgeneric embodiments can be used as squalene synthetase inhibitors, antifungal agents, and hypotriglyceridemic agents. Preferred uses of the different subgeneric embodiments are listed below each of the following formulae.

Further subgeneric embodiments of the present invention include the following:

(1) 4,1-Benzoxazepin-2-one derivatives represented by the formula (I):

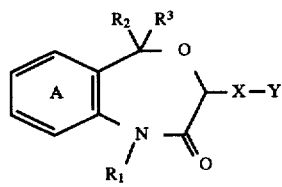

, wherein $R^1$ stands for hydrogen atom or an optionally substituted hydrocarbon group; $R_2$ and $R_3$ independently stand for hydrogen atom, an optionally substituted lower alkyl group, an optionally substituted phenyl group or an optionally substituted aromatic heterocyclic group; X stands for a bond or a spacer having the chain length of 1 to 7 atoms; Y stands for an optionally esterified or thioesterified carboxyl group, an optionally substituted hydroxyl group, an optionally substituted amino group, an optionally substituted phenyl group, an optionally substituted carbamoyl group or a N-containing heterocyclic residue having hydrogen atom capable of being deprotonated; provided that, when X is methylene and $R_1$ is not an alkyl group having carbon atoms of more than 4, Y is neither carboxyl group nor alkoxycarbonyl group; and the ring A may optionally be substituted, or salts thereof, (2) 4,1-Benzoxazepin-2-one derivatives represented by the formula (I'):

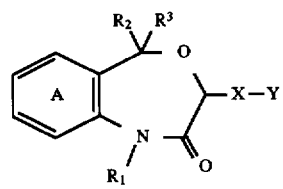

, wherein $R^1$ stands for hydrogen atom or an optionally substituted hydrocarbon group; $R_2$ and $R_3$ independently stand for hydrogen atom, an optionally substituted lower alkyl group, an optionally substituted phenyl group or an optionally substituted aromatic heterocyclic group; X stands for a bond or a spacer having the chain length of 1 to 7 atoms; Y stands for an optionally esterified or thioesterified carboxyl group, an optionally substituted hydroxyl group, an optionally substituted amino group, an optionally substituted phenyl group, an optionally substituted carbamoyl group or a N-containing heterocyclic residue having hydrogen atom capable of being deprotonated; provided that, when X is methylene, Y is neither carboxyl group nor alkoxycarbonyl group; and the ring A may optionally be substituted, or salts thereof, (3) a squalene synthetase inhibitor comprising as an active ingredient a 4,1-Benzoxazepin-2-one derivative represented by the formula (I"):

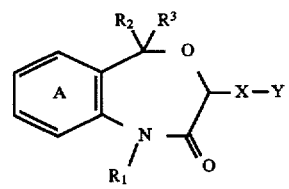

, wherein $R^1$ stands for hydrogen atom or an optionally substituted hydrocarbon group; $R_2$ and $R_3$ independently stand for hydrogen atom, an optionally substituted lower alkyl group, an optionally substituted phenyl group or an optionally substituted aromatic heterocyclic group; X stands for a bond or a spacer having the chain length of 1 to 7 atoms; Y stands for an optionally esterified or thioesterified carboxyl group, an optionally substituted hydroxyl group, an optionally substituted amino group, an optionally substituted phenyl group, an optionally substituted carbamoyl group or a N-containing heterocyclic residue having hydrogen atom capable of being deprotonated; and the ring A may optionally be substituted, or a salt thereof, and (4) a fungal growth inhibitor comprising as an active ingredient a 4,1-Benzoxazepin-2-one derivative represented by the formula (I"):

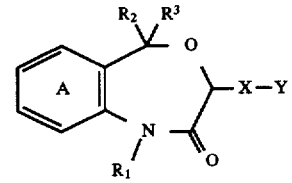

, wherein $R^1$ stands for hydrogen atom or an optionally substituted hydrocarbon group; $R_2$ and $R_3$ independently stand for hydrogen atom, an optionally substituted lower alkyl group, an optionally substituted phenyl group or an optionally substituted aromatic heterocyclic group; X stands for a bond or a spacer having the chain length of 1 to 7 atoms; Y stands for an optionally esterified or thioesterified carboxyl group, an optionally substituted hydroxyl group, an optionally substituted amino group, an optionally substituted phenyl group, an optionally substituted carbamoyl group or a N-containing heterocyclic residue having hydrogen atom capable of being deprotonated; and the ring A may optionally be substituted, or a salt thereof.

Further, the present invention is to provide a method of producing the novel compounds represented by the formula (I) and (I') or salts thereof.

In the above-mentioned formulae (I), (I') and (I"), as the hydrocarbon group of "optionally substituted hydrocarbon group" shown by $R_1$, mention is made of aliphatic chain hydrocarbon groups, alicyclic hydrocarbon group and aryl group, among others, with preference given to aliphatic chain hydrocarbon groups.

A further aspect of the present invention is compounds of the formulae (I), (I'), and (I") wherein the chiral carbon atom directly bonded to X possesses the R configuration.

Another aspect of the present invention is a compound of the formula

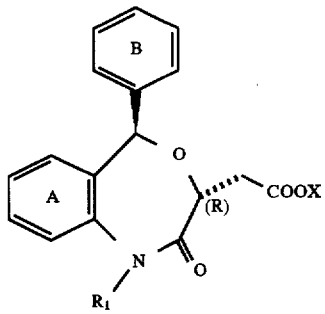

wherein $R_1$ is a lower alkyl, preferably isobutyl or neopentyl; X is hydrogen, preferably chlorine, or a metal ion, preferably a sodium ion or a potassium ion; ring A is phenyl substituted with halogen; and ring B is phenyl substituted with a lower alkoxy, preferably methoxy or ethoxy.

DETAILED DESCRIPTION OF THE INVENTION

In the above formulae (Ir), (Ir'), (I), (I') and (I"), as the hydrocarbon group of the "optionally substituted hydrocarbon group" shown by $R^1$, mention is made of aliphatic chain hydrocarbon groups, alicyclic hydrocarbon group and aryl group, among others, with preference given to aliphatic chain hydrocarbon groups.

As the aliphatic chain hydrocarbon group of said hydrocarbon group, mention is made of straight-chain or branched aliphatic hydrocarbon groups, for example, alkyl group, alkenyl group and alkynyl group, with preference given to lower alkyl group, lower alkenyl group and lower alkynyl group. As the lower alkyl group, $C_{1-7}$ lower alkyl groups are preferable, which are exemplified by methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylpropyl, 3,3-dimethylbutyl, 2-ethylbutyl and 1-ethylpropyl, with preference given to $C_{2-5}$ alkyl groups, more preferably $C_{4-5}$ alkyl groups. As the lower alkenyl group, $C_{2-6}$ lower alkenyl groups are preferable, which are exemplified by vinyl, allyl, 2-methylallyl isopropenyl, 1-propenyl, 2-methyl-1-propenyl, 2-methyl2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5- hexenyl. Among them, vinyl, allyl, isopropenyl, 2-methylallyl, 2-methyl-1-propenyl, 2-methyl-2-propenyl, and 3-methyl-2-butenyl are especially preferable. As the lower alkynyl group, $C_{1-6}$ lower alkynyl groups are preferable, which are exemplified by ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Among them, ethynyl, 1-propynyl and 2-propynyl are especially preferable.

As the alicyclic hydrocarbon group of the said hydrocarbon group, mention is made of saturated or unsaturated alicyclic hydrocarbon groups, which are exemplified by cycloalkyl group, cycloalkenyl group or cycloalkadienyl group. As the cycloalkyl group, $C_{3-9}$ cycloalkyl groups are preferable, which are exemplified by cyclopropyl, cyclobutyl, cyclopentyl, cyclohexyl, cycloheptyl, cyclooctyl and cyclononyl. Among them, $C_{3-6}$ cycloalkyl groups such as cyclopropyl, cyclobutyl, cyclopentyl and cyclohexyl are especially preferable. Examples of the cycloalkenyl group include 2-cyclopenten-1-yl, 3-cyclopenten-1-yl, 2-cyclohexen-1-yl, 3-cyclohexen-1-yl, 1-cyclobuten-1-yl and 1-cyclopenten-1-yl. Examples of the cycloalkadienyl group include 2,4-cyclopentadien-1-yl, 2,4-cyclohexadien-1-yl, and 2,5-cyclohexadien-1-yl.

As the aryl group of said hydrocarbon group, mention is made of monocyclic or condensed polycyclic aromatic hydrocarbon groups, which are exemplified by phenyl, naphthyl, anthryl, phenanthryl and acenaphthylenyl. Among them, phenyl, 1-naphthyl and 2-naphthyl are especially preferable.

As the substituent of "optionally substituted hydrocarbon group" shown by $R_1$, mention is made of optionally substituted aryl groups, optionally substituted cycloalkyl groups or cycloalkenyl groups, optionally substituted heterocyclic groups, optionally substituted amino groups, optionally substituted hydroxyl groups, optionally substituted thiol groups and halogen atoms (e.g. fluorine, chlorine, bromine and iodine). Number of these optional substituents ranges from 1 to 5 (preferably 1 to 3). As the aryl group of said optionally substituted aryl group, mention is made of phenyl, naphthyl, anthryl, phenanthryl and acenaphthylenyl. Among them, phenyl, 1-naphthyl and 2-naphthyl are preferable. As the substituent on said optionally substituted aryl group, mention is made of $C_{1-3}$ alkoxy groups (e.g. methoxy, ethoxy and propoxy), halogen atoms (e.g. fluorine, chlorine bromine and iodine) and $C_{1-3}$ alkyl groups (e.g. methyl, ethyl and propyl). Number of these optional substituents ranges from 1 to 2. As the cycloalkyl group of said optionally substituted cycloalkyl group, mention is made of $C_{3-7}$ cycloalkyl groups such as cyclopropyl, cyclobutyl, cyclopentyl, cyclohexyl and cycloheptyl. Kinds and number of the substituents on said optionally substituted cycloalkyl group are the same as those mentioned for the substituents in the above-mentioned optionally substituted aryl groups. As the cycloalkenyl group of said optionally substituted cycloalkenyl group, mention is made of $C_{3-6}$ cycloalkenyl groups including cyclopropanyl, cyclobutenyl, cyclopentenyl and cyclohexenyl. Kinds and number of the substituents on said optionally substituted cycloalkenyl group are the same as those mentioned for the substituents in the above-mentioned optionally substituted aryl groups. As the heterocyclic group of said optionally substituted heterocyclic group, mention is made of an aromatic heterocyclic group and a saturated or unsaturated non-aromatic heterocyclic group (aliphatic heterocyclic group) having at least one hetero atom selected from oxygen, sulfur and nitrogen, with preference given to an aromatic heterocyclic group. As said aromatic heterocyclic group, mention is made of aromatic monocyclic heterocyclic groups (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.) and aromatic condensed heterocyclic groups (e.g. benzofuranyl, isobenzofuranyl, benzo[b] thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), with preference given to furyl, thienyl, pyridyl, pyrimidinyl, pyrazinyl, indolyl and isoindolyl. As said non-aromatic heterocyclic group, mention is made of, for example, oxiranyl, azetidinyl, oxetanyl, thiethanyl, pyrrolidinyl, tetrahydrofuryl, thioranyl, piperidyl, tetrahydropyranyl, morpholinyl, thiomorpholinyl, piperazinyl, etc. As the substituent of said optionally substituted heterocyclic group, mention is made of $C_{1-3}$ alkyl groups (e.g. methyl, ethyl and propyl). As the substituent of said optionally substituted amino group, optionally substituted hydroxyl group or optionally substituted thiol group, mention is made of $C_{1-3}$ alkyl groups (e.g. methyl, ethyl and propyl). In the case where the hydrocarbon group in the optionally substituted hydrocarbon group shown by $R_1$ is an alicyclic hydrocarbon group or aryl group, it may further have a $C_{1-3}$ alkyl group (e.g. methyl, ethyl and propyl).

Further examples of $R_1$ include optionally substituted $C_{1-6}$ acyl groups such as formyl, acetyl, propionyl, butyryl, isobutyryl, valeryl, isovaleryl, pivaloyl, hexanoyl, dimethylacetyl, and trimethylacetyl. Said acyl group may have one to five substituents at any possible position. Such substituents include halogen atoms (e.g. fluorine, chlorine, and bromine).

In the above-mentioned formulae, as the optionally substituted lower alkyl groups shown by $R_2$ and $R_3$, mention is made of $C_{1-6}$ lower alkyl groups (e.g. methyl, ethyl, n-propyl, isopropyl, butyl, isobutyl, sec-butyl, tert-butyl, pentyl, isopentyl, neopentyl, hexyl and isohexyl), preferably $C_{1-4}$ alkyl groups such as methyl, ethyl, propyl, isopropyl, butyl and t-butyl. As the substituent of said optionally substituted lower alkyl group, mention is made of halogen atoms (e.g. fluorine, chlorine, bromine and iodine), $C_{1-4}$ lower alkoxy groups (e.g. methoxy, ethoxy, propoxy, isopropoxy, butoxy and t-butoxy), among others.

Substituents of "optionally substituted phenyl group" shown by $R_2$ and $R_3$ are independently exemplified by halogen atom (e.g. fluorine, chlorine, bromine or iodine), optionally substituted $C_{1-4}$ lower alkyl groups (e.g. methyl, ethyl, propyl, isopropyl, butyl and t-butyl), optionally substituted $C_{1-4}$ lower alkoxy groups (e.g. methoxy, ethoxy, propoxy, isopropoxy, butoxy and t-butoxy), optionally substituted hydroxyl group, nitro group and cyano group, and "optionally substituted phenyl group" may have 1 to 3 of these substituents. As the substituent of said optionally substituted lower ($C_{1-4}$) alkyl group or optionally substituted ($C_{1-4}$) alkoxy group, mention is made of, among others, halogen atoms (e.g. fluorine, chlorine, bromine, iodine), and 1 to 3 of them may be substituted on optional positions. As the substituent of optionally substituted hydroxyl group, mention is made of, among others, lower ($C_{1-4}$) alkyl groups (e.g. methyl, ethyl, propyl, isopropyl, butyl and t-butyl), $C_{3-6}$ cycloalkyl groups (e.g. cyclopropyl, cyclobutyl, cyclopentyl and cyclohexyl), aryl groups (e.g. phenyl, 1-naphthyl and 2-naphthyl) and aralkyl groups (e.g. benzyl, phenethyl). Further, two adjoining substituents on the phenyl group may cooperate therewith to form a ring. Examples of such rings are the following formulae:

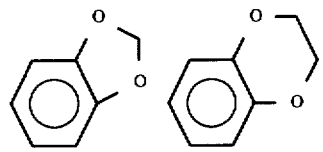

The above ring formed by two adjoining substituents may itself be substituted with a lower ($C_{1-3}$) alkyl (e.g. methyl, ethyl, propyl, and isopropyl) and the like.

As the aromatic heterocyclic group of "optionally substituted aromatic heterocyclic group" shown by $R_2$ and $R_3$, mention is made of the same aromatic heterocyclic groups specified for $R_1$. Among them, furyl, thienyl, imidazolyl, pyridyl, pyrimidinyl, pyrazinyl, indolyl, and isoindolyl are preferred. As the substituent of said aromatic heterocyclic group, mention is made of lower $C_{1-3}$ alkyl groups (e.g. methyl, ethyl, and propyl), among others.

Among the above-exemplified groups represented by $R_2$ and $R_3$, optionally substituted phenyl groups, substituted phenyl groups are preferable, with greater preference given to a phenyl group substituted with halogen and lower alkoxy. Also, either $R_2$ or $R_3$ is preferably hydrogen.

In the above formulae (Ir), as the "a substituent comprising an optionally esterified carboxyl group" shown by X', mention is made of optionally esterified carboxyl groups and a substituent having an optionally esterified carboxyl group, etc. Said optionally esterified carboxyl groups are substantially the same as those in the case of the below-mentioned optionally esterified carboxyl groups shown by Y.

As the "a substituent comprising an optionally substituted carbamoyl group" shown by X', mention is made of optionally substituted carbamoyl groups and a substituent having an optionally substituted carbamoyl group, etc. Said optionally substituted carbamoyl groups are substantially the same as those in the case of the below-mentioned optionally substituted carbamoyl groups shown by Y.

As the "a substituent comprising an optionally substituted hydroxyl group" shown by X', mention is made of optionally substituted hydroxyl groups and a substituent having an optionally substituted hydroxyl group, etc. Said optionally substituted hydroxyl groups are substantially the same as those in the case of the below-mentioned optionally substituted hydroxyl groups shown by Y.

As the "a substituent comprising an optionally substituted amino group" shown by X', mention is made of optionally substituted amino groups and a substituent having an optionally substituted amino group, etc. Said optionally substituted amino groups are substantially the same as those in the case of the below-mentioned optionally substituted amino groups shown by Y.

As the "substituent comprising an optionally substituted heterocyclic radical having a protonizable hydrogen" shown by X', mention is made of an optionally substituted heterocyclic radical having a protonizable hydrogen and a substituent having an optionally substituted heterocyclic radical having a protonizable hydrogen, etc. Said optionally substituted heterocyclic radicals are substantially the same as those in the case of the below-mentioned optionally substituted heterocyclic radicals shown by Y.

Examples of X' include groups represented by the formula (a)

wherein X is a bond or a divalent or trivalent atomic chain; Y is an optionally esterified carboxyl group, an optionally substituted carbamoyl group, an optionally substituted hydroxyl group, an optionally substituted amino group or an optionally substituted heterocyclic radical having a protonizable hydrogen; the symbol ......... is a single or double bond.

In the formula (a), as the "divalent atomic chain" shown by X, mention is made of, preferably, any one of divalent chains having 1 to 7 atoms, more preferably 1 to 4, constituting the straight-chain, and they may have side chains.

In addition, as X, mention is made of a carbon chain containing a double bond or —L—C(OH)— (wherein L is a bond or a straight-chain or branched alkylene chain). As said "carbon chain containing double bond", mention is made of, preferably, those in which the carbon number constituting the straight-chain portion ranges from 1 to 7, more preferably 1 to 4, and they may optionally have a side chain. While the double bond at said carbon chain is contained in the straight-chain portion and/or branched chain portion, it is contained preferably in the straight-chain portion. Number of the double bond contained in said carbon chain is not restricted as far as possible, it ranges preferably from 1 to 2.

Examples of carbon chains containing said double bond include methine, vinylene, propenylene, butenylene, butadienylene, methylpropenylene, ethylpropenylene, propylpropenylene, methylbutenylene, ethylbutenylene, propylbutenylene, methylbutadienylene, ethylbutadienylene, propylbutadienylene, pentenylene, hexenylene, heptenylene, hexadienylene and heptadienylene, preferably methine, vinylene, propenylene, butenylene and butadienylene. Herein, when said carbon chain is trivalent, it binds to a carbon atom on Ring J' at any possible position by a double bond.

Examples of the "straight-chain or branched alkylene chain" shown by L include straight-chain or branched $C_{1-6}$ alkylene chain, more specifically, divalent ones such as methylene, ethylene, trimethylene, tetramethylene, pentamethylene, hexamethylene, propylene, ethylmethylene, ethylethylene, propylethylene, butylethylene, methyltetramethylene and methyltrimethylene, and, preferably, $C_{1-3}$ ones such as methylene, ethylene, trimethylene and propylene.

Among the above-exemplified groups shown by X', the groups represented by the formula (b)

—X₁—Y wherein $X_1$ is a bond or a divalent atomic chain; Y is an optionally esterified carboxyl group, an optionally substituted carbamoyl group, an optionally substituted hydroxyl group, an optionally substituted amino group or an optionally substituted heterocyclic radical having a protonizable hydrogen, are preferable.

in the formula (b), the "divalent atomic chains" shown by $X_1$ are substantially the same as those in the case of the above-mentioned divalent atomic chains shown by X.

In the formulae (a) and (b), as the "divalent atomic chain" shown by X or X1, more preferably, mention is made of straight-chain or branched alkylene chain, in which the carbon number constituting the straight-chain ranges from 1 to 7 (preferably from 1 to 4). Examples of said alkylene chain include divalent ones such as methylene, ethylene, trimethylene, tetramethylene, pentamethylene, hexamethylene, heptamethylene, propylene, ethylmethylene, ethylethylene, propylethylene, butylethylene, methyltetramethylene and methyltrimethylene, and, preferably $C_{1-4}$ ones such as methylene, ethylene, trimethylene and propylene.

As the spacer having a chain length of 1 to 7 atoms shown by X, any one can be exemplified, so long as it is a divalent chain in which the number of atoms constituting the straight chain is 1 to 7, and it may have a side chain. For example, said spacer includes one represented by the following formula:

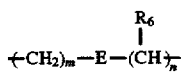

wherein m and n denote independently 0, 1, 2 or 3; E stands for a bond or oxygen atom, sulfur atom, sulfoxide, sulfone,

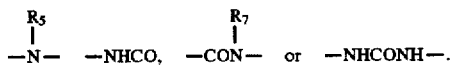

Herein, $R_6$ and $R_7$ independently stand for hydrogen atom, an optionally substituted lower alkyl group, an optionally substituted aralkyl group or an optionally substituted phenyl group. And, $R_5$ stands for hydrogen atom, a lower alkyl group, aralkyl group or acyl group.

As the alkyl groups of "optionally substituted lower alkyl groups" shown by $R_6$ and $R_7$, mention is made of $C_{1-6}$ straight-chain or branched lower alkyl groups (e.g. methyl, ethyl, n-propyl, isopropyl, n-butyl, isobutyl, t-butyl, n-pentyl, isopentyl, neopentyl, etc.). As the substituent of said optionally substituted lower alkyl group, mention is made of aromatic heterocyclic groups (e.g. furyl, thienyl, pyridyl, pyrimidinyl, pyrazinyl, indolyl, imidazolyl and isoindolyl), optionally substituted amino groups, optionally substituted hydroxyl groups, optionally substituted thiol groups, optionally esterified carboxyl groups and halogen atoms (e.g. fluorine, chlorine, bromine and iodine). As the substituent of optionally substituted amino group, optionally substituted hydroxyl group or optionally substituted thiol group, mention is made of lower ($C_{1-3}$) alkyl groups (e.g. methyl, ethyl and propyl). As the optionally esterified carboxyl group, mention is made of methoxycarbonyl, ethoxycarbonyl, propoxycarbonyl, phenoxycarbonyl, 1-naphtoxycarbonyl, 2-naphtoxycarbonyl, with preference given to methoxycarbonyl, ethoxycarbonyl, propoxycarbonyl.

As the aralkyl groups of "optionally substituted aralkyl groups shown by $R_6$, and $R_7$, mention is made of benzyl, naphthylmethyl, phenylethyl, phenylpropyl, phenylbutyl, etc. As the substituent of said "optionally substituted aralkyl groups", mention is made of halogen atoms (e.g. fluorine, chlorine, bromine, iodine), $C_{1-3}$ alkoxy groups (e.g. methoxy, ethoxy, propoxy, etc.), hydroxyl group, amino group, carboxyl group, sulfhydryl, etc.

As the substituent of the optionally substituted phenyl group shown by $R_6$, and $R_7$, mention is made of halogen atoms (e.g. fluorine, chlorine, bromine and iodine), $C_{1-3}$ alkoxy groups (e.g. methoxy, ethoxy, propoxy, etc.) and $C_{1-3}$ alkyl groups (e.g. methyl, ethyl, propyl, etc.).

$R_6$ may each be different depending on the corresponding methylene chains.

And, examples of "lower alkyl group" and "aralkyl group" shown by $R_5$ include a $C_{1-4}$ lower alkyl group (e.g. methyl, ethyl, propyl, butyl, t-butyl, etc.), a $C_{7-15}$ aralkyl group (e.g. benzyl, phenethyl, phenylpropyl, phenylbutyl, naphthylmethyl, etc.).

As the acyl group shown by $R_5$, mention is made of lower alkanoyl groups (formyl, acetyl, propionyl, butyryl, isobutyryl, valeryl, isovaleryl, pivaloyl and hexanoyl), lower alkenoyl groups (acryloyl, methacryloyl, crotonoyl and isocrotonoyl), cycloalkanecarbonyl (cyclopropanecarbonyl, cyclobutanecarbonyl, cyclopentanecarbonyl and cyclohexanecarbonyl), lower alkanesulfonyl groups (mesyl, ethanesulfonyl and propanesulfonyl), aroyl groups (benzoyl, p-toluoyl, 1-naphthoyl and 2-naphthoyl), aryl lower alkanoyl groups (phenylacetyl, phenylpropionyl, hydroatropoyl and phenylbutyryl), aryl lower alkenoyl groups (cinnamoyl and atropoyl) and arenesulfonyl groups (benzenesulfonyl and p-toluenesulfonyl), among others.

Examples of optionally esterified carboxyl group shown by Y include lower alkoxycarbonyl groups (methoxycarbonyl, ethoxycarboxyl, propoxycarbonyl, isopropoxycarbonyl, butoxycarbonyl, tert-butoxycarbonyl, sec-butoxycarbonyl, pentyloxycarbonyl, isopentyloxycarbonyl, neopentyloxycarbonyl and tert-pentyloxycarbonyl) and aryloxycarbonyl groups (phenoxycarbonyl, 1-naphtoxycarbonyl and benzyloxycarbonyl).

Said lower alkoxycarbonyl groups may have 1 or more substituents at any possible positions. Examples of such substituents include optionally substituted hydroxyl groups, optionally esterified carboxyl groups, optionally substituted carbamoyl groups, optionally substituted phenyl groups, optionally substituted $C_{3-6}$ cycloalkyl groups (e.g. cyclopropyl, cyclobutyl, cyclopentyl and cyclohexyl), lower $C_{1-3}$ alkenyl groups (e.g. vinyl, allyl, etc.) and 5-membered heterocyclic residue containing one to three of oxygen atom. As the substituent of said optionally substituted hydroxyl group, mention is made of lower alkanoyl groups (e.g. pivaloyl, etc.) and optionally esterified carboxyl groups (e.g. methoxycarbonyl, ethoxycarboxyl, propoxycarbonyl, isopropoxycarbonyl and cyclohexyloxycarbonyl). As the substituent of said optionally esterified carboxyl group, mention is made of lower $C_{1-4}$ alkoxycarbonyl groups (e.g. methoxycarbonyl, ethoxycarbonyl, propoxycarbonyl, isopropoxycarbonyl, butoxycarbonyl tert-butoxycarbonyl and sec-butoxycarbonyl). As the substituent of said optionally substituted carbamoyl group, mention is made of lower $C_{1-3}$ alkyl groups (e.g. methyl, ethyl and propyl), $C_{3-6}$ cycloalkyl groups (e.g. cyclopropyl, cyclobutyl, cyclopentyl and cyclohexyl), phenyl group, benzyl group and optionally esterified carboxyl groups (e.g. methoxycarbonyl, ethoxycarbonyl, propoxycarbonyl). As the substituents of said optionally substituted phenyl group or optionally substituted $C_{3-6}$ cycloalkyl group, mention is made of lower $C_{1-3}$ alkyl groups (e.g. methyl, ethyl and propyl) and lower $C_{1-3}$ alkoxy groups (e.g. methoxy, ethoxy and propoxy). Said 5-membered heterocyclic residue may have 1 or more substituents at any possible positions. Examples of such substituents include lower $C_{1-3}$ alkyl groups (e.g. methyl, ethyl and propyl) and oxo. Further, said heterocyclic group may cooperate with a benzen ring to form a fused ring.

Said aryloxycarbonyl group may have 1 or more substituents at any possible positions. Examples of such substituents include lower $C_{1-3}$ alkyl groups (e.g. methyl, ethyl and propyl), lower $C_{1-3}$ alkoxy groups (e.g. methoxy, ethoxy and propoxy) and optionally esterified carboxyl groups (e.g. methoxycarbonyl, ethoxycarbonyl, propoxycarbonyl).

Also, the optionally esterified carboxyl group shown by Y may be thioesterified.

Exemplary substituents of optionally substituted hydroxyl groups shown by Y include lower $C_{1-4}$ alkyl groups (e.g. methyl, ethyl, propyl, isopropyl, butyl and t-butyl), $C_{3-6}$ cycloalkyl groups (cyclopropyl, cyclobutyl, cyclopentyl and cyclohexyl), optionally substituted aryl groups (e.g. phenyl, 1-naphthyl and 2-naphthyl) and optionally substituted aralkyl groups (e.g. benzyl and phenethyl). As substituents of said optionally substituted aryl groups and optionally substituted aralkyl groups, mention is made of halogen atoms (e.g. fluorine, chlorine, bromine, iodine), and carboxyl groups optionally esterified with lower $(C_{1-4})$ alkyl (e.g. methyl, ethyl, propyl, isopropyl, butyl, and t-butyl).

Exemplary substituents of optionally substituted amino groups shown by Y include lower $C_{1-4}$ alkyl groups (e.g. methyl, ethyl, propyl, isopropyl, butyl and t-butyl), $C_{3-6}$ cycloalkyl groups (cyclopropyl, cyclobutyl, cyclopentyl and cyclohexyl), optionally substituted aryl groups (e.g. phenyl, 1-naphthyl and 2-naphthyl) and optionally substituted aralkyl groups (e.g. benzyl and phenethyl). As substituents of said optionally substituted aryl groups and optionally substituted aralkyl groups, mention is made of halogen atoms (e.g. fluorine, chlorine, bromine, iodine), and carboxyl groups optionally esterified with lower $(C_{1-4})$ alkyl (e.g. methyl, ethyl, propyl, isopropyl, butyl, and t-butyl). Also, two substituents on a nitrogen atom may form a cyclic amino group taken together with the nitrogen atom. Examples of the cyclic amino group include 1-azetidinyl, 1-pyrrolidinyl, piperidino, morpholino, 1-piperazinyl, and 1-piperazinyl having a lower $C_{1-3}$ alkyl group (e.g. methyl, ethyl, propyl, etc.), an aralkyl group (e.g. benzyl, phenethyl, etc.), an aryl group (e.g. phenyl, etc.) or the like at the 4-position.

Example substituents of optionally substituted phenyl group shown by Y include optionally substituted lower $C_{1-4}$ alkyl groups (e.g. methyl, ethyl, propyl, isopropyl, butyl and t-butyl), lower $C_{1-4}$ alkoxy groups (e.g. methoxy, ethoxy, propoxy, isopropoxy, butoxy, t-butoxy), optionally esterified carboxyl groups (e.g. methoxycarbonyl, ethoxycarbonyl, propoxycarbonyl, isopropoxycarbonyl, butoxycarbonyl, tert-butoxycarbonyl and sec-butoxycarbonyl), optionally substituted phenyl groups, optionally substituted amino groups and a N-containing heterocyclic residue having hydrogen atom capable of being deprotonated. As the substituent of said optionally substituted lower $C_{1-4}$ alkyl group or said optionally substituted phenyl group, mention is made of optionally esterified carboxyl groups (e.g. methoxycarbonyl, ethoxycarbonyl, propoxycarbonyl, isopropoxycarbonyl, butoxycarbonyl, tert-butoxycarbonyl and sec-butoxycarbonyl). As the substituent of said optionally substituted amino group, mention is made of lower $C_{1-3}$ alkyl groups (e.g. methyl, ethyl and propyl). Said N-containing heterocyclic residue includes tetrazol-5-yl, 2,5-dihydro-5-oxo-1,2,4-oxadiazol-3-yl, 2,5-dihydro-5-oxo-1,2,4-thiadiazol-3-yl.

Exemplary substituents of optionally substituted carbamoyl groups shown by Y include optionally substituted lower $C_{1-6}$ alkyl groups (e.g. methyl, ethyl, propyl, isopropyl, butyl, and t-butyl), optionally substituted $C_{3-6}$ cycloalkyl groups (cyclopropyl, cyclobutyl, cyclopentyl and cyclohexyl), optionally substituted aryl group (e.g. phenyl, 1-naphthyl, 2-naphthyl, etc.), optionally substituted aralkyl groups (e.g. benzyl, phenethyl, etc.), and, one or two of these substituents may be independently substituted. As substituents of said optionally substituted lower $(C_{1-6})$alkyl and optionally substituted $C_{3-6}$ cycloalkyl group, mention is made of a carboxyl group optionally esterified with a lower (C$_{1-5}$) alkyl (e.g. methyl, ethyl, propyl, isopropyl, butyl, t-butyl, pentyl, isopentyl, neopentyl, etc.), aromatic heterocyclic groups (e.g. furyl, thienyl, indolyl, isoindolyl, pyrazinyl, pyridyl, pyrimidyl, imidazolyl, etc.), amino group, hydroxyl group, phenyl group, etc., and one to three of these substituents may be independently substituted. As substituents of said optionally substituted aryl groups and optionally substituted aralkyl groups, mention is made of halogen atoms (e.g. fluorine, chlorine, bromine, iodine), carboxyl groups optionally esterified with a lower (C$_{1-4}$) alkyl (e.g. methyl, ethyl, propyl, isopropyl, butyl, t-butyl, etc.). Also, two substituents on a nitrogen atom may form a cyclic amino group taken together with the nitrogen atom. Examples of such cyclic amino groups include 1-azetidinyl, 1-pyrrolidinyl, piperidino, morpholino, 1-piperazinyl, etc.

As heterocyclic radicals of the "optionally substituted heterocyclic radical having a protonizable hydrogen" shown by Y, mention is made of 5–7 membered (preferably 5-membered) monocyclic heterocyclic radicals containing at least one hetero atom selected from the group consisting of N, S and O, more preferably N-containing heterocyclic radicals. Especially, tetrazol-5-yl and groups represented by the formula

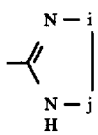

, wherein i stands for —O— or —S—; j stands for >C=O, >C=S or >SO$_2$ (especially 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl) are preferable.

Examples of N-containing heterocyclic residues having a hydrogen atom capable of being protonated shown by Y also include tetrazol-5-yl, 2,5-dihydro-5-oxo-1,2,4-oxadiazol3-yl, 2,5-dihydro-5-oxo-1,2,4-thiadiazol-3-yl.

Said heterocyclic radical may be protected with an optionally substituted lower alkyl (preferably C$_{1-4}$ alkyl), acyl, etc. As said optionally substituted lower alkyl, mention is made of methyl, triphenylmethyl, methoxymethyl, ethoxymethyl, p-methoxybenzyl, p-nitrobenzyl, etc. Examples of said acyl include lower (C$_{2-5}$) alkanoyl, benzoyl, etc.

As the substituent of ring A, mention is made of halogen atoms (e.g. fluorine, chlorine, bromine, iodine), C$_{1-4}$ optionally substituted lower alkyl groups (e.g. methyl, ethyl, propyl, butyl and tert-butyl), C$_{1-4}$ optionally substituted lower alkoxy groups (e.g. methoxy, ethoxy, propoxy, isopropoxy, butoxy and tert-butoxy), nitro group and cyano group. The ring A may have 1 to 3, preferably one or two, of these substituents. And, these substituents may form a ring with each of the adjacent substituents. As the substituent of said optionally substituted lower alkyl group or optionally substituted lower alkoxy group, mention is made of halogen atoms (e.g. fluorine, chlorine, bromine, iodine), and 1 to 3 of these halogen atoms may be substituted on an optional position.

And, when X is shown by the formula

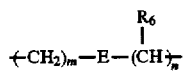

, wherein symbols are of the same meaning as defined above, E is preferably a bond or —CONH—. When E is —CONH—, preferably m=1, n=1 or m=2, n=1, especially m=1, n=1. In this case, R$_6$ is preferably hydrogen atom, benzyl and 3-indolyl methyl, especially hydrogen atom and 3-indolyl methyl. When E is —CONH—, Y is preferably carboxyl group and esterified carboxyl group, especially carboxyl group.

Further, preferable examples of substituents of the ring A include no substituent, lower alkoxy or a halogen atom, and methoxy or chlorine atom is especially preferable.

As salts of the compound (I), (I') or (I''), mention is made of pharmacologically acceptable salts including inorganic salts such as hydrochloride, hydrobromide, sulfate, nitrate, phosphate, etc., organic acid salts such as acetate, tartrate, citrate, fumarate, maleate, toluenesulfonate, methanesulfonate, etc., metal salts such as sodium salt, potassium salt, calcium salt, aluminiun salt, etc. and basic salts such as triethylamine salt, guanidine salt, ammonium salt, hydrazine salt, quinine salt, cinchonine salt, etc.

Further, the present invention provides a method of producing a compound represented by the formula (I) or the formula (I'):

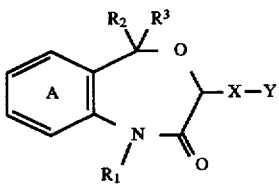

, wherein each of the symbols is of the same meaning as defined above or a pharmaceutically acceptable salt thereof, by subjecting a compound represented by the following formula:

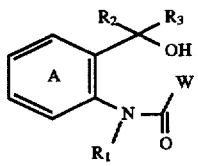

wherein W is

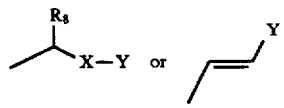

wherein R$_8$ is halogen (e.g. fluorine, chlorine, bromine and iodine) or —OSO$_3$CH$_3$ or other symbols are of the same meaning as defined above, to a cyclization reaction.

Methods of producing compounds of this invention are described below:

Among the compounds of formula (I) and (I'), compounds represented by the formula (Ia)

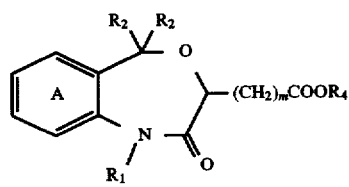

, wherein R$_4$ stands for a C$_{1-8}$ alkyl group or aralkyl group, and other symbols are of the same meaning as defined above, can be produced by the following methods.

2-aminobenzophenones as the starting material can be synthesized by, or in accordance with, the method described in D. A. Walsh, Synthesis, 677 (1980) or the method cited in said reference.

Among the above-exemplified groups shown by X', an alkyl group substituted with an optionally esterified carboxyl group or an alkyl group substituted with an optionally substituted heterocyclic radical having a protonizable hydrogen are preferable.

In the formulae (Ir), as aromatic heterocyclic rings shown by Ring A', mention is made of aromatic heterocyclic groups described in detail referring to $R_1$. Among them, groups represented by the formulae

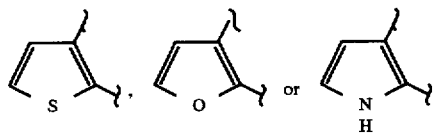

are preferable.

As substituents of the "optionally substituted benzene rings" and "optionally substituted aromatic heterocyclic groups" shown by Ring A', mention is made of halogen (e.g. fluorine, chlorine, bromine, iodine), $C_{1-4}$ optionally substituted lower alkyl groups (e.g. methyl, ethyl, propyl, butyl, tert-butyl, etc.), $C_{1-4}$ optionally substituted lower alkoxy groups (methoxy, ethoxy, propoxy, isopropoxy, butoxy, tert-butoxy, etc.), hydroxy, nitro group, cyano, etc. the ring A may have 1 to 3 of these substituents, preferably 1 to 2. And, these substituents may form a ring, taken together with respectively adjacent substituents. As substituents of said optionally substituted lower alkyl groups or those of optionally substituted lower alkoxy groups, mention is made of halogen atoms (e.g. fluorine, chlorine, bromine, iodine), etc., which may have 1 to 3 substituents at optional positions. As rings A, those which are substituted with methoxy or chlorine atom are preferable, especially those substituted with chlorine are preferable.

In the formula (Ir'), as substituents of the "optionally substituted benzene rings" shown by Ring A, mention is made of halogen (e.g. fluorine, chlorine, bromine, iodine), $C_{1-4}$ optionally substituted lower alkyl groups (e.g. methyl, ethyl, propyl, butyl, tert-butyl, etc.), $C_4$ optionally substituted lower alkoxy groups (methoxy, ethoxy, propoxy, isopropoxy, butoxy, tert-butoxy, etc.), hydroxy, nitro group, cyano, etc. the Ring A may have 1 to 3 of these substituents, preferably 1 to 2. And, these substituents may form a ring, taken together with respectively adjacent substituents. As substituents of said optionally substituted lower alkyl groups or those of optionally substituted lower alkoxy groups, mention is made of halogen atoms (e.g. fluorine, chlorine, bromine, iodine), etc., which may have 1 to 3 substituents at optional positions. As rings B, those which are substituted with methoxy or chlorine atom are preferable, especially those substituted with chlorine are preferable.

In the formula (Ir), as heterocyclic rings of the "7- or 8-membered heterocyclic ring containing at most three ring constituting hetero atoms" shown by ring J', mention is made of saturated or unsaturated 7- or 8-membered heterocyclic rings containing, as the atoms constituting the cyclic ring, at least one hetero-atom selected from O, S(O)$_q$ (q is 0, 1 or 2) and N, provided that the number of hetero atoms in the atoms constituting the cyclic system (ring constituting atoms) of said heterocyclic ring is at most three.

And, the ring J' may optionally have, besides the groups represented by $R_1$, $R_2$, $R_3$ and X', one or two appropriate substituents at any possible position. As said substituent, when it binds to a nitrogen atom on the ring J', mention is made of $C_{1-6}$ straight-chain or branched alkyl groups (e.g. methyl, ethyl, n-propyl, isopropyl, n-butyl, isobutyl, tert-butyl, n-pentyl, isopentyl, neopentyl, etc.), acyl groups such as $C_{1-4}$ acyl groups (e.g. formyl, acetyl, propionyl, butyroyl, etc.), etc. Said alkyl or said acyl may have one to five of halogen atoms (e.g. fluorine, chlorine, bromine, iodine). And, when said substituent binds to a carbon atom or the ring J', mention is made of oxo, thioxo, an optionally substituted hydroxyl group, an optionally substituted amino group, etc. Said optionally substituted hydroxyl group and said optionally substituted amino group are substantially the same as the "optionally substituted hydroxyl group and the "optionally substituted amino group shown by Y.

The ring J' is preferably substituted with oxo or thioxo, besides the groups of $R_1$, $R_2$, $R_3$ and X', at any possible position.

As the condensed ring composed of Ring A' and Ring J', mention is made of

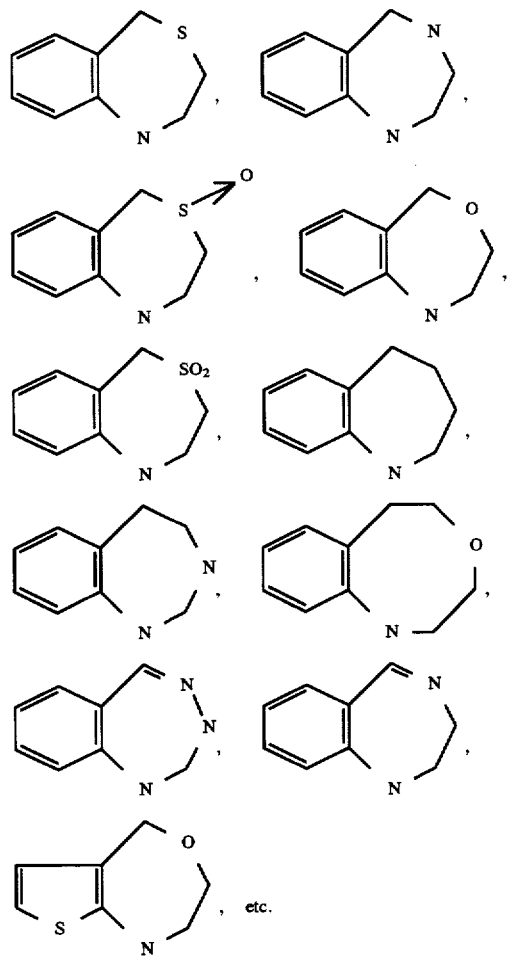

The formula (Ir) is preferably one represented by the formula (Ir$_a$):

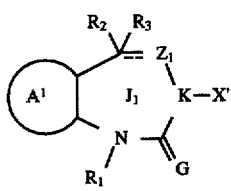

wherein $R_1$, $R_2$, $R_3$, X' and Ring A' are of the same meaning as defined above; Ring $J_1$ is a 7-membered heterocyclic ring; $Z_1$ is =N—, —N($R_7$)— (wherein $R_7$ is hydrogen, alkyl group or acyl group), —S(O)$_q$— (wherein q is 0, 1 or 2), —CH$_2$— or —O—; K is C or N; G is O or S; the symbol ......... is a double bond when $Z_1$ is =N—, while a single bond when $Z_1$ is not =N—.

In the formula (Ir$_a$), as alkyl groups shown by $R_7$, mention is made of $C_{1-6}$ straight-chain or branched lower alkyl groups (e.g. methyl, ethyl, n-propyl, isopropyl, n-butyl, isobutyl, tert-butyl, n-pentyl, isopentyl, neopentyl, etc.), which may optionally be substituted with 1 to 5 halogen atoms (e.g. fluorine, chlorine, bromine, iodine).

As acyl groups shown by $R_7$, mention is made of $C_{1-4}$ acyl groups (e.g. formyl, acetyl, propionyl, butyroyl, etc.), which may optionally be substituted with 1 to 5 halogen atoms (e.g. fluorine, chlorine, bromine, iodine).

The formula (Ir$_a$) is preferably one represented by the formula (Ir$_b$):

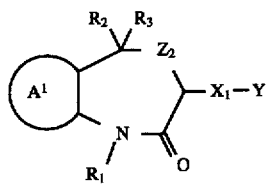

wherein $R_1$, $R_2$, $R_3$, $X_1$, Y and Ring A' are of the same meaning as defined above; $Z_2$ is S(O)$_q$— (wherein q is 0, 1 or 2) or O.

The formula (Ir) is more preferably one represented by the formula (Ir").

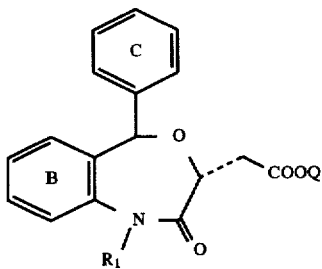

wherein $R_1$ and Ring B are of the same meaning as defined above; Q is hydrogen or a metal ion; Ring B is an optionally substituted phenyl group. Here, the formula (Ir") shows a trans-isomer in which the substituents at 3- and 5-positions are oriented in the adverse directions to each other relative to the face of 7-membered ring. And (R) shows (R)-configuration.

In the formula (Ir"), as the metal ion shown by Q, mention is made of sodium salt, potassium salt, calcium salt and aluminium salt, etc, preferably sodium salt, potassium salt.

Examples of the "optionally substituted phenyl group" shown by ring C are substantially the same as those in the case of the above-mentioned "optionally substituted phenyl group" shown by $R_2$ and $R_3$.

The compounds in this invention are specifically disclosed as follows:

(3R, 5S)-7-cyano-5-(2,3-dimethoxyphenyl)-1-neopentyl-2-oxo-1,2,3,5-tetrahydro-4,1-benzoxazepine-3-acetic acid, (3R, 5S)-7-cyano-5-(2,4-dimethoxyphenyl)-1-neopentyl-2-oxo-1,2,3,5-tetrahydro-4,1-benzoxazepine-3-acetic acid, (3R, 5S)-7-cyano-5-(2,3-methylenedioxyphenyl)-1-neopentyl-2-oxo-1,2,3,5-tetrahydro-4,1-benzoxazepine-3-acetic acid, (3R, 5S)-7-cyano-5-(2,3-ethylenedioxyphenyl)-1-neopentyl-2-oxo-1,2,3,5-tetrahydro-4,1-benzoxazepine-3-acetic acid, (3R, 5S)-7-cyano-5-(2,3-dimethoxyphenyl)-1-isobutyl-2-oxo-1,2,3,5-tetrahydro-4,1-benzoxazepine-3-acetic acid, (3R, 5S)-7-cyano-5-(2,4-dimethoxyphenyl)-1-isobutyl-2-oxo-1,2,3,5-tetrahydro-4,1-benzoxazepine-3-acetic acid, (3R, 5S)-7-cyano-5-(2,3-methylenedioxyphenyl)-1-isobutyl-2-oxo-1,2,3,5-tetrahydro-4,1-benzoxazepine-3-acetic acid, (3R, 5S)-7-cyano-5-(2,3-ethylenedioxyphenyl)-1-isobutyl-2-oxo-1,2,3,5-tetrahydro-4,1-benzoxazepine-3-acetic acid, (3R, 5S)-7-chloro-5-(2,3-dimethoxyphenyl)-1-neopentyl-2-oxo-1,2,3,5-tetrahydro-4,1-benzoxazepine-3-acetic acid, (3R, 5S)-7-chloro-5-(2,4-dimethoxyphenyl)-1-neopentyl-

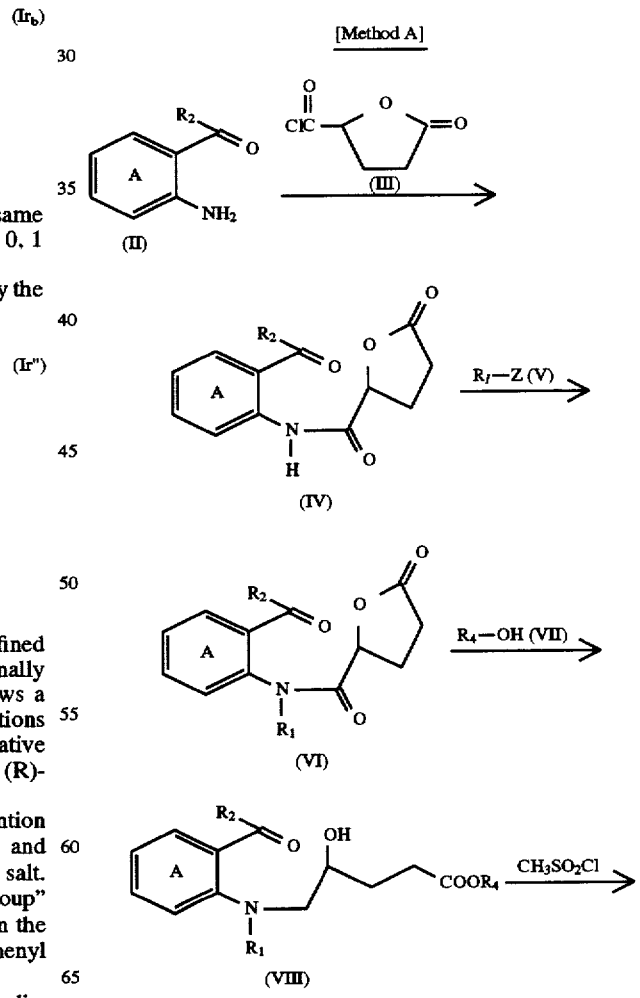

[Method A]

-continued
[Method A]
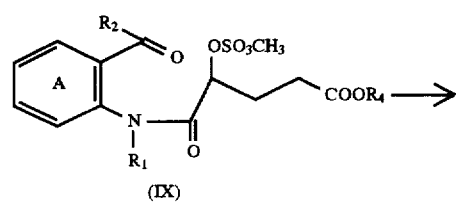
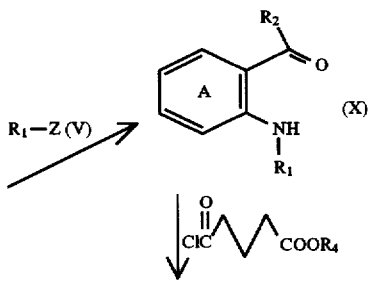
[Method B]
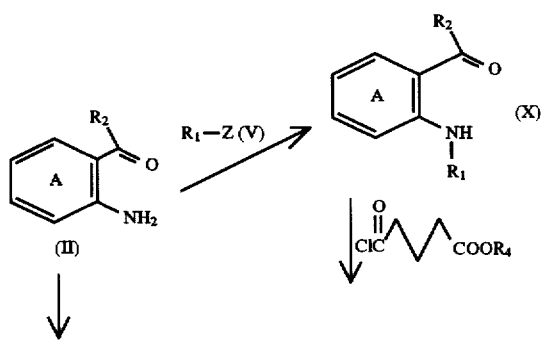
[Method B]
-continued
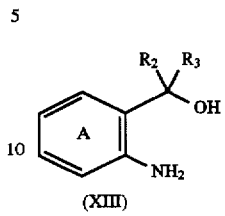 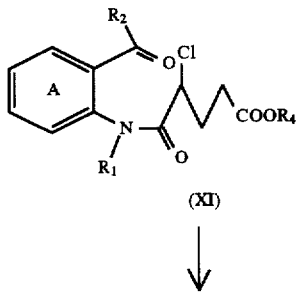
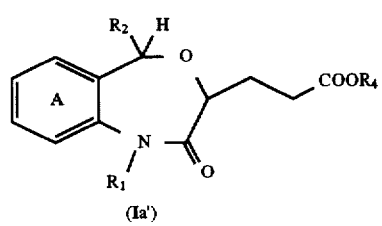
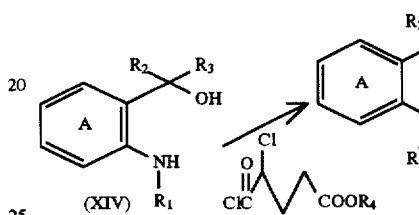
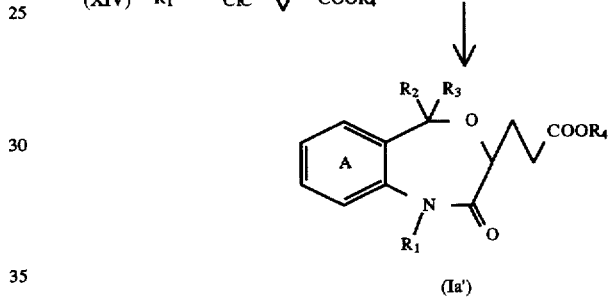
[Method C]
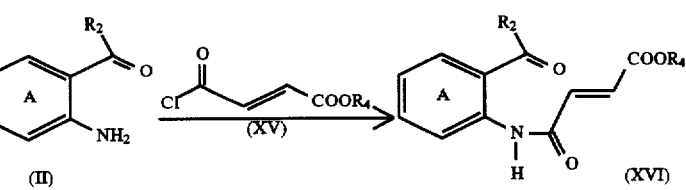
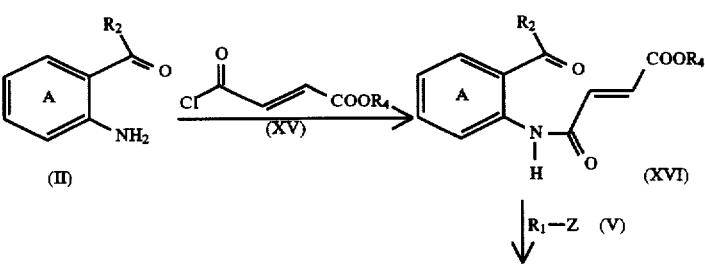
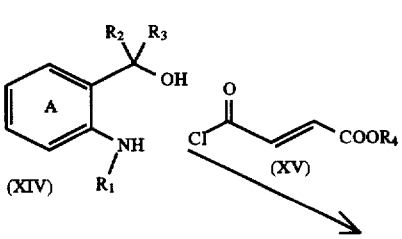

-continued
[Method C]

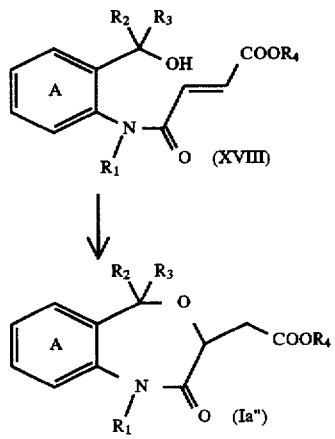

, wherein Z stands for a halogen atom, and other symbols are of the same meaning as defined above.

The reactions from the formula (II) to the formula (IV) and from the formula (VIII) to the formula (IX) in the above-mentioned [Method A] or those from the formula (X) to the formula (XI) and from the formula (XIV) to the formula (XII) in the above-mentioned [Method B] can be carried out by utilizing a per se known acylation reaction. For example, the acylation reaction of this invention can be conducted in a solvent exemplified by an ether-type solvent such as diethyl ether, tetrahydrofuran, dioxane, etc., a halogen-type solvent such as dichloromethane, dichloroethane, chloroform, carbon tetrachloride, etc., a hydrocarbon-type solvent such as benzene, toluene, hexane, heptane, etc., dimethylformamide, dimethyl sulfoxide, etc., and, depending on necessity, in the presence of water and a base (e.g. an organic base such as 4-dimethylaminopyridine, triethylamine, triethylenediamine, tetramethylethylenediamine, etc. an inorganic base such as sodium hydrogencarbonate, potassium hydrogencarbonate, sodium carbonate, potassium carbonate, sodium hydroxide, potassium hydroxide, etc, sodium hydride, potassium hydride), among others. Relative to one mole of a compound represented by the formulae (II), (VIII), (X) and (XIV), acid chloride and methanesulfonyl chloride by the formula (III) and ester of 4-chloroformyl butyric acid are usually employed in an amount of 1 to 10 mol., preferably 1 to 3 mol. And, the reaction time usually ranges from about 1 to 48 hours, preferably from about 5 to 10 hours. The reaction temperature ranges from −50° to 100° C., preferably from about 0° to 50° C.

And, the reaction from the formula (IV) to the formula (VI) in [Method A] and the reactions from the formula (II) to the formula (X) and from the formula (XIII) to the formula (XIV) in [Method B] can be carried out in an ether type solvent such as diethyl ether, tetrahydrofuran, dioxane etc., a hydrocarbon type solvent such as benzene, toluene, hexane, heptane etc., an alcohol type solvent such as methanol, ethanol, propanol, butanol etc., acetone or dimethylformamide, and, depending on necessity, in the presence of a base (e.g. sodium hydrogencarbonate, potassium hydrogencarbonate, sodium carbonate, potassium carbonate, sodium hydride, potassium hydride or the like). Relative to one mole of a compound represented by the formula (II), the formula (IV) or the formula (XIII), a compound represented by the formula (V) is employed usually in an amount ranging from 1 to 10 mol., preferably about 1 to 2 mol. The reaction temperature ranges from 0° to 100° C., preferably from about 20° to 50° C. The reaction time ranges usually from 1 to 24 hours, preferably about 3 to 10 hours.

And, the reduction reaction of carbonyl group from the formula (IX) to the formula (Ia') in [Method A], from the formula (II) to the formula (XIII) and from the formula (XI) to the formula (XII) in [Method B] can be conducted in a protonic solvent (e.g. methanol, ethanol, propanol, butanol, etc.) or a non-protonic solvent (e.g. ethyl ether, tetrahydrofuran, dioxane, etc.) in the presence of a metal hydrogen complex (e.g. lithium aluminum hydride, sodium aluminum hydride, sodium triethoxyaluminium hydride, sodium borohydride, etc.). Relative to one each mol. of compounds shown by the formula (IX), the formula (II) and the formula (XI), such a metal hydrogen complex as mentioned above is employed in an amount, usually ranging from 0.3 to 5 mol. equivalents, preferable from 0.5 to 2 mol. equivalents. The reaction temperature ranges from −20° to 100° C., preferably from 20° to 50° C.

The cyclization reaction to the formula (Ia') from the formula (XII) in [Method B] can be carried out in a solvent, for example, an ether type solvent such as diethyl ether, tetrahydrofuran, dioxane, etc., a hydrocarbon type solvent such as benzene, toluene, hexane, heptane, etc., an alcohol type solvent such as methanol, ethanol, propanol, butanol, etc., acetone, dimethylformamide or the like, in the presence of, depending on necessity, a base (e.g. sodium hydrogencarbonate, potassium hydrogencarbonate, sodium carbonate, potassium carbonate, sodium hydride, potassium hydride, etc.). Relative to one mol. of a compound shown by the formula (XII), a base as exemplified above is employed in an amount usually ranging from 1 to 5 mol., preferable from about 1 to 2 mol. The reaction temperature ranges usually from −20° to 200° C., preferably from 20° to 100° C. The reaction time ranges usually from 1 to 20 hours, preferably from 2 to 5 hours.

The reaction from the formula (VI) to (VIII) in [Method A] can be conducted in an alcohol shown by the formula (VII), and, depending on necessity, in the presence of an inorganic acid such as nitric acid, hydrochloric acid, hydrobromic acid or sulfuric acid, or an organic acid such as toluenesulfonic acid or methanesulfonic acid, at temperatures ranging from −20° to 100° C., preferably from 20° to 50° C. The reaction time ranges from 10 to 100 hours, preferably from 10 to 48 hours.

The compound shown by the formula (Ia") can be produced in accordance with a conventional method.

Among the compounds shown by the formula (I) and (I'), a compound represented by the formula (Ib)

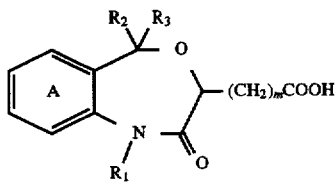

, wherein symbols are of the same meaning as defined above, can be produced by subjecting a compound shown by the formula (Ia) to hydrolysis, for example, by processing a compound shown by the formula (Ia) with an acid or a base. More specifically, a compound shown by the formula (Ia) is processed in an aqueous solution of a mineral acid (e.g. nitric acid, hydrochloric acid, hydrobromic acid, iodic acid, sulfuric acid or the like) or an alkali metal hydroxide (sodium hydroxide, potassium hydroxide, barium hydroxide, lithium hydroxide) at temperatures ranging from 0° to 150° C., preferably from 20° to 50° C. The strength of the acid or the base ranges usually from 1 to 10N, preferably from 4 to 10N. The reaction time varies with the reaction temperature, but usually ranges from 1 to 24 hours, preferably from about 2 to 10 hours.

A compound shown by the formula (Ib')

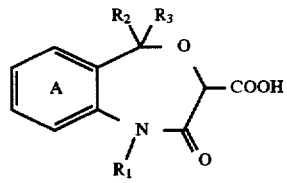

, wherein symbols are of the same meaning as defined above, can be produced by subjecting a compound shown by the formula (Ic')

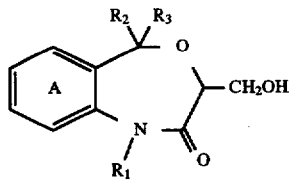

, wherein symbols are of the same meaning as defined above, to oxidation. The solvent then to be used may be any one so long as it does not hamper the reaction, which is exemplified by acetone, dioxane, tetrahydrofuran, dichloromethane, dichloroethane or chloroform. As the oxidizing agent, permanganate, chromic acid or nickel peroxide can be used, for example. In this case, the oxidizing agent is used in an amount ranging from 0.5 to 20 mol. equivalents, preferably from 1 to 3 mol. equivalents, relative to one mol. of the compound shown by the formula (Ic'), the reaction temperature ranges from 0° to 100° C., preferably from 15° to 50° C. and the reaction time ranges from 0.5 to 5 hours, preferably from about 1 to 2 hours.

Among the compounds to be used as intermediates for synthesizing a compound of formula (I) or (I'), a compound shown by the formula (XIX)

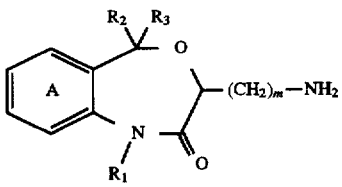

, wherein symbols are of the same meaning as defined above, can be produced by allowing a compound shown by the formula (Ib) to react with diphenylphosphoryl azide in a solvent in the presence of a base, then by processing the resultant with an acid in a solvent. The solvent to be used in the reaction between a compound shown by the formula (Ib) and diphenylphosphoryl azide may be any one, so long as it does not hamper the reaction, which is exemplified by dimethylformamide, a halogen-type solvent such as dichloromethane, chloroform or dichloroethane and an ether-type solvent such as ether, tetrahydrofuran or dioxane. Typical examples of the base to be employed include triethylamine, 4-dimethylaminopyridine, triethylenediamine and tetramethylethylenediamine. Relative to 1 mol. of a compound shown by the formula (Ib), 1 to 10 mol. equivalents, preferably about 1.5 to 3 mol. equivalents, of diphenylphosphoryl azide is employed. The reaction temperature ranges from −20° to 50° C. preferably from 0° to 20° C. and the reaction time ranges from 0.5 to 5 hours, preferably from about 1 to 2 hours.

In the case of processing the product obtained by the above-described reactions, the solvent to be used is exemplified by water, dioxane, dimethylformamide etc., and, as the acid to be employed, a mineral acid such as sulfuric acid, hydrochloric acid, nitric acid or hydrobromic acid can be exemplified. The reaction temperature ranges from 20° to 200° C., preferably from about 50° to 100° C. and the reaction time ranges from 0.5 to 5 hours, preferably from about 1 to 2 hours.

Among the compounds represented by the formula (I) and (I'), a compound shown by the formula (Ic)

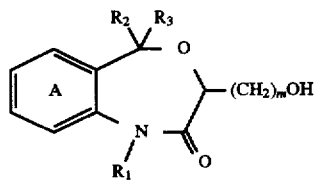

, wherein symbols are of the same meaning as defined above, can be produced by subjecting a compound shown by the formula (Ia) to reduction. More specifically, the compound shown by the formula (Ic) can be produced by processing the compound shown by the formula (Ia) with a metal hydride complex (e.g. lithium aluminum hydride, sodium aluminum hydride, sodium borohydride) in a protonic solvent (e.g. methanol, ethanol, propanol, butanol etc.) or a non-protonic solvent (e.g. ethyl ether, tetrahydrofuran, dioxane etc.) Relative to one mol. of the compound shown by the formula (Ia), such a metal hydride complex compound is used in an amount ranging usually from 0.3 to 5 mol. equivalents, preferably from 0.5 to 2 mol. equivalents. The reaction temperature ranges from −20° C. to 100° C., preferably from 0° to 20° C. The reaction time ranges from 0.5 to 10 hours, preferably from about 1 to 3 hours.

And, a compound shown by the formula (Ic) can be produced also by converting the amine portion of a compound shown by the formula (XIX) into hydroxyl group. For example, a compound of the formula (Ic) can be produced by adding sodium nitrite to a compound of the formula (XIX) in a solvent in the presence of an acid then by processing the resultant azide compound in a solvent in the presence of a base. In the method of azidation, for example, 0.5 to 3, preferably 1 to 1.5, mol. equivalents of sodium nitrite, is employed relative to 1 mol. of a compound of (XIX). As the acid, any one can be employed so long as it does not hamper the reaction, typically exemplified by acetic acid and sulfuric acid. The reaction temperature ranges form −20° to 20° C., preferably 0° to 5° C., and the reaction time ranges from 5 to 60 minutes, preferably about 10 to 30 minutes. The method of converting the azide of thus-obtained azide compound into hydroxyl group comprises, for example, use of, as the base, for example, sodium hydrogencarbonate, potassium hydrogencarbonate, sodium carbonate, potassium carbonate, sodium hydroxide, potassium hydroxide or the like in water or an aqueous organic solvent (e.g. an alcohol-type solvent such as methanol, ethanol, propanol, butanol or the like, an ether-type solvent such as tetrahydrofuran, dioxane or the like, dimethylformamide, etc.). The reaction temperature ranges from 20° to 200° C., preferably from 50° to 100° C., and the reaction time ranges from 5 minutes to 2 hours, preferably from about 15 to 30 minutes.

The compound shown by the formula (XX)

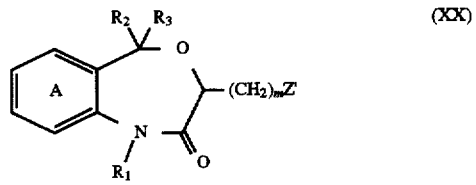

, wherein Z' stands for halogen (chlorine, bromine, iodine) and other symbols are of the same meaning as defined above, which is an intermediate for synthesizing the compound of the formula (I), can be produced by, like the method employed in the case of producing the compound (Ic) from the compound (XIX), subjecting a compound shown by the formula (XIX) to diazotization with sodium nitrite in hydrochloric acid, hydrobromic acid or hydroiodic acid, then by heating thus diazotized compound. The reaction temperature ranges from 20° to 200° C., preferably form 50° to 100° C., and the reaction time ranges from 5 minutes to 2 hours, preferably from about 15 to 30 minutes.

Among the compounds represented by the formula (I) and (I'), a compound shown by the formula (Id)

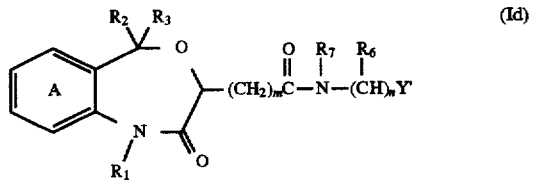

, wherein Y' stands for, among the definitions given to Y as above, esterified carboxyl group and hydroxyl group, and other symbols are of the same meaning as defined above, can be produced by subjecting a compound shown by the formula (Ib) to condensation with a compound represented by the formula (XXI)

, wherein symbols are of the same meaning as defined above, more specifically, the compound (Ib) and the compound (XXI) are subjected to condensation in a solvent by using a condensing agent, and, upon necessity, in the presence of a base. The solvents to be employed are exemplified by hydrocarbon-type solvents such as benzene, toluene, hexane, heptane etc., halogen-type solvents such as dichloromethane, dichloroethane, chloroform, carbon tetrachloride etc., ether-type solvents such as ethyl ether, tetrahydrofuran, dioxane, etc., acetonitrile, dimethylformamide, etc. As the base, use is made of, among others, triethylamine, 4-dimethyl aminopyridine, triethylenediamine and tetramethyl ethylenediamine. As condensing agents, mention is made of those to be employed for peptide synthesis, which are exemplified by, among others, cyclohexyl carbodiimide, diethyl cyanophosphate and 1-ethyl-3-(3-dimethylaminopropyl)carbodiimide. Relative to one mol. of the compound shown by the formula (Ib), a compound represented by the formula (XXI) is used in an amount ranging from 0.5 to 2 mol. equivalents, preferably from 1 to 1.2 mol. equivalent, and a condensing agent is used in an amount ranging from 0.5 to 5 mol. equivalents, preferably 1 to 2 mol. equivalents. The reaction temperature ranges from 0° to 100° C., preferably from 20° to 50° C., and the reaction time ranges from 0.5 to 24 hours, preferably from about 1 to 5 hours.

Among the compounds represented by the formula (I) and (I'), a compound shown by the formula (Ie)

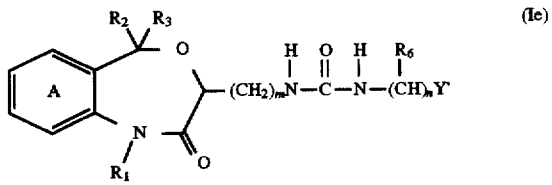

, wherein symbols are of the same meaning as defined above, can be produced by allowing a compound (Ib) to react with diphenyl phosphoryl azide in a solvent in the presence of a base, then by allowing the resultant compound to react with a compound (XXI). As the solvent to be employed in the reaction between the compound (Ib) and diphenyl phosphoryl azide, any one can be used so long as it does not hamper the reaction, which is exemplified by dimethylformamide or a halogen-type solvent such as dichloromethane, chloroform, dichloroethane etc., and an ether-type solvent such as ether, tetrahydrofuran, dioxane etc. The base to be employed is typically exemplified by triethylamine, 4-dimethyl aminopyridine, triethylene diamine or tetramethyl ethylenediamine. Relative to one mol. of the compound shown by the formula (Ib), 1–10, preferably about 1.5 to 3 mol. equivalents of diphenyl phosphoryl azide is employed. The reaction temperature ranges from −20° to 50° C., preferably from 0° to 20° C., and the reaction time ranges from 0.5 to 5 hours, preferably from about 1 to 2 hours.

The solvent to be employed in the reaction between the compound obtained thus above and a compound shown by the formula (XXI) is exemplified by a halogen-type solvent such as dichloromethane, dichloroethane, chloroform etc., an ether-type solvent such as ether, tetrahydrofuran, dioxane etc., acetonitrile, dimethylformamide, among others. And, depending on necessity, a base is employed. As the base, mentioned is made of an organic base including triethylamine, 4-dimethyl aminopyridine, triethylenediamine and tetramethyl ethylenediamine. Relative to one mol. of the compound (Ib), 0.5 to 3, preferably 1 to 1.5, mol. equivalents of the compound (XXI). The reaction temperature ranges from 0° to 150° C., preferably from 30° to 100° C., and the reaction time ranges from 0.5 to 24, preferably about 1 to 3, hours.

Among the compounds represented by the formula (I) and (I'), a compound shown by the formula (If)

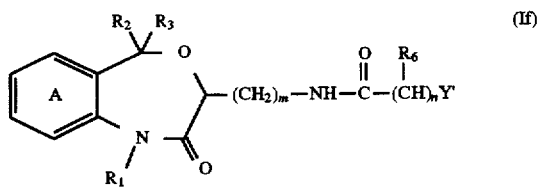

, wherein symbols are of the same meaning as defined above, can be produced by subjecting a compound of (XIX) to condensation with a compound represented by the formula (XXII)

, wherein symbols are of the same meaning as defined above. This reaction can be conducted in completely the same manner as in the production of the compound (Id).

Among the compounds represented by the formula (I) and (I'), a compound shown by the formula (Ig)

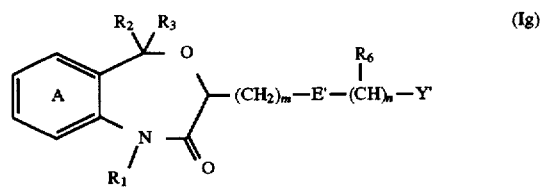

, wherein E' stands for, among the definitions given above, oxygen atom or —NH—, and other symbols are of the same meaning as defined above, can be produced by allowing a compound shown by the formula (Ic) or a compound shown by the formula (XIX) to react with a compound represented by the formula (XXIII)

, wherein symbols are of the same meaning as defined above. More specifically, the compound (Ic) or the compound (XIX) is allowed to react with the compound (XXIII) in an alcohol-type solvent such as methanol, ethanol, propanol, butanol etc., an ether-type solvent such as diethyl ether, tetrahydrofuran, dioxane etc. or dimethylformamide, among others, in the presence of a base including an inorganic base such as sodium hydrogencarbonate, potassium hydrogencarbonate, sodium carbonate, potassium carbonate etc., an organic base such as triethylamine, 4-dimethyl aminopyridine, triethylenediamine, tetramethyl ethylenediamine etc. or sodium hydride. Relative to one mol. of the compound (Ic) or (XIX), 0.5 to 1.5 mol. equivalent of the compound (XXIII) is used, and, relative to one mol. of the compound (Ic) or (XIX), 1 to 5, preferably 1 to 2, mol. equivalents of the base is used. The reaction temperature ranges from 0° to 200° C., preferably from 20° to 100° C., and the reaction time ranges from 0.5 to 24 hours, preferably from about 1 to 3 hours.

Among the compounds represented by the formula (I) and (I'), a compound shown by the formula (Ih)

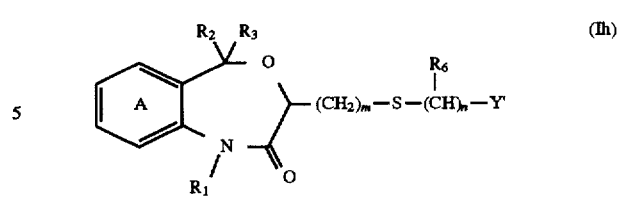

, wherein symbols are of the same meaning as defined above, can be produced by allowing a compound (XX) to react with a compound represented by the formula (XXV)

, wherein symbols are of the same meaning as defined above. The solvent to be employed is a non-protonic solvent exemplified by ethyl ether, tetrahydrofuran, dioxane, acetonitrile, dimethylformamide or the like. Depending on necessity, an inorganic base such as sodium hydrogencarbonate, potassium hydrogencarbonate, sodium carbonate or potassium carbonate, an organic base such as triethylamine, 4-dimethyl aminopyridine, triethylenediamine or tetramethyl ethylenediamine, sodium hydride, cesium fluoride or the like may be used. Relative to one mol. of the compound (XX), 0.5 to 5, preferably 1 to 2, mol. equivalents of the compound (XXV) is employed. The reaction temperature ranges from 0° to 200° C. preferably 20° to 100° C., and the reaction time ranges from 10 minutes to 5 hours, preferably from about 30 minutes to 2 hours.

Among the compounds represented by the formula (I) and (I'), a compound shown by the formula (Ii)

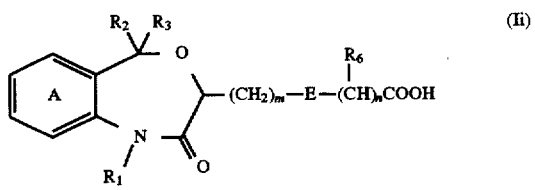

, wherein symbols are of the same meaning as defined above, can be produced by subjecting a compound represented by the formula (Ij)

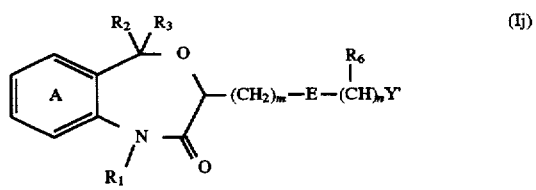

, wherein Y" stands for, among the groups defined by Y as above, esterified carboxyl group, and other symbols are of the same meaning as defined above, to hydrolysis. More specifically, the hydrolysis is conducted in a solvent such as water, methanol, ethanol, propanol or butanol in the presence of an alkali metal hydroxide (e.g. sodium hydroxide, potassium hydroxide, barium hydroxide or lithium hydroxide), sodium hydrogencarbonate, potassium hydrogencarbonate, sodium carbonate or potassium carbonate, or, in the presence of a mineral acid (e.g. nitric acid, hydrochloric acid, hydrobromic acid, iodic acid or sulfuric acid) or trifluoroacetic acid, at temperatures ranging from 10° to 150° C., preferably from 10° to 50° C. While the reaction time varies with the reaction temperature, it ranges usually from 1 to 24 hours, preferably from about 2 to 10 hours.

While the compound represented by the formula (I") of this invention has a squalene synthetase inhibiting action and an antifungal action, among the compounds used in the present invention, there are compounds capable of inhibiting other enzymes in the pathway of cholesterol biosynthesis. In any event, the compound represented by the formula (I") of this invention inhibits biosynthesis of cholesterol, which is useful for the prophylaxis or therapy of hypercholesteremia or coronary sclerosis of meals (e.g. mouse, rat, rabbit, dog, cat, cow, pig and human being) and, further, for the prophylaxis or therapy of fungus infections.

Said compound (I") can be administered to man orally or non-orally. The orally administrable compositions may be in a solid or liquid form, more specifically tablets (including sugar-coated tablets and film-coated tablets), syrups, emulsions, suspensions or the like. These compositions can be prepared by a per se known method and contain carriers or excipients conventionally used in the field of pharmaceutical preparation, for example, carriers or excipients such as lactose, starch, sucrose or magnesium stearate for preparing tablets.

The non-orally administrable compositions are exemplified by injections and suppositories, and the injections include hypodermic injections, intradermal injections and intramuscular injections. These injections can be prepared by a per se known method, more specifically, by suspending or emulsifying the compound of this invention in a sterile water or oil conventionally used for preparing injectable compositions. The aqueous liquid to be used for preparation of injections include physiological saline solution and isotonic solution, and, depending on necessity, a suitable suspending agent such as sodium carboxymethyl cellulose, a non-ionic surfactant or the like may be jointly used. As the oil, mention is made of sesame oil, soybean oil, etc., and benzyl benzoate, benzyl alcohol etc. as a solubilizer may be jointly used. Injections thus prepared are, in general, filled in appropriate ampoules.

The compound represented by the formula (I") or a salt thereof can be used safely with low toxicity. Although the daily dose varies depending on the condition and weight of the patient, kind of the compound, route of administration and other factors, for example, in the case of administering the compound of the present invention for the therapy of hypercholesteremia, a daily oral dosage per adult human is about 1 to 500 mg, preferably about 10 to 200 mg. Within this range, no toxicity is observed at all.

The compound of the formula (I") for squalene synthetase inhibition is effectively administered to a mammal, e.g., human, in a therapeutically effective amount which is generally provided with an oral daily dosage per adult of from about 1 to about 500 mg, preferably about 10 to 200 mg. In terms of a non-oral dosage range such as for an injection or suppository, therapeutically effective amount is generally in the range of from about 0.1 to about 100 mg/day, preferably about 1 to 20 mg/day.

The present invention compounds also demonstrate broad spectrum antifungal activity as determined by broth or agar dilution methods.

In case of administering the compound of the present invention for the therapy of fungus infections, generally from 2 to 5 mg/kg should be employed as a unit dosage in an antifungal treatment.

The compound of the formula (I") for fungus treatment is effectively administered to a mammal, e.g., human, in a therapeutically effective amount which is generally provided with an oral daily dosage per adult of from about 0.1 to about 100 mg, preferably about 1 to 50 mg. In terms of a non-oral dosage range such as for an injection or suppository, a therapeutically effective amount is generally in the range of from about 0.1 to about 100 mg/day, preferably about 1 to 50 mg/day.

Abbreviations for amino acids, and other used in the present specification are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated.

Trp or Y: Tryptophan
Ser or S: Serine
Asp or D: Aspartic acid
Glu or E: Glutamic acid
Me: Methyl
Et: Ethyl
Ph: Phenyl

[EXAMPLES]

The following examples, reference examples, formulation examples and test examples are intended to illustrate the present invention in further detail and should by no means be construed as defining the metes and bounds of the invention.

In the following description, two types of racemic diastereomers are obtained depending of the kinds of compounds, which is due to the presence of asymmetric carbon atoms at 3- and 5-positions. Isomers in which the substituents at 3- and 5-positions are oriented in the same direction relative to the face of 7-membered ring are named cis-isomers, while those in which the substituents at 3- and 5-positions are oriented in the adverse directions to each other are named trans-isomers.

Reference Example 1

Trans-7-chloro-5-(2-chlorophenyl)-1,2,3,5-tetrahydro-1-methyl-2-oxo-4,1-benzoxazepine-3-acetic acid ethyl ester (1) Ethyl 3-[N-[2-(2-chlorobenzoyl)-4-chlorphenyl] carbamoyl]acrylate To a suspension of 5.0 g of 2-amino-5-chloro-2'-chlorobenzophenone and 2.5 g of sodium hydrogencarbonate in 100 ml of methylene chloride was added dropwise 3.3 g of monoethyl ester of fumaric acid semi-chloride in the course of 30 minutes. The mixture was stirred for 2 hours at room temperature, to which was then added water, followed by shaking. The organic layer was separated, which was dried over anhydrous sodium sulfate, followed by distilling off the solvent under reduced pressure to leave 4.8 g of 3-[N-[2-(2-chlorobenzoyl)-4-chlorophenyl]carbamoyl] acrylic acid ethyl ester as crystals, m.p. 113°–114° C.

Elemental Analysis for $C_{19}H_{15}Cl_2NO_4$: Calcd.: C 58.18; H 3.85; N 3.57 Found: C 58.27; H 3.88; N 3.48

(2) Ethyl ester of 3-[N-[2-(2-chlorobenzoyl)-4-chlorophenyl]-N-methylcarbamoyl] acrylic acid To a suspension of 0.15 g of sodium hydride in 20 ml of N,N-dimethylformamide was added, while stirring under ice-cooling, 3.0 g of the crystals obtained above. The mixture was stirred for 10 minutes at 0° C. to which was added 2.0 g of methyl iodide, then the mixture was stirred for 2 hours at room temperature. The reaction mixture was poured into ice-water, which was subjected to extraction with ethyl acetate. The ethyl acetate layer was washed with water and dried, from which the solvent was distilled off under reduced pressure to leave 2.8 g of ethyl ester of 3-[N-[2-(2-chlorobenzoyl)-4-chlorophenyl]-N-methylcarbamoyl] acrylic acid as an oily product.

IRv$_{max}^{Neat}$cm$^{-1}$: 1725(C=O) 1670(C=O), 1490, 1370, 1300, 1180, 1115, 920, 740

$^1$H-NMR spectrum (200 MHz, CDCl$_3$) δ: 1.27(3H,t,CH$_2$CH$_3$), 3.18(3H,s,—N CH$_3$), 4.18(2H,q, CH$_2$CH$_3$), 6.78(2H, d,—CH=CH—), 7.1–7.7(7H,m)

(3) Ethyl ester of 3-[N-[4-chloro-2-(α-hydroxy-2-chlorobenzyl)phenyl]-N-methylcarbamoyl] acrylic acid In 50 ml of methanol was dissolved 2.8 g of the oily product obtained above, to which was added 0.2 g of sodium borohydride, and the mixture was stirred for 30 minutes at room temperature. The reaction mixture was concentrated under reduced pressure, which was subjected to extraction with ethyl acetate. The organic layer was washed with water, dried and subjected to distillation under reduced pressure. Crystallization of the residue afforded 2.4 g of ethyl ester of 3-[N-[4-chloro-2-(α-hydroxy-2-chlorobenzyl)phenyl]-N-methylcarbamoyl] acrylic acid, m.p. 128°–130° C.

Elemental Analysis for C$_{20}$H$_{19}$Cl$_2$NO$_4$·¼H$_2$O: Calcd.: C 58.19; H, 4.76; N 3.39 Found: C 58.38; H, 4.79; N 3.31

(4) Ethyl trans-7-chloro-5-(2-chlorophenyl)-1,2,3,5-tetrahydro-1-methyl-2-oxo-4,1-benzoxazepine-3-acetate In 30 ml of ethanol was dissolved 2.2 g of the crystals obtained above, to which was added 1.5 g of potassium carbonate, and the mixture was stirred for 3 hours at room temperature. The reaction mixture was concentrated under reduced pressure. To the concentrate was added water, which was subjected to extraction with ethyl acetate. The organic layer was washed with water and dried, followed by distilling off the solvent under reduced pressure. The residue was purified by means of a silica gel chromatography (eluent, hexane:ethyl acetate=3:1) to afford 1.85 g of ethyl ester of trans-7-chloro-5-(2-chlorophenyl)-1,2,3,5-tetrahydro-1-methyl-2-oxo-4,1-benzoxazepine-3-acetic acid as crystals, m.p. 147°–148° C.

Elemental Analysis for C$_{20}$H$_{19}$Cl$_2$NO$_4$: Calcd.: C 58.84; H 4.69; N 3.43 Found: C 58.76; H 4.79; N 3.28

Reference Example 2

Ethyl trans-7-chloro-5-(2-chlorophenyl)-1-cyclohexylmethyl-1,2,3,5-tetrahydro-2-oxo-4,1-benzoxazepine-3-acetate (1) N-cyclohexylmethyl-4-chloro-2-[α-hydroxy-(2-chlorophenyl)methyl]aniline In 50 ml of glacial acetic acid was dissolved 5.0 g of 4-chloro-2-[α-hydroxy-(2-chlorophenyl)methyl]aniline. To the solution was added 2.5 g of cyclohexane carboxaldehyde. To the mixture was added, while stirring under ice-cooling, 1.06 g of sodium borohydride in the course of 40 minutes. The reaction mixture was poured into ice-water, which was subjected to extraction with ethyl acetate. The organic layer was washed with a dilute aqueous solution of sodium hydroxide, then with water, followed by drying. The solvent was distilled off under reduced pressure to leave 6.2 g of N-cyclohexylmethyl-4-chloro-2-[α-hydroxy-(2-chlorophenyl)methyl]aniline as crystals, m.p. 91°–92° C.

Elemental Analysis for C$_{20}$H$_{23}$Cl$_2$NO: Calcd.: C 65.94; H 6.36; N 3.84 Found: C 65.79; H 6.32; N 3.71

(2) Ethyl ester of 3-[N-[4-chloro-2-(α-hydroxy-2-chlorophenylmethyl)phenyl]-N-cyclohexylmethylcarbamoyl]acrylic acid In 80 ml of methylene chloride was dissolved 6.0 g the crystals obtained above. To the solution was added dropwise, while stirring under ice-cooling, 2.8 g of monoethyl ester of fumaric acid chloride (a solution in 20 l of methylene chloride) in the course of 30 minutes. The reaction mixture was stirred for 20 minutes at room temperature, which was washed with water, dried and subjected to concentration under reduced pressure. The concentrate was purified by means of a silica gel chromatography (eluent, hexane:ethyl acetate=3:1) to afford 6.5 g of ethyl ester of 3-[N-[4-chloro-2-(α-hydroxy-2-chlorophenylmethyl)phenyl]-N-cyclohexylmethylcarbamoyl] acrylic acid as an oily product.

IRv$_{max}^{Neat}$cm$^{-1}$: 3400(OH) 2940, 1730(C=O), 1660 (C=O), 1630, 1300, 1180, 1040

$^1$H-NMR spectrum (200 MHz, CDCl$_3$) δ: 0.8–2.0(14H, multipliet, CH$_2$CH$_3$, -cyclohexane), 2.6–3.5(2H, multiplet, —N CH$_2$-cyclohexane), 4.0–4.5(2H, multiplet, CH$_2$CH$_3$), 6.05–7.7(10H, multiplet)

(3) Ethyl ester of trans-7-chloro-5-(2-chlorophenyl)-1-cyclohexylmethyl-1,2,3,5-tetrahydro-2-oxo-4,1-benzoxazepine-3-acetic acid In 100 ml of ethanol was dissolved 6.5 g of the oily product obtained above, to which was added 5 g of potassium carbonate, and the mixture was stirred for 15 hours at room temperature. The reaction mixture was concentrated under reduced pressure. The concentrate was subjected to extraction with ethyl acetate. The organic layer was washed with water and dried, from which was distilled off the solvent under reduced pressure. The residue was purified by means of a silica gel chromatography (eluent, hexane:ethyl acetate =8:1) to afford 5.2 g of ethyl ester of 3,5-trans-7-chloro-5-(2-chlorophenyl)-1-cyclohexylmethyl-1,2,3,5-tetrahydro-2-oxo-4,1-benzoxazepine-3-acetic acid as a powdery product.

IRv$_{max}^{Neat}$cm$^{-1}$: 2940, 1740(C=O), 1680(C=O), 1600, 1490, 1380, 1270

Elemental Analysis for C$_{26}$H$_{29}$Cl$_2$NO$_4$: Calcd.: C 63.68; H 5.96; N 2.86 Found: C 63.48; H 5.98; N 2.71

Reference Example 3

By substantially the same procedure as in Reference Example 2, compounds shown in Table 1 through Table 4 were obtained.

TABLE 1

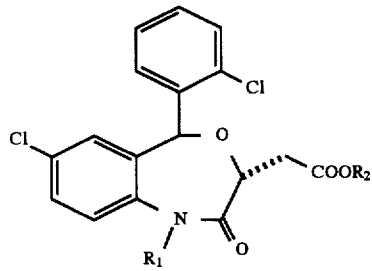

| Compd. No. | $R_1$ | $R_2$ | m.p. (°C.) | Formula | Elemental Analysis (Found) C | H | N |
|---|---|---|---|---|---|---|---|
| 1 | H | $C_2H_5$ | 148–150 | $C_{19}H_{17}Cl_2NO_4$ | 57.88 (57.92) | 4.35 (4.60) | 3.55 (3.33) |
| 2 | —CH₂—C₆H₅ | $C_2H_5$ | 126–127 | $C_{26}H_{23}Cl_2NO_4$ | 64.47 (64.67) | 4.79 (4.65) | 2.89 (2.91) |
| 3 | —CH₂—(2-OCH₃-C₆H₄) | $C_2H_5$ | oil | $C_{27}H_{25}Cl_2NO_5$ | IR $\nu_{max}^{neat}$ cm$^{-1}$: 2980, 1735(CO), 1680(CO) $^1$H-NMR(CDCl$_3$)δ: 1.26(3H, t, CH$_2$CH$_3$), 2.82(1H,dd), 3.13(1H, dd) 3.67(3H, s, OCH$_3$), 4.16(2H, q, CH$_2$CH$_3$), 4.51(1H, dd, C$_3$—H) | | |
| 4 | —CH₂—(4-OCH₃-C₆H₄) | $C_2H_5$ | 135–136 | $C_{27}H_{25}Cl_2NO_5$ | 63.04 (62.84) | 4.90 (5.02) | 2.72 (2.70) |

TABLE 2

| Compd. No. | $R_1$ | $R_2$ | m.p. (°C.) | Formula | Elemental Analysis (Found) C  H  N |
|---|---|---|---|---|---|
| 5 | —CH₂CH₂—C₆H₅ | $C_2H_5$ | oil | $C_{27}H_{25}Cl_2NO_4$ | IR $\nu_{max}^{neat}$ cm$^{-1}$: 3000, 1740 (CO), 1680(CO), 1490, 1170 $^1$H-NMR(CDCl$_3$) δ: 1.26 (3H, t, CH$_2$CH$_3$), 3.8(1H, dd, C$_3$—H), 4.15(2H, q, CH$_2$CH$_3$), 6.04(1H, s, C$_5$—H) |
| 6 | —H₂C—(1-naphthyl) | $C_2H_5$ | 142–143 | $C_{30}H_{25}Cl_2NO_4$ | 67.42  4.71  2.62 (67.38) (4.89) (2.45) |
| 7 | —CH(CH₃)₂ | $C_2H_5$ | oil | $C_{22}H_{23}Cl_2NO_4$ | IR $\nu_{max}^{neat}$ cm$^{-1}$: 2980, 1740 (CO), 1670 (CO) $^1$H-NMR(CDCl$_3$) δ: 1.1–1.6(9H, m, CH$_2$CH$_3$, CH(CH$_3$)$_2$), 2.77(1H, dd), 3.07 (1H, dd), 4.13 (2H, q,), 4.33 (1H, t, C$_3$—H), 6.01 (1H, s, C$_5$—H) |

TABLE 2-continued

| Compd. No. | $R_1$ | $R_2$ | m.p. (°C.) | Formula | Elemental Analysis (Found) C | H | N |
|---|---|---|---|---|---|---|---|
| 8 | 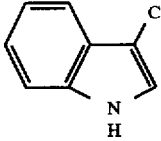 | $C_2H_5$ | 186–187 | $C_{28}H_{24}Cl_2N_2O_4$ | 64.25 (64.02) | 4.62 (4.69) | 5.35 (5.39) |

TABLE 3

| Compd. No. | $R_1$ | $R_2$ | m.p. (°C.) | Formula | Elemental Analysis (Found) C | H | N |
|---|---|---|---|---|---|---|---|
| 9 | $-C_2H_5$ | $C_2H_5$ | 119–120 | $C_{21}H_{21}Cl_2NO_4$ | 59.73 (59.60) | 5.01 (4.95) | 3.32 (3.35) |
| 10 | cyclopentyl | $C_2H_5$ | oil | $C_{24}H_{25}Cl_2NO_4$ | $^1$H-NMR(CDCl$_3$) δ: 1.25 (3H, t, CH$_2$CH$_3$), 1.5–2.4 (8H, m), 2.78, 3.05(2H, both dd); 4.15(2H, m), 4.31 (1H, dd, C$_3$—H), 4.69 (1H, t), 6.01(1H, s, C$_5$—H), 6.50(1H, d, C$_6$—H), 7.2–7.6(6H, m) | | |
| 11 | —CH$_2$-furyl | $C_2H_5$ | oil | $C_{24}H_{21}Cl_2NO_5$ | $^1$H-NMR(CDCl$_3$) δ: 1.24 (3H, t, CH$_3$), 2.82, 3.10 (2H, both both dd), 4.14 (2H, q, CH$_2$CH$_3$), 4.46 (1H, dd, C$_3$—H), 4.85, 5.5 (2H, both d), 5.93(1H, s, C$_5$—H), 6.2–6.5(3H, m), 7.2–7.7(7H, m) | | |

TABLE 4

| Compd. No. | $R_1$ | $R_2$ | m.p. (°C.) | Formula | Elemental Analysis (Found) C | H | N |
|---|---|---|---|---|---|---|---|
| 12 | —CH$_2$—CH=C(CH$_3$)$_2$ | $C_2H_5$ | oil | $C_{24}H_{25}Cl_2NO_4$ | $^1$H-NMR(CDCl$_3$) δ: 1.25 (3H, t, CH$_3$), 1.65(6H, d, CH$_3$×2), 2.8, 3.8(2H, both dd), 4.05–4.3(3H, m), 4.42 (1H, dd) 4.9–5.4(2H, m), 6.0(1H, s, C$_5$—H), 6.49 (1H, d), 7.2–7.7(6H, m) | | |
| 13 | —CH$_2$—C(CH$_3$)=CH$_2$ | $C_2H_5$ | oil | $C_{23}H_{23}Cl_2NO_4$ | $^1$H-NMR(CDCl$_3$) δ: 1.25 (3H, t, CH$_3$), 1.82(3H, s, CH$_3$), 2.80, 3.13(2H, both dd), 4.13(2H, q, CH$_2$CH$_3$), 4.40, 4.67(2H, both d), 4.53(1H, dd, C$_8$—H), 4.97(2H, m), 6.05(1H, s), 6.5(1H, d), 7.2–7.8(6H, m) | | |
| 14 | —CH$_2$—CH=CH$_2$ | $C_2H_5$ | 126–127 | $C_{22}H_{21}Cl_2NO_4$ | 60.84 (60.91) | 4.87 (4.90) | 3.23 (3.06) |
| 15 | —CH$_2$C≡CH | $C_2H_5$ | oil | $C_{22}H_{19}Cl_2NO_4$ | $^1$H-NMR(CDCl$_3$) δ: 1.25 (3H, t, CH$_3$), 2.82, 3.08 (2H, both dd), 4.14(2H, q, CH$_2$CH$_3$), 4.47(1H, dd, C$_3$—H), 4.55, 4.95(2H, both dd), 6.10(1H, s, C$_5$—H), 6.53(1H, d), 7.3–7.75(7H, m) | | |
| 16 | —CH$_2$CH$_2$CH$_3$ | $C_2H_5$ | oil | $C_{22}H_{23}Cl_2NO_4$ | $^1$H-NMR(CDCl$_3$) δ: 0.97 (3H, t, CH$_3$), 1.25(3H, t), 1.5–1.9(2H, m), 2.78, 3.07 (2H, both dd), 3.53(1H, m), | | |

TABLE 4-continued

| Compd. | | | m.p. | | Elemental Analysis (Found) | | |
|---|---|---|---|---|---|---|---|
| No. | $R_1$ | $R_2$ | (°C.) | Formula | C | H | N |
| | | | | | 4.13(2H, dq), 4.4(2H, m), 6.03(1H, s), 6.50(1H, d), 7.2–7.8(6H, m) | | |

Example 1

By substantially the same procedure as in Reference Example 2, compounds shown in Table 5 and Table 6 were obtained

TABLE 5

| Compd. | | | m.p. | | Elemental Analysis (Found) | | |
|---|---|---|---|---|---|---|---|
| No. | $R_1$ | $R_2$ | (°C.) | Formula | C | H | N |
| 1 | —$(CH_2)_6CH_3$ | $C_2H_5$ | 80–81 | $C_{16}H_{31}Cl_2NO_4$ | 63.42 (63.58) | 6.35 (6.58) | 2.84 (2.79) |
| 2 | —$CH_2CH(CH_3)_2$ | $C_2H_5$ | oil | $C_{23}H_{25}Cl_2NO_4$ | $^1$H-NMR(CDCl$_3$) δ: 0.92, 1.03(6H, both d, CH$_3$), 1.25(3H, t, CH$_3$), 1.98(1H, m), 2.8, 3.06(2H, both dd), 3.45(1H, dd), 4.13(2H, q), 4.2–4.5(2H, m), 6.14(1H, s, C$_5$—H), 6.51(1H, d) 7.2–7.8(6H, m) | | |
| 3 | —$CH_2CH(C_2H_5)_2$ | $C_2H_5$ | oil | $C_{25}H_{29}Cl_2NO_4$ | $^1$H-NMR(CDCl$_3$) δ: 0.85, 0.89(6H, both t, CH$_3$), 1.25 (3H, t, CH$_3$), 1.2–1.7 (4H, m), 2.8, 3.05(2H, both dd), 4.14(2H, q, $\underline{CH_2}$CH$_3$), 3.45(1H, dd), 4.45(2H, m), 6.11(1H, s, C$_5$—H), 6.51 (1H, d), 7.2–7.8(6H, m) | | |
| 4 | —$CH_2C(CH_3)_3$ | $C_2H_5$ | 101–102 | $C_{24}H_{27}Cl_2NO_4$ | 62.07 (62.36) | 5.86 (5.87) | 3.02 (2.99) |
| 5 | —$(CH_2)_2CH(CH_3)_2$ | $C_2H_5$ | oil | $C_{24}H_{27}Cl_2NO_4$ | $^1$H-NMR(CDCl$_3$) δ: 0.91, 0.92(6H, both t. CH$_3$), 1.25 (3H, t, CH$_3$), 1.4–1.8(3H, m), 2.79, 3.06(2H, both dd), 3.55(1H, m), 4.05–4.6(4H, m), 6.01(1H, s, C$_5$—H), 6.51(1H, d), 7.2–7.8(6H, m) | | |

TABLE 6

| Compd. | | | m.p. | | Elemental Analysis (Found) | | |
|---|---|---|---|---|---|---|---|
| No. | $R_1$ | $R_2$ | (°C.) | Formula | C | H | N |
| 6 | —$CH(C_2H_5)_2$ | $C_2H_5$ | oil | $C_{24}H_{27}Cl_2NO_4$ | $^1$H-NMR(CDCl$_3$) δ: 0.98, 1.04(6H, both t, CH$_3$), 1.24(3H, t), 1.6–2.1(4H, m), 2.76, 3.1(2H, both dd), 4.13, (2H, q, O$\underline{CH_2}$CH$_3$), 4.2–4.4(2H, m), 6.09(1H, s, C$_5$—H), 6.51(1H, d) 7.2–7.8(6H, m) | | |
| 7 | —$(CH_2)_3CH_3$ | $C_2H_5$ | oil | $C_{23}H_{25}Cl_2NO_4$ | 1H-NMR(CDCl$_3$) δ: 0.91(3H, t), 1.25(3H, t), 1.3–1.8(4H, m), 2.78, 3.06(2H, both dd), 3.45–3.63 (1H, m), 4.13(2H, dq), 4.35–4.55(2H, m), 6.03(1H, s), 6.51(1H, d), 7.2–7.75(6H, m) | | |

In Table 7 through Table 12, physicochemical properties of intermediates obtained in Reference Example 3 and Example 1 are shown.

TABLE 7

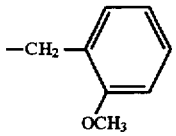

| R | m.p. (°C.) | Formula | Elemental Analysis (Found) C | H | N |
|---|---|---|---|---|---|
| 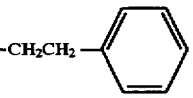 —CH₂—(2-OCH₃-C₆H₄) | oil | $C_{21}H_{19}Cl_2NO_2$ | ¹H-NMR(CDCl₃) δ: 3.77(3H, s, OCH₃), 4.29(2H, s), 6.08(1H, s), 6.55–7.5(11H, m) | | |
| —CH₂CH₂—C₆H₅ | 119–120 | $C_{21}H_{19}Cl_2NO$ | 67.75 (67.83) | 5.14 (5.12) | 3.76 (3.71) |
| 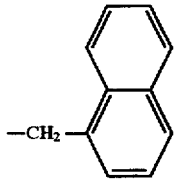 —CH₂—(1-naphthyl) | oil | $C_{24}H_{19}Cl_2NO$ | ¹H-NMR(CDCl₃) δ: 4.73(2H, s), 6.09(1H, s), 6.6–8.0(14H, m) | | |
| —CH(CH₃)₂ | oil | $C_{16}H_{17}Cl_2NO$ | NMR(CDCl₃) δ: 1.12(3H, d), 1.18 (3H, d), 3.6(1H, m), 6.07(1H, m), 6.5–7.5(7H, m) | | |
| 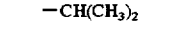 (3-indolylmethyl)— | oil | $C_{22}H_{18}Cl_2N_2O$ | ¹H-NMR(CDCl₃) δ: 4.45(2H, s, CH₂-indol), 6.05(1H, s), 6.5–8.2 (12H, m) | | |

TABLE 8

| R | m.p. (°C.) | Formula | Elemental Analysis (Found) C | H | N |
|---|---|---|---|---|---|
| —(CH₂)₆CH₃ | oil | $C_{20}H_{25}Cl_2NO$ | ¹H-NMR(CDCl₃) δ: 0.87(3H, t, CH₃), 1.0–1.7(10H, m), 2.8–3.1 (2H, m), 6.1–7.7(8H, m) | | |
| —CH₂CH(CH₃)₂ | 87–88 | $C_{17}H_{18}Cl_2NO$ | 62.97 (62.97) | 5.91 (6.05) | 4.32 (4.44) |
| 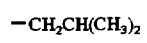 cyclopentyl | oil | $C_{18}H_{19}Cl_2NO$ | ¹H-NMR(CDCl₃) δ: 1.2–2.2(8H, m), 3.75(1H, m), 6.05(1H, s), 6.5–7.5(7H, m) | | |
|  —CH₂—(2-furyl) | oil | $C_{19}H_{15}Cl_2NO_2$ | ¹H-NMR(CDCl₃) δ: 3.7(2H, m), 5.9–6.2(3H, m), 6.8–7.5(8H, m) | | |

TABLE 8-continued

| R | m.p. (°C.) | Formula | Elemental Analysis (Found) | | |
|---|---|---|---|---|---|
| | | | C | H | N |
| $-CH_2CH(C_2H_5)_2$ | oil | $C_{19}H_{23}Cl_2NO$ | $^1$H-NMR(CDCl$_3$) δ: 0.7–1.6(10H, m), 2.97(2H, d), 6.11(1H, s), 6.6 (1H, d), 6.9–7.5(6H, m) | | |
| $-CH_2C(CH_3)_3$ | 110–111 | $C_{18}H_{21}Cl_2NO$ | 63.91 (64.12) | 6.26 (6.30) | 4.14 (4.31) |
| $-(CH_2)_2CH(CH_3)_2$ | oil | $C_{18}H_{21}Cl_2NO$ | $^1$H-NMR(CDCl$_3$) δ: 0.90, 0.93(6H, both d, CH$_3$), 1.4–1.8 (3H, m), 3.09(2H, t), 6.12(1H, s), 6.60(1H, d), 6.90(1H, d), 7.1–7.5(5H, m) | | |

TABLE 9

| R | p.m. (°C.) | Formula | Elemental Analysis (Found) | | |
|---|---|---|---|---|---|
| | | | C | H | N |
| $-CH_2CH=C(CH_3)_2$ | oil | $C_{18}H_{19}Cl_2NO$ | $^1$H-NMR(CDCl$_3$) δ: 1.66, 1.73 (6H, both s, CH$_3$), 3.66(2H, d), 6.01(1H, s), 6.59(1H, d), 8.22(1H, d), 7.1–7.5(6H, m) | | |
| $-CH_2C(CH_3)=CH_2$ | oil | $C_{17}H_{17}Cl_2NO$ | $^1$H-NMR(CDCl$_3$) δ: 1.72(3H, s, CH$_3$), 3.68(2H, s), 4.85(2H, m), 6.15(1H, s), 6.55(1H, d), 6.86(1H, d), 7.05–7.5(5H, m) | | |
| $-CH(C_2H_5)_2$ | oil | $C_{18}H_{21}Cl_2NO$ | $^1$H-NMR(CDCl$_3$) δ: 0.75(3H, t, CH$_3$), 0.88(3H, t, CH$_3$), 1.1–1.7(4H, m), 3.2(1H, m), 6.1(1H, s), 6.5–7.5(7H, m) | | |
| $-CH_2-CH=CH_2$ | oil | $C_{18}H_{15}Cl_2NO$ | $^1$H-NMR(CDCl$_3$) δ: 3.8(2H, m), 5.1–6.0(3H, m) 6.16(1H, s), 6.55–7.5(7H, m), 6.82(1H, d) | | |
| $-CH_2C\equiv CH$ | oil | $C_{18}H_{13}Cl_2NO$ | $^1$H-NMR(CDCl$_3$) δ: 3.95(2H, d), 6.14(1H, s), 6.73(1H, d), 6.8(1H, d), 7.1–7.6(6H, m) | | |
| $-CH_2CH_2CH_3$ | oil | $C_{16}H_{17}Cl_2NO$ | $^1$H-NMR(CDCl$_3$) δ: 0.95(3H, t), 1.65(2H, m), 3.06(2H, t), 6.12(1H, s), 6.55–7.5(8H, m) | | |
| $-(CH_2)_3CH_3$ | oil | $C_{17}H_{19}Cl_2NO$ | $^1$H-NMR(CDCl$_3$) δ: 0.92(3H, t), 1.2–1.7(4H, m), 3.07(2H, t), 6.10(1H, s), 6.59(1H, d), 6.87(1H, d), 7.1–7.5(5H, m) | | |

TABLE 10

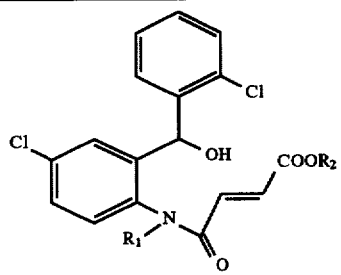

| R$_1$ | R$_2$ | m.p. (°C.) | Formula | Elemental Analysis (Found) | | |
|---|---|---|---|---|---|---|
| | | | | C | H | N |
| $-CH_2$-(2-OCH$_3$-C$_6$H$_4$) | $-C_2H_5$ | oil | $C_{27}H_{25}Cl_2NO_5$ | $^1$H-NMR(CDCl$_3$) δ: 1.2(3H, t, CH$_2$CH$_3$), 3.5(3H, s, OCH$_3$), 4.06(2H, q, CH$_2$CH$_3$), 4.68(1H, d), 5.55(1H, d), 6.0–7.7(14H, m) | | |
| $-CH_2$-(4-OCH$_3$-C$_6$H$_4$) | $-C_2H_5$ | oil | $C_{27}H_{25}Cl_2NO_5$ | $^1$H-NMR(CDCl$_3$) δ: 1.2(3H, t, CH$_2$CH$_3$), 3.76(3H, s, OCH$_3$), 4.05(2H, q, CH$_2$CH$_3$), 4.24(1H, d), 5.65(1H, d) 6.1–7.6(14H, m) | | |

TABLE 10-continued

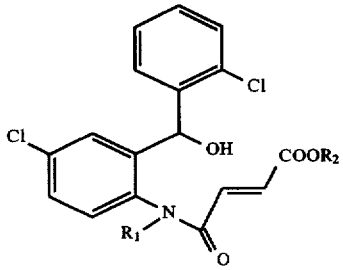

| R₁ | R₂ | m.p. (°C.) | Formula | Elemental Analysis (Found) C, H, N |
|---|---|---|---|---|
| —CH₂CH₂—(phenyl) | —C₂H₅ | oil | C₂₇H₂₅Cl₂NO₄ | ¹H-NMR(CDCl₃) δ: 1.1–1.4(3H, m), 2.7–4.7(6H, m), 6.0–7.7 (15H, m) |

TABLE 11

| R₁ | R₂ | m.p. (°C.) | Formula | Elemental Analysis (Found) C, H, N |
|---|---|---|---|---|
| —CH₂-(1-naphthyl) 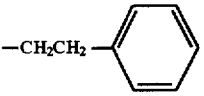 | —C₂H₅ | oil | C₃₀H₂₅Cl₂NO₄ | ¹H-NMR(CDCl₃) δ: 1.13 (3H, t, CH₂CH₃) 4.1(2H, q, CH₂CH₃), 5.02(1H, d), 5.9–8.2(18H, m) |
| —CH₂-(indol-3-yl) 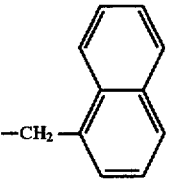 | —C₂H₅ | oil | C₂₈H₂₄Cl₂N₂O₄ | ¹H-NMR(CDCl₃) δ: 1.1–1.4(3H, m), 3.9–4.3 (2H, m), 4.6–5.8(2H, m), 6.0–8.4(15H, m) |
| —C₂H₅ | —C₂H₅ | oil | C₂₁H₂₁Cl₂NO₄ | ¹H-NMR(CDCl₃) δ: 0.9–1.5(6H, m), 3.5– 4.5(4H, m), 6.0–7.9(10H, m) |
| —(CH₂)₆CH₃ | —C₂H₅ | oil | C₂₆H₃₁Cl₂NO₄ | ¹H-NMR(CDCl₃) δ: 0.85 (3H, t, CH₃), 0.95– 1.7(13H, m), 2.7–4.5(4H, m) 6.0–7.7(10H, m) |
| —CH₂CH(CH₃)₂ | —C₂H₅ | 136–138 | C₂₃H₂₅Cl₂NO₄ | 61.34  5.59  3.11 (61.26) (5.71) (3.06) |
| cyclopentyl 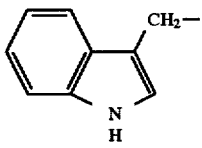 | —C₂H₅ | 192–194 | C₂₄H₂₅Cl₂NO₄ | 62.34  5.45  3.03 (62.05) (5.50) (3.07) |
| —CH₂-(furan-2-yl)  | —C₂H₅ | oil | C₂₄H₂₁Cl₂NO₅ | ¹H-NMR(CDCl₃) δ: 1.27 (3H, m, CH₃), 3.6(1H, m), 4.15(2H, m, CH₂), 5.35 (1H, m), 5.9–8.0(13H, m) |

TABLE 12

| $R_1$ | $R_2$ | m.p. (°C.) | Formula | Elemental Analysis (Found) C | H | N |
|---|---|---|---|---|---|---|
| —CH$_2$CH(C$_2$H$_5$)$_2$ | —C$_2$H$_5$ | oil | C$_{25}$H$_{29}$Cl$_2$NO$_4$ | $^1$H-NMR(CDCl$_3$) δ: 0.6–1.7(14H, m), 2.7–4.6(4H, m), 5.9–7.7(10H, m) | | |
| —CH$_2$C(CH$_3$)$_3$ | —C$_2$H$_5$ | oil | C$_{24}$H$_{27}$Cl$_2$NO$_4$ | $^1$H-NMR(CDCl$_3$) δ: 0.7–1.4(12H, m), 2.8–4.6(4H, m), 6.1–7.7(10H, m) | | |
| —(CH$_2$)$_2$CH(CH$_3$)$_2$ | —C$_2$H$_5$ | oil | C$_{24}$H$_{27}$Cl$_2$NO$_4$ | $^1$H-NMR(CDCl$_3$) δ: 0.6–1.7(12H, m), 2.6–4.6(4H, m), 5.9–7.7(10H, m) | | |
| —CH$_2$—CH=C(CH$_3$)$_2$ | —C$_2$H$_5$ | oil | C$_{23}$H$_{23}$Cl$_2$NO$_4$ | $^1$H-NMR(CDCl$_3$) δ: 1.1–1.9(9H, m), 3.9–4.9(4H, m), 6.0–7.7(11H, m) | | |
| —CH$_2$—C(CH$_3$)=CH$_2$ | —C$_2$H$_5$ | oil | C$_{24}$H$_{27}$Cl$_2$NO$_4$ | $^1$H-NMR(CDCl$_3$) δ: 1.25(3H, m), 1.75(3H, m), 3.0–5.2(6H, m), 5.9–7.9(10H, m) | | |
| —CH(C$_2$H$_5$)$_2$ | —C$_2$H$_5$ | oil | C$_{22}$H$_{21}$Cl$_2$NO$_4$ | $^1$H-NMR(CDCl$_3$) δ: 1.15–1.4(3H, m, CH$_3$), 3.1–6.0(7H, m), 6.1–7.7(10H, m) | | |
| —CH$_2$—C≡CH | —C$_2$H$_5$ | 132–133 | C$_{22}$H$_{19}$Cl$_2$NO$_4$ | 61.12 (61.02) | 4.43 (4.67) | 3.24 (3.13) |
| —CH$_2$CH$_2$CH$_3$ | —C$_2$H$_5$ | oil | C$_{22}$H$_{23}$Cl$_2$NO$_4$ | $^1$H-NMR(CDCl$_3$) δ: 0.77, 0.86(3H, both d), 1.22, 1.24 (3H, both t), 1.4–1.9(2H, m), 2.6–4.5(4H, m), 6.0–7.6 (10H, m) | | |
| —(CH$_2$)$_3$CH$_3$ | —C$_2$H$_5$ | oil | C$_{23}$H$_{25}$Cl$_2$NO$_4$ | $^1$H-NMR(CDCl$_3$) δ: 0.7–1.9(10H, m), 2.6–4.5(4H, m), 5.9–7.7(10H, m). | | |

Reference Example 4

Trans-7-chloro-5-(2-chlorophenyl)-1-methyl-1,2,3,5-tetrahydro-2-oxo-4,1-benzoxazepine-3-acetic acid In a mixture of 10 ml of methanol and 4 ml of water was suspended 0.5 g of ethyl ester of 3,5-trans-7-chloro-5-(2-chlorophenyl)-1-methyl-1,2,3,5-tetrahydro-2-oxo-4,1-benzoxazepine-3-acetic acid. To the suspension was added 0.8 g of potassium carbonate, and the mixture was stirred for 3 hours at 60° C. The reaction mixture was concentrated under reduced pressure, to which was added water, followed by extraction with ether. The aqueous layer was acidified with dilute hydrochloric acid, followed by extraction with ethyl acetate. The organic layer was washed with water and dried, followed by concentration under reduced pressure. The concentrate was purified by means of a silica gel chromatography to afford 0.21 g of 3,5-trans-7-chloro-5-(2-chlorophenyl)-1-methyl-1,2,3,5-tetrahydro-2-oxo-4,1-benzoxazepine-3-acetic acid as crystals, m.p. 211°–213° C.

Elemental Analysis for C$_{18}$H$_{15}$Cl$_2$NO$_4$: Calcd.: C 56.86; H 3.98; N 3.68 Found: C 56.86; H 4.24; N 3.53

Reference Example 5

By substantially the same procedure as in Reference Example 4, compounds shown in Table 13 through Table 15 were obtained.

TABLE 13

| Compd. No. | R | m.p. (°C.) | Formula | Elemental Analysis (Found) C | H | N |
|---|---|---|---|---|---|---|
| 1 | —CH$_2$—C$_6$H$_5$ | 175–178 | C$_{24}$H$_{19}$Cl$_2$NO$_4$ | 63.17 (63.18) | 4.20 (4.24) | 3.07 (3.23) |
| 2 | —CH$_2$—C$_6$H$_4$—OCH$_3$ | 213–214 | C$_{25}$H$_{21}$Cl$_2$NO$_5$ | 61.74 (61.55) | 4.35 (4.55) | 2.88 (2.79) |

TABLE 13-continued

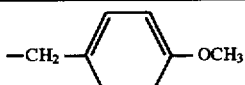

| Compd. No. | R | m.p. (°C.) | Formula | Elemental Analysis (Found) | | |
|---|---|---|---|---|---|---|
| | | | | C | H | N |
| 3 | —CH₂—⟨benzene⟩—OCH₃ | 165–167 | C₂₅H₂₁Cl₂NO₅ | 61.74 (61.49) | 4.35 (4.47) | 2.88 (2.84) |

TABLE 14

| Compd. No. | R | p.m. (°C.) | Formula | Elemental Analysis (Found) | | |
|---|---|---|---|---|---|---|
| | | | | C | H | N |
| 4 | —CH₂CH₂—⟨phenyl⟩ | 212–214 | C₂₅H₂₁Cl₂NO₄ | 63.84 (63.94) | 4.50 (4.71) | 2.98 (3.17) |
| 5 | —CH₂—⟨naphthyl⟩ | 243–244 | C₂₈H₂₁Cl₂NO₄ | 66.41 (66.27) | 4.18 (4.05) | 2.77 (2.65) |
| 6 | —CH₂—⟨cyclohexyl⟩ | 241–242 | C₂₄H₂₅Cl₂NO₄ | 62.34 (62.27) | 5.45 (5.45) | 3.03 (3.02) |
| 7 | —CH(CH₃)₂ | 208–209 | C₂₀H₁₉Cl₂NO₄ | 58.84 (58.78) | 4.69 (4.83) | 3.43 (3.38) |

TABLE 15

| Compd. No. | R | p.m. (°C.) | Formula | Elemental Analysis(Found) | | |
|---|---|---|---|---|---|---|
| | | | | C | H | N |
| 8 | —C₂H₅ | 215–216 | C₁₉H₁₇Cl₂NO₄ | 51.88 (57.67) | 4.35 (4.27) | 3.55 (3.54) |
| 9 | ⟨cyclopentyl⟩ | 224–225 | C₂₂H₂₁Cl₂NO₄ | 60.84 (60.64) | 4.87 (4.94) | 3.22 (3.32) |
| 10 | —CH₂—⟨furyl⟩ | 190–191 | C₂₂H₁₇Cl₂NO₅ | 59.21 (58.99) | 3.84 (3.78) | 3.14 (3.10) |
| 11 | —CH₂—CH=C(CH₃)₂ | 154– | C₂₂H₂₁Cl₂NO₄ | 60.84 | 4.87 | 3.22 |

TABLE 15-continued

| Compd. No. | R | p.m. (°C.) | Formula | Elemental Analysis(Found) C | H | N |
|---|---|---|---|---|---|---|
| | | 155 | | (60.54) | (5.15) | (3.31) |
| 12 | —CH$_2$—C(CH$_3$)=CH$_2$ | 241–242 | C$_{21}$H$_{19}$Cl$_2$NO$_4$ | 60.01 (59.76) | 4.56 (4.73) | 3.33 (3.22) |
| 13 | —CH$_2$—CH=CH$_2$ | 199–200 | C$_{20}$H$_{17}$Cl$_2$NO$_4$ | 59.13 (58.88) | 4.22 (4.30) | 3.45 (3.58) |
| 14 | —CH$_2$—C≡CH | 184–155 | C$_{20}$H$_{15}$Cl$_2$NO$_4$ | 59.42 (59.18) | 3.74 (3.75) | 3.46 (3.23) |
| 15 | —CH$_2$CH$_2$CH$_3$ | 189–190 | C$_{20}$H$_{19}$Cl$_2$NO$_4$ | 58.84 (58.18 | 4.69 4.95 | 3.43 3.60) |

Example 2

By substantially the same procedure as in Reference Example 4, compounds shown in Table 16, were obtained.

TABLE 16

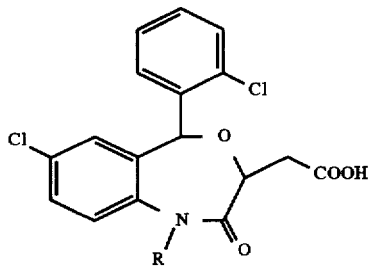

| Compd. No. | R | p.m. (°C.) | Formula | Elemental Analysis(Found) C | H | N |
|---|---|---|---|---|---|---|
| 1 | —(CH$_2$)$_6$CH$_3$ | 188–189 | C$_{24}$H$_{27}$Cl$_2$NO$_4$ | 62.07 (62.21) | 5.86 (5.83) | 3.02 (3.00) |
| 2 | —CH$_2$CH(CH$_3$)$_2$ | 220–221 | C$_{21}$H$_{21}$Cl$_2$NO$_4$ | 59.73 (59.98) | 5.01 (5.24) | 3.32 (3.14) |
| 3 | —CH$_2$CH(C$_2$H$_5$)$_2$ | 188–189 | C$_{23}$H$_{25}$Cl$_2$NO$_4$ | 61.34 (61.39) | 5.60 (5.74) | 3.11 (2.99) |
| 4 | —CH$_2$—C(CH$_3$)$_3$ | 247–248 | C$_{22}$H$_{23}$Cl$_2$NO$_4$ | 60.56 (60.55) | 5.3 (5.47) | 3.21 (3.11) |
| 5 | —(CH$_2$)$_2$CH(CH$_3$)$_2$ | 166–167 | C$_{22}$H$_{23}$Cl$_2$NO$_4$ | 60.56 (60.40) | 5.31 (5.49) | 3:2 (3.22) |
| 6 | —CH(C$_2$H$_5$)$_2$ | 220–221 | C$_{22}$H$_{23}$Cl$_2$NO$_4$ | 60.56 (60.45) | 5.31 (5.29) | 3.21 (3.20) |
| 7 | —(CH$_2$)$_3$CH$_3$ | 195–196 | C$_{21}$H$_{21}$Cl$_2$NO$_4$ | 59.73 (59.68 | 5.01 4.97 | 3.32 3.54) |

Reference Example 6

Trans-1-benzyl-7-chloro-5-phenyl-2-oxo-1,2,3,5-tetrahydro-4,1-benzoxazepine-3-acetic acid 0.3 g of the ethyl ester of trans-1-benzyl-7-chloro-5-phenyl-2-oxo-1,2,3,5-tetrahydro-4,1-benzoxazepine-3-acetic acid disclosed in JPA S57(1982)-35576 was subjected to hydrolysis in the manner to be described in the following Reference Example 4 to afford 0.12 g of trans-1-benzyl-7-chloro-5-phenyl-2-oxo-1,2,3,5-tetrahydro-4,1-benzoxazepine-3-acetic acid as a white powdery product.

Example 3

Ethyl ester of trans-1-isobutyl-2-oxo-5-(o-tolyl)-1,2,3,5-tetrahydro-4,1-benzoxazepine-3-acetic acid (1) 2-Isobutylamino-α-(o-tolyl)benzyl alcohol Using 2-amino-α-(o-tolyl)benzyl alcohol (2.5 g) and isobutyl aldehyde (1.17 ml), reaction is conducted in substantially the same manner as in Reference Example 2 (1) to give 2-isobutylamino-α-(o-tolyl)benzyl alcohol (3.1 g) as an oily product.

IRv$_{max}$$^{Neat}$cm$^{-1}$: 3400(OH); 1720, 1655, 1630(C=O, C=C)

$^1$H-NMR(CDCl$_3$) δ: 0.7–1.1(6H,m), 1.21(3H,t,J=7.0 Hz), 1.5–2.0(1H,m), 2.29(3H,s), 2.0–2.3 and 2.9–3.1(1H, each m), 3.9–4.5(3H,m), 5.9–6.4(2H,m), 6.6–6.9(1H,m), 6.95–7.9(8H,m)

(2) Ethyl ester of 3-[N-[2-(α-hydroxy-2-methylbenzyl)phenyl-N-isobutyl]carbamoyl]acrylic acid In substantially the same manner as in Reference Example 2 (2), 2-isobutylamino-α-(o-tolyl)benzyl alcohol (1.3 g) obtained in (1) above was allowed to react with fumaric acid chloride monoethyl ester to give ethyl ester of 3-[N-[2-(α-hydroxy-2-methylbenzyl)phenyl-N- isobutyl]carbamoyl] acrylic acid (3.1 g) as an oily product.

IRν$_{max}^{Neat}$cm$^{-1}$: 3400(OH); 1720, 1655, 1630(C=C, C=O)

$^1$H-NMR spectrum (200 MHz, CDCl$_3$) δ: 0.7–1.1(6H,m), 1.21(3H,t,J=7.0 Hz), 1.5–2.0(1H,m), 2.29(3H,s), 2.0–2.3 and 2.9–3.1(1H, each m), 3.9–4.5(3H,m), 5.9–6.4(2H,m), 6.6–6.9(1H,m), 6.95–7.9(8H,m)

(3) Ethyl ester of trans-1-isobutyl-2-oxo-5-(o-tolyl)-1,2,3,5-tetrahydro-4,1-benzoxazepine-3-acetic acid In the same manner as in Reference Example 2 (3), ethyl ester of 3-[N-[2-(α-hydroxy-2-methylbenzyl) phenyl-N-isobutyl]carbamoyl]acrylic acid (1.8 g) was subjected to reaction. The reaction product was crystallized from water-ethanol to give ethyl ester of trans-1-isobutyl-2-oxo-5-(o-toluyl)-1,2,3,5-tetrahydro-4,1-benzoxazepine-3-acetic acid (2.41 g) as prisms, 88° C.–90° C.

IRν$_{max}^{KBr}$cm$^{-1}$: 1730, 1670(C=O)

Elemental Analysis for C$_{24}$H$_{29}$NO$_4$: Calcd.: C 72.89; H 7.39; N 3.54 Found: C 73.18; H 7.25; N 3.54

Example 4

By substantially the same synthetic procedure as in Example 3, compounds listed in Table 17 and Table 18 were obtained.

TABLE 17

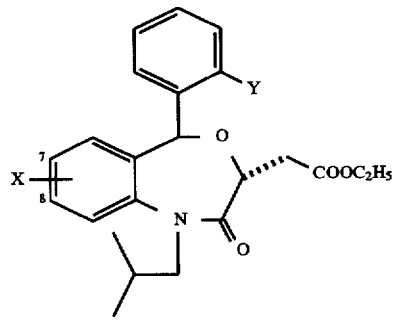

| Compd. No. | X | Y | m.p. (°C.) | Formula | Elemental Analysis(Found) C | H | N |
|---|---|---|---|---|---|---|---|
| 1 | H | Cl | 99–100 | C$_{23}$H$_{26}$ClNO$_4$ | 66.42 (66.20) | 6.30 (6.57) | 3.37 (3.42) |
| 2 | (7)-CH$_3$ | Cl | oil | C$_{24}$H$_{28}$ClNO$_4$ | $^1$H-NMR(CDCl$_3$) δ: 0.92, 1.03(6H, both d, CH$_3$), 1.25(3H, t, CH$_2$CH$_3$), 2.19(3H, s, CH$_3$), 2.8, 3.03(2H, both dd), 3.45(1H, dd), 4.13 (2H, q, CH$_2$CH$_3$), 4.2–4.5(2H, m), 6.16(1H, s, C$_5$—H), 6.31(1H, s, C$_8$—H), 7.1–7.8 (6H, m) | | |
| 3 | (7)-Cl | F | oil | C$_{23}$H$_{25}$ClFNO$_4$ | $^1$H-NHR(CDCl$_3$) δ: 0.89; 0.97(6H, both d, CH$_3$), 1.26(3H, t, CH$_2$CH$_3$), 2.04(1H, m), 2.78, 3.07(2H, both dd), 3.4(1H, dd), 4.13(2H, q), 4.2–4.5(2H, m), 6.13(1H, s, C$_5$—H), 6.63(1H, d), 7.0–7.7(6H, m) | | |

TABLE 18

| Compd. No. | X | Y | m.p. (°C.) | Formula | Elemental Analysis(Found) C | H | N |
|---|---|---|---|---|---|---|---|
| 4 | (7)-CH$_2$CH$_2$ \| CH$_2$-(8) | Cl | oil | C$_{26}$H$_{30}$ClNO$_4$ | $^1$H-NMR(CDCl$_3$) δ: 0.93, 1.04(6H, both d), 1.9–2.2 3H, m), 2.7–3.15(6H, m), 3.48(1H, dd), 4.0–4.5(4H, m), 6.16(1H, s, C$_5$—H), 6.35(1H, s, C$_8$—H), 7.1–7.8(5H, m) | | |
| 5 | H | F | oil | C$_{23}$H$_{26}$FNO$_4$ | $^1$H-NMR(CDCl$_3$) δ: 0.89, (3H, d), 0.98(3H, d), 1.24 (3H, t), 1.9–2.2(1H, m), 2.78(1H, dd), 3.06(1H, dd), 3.46,(1H, dd), 4.13(2H, q), | | |

TABLE 18-continued

| Compd. No. | X | Y | m.p. (°C.) | Formula | Elemental Analysis(Found) | | |
|---|---|---|---|---|---|---|---|
| | | | | | C | H | N |
| | | | | | 4.25–4.5(2H, m), 6.18(1H, s), 6.67(1H, d), 6.9–7.75(7H, m) | | |
| 6 | H | OCH₃ | 132–133 | C₂₄H₂₉NO₅ | 70.05 (70.20) | 7.10 (7.13) | 3.40 (3.56) |

In Table 19 through Table 22, physicochemical properties of intermediates are shown.

TABLE 19

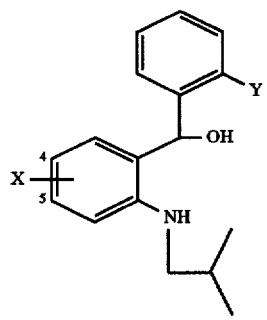

| X | Y | m.p. (°C.) | Formula | Elemental Analysis (Found) | | |
|---|---|---|---|---|---|---|
| | | | | C | H | N |
| H | Cl | oil | C₁₇H₂₀ClNO | ¹H-NMR(CDCl₃) δ: 0.8–1.1(6H, m), 1.9(1H, m), 2.95(2H, d), 5.29 (1H, s), 6.17(1H, s), 6.5–7.6(7H, m) | | |
| (4)-CH₃ | Cl | oil | C₁₈H₂₂ClNO | ¹H-NMR(CDCl₃) δ: 0.8–1.1(6H, m), 1.85(1H, m), 2.18(3H, s, CH₃), 2.91 (2H, d), 6.16(1H, s), 6.55–7.6(7H, m) | | |
| (4)-Cl | F | oil | C₁₇H₁₉ClFNO | ¹H-NMR(CDCl₃) δ: 0.8–1.1(6H, m, CH₃), 1.85(1H, m), 2.89(2H, d, NHCH₂), 6.05(1H, s), 6.57(1H, d), 6.9–7.5 (6H, m) | | |

TABLE 20

| X | Y | m.p. (°C.) | Formula | Elemental Analysis (Found) | | |
|---|---|---|---|---|---|---|
| | | | | C | H | N |
| (4)-CH₂CH₂  \| CH₂-(5) | Cl | oil | C₂₀H₂₄ClNO | ¹H-NMR(CDCl₃) δ: 0.8–1.1(6H, m), 1.7–2.1(3H, m), 2.6–3.0 (6H, m), 6.17(1H, s), 6.62(1H, s), 6.68(1H, s), 7.2–7.6(4H, m) | | |
| H | F | oil | C₁₇H₂₀FNO | ¹H-NMR(CDCl₃) δ: 0.95(6H, d, J=6.6Hz), 1.8–2.1(1H, m), 2.93 (2H, d, J=6.6Hz), 6.11(1H, s), 6.55–6.75(2H, m), 6.9–7.5(6H, m) | | |
| H | OCH₃ | oil | C₁₈H₂₃NO₂ | ¹H-NMR(CDCl₃) δ: 0.94(6H, d, J=6.6Hz), 1.75–2.05 (1H, m), 2.94(2H,d), 3.86(3H, s), 6.02(1H, s), 6.5–6.75(2H, m), 6.85–7.0(3H, m), 7.1–7.4(3H, m) | | |

TABLE 21

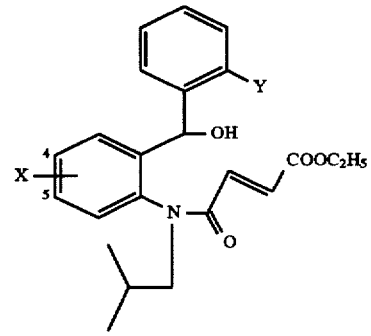

| X | Y | m.p. (°C.) | Formula | Elemental Analysis (Found) | | |
|---|---|---|---|---|---|---|
| | | | | C | H | N |
| H | Cl | oil | C₂₃H₂₆ClNO₄ | ¹H-NMR(CDCl₃) δ: 0.7–1.4(9H, m), 1.9(1H, m), 2.6–4.5(4H, m) 6.1–7.7(1H, m) | | |
| (4)-CH₃ | Cl | oil | C₂₄H₂₈ClNO₄ | ¹H-NMR(CDCl₃) δ: 0.7–1.4(9H, m), 1.8–3.2(5H, m), 4.0–4.5(3H, m), 6.0–7.6(10H, m) | | |
| (4)-Cl | F | oil | C₂₃H₂₅ClFNO₄ | ¹H-NMR(CDCl₃) δ: 0.7–1.4(9H, m), 1.85(1H, m), 2.5–4.4(4H, m), 5.9–7.9(10H, m) | | |

TABLE 22

| X | Y | m.p. (°C.) | Formula | Elemental Analysis (Found) | | |
|---|---|---|---|---|---|---|
| | | | | C | H | N |
| (4)-CH₂CH₂<br>\|<br>CH₂-(5) | Cl | oil | C₂₆H₃₀ClNO₄ | ¹H-NMR(CDCl₃) δ: 0.7–1.4(9H, m), 1.8–2.3(3H, m), 2.1–3.2 (5H, m), 4.0–4.5(3H, m), 5.95–7.7(9H, m), | | |
| H | F | oil | C₂₃H₂₈FNO₄ | ¹H-NMR(CDCl₃) δ: 0.75–1.15(6H, m), 1.20(3H, t, J=7.0Hz), 1.5–2.1(1H, m), 2.6–2.8, 2.95–3.15(1H, both m), 4.0–4.5(3H, m), 6.0–6.5(2H, m), 6.7–7.8(9H, m) | | |
| H | OCH₃ | oil | C₂₄H₂₉NO₅ | ¹H-NMR(CDCl₃) δ: 0.7–1.1(6H, m), 1.20(3H, t, J=7.1Hz), 1.7–2.0 (1H, m), 2.5–3.2(2H, m), 3.74, 3.78(3H, s), 4.0–4.45(3H, m), 6.0–6.5(2H, m), 6.7–5(9H, m) | | |

Example 5

Trans-1-isobutyl-2-oxo-5-(o-tolyl)-1,2,3,5-tetrahydro-4,1-benzoxazepine-3-acetic acid In substantially the same manner as in Reference Example 4, ethyl ester of trans-1-isobutyl-2-oxo-5-(o-tolyl)-1,2,3,5-tetrahydro-4,1-benzoxazepine-3-acetic acid (2.0 g) obtained in Example 3 was subjected to hydrolysis to give trans-1-isobutyl-2-oxo-5-(o-tolyl)-1,2,3,5-tetrahydro-4,1-benzoxazepine-3-acetic acid (1.23 g) as prisms, m.p. 192° C.–195° C.

IRν$_{max}^{Neat}$cm⁻¹: 1735, 1650(C=O)

Elemental Analysis for C₂₂H₂₅NO₄: Calcd.: C 71.91; H 6.66; N 3.81 Found: C 71.86; H 6.78; N 3.80

Example 6

In substantially the same manner as in Reference Example 4, using compounds obtained in Example 4, compounds listed in Table 23 were obtained.

TABLE 23

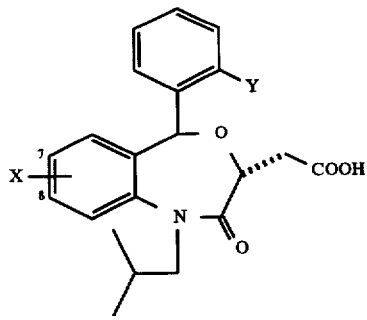

| | | m.p. | | Elemental Analysis (Found) | | |
|---|---|---|---|---|---|---|
| X | Y | (°C.) | Formula | C | H | N |
| H | Cl | 192–193 | C₂₁H₂₂ClNO₄ | 65.03 (64.73) | 5.72 (5.63) | 3.61 (3.76) |
| (7)-CH₃ | Cl | 166–167 | C₂₂H₂₄ClNO₄ | 65.75 (65.78) | 6.02 (6.02) | 3.49 (3.72) |
| (7)-Cl | F | 153–154 | C₂₁H₂₁ClFNO₄ | 62.15 (62.17) | 5.22 (5.19) | 3.45 (3.50) |

TABLE 23-continued

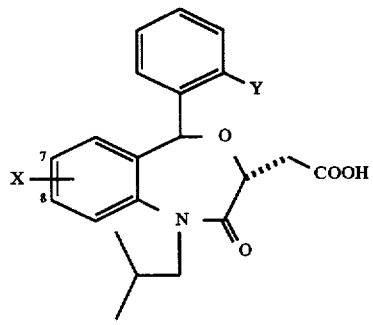

| X | Y | m.p. (°C.) | Formula | Elemental Analysis (Found) | | |
|---|---|---|---|---|---|---|
| | | | | C | H | N |
| (7)-CH$_2$CH$_2$<br>\|<br>CH$_2$-(8) | Cl | 170–171 | C$_{24}$H$_{28}$ClNO$_4$ | 66.66<br>(66.61) | 6.18<br>(6.27) | 3.24<br>(3.12) |
| H | F | 185–187 | C$_{21}$H$_{22}$FNO$_4$ | 67.91<br>(67.93) | 5.97<br>(6.01) | 3.77<br>(3.65) |
| H | OCH$_3$ | 243–245 | C$_{22}$H$_{26}$NO$_5$ | 68.91<br>(68.89) | 6.57<br>(6.60) | 3.65<br>(3.74) |

Example 7

Trans-7-chloro-5-(2-chlorophenyl)-1-isobutyl-2-oxo-1,2,3,5-tetrahydro-4,1-benzoxazepine-3-acetic acid pivaloyloxymethyl ester In N,N-dimethylformamide (10 ml) was dissolved trans-7-chloro-5-(2-chlorophenyl)-1-isobutyl-2-oxo-1,2,3,5-tetrahydro-4,1-benzoxazepine-3-acetic acid (0.5 g) obtained in Example 2. To the solution were added pivaloyloxymethyl chloride (0.43 ml), N,N-diisobutyl ethylamine (0.52 ml) and KI (0.2 g). The mixture was stirred at room temperature overnight. To the reaction mixture were added water (100 ml) and ethyl acetate (100 ml), followed by extraction. The ethyl acetate layer was washed with an aqueous solution of potassium hydrogensulfate, an aqueous solution of sodium hydrogencarbonate and water, successively, which was dried over anhydrous magnesium sulfate. The solvent was then distilled off under reduced pressure. The residue was purified by means of a silica gel column chromatography (hexane:ethyl acetate=10:1 to 5:1) to afford trans-7-chloro-5-(2-chlorophenyl)-1-isobutyl-2-oxo-1,2,3,5-tetrahydro-4,1-benzoxazepine-3-acetic acid pivaloyloxymethyl ester (0.55 g).

IRv$_{max}$$^{Neat}$cm$^{-1}$: 1750, 1675(C=O)

Elemental Analysis for C$_{27}$H$_{31}$Cl$_2$NO$_6$: Calcd.: C 60.45; H 5.82; N 2.61 Found: C 60.38; H 5.93; N 2.48

Reference Example 7

Ethyl ester of trans-7-chloro-5-(2-chlorophenyl)-1-(2,4-dimethoxybenzyl)-2-oxo-1,2,3,5-tetrahydro-4,1-benzoxazepine-3-acetic acid (1) 5-Chloro-α-(2-chlorophenyl)-2-(2,4-dimethoxybenzyl) aminobenzyl alcohol To a solution of 2-amino-5-chloro-α-(2-chloro phenyl) benzyl alcohol (5.0 g) and 2,4-dimethoxy benzaldehyde (3.72 g) in acetic acid (50 ml) was added, under ice-cooling, sodium borohydride (0.94 g). The mixture was stirred for one hour at room temperature, which was poured into water (200 ml), followed by extraction with ethyl acetate (200 ml×2). The ethyl acetate layer was washed with 1N sodium hydroxide, which was dried over anhydrous magnesium sulfate, followed by distilling off the solvent under reduced pressure. The residue was purified by means of a silica gel column chromatography (hexane:ethyl acetate=5:1) to give 5-chloro-α-(2-chlorophenyl)-2-(2,4-dimethoxybenzyl) aminobenzyl alcohol (7.5 g) as an oily product.

$^1$H-NMR (CDCl$_3$) δ: 3.78(3H,s), 3.79(3H,s), 3.65–3.95 (1H,m), 4.27(2H,s), 6.15(1H,s), 6.35–7.55(10H,m) (2) Ethyl ester of 3-[N-[4-chloro-2-(2-chloro-α-hydroxybenzyl) phenyl]-N-(2,4-dimethoxybenzyl)carbamoyl] acrylic acid A solution of fumaric acid monoethyl ester (2.24 g) and thionyl chloride (3.4 ml) in toluene (10 ml) was stirred for 30 minutes at 90° C. Then the solvent was distilled off under reduced pressure to leave acid chloride of fumaric acid monoethyl ester. This product and 5-chloro-α-(2-chlorophenyl)-2-(2,4-dimethoxybenzyl)aminobenzyl alcohol (5.0 g) obtained in (1) were dissolved in methylene chloride (100 ml). To the solution was added sodium hydrogencarbonate (2.01 g), and the mixture was stirred for 30 minutes at room temperature. The reaction mixture was washed with water and dried over anhydrous magnesium sulfate, then the solvent was distilled off under reduced pressure. The residue was purified by means of a silica gel column chromatography (hexane:ethyl acetate=2:1) to give 3- [N-[4-chloro-2-(2-chloro-α-hydroxybenzyl)phenyl]-N-(2,4-dimethoxybenzyl)carbamoyl]acrylic acid ethyl ester (5.5 g) as an oily product.

IRv$_{max}$$^{Neat}$cm$^{-1}$: 3390(OH); 1720, 1610(C=O); 1655 (C=C)

$^1$H-NMR spectrum (200 MHz,CDCl$_3$) δ: 1.2–1.4(3H,m), 3.4–3.9(6H,m), 3.95–4.4(3H,m), 4.45–4.75(1H,m), 5.25–5.6(1H,m), 6.0–8.05(13H,m)

(3) Trans-7-chloro-5-(2-chlorophenyl)-1-(2,4-dimethoxybenzyl)-2-oxo-1,2,3,5-tetrahydro-4,1-benzoxazepine-3-acetic acid ethyl ester In ethanol (50 ml) was dissolved 3-[N-[4-chloro-2-(2-chloro-α-hydroxybenzyl)phenyl]-N-(2,4-dimethoxybenzyl) carbamoyl]acrylic acid ethyl ester (5.5 g) obtained in (2). To the solution was added potassium carbonate (1.4 g), and the mixture was stirred for 2 hours. To the reaction mixture were added water (200 ml) and ethyl acetate (300 ml). The mixture was subjected to extraction. The ethyl acetate layer was washed with water and dried over anhydrous magnesium sulfate, then the solvent was distilled off under reduced pressure. The residue was purified by means of a silica gel column chromatography to afford trans-7-chloro-5-(2-chlorophenyl)-1-(2,4-dimethoxybenzyl)-2-oxo-1,2,3,5-tetrahydro-4,1-benzoxazepine-3-acetic acid ethyl ester as an oily product.

IRv$_{max}^{Neat}$cm$^{-1}$: 1730, 1675(C=O)

Elemental Analysis for $C_{28}H_{27}Cl_2NO_6$: Calcd.: C 61.77; H 5.00; N 2.57 Found: C 62.06; H 5.26; N 2.61

Reference Example 8

Trans-7-chloro-5-(2-chlorophenyl)-1-(2,4-dimethoxybenzyl)-2-oxo-1,2,3,5-tetrahydro-4,1-benzoxazepine-3-acetic acid To a solution of trans-7-chloro-5-(2-chlorophenyl)-1-(2,4-dimethoxybenzyl)-2-oxo-1,2,3,5-tetrahydro-4,1-benzoxazepine-3-acetic acid ethyl ester (1.0 g) obtained in Reference Example 7 in methanol (20 ml) was added an aqueous solution (10 ml) of potassium carbonate (0.51 g), followed by stirring for one hour at 60° C. The reaction mixture was acidified with 1N hydrochloric acid (50 ml), which was subjected to extraction with ethyl acetate (100 ml). The ethyl acetate layer was washed with water and dried over anhydrous magnesium sulfate, then the solvent was distilled off under reduced pressure. The residue was purified by means of a silica gel column chromatography (hexane:ethyl acetate=1:1~hexane:methylene chloride:ethanol =5:5:1) to afford trans-7-chloro-5-(2-chlorophenyl)-1-(2,4-dimethoxybenzyl)-2-oxo-1,2,3,5-tetrahydro-4,1-benzoxazepine-3-acetic acid (0.43 g) as a powdery product.

IRv$_{max}^{KBr}$cm$^{-1}$: 1715, 1670(C=O)

Elemental Analysis for $C_{26}H_{23}Cl_2NO_6$: Calcd.: C 60.48; H 4.49; N 2.71 Found: C 60.21; H 4.73; N 2.72

Example 8

Ethyl ester of 1-benzyl-2-oxo-5-phenyl-1,2,3,5-tetrahydro-4,1-benzoxazepine-3-propionic acid (1) 2-(5-Oxotetrahydrofuran-2-carbonyl)aminobenzophenone A mixture of 4.9 g of 5-oxotetrahydrofuran-2-carboxylic acid and 5.5 ml of thionyl chloride was subjected to reflux for 2 hours. Thionyl chloride was then distilled off under reduced pressure to leave 5-oxotetrahydrofuran-2-carbonyl chloride. This product was mixed with 5.0 g of 2-aminobenzophenone, 200 ml of ethyl acetate and 200 ml of a saturated aqueous solution of sodium hydrogencarbonate, which was stirred for one hour at room temperature. The ethyl acetate layer was washed with water and dried over anhydrous magnesium sulfate, then the solvent was distilled off under reduced pressure. The residue was purified by means of a silica gel column chromatography (eluent, hexane:ethyl acetate=2:1) to give 2-(5-oxotetrahydrofuran-2-carbonyl)aminobenzophenone (6.5 g) as needles, m.p. 100° C.–102° C.

IRv$_{max}^{KBr}$cm$^{-1}$: 3300(NH) 1790, 1690, 1640(C=O)

Elemental Analysis for $C_{18}H_{15}NO_4$: Calcd.: C 69.89; H 4.88; N 4.53 Found: C 69.98; H 5.01; N 4.41

(2) 2-[N-benzyl-N-(5-oxotetrahydrofuran-2-carbonyl)]aminobenzophenone

In 20 ml of N,N-dimethylformamide was dissolved 3.0 g of 2-(5-oxotetrahydrofuran-2-carbonyl) aminobenzophenone obtained in (1). To the solution were added 1.73 ml of benzyl bromide, 2.67 g of potassium carbonate and 0.1 g of tetrabutyl ammonium iodide. The mixture was stirred overnight at room temperature. The reaction mixture was subjected to extraction with a mixture of 200 ml of ethyl acetate and 100 ml of water. The ethyl acetate layer was washed with 0.1N hydrochloric acid and an aqueous solution of sodium hydrogencarbonate, which was then dried over anhydrous magnesium sulfate. The solvent was distilled off under reduced pressure. The residue was purified by means of a silica gel column chromatography (eluent, hexane:ethyl acetate=2:1) to give crystals. Recrystallization from hexane-ethyl acetate afforded 2-[N-benzyl-N-(5-oxotetrahydrofuran-2-carbonyl)] aminobenzophenone (3.71 g) as needles, m.p. 142°–143° C.

IRv$_{max}^{KBr}$cm$^{-1}$: 1780, 1660, 1650(C=O)

Elemental Analysis for $C_{25}H_{21}NO_4$: Calcd.: C 75.17; H 5.30; N 3.51 Found: C 75.05; H 5.59; N 3.49

(3) 2-[N-benzyl-N-(4-ethoxycarbonyl-2-hydroxy)butyryl]aminobenzophenone

In 100 ml of ethanol was dissolved 5.0 g of 2-[N-benzyl-N-(5-oxotetrahydrofuran-2-carbonyl)]aminobenzophenone obtained in (2). To the solution was added 0.2 ml of conc. sulfuric acid, and the mixture was left standing for 7 days. Ethanol Was distilled off under reduced pressure. The residue was subjected to extraction with a mixture of 100 ml of water and 200 ml of ethyl acetate. The ethyl acetate layer was washed with an aqueous solution of sodium hydrogencarbonate, which was then dried over anhydrous magnesium sulfate. The solvent was then distilled off under reduced pressure. The residue was purified by means of a silica gel column chromatography (eluent, hexane:ethyl acetate=2:1) to afford 2.8 g of 2-[N-benzyl-N-(4-ethoxycarbonyl-2-hydroxy)butyryl]aminobenzophenone as an oily product.

IRv$_{max}^{Neat}$cm$^{-1}$: 3440(OH) 1735, 1670(C=O)

Mass spectrum (m/e): 445 (M$^+$)

$^1$H-NMR spectrum (200 MHz,CDCl$_3$) δ: 1.20(3H,t,J=7.2 Hz), 1.65–2.0(2H,m), 2.2–2.6(2H,m), 3.65–3.7(1H,br), 4.05 (2H,q,J=7.2 Hz), 4.0–4.35(1H,m), 4.69(1H,d,J=14.4 Hz), 4.87(1H,d,J=14.4 Hz), 6.9–7.9(14H,m)

(4) 2-[N-benzyl-N-(4-ethoxycarbonyl-2-methanesulfonyloxy)butyryl]aminobenzophenone 2-[N-Benzyl-N-(4-ethoxycarbonyl-2-hydroxy)butyryl] aminobenzophenone (2.8 g) obtained in (3) was dissolved in 30 ml of ethyl acetate. To the solution were added, under ice-cooling, 0.73 ml of methanesulfonyloxy chloride and 1.31 ml of triethylamine. The mixture was stirred for 2 hours at room temperature. The reaction mixture was then washed with 1N HCl and an aqueous solution of sodium hydrogencarbonate, successively, which was dried over anhydrous magnesium sulfate, followed by distilling off the solvent under reduced pressure. The residue was purified by means of a silica gel column chromatography (eluent, hexane:ethyl acetate=2:1) to afford 3.2 g of 2-[N-benzyl-N-(4-ethoxycarbonyl-2-methanesulfonyloxy) butyryl] aminobenzophenone as an oily product.

IRv$_{max}^{Neat}$cm$^{-1}$: 1730, 1670(C=O)

Mass spectrum (m/e): 523 (M$^+$)

$^1$H-NMR spectrum (200 MHz,CDCl$_3$) δ: 1.1–1.35(3H, m), 2.0–2.6(4H,m), 3.14+3.38(3H,each s), 3.9–4.7(3H,m), 4.93(d,J=14.2 Hz)+5.53(d,J=14.8 Hz)(1H), 5.05–5.15(m) 5.15–5.3(m)(1H), 7.0–7.85(14H,m)

(5) Ethyl-cis-1-benzyl-2-oxo-5-phenyl-1,2,3,5-tetrahydro-4,1-benzoxazepine-3-propionate and ethyl-trans-1-benzyl-2-oxo-5-phenyl-1,2,3,5-tetrahydro-4,1-benzoxazepine-3-propionate In 30 ml of ethanol was dissolved 3.2 g of 2-[N-benzyl-N-(4-ethoxycarbonyl-2-methanesulfonyloxy) butyryl] aminobenzophenone obtained in (4). To the solution was added, under ice-cooling, 0.32 g of sodium borohydride. The reaction mixture was stirred for 45 minutes at 50° C., followed by cooling the reaction mixture to room temperature. The reaction mixture was acidified by the addition of 100 ml of 1N HCl, which was subjected to extraction with 200 ml of ethyl acetate. The extract solution was washed with an aqueous solution of sodium hydrogencarbonate, dried over magnesium sulfate, then the solvent was distilled off under reduced pressure. The residue was purified by means of a silica gel column chromatography (eluent, hexane:ethyl acetate=10:1 to 5:1) to afford, as the first fraction, 0.73 g of ethyl ester of cis-1-benzyl-2-oxo-5-phenyl-1,2,3,5-tetrahydro-4,1-benzoxazepine-3-propionic acid as needles, m.p. 107° C.–108° C.

IRv$_{max}$$^{KBr}$cm$^{-1}$: 1735, 1670(C=O)

Elemental Analysis for C$_{27}$H$_{27}$NO$_4$: Calcd.: C 75.50; H 6.34; N 3.26 Found: C 75.21; H 6.44; N 3.27

$^1$H-NMR spectrum (200 MHz,CDCl$_3$) δ: 1.21(3H,t,J=7.2 Hz), 2.2–2.4(2H,m), 2.55(2H,t,J=7.0 Hz), 3.72(1H,d,J=16.0 Hz), 4.10(2H,q,J=7.2 Hz), 4.23(1H,t,J=6.5 Hz), 4.70(1H,d, J=16.0 Hz), 5.95(1H,s), 7.0–7.5(14H,m)

As the second fraction, 0.3 g of ethyl ester of trans-1-benzyl-2-oxo-5-phenyl-1,2,3,5-tetrahydro-4,1-benzoxazepine-3-propionic acid as an oily product.

IRv$_{max}$$^{Neat}$cm$^{-1}$: 1730, 1670(C=O)

Mass spectrum (m/e): 429 (M$^+$)

$^1$H-NMR spectrum (200 MHz,CDCl$_3$) δ: 1.17(3H,t,J=7.1 Hz), 2.05–2.4(2H,m), 2.49(2H,t,J=7.0 Hz), 4.06(2H,q,J=7.1 Hz), 3.95–4.05(1H,m), 4.86(1H,d,J=14.6 Hz), 5.46(1H,s), 5.50(1H,d,J=14.6 Hz), 6.53(1H,d,J=7.8 Hz), 7.0–7.45(13H, m)

Example 9

Ethyl ester of cis-1-benzyl-7-chloro-5-(2-chlorophenyl)-2-oxo-1,2,3,5-tetrahydro-4,1-benzoxazepine-3-propionic acid (1) 2',5-Dichloro-2-(5-oxotetrahydrofuran-2-carbonyl) aminobenzophenone In substantially the same manner as in Example 8 (1), 15 g of 2-amino-2',5-dichlorobenzophenone was allowed to react with 5-oxotetrahydrofuran-2-carbonyl chloride to afford 18.1 g of 2',5-dichloro-2-(5-oxotetrahydrofuran-2-carbonyl) aminobenzophenone, m.p. 170° C.–173° C.

IRv$_{max}$$^{KBr}$cm$^{-1}$: 3250(NH), 1775, 1695, 1640(C=O)

Elemental Analysis for C$_{18}$H$_{13}$Cl$_2$NO$_4$: Calcd.: C 57.16; H 3.46; N 3.70 Found: C 57.29; H 3.55; N 3.57

(2) 2-[N-benzyl-N-(5-oxotetrahydrofuran-2-carbonyl)] amino-2',5-dichlorobenzophenone In substantially the same manner as in Example 8 (2), 20 g of 2',5-dichloro-2-(5-oxotetrahydrofuran-2-carbonyl) aminobenzophenone obtained in (1) was allowed to react with benzyl bromide to afford 24.5 g of 2-[N-benzyl-N-(5-oxotetrahydrofuran-2-carbonyl)]amino-2',5-dichlorobenzophenone as an oily product.

IRv$_{max}$$^{Neat}$cm$^{-1}$: 1780, 1670(C=O)

$^1$H-NMR spectrum (200 MHz,CDCl$_3$) δ: 2.1–2.55(2H, m), 2.65–3.0(2H,m), 4.01(d,J=14.4 Hz)+4.29(d,J=14.4 Hz) (1H), 4.75–4.9(1H,m), 5.29(d=14.4 Hz)+5.47(d,J=14.4 Hz) (1H), 6.6–7.6(13H,m)

(3) 2-[N-benzyl-N-(4-ethoxycarbonyl-2-hydroxy)butyryl] amino-2',5-dichlorobenzophenone 23 g of 2-[N-benzyl-N-(5-oxotetrahydrofuran-2-carbonyl)]amino-2',5-dichlorobenzophenone obtained in (2) was subjected to substantially the same reaction as in Example 8 (3) to afford 17 g of 2-[N-benzyl-N-(4-ethoxycarbonyl-2-hydroxy)butyryl]amino-2',5-dichlorobenzophenone.

IRv$_{max}$$^{Neat}$cm$^{-1}$: 1730, 1660(C=O)

$^1$H-NMR spectrum (200 MHz,CDCl$_3$) δ: 1.1–1.35(3H, m), 1.6–2.0(2H,m), 2.3–2.8(2H,m), 3.9–4.8(4H,m), 5.34(d, J=14.4 Hz)+5.69(d,J=14.4 Hz)(1H), 6.8–7.6(12H,m)

(4) 2-[N-benzyl-N-(4-ethoxycarbonyl-2-methanesulfonyloxy)butyryl]amino-2',5-dichlorobenzophenone In substantially the same manner as in Example 8 (4), 17 g of 2-[N-benzyl-N-(4-ethoxycarbonyl-2-hydroxy)butyryl] amino-2',5-dichlorobenzophenone was allowed to react with methanesulfonyl chloride to afford 19 g of 2-[N-benzyl-N-(4-ethoxycarbonyl-2-methanesulfonyloxy)butyryl]amino-2',5-dichlorobenzophenone as an oily product.

IRv$_{max}$$^{Neat}$cm$^{-1}$: =1730, 1675(C=O)

$^1$H-NMR spectrum (200 MHz,CDCl$_3$) δ: 1.1–1.35(3H, m), 1.9–2.6(4H,m), 3.17+3.32(3H,each s), 4.85–5.0(m)+ 5.05–5.15(m)(1H), 5.45(d,J=14.4 Hz)+5.72(d,J=14.4 Hz) (1H), 6.9–7.6(12H,m)

(5) Ethyl ester of cis-1-benzyl-7-chloro-5-(2-chlorophenyl) -2-oxo-1,2,3,5-tetrahydro-4,1-benzoxazepine-3-propionic acid and ethyl ester of trans-1-benzyl-7-chloro-5-(2-chlorophenyl)-2-oxo-1,2,3,5-tetrahydro-4,1-benzoxazepine-3-propionic acid 19 g of 2-[N-benzyl-N-(4-ethoxycarbonyl-2-methane sulfonyloxy)butyryl]amino-2',5-dichlorobenzophenone was subjected to substantially the same reaction as in Example 8 (5). The reaction mixture was purified by means of a silica gel column chromatography. As the first fraction, 3.1 g of ethyl ester of cis-1-benzyl-7-chloro-5-(2-chlorophenyl)-2-oxo-1,2,3,5-tetrahydro-4,1-benzoxazepine-3-propionic acid was obtained in the form of an oily product.

IRv$_{max}$$^{Neat}$cm$^{-1}$: 1730, 1670(C=O)

As the second fraction, 3.3 g of ethyl ester of trans-1-benzyl-7-chloro-5-(2-chlorophenyl)-2-oxo-1,2,3,5-tetrahydro-4,1-benzoxazepine-3-propionic acid as prisms, m.p. 122° C.–123° C.

IRv$_{max}$$^{Neat}$cm$^{-1}$: 1740, 1670(C=O)

Elemental Analysis for C$_{27}$H$_{25}$Cl$_2$NO$_4$: Calcd.: C 65.07; H 5.06; N 2.81 Found: C 65.30; H 5.09; N 2.81

Example 10

Ethyl ester of 7-chloro-5-(2-chlorophenyl)-1-methyl-2-oxo-1,2,3,5-tetrahydro-4,1-benzoxazepine-3-propionic acid (1) 2',5-Dichloro-2-[N-methyl-N-(5-oxotetrahydrofuran-2-carbonyl)]aminobenzophenone In 100 ml of acetone was dissolved 15 g of 2',5-dichloro-2-(5-oxotetrahydrofuran-2-carbonyl)aminobenzophenone obtained in Example 9 (1). To the solution were added 4.96 ml of methyl iodide and 11 g of potassium carbonate, and the mixture was stirred for 3 days at room temperature. The reaction mixture Was subjected to distillation under reduced pressure. The residue was subjected to extraction by the addition of 200 ml of water and 300 ml of ethyl acetate. The ethyl acetate layer was washed with water and dried over anhydrous magnesium sulfate, then the solvent was distilled off under reduced pressure. The residue was purified by means of a silica gel chromatography (eluent, hexane:ethyl acetate=2:1 to 1:1) to afford 13.5 g of 2',5-dichloro-2-[N-methyl-N-(5-oxotetrahydrofuran-2-carbonyl)] aminobenzophenone as an oily product.

IRv$_{max}$$^{Neat}$cm$^{-1}$: 1780,1675(C=O)

$^1$H-NMR spectrum (200 MHz,CDCl$_3$) δ: 2.1–3.0(4H,m), 3.08+3.14(3H,each s), 4.75–4.9(1H,m), 7.1–7.7(7H,m)

(2) 2',5-Dichloro-2-[N-(4-ethoxycarbonyl-2-hydroxy) butyryl-N-methyl]aminobenzophenone 13.5 g of 2',5-dichloro-2-[N-methyl-N-(5-oxotetrahydro furan-2-carbonyl)]aminobenzophenone was subjected to substantially the same reaction as in Example 8 (3) to afford 9.5 g of 2',5-dichloro-2-[N-(4-ethoxycarbonyl-2-hydroxy) butyryl-N-methyl]aminobenzophenone as an oily product.

IRv$_{max}^{Neat}$cm$^{-1}$: 1730, 1670, 1660(C=O)

$^1$H-NMR spectrum (200 MHz, CDCl$_3$) δ: 1.1–1.4(3H,m), 1.5–1.9(2H,m), 2.0–2.75(2H,m), 3.0–3.5(3H,m), 3.95–4.5 (4H,m), 7.2–7.7(7H.,)

(3) 2',5-Dichloro-2-[N-(4-ethoxycarbonyl-2-methanesulfonyloxy)butyryl-N-methyl] aminobenzophenone In substantially the same manner as in Example 8 (4), 9.5 g of 2',5-dichloro-2-[N-(4-ethoxycarbonyl-2-hydroxy) butyryl-N-methyl]aminobenzophenone obtained in (2) was allowed to react with methanesulfonyl chloride to give 11.0 g of 2',5-dichloro-2-[N-(4-ethoxycarbonyl-2-methanesulfonyloxy)butyryl-N-methyl] aminobenzophenone as an oily product.

IRv$_{max}^{Neat}$cm$^{-1}$: 1730, 1680(C=O)

$^1$H-NMR spectrum (200 MHz, CDCl$_3$) δ: 1.1–1.35(3H, m), 1.9–2.7(4H,m), 3.0–3.7(6H,m), 3.9–4.25(2H,m), 4.9–5.7(1H,m), 7.3–7.75(7H,m)

(4) Ethyl ester of 7-chloro-5-(2-chlorophenyl)-1-methyl-2-oxo-1,2,3,5-tetrahydro-4,1-benzoxazepine-3-propionic acid 11.0 g of 2',5-dichloro-2-[N-(4-ethoxycarbonyl-2-methanesulfonyloxy)butyryl-N-methyl] aminobenzophenone obtained in (3) was subjected to substantially the same reaction in Example 8 (5), and the reaction product was purified by means of a silica gel column chromatography to give 4.17 g of the mixture of cis- and trans-isomers of ethyl ester of 7-chloro-5-(2-chlorophenyl)-1-methyl-2-oxo-1,2,3,5-tetrahydro-4,1-benzoxazepine-3-propionic acid as an oily product.

IRv$_{max}^{Neat}$cm$^{-1}$: 1735, 1675(C=O)

$^1$H-NMR spectrum (200 MHz,CDCl$_3$) δ: 1.19(3H,t,J=7.2 Hz), 1.21(3H,t,J=7.2 Hz), 2.0–2.4(4H,m), 2.4–2.6(4H,m), 3.15(3H,s), 3.51(3H,s), 3.95–4.2(5H,m), 4.36(1H,t,J=6.6 Hz), 5.99(1H,s), 6.16(1H,s), 6.50(1H,d,J=2.4 Hz), 7.05–7.8 (13H,m)

Example 11

Ethyl ester of 1-benzyl-5-(4-methoxyphenyl)-2-oxo-1,2,3,5-tetrahydro-4,1-benzoxazepine-3-propionic acid (1) 4'-Methoxy-2-(5-tetrahydrofuran-2-carbonyl)aminobenzophenone In substantially the same manner as in Example 8 (1), 8 g of 2-amino-4'-methoxybenzophenone was allowed to react with 5-oxotetrahydrofuran-2-carbonyl chloride to give 12 g of 4'-methoxy-2-(5-oxotetrahydrofuran-2-carbonyl) aminobenzophenone as an oily product.

IRv$_{max}^{Neat}$cm$^{-1}$: 1780, 1685, 1625(C=O)

$^1$H-NMR spectrum (200 MHz,CDCl$_3$) δ: 2.3–2.8(4H,m), 3.89(3H,s), 4.9–5.05(1H,m), 6.9–7.85(7H,m), 8.5–8.6(1H, m), 11.2(1H,br)

(2) 2-[N-benzyl-N-(5-oxotetrahydrofuran-2-carbonyl)] amino-4'-methoxybenzophenone In substantially the same manner as in Example 8 (2), 12 g of 4'-methoxy-2-(5-oxotetrahydrofuran-2-carbonyl) aminobenzophenone obtained in (1) was allowed to react with benzyl bromide to give 13.2 g of 2[N-benzyl-N-(5-oxotetrahydrofuran-2-carbonyl)]amino-4'-methoxybenzophenone as prisms, m.p. 137° C.–138° C.

IRv$_{max}^{KBr}$cm$^{-1}$: 1775, 1660, 1645(C=O)

Elemental Analysis for C$_{26}$H$_{23}$NO$_5$: Calcd.: C 72.71; H 5.40; N 3.26 Found: C 72.98; H 5.46; N 3.22

(3) 2-[N-benzyl-N-(4-ethoxycarbonyl-2-hydroxy)butyryl] amino-4'-methoxybenzophenone 13.0 g of 2-[N-benzyl-N-(5-oxotetrahydrofuran-2-carbonyl)]amino-4'-methoxybenzophenone obtained in (2) was subjected to substantially the same reaction as in Example 8 (3) to give 10.5 g of 2-[N-benzyl-N-(4-ethoxycarbonyl-2-hydroxy)butyryl]amino-4'-methoxybenzophenone as an oily product.

IRv$_{max}^{Neat}$cm$^{-1}$: 1730, 1650(C=O)

$^1$H-NMR spectrum (200 MHz,CDCl$_3$) δ: 1.1–1.35(3H, m), 1.7–2.1(2H,m), 2.2–2.55(2H,m), 3.88(3H,s), 3.9–4.3 (3H,m), 4.52(1H,d,J=14.4 Hz), 4.99(1H,d,J=14.4 Hz), 6.8–7.9(13H,m)

(4) 2-[N-benzyl-N-(4-ethoxycarbonyl-2-methanesulfonyloxy)butyryl]amino-4'-methoxybenzophenone In substantially the same manner as in Example 8 (4), 10.5 g of 2-[N-benzyl-N-(4-ethoxycarbonyl-2-hydroxy)butyryl] amino-4'-methoxybenzophenone was allowed to react with methanesulfonyl chloride to give 8.5 g of 2-[N-benzyl-N-(4-ethoxycarbonyl-2-methanesulfonyloxy)butyryl]amino-4'-methoxybenzophenone as an oily product.

IRv$_{max}^{Neat}$cm$^{-1}$: 1730, 1670, 1660(C=O)

$^1$H-NMR spectrum (200 MHz,CDCl$_3$) δ: 1.1–1.3(3H,m), 2.0–2.6(4H,m), 3.14+3.38(3H,each s), 3.89+3.91(3H,each s), 3.9–4.6(3H,m), 4.9–5.65(2H,m), 6.8–7.9(13H,m)

(5) Ethyl ester of cis-1-benzyl-5-(4-methoxyphenyl-2-oxo-1,2,3,5-tetrahydro-4,1-benzoxazepine-3-propionic acid and ethyl ester of trans-1-benzyl-5-(4-methoxyphenyl)-2-oxo-1,2,3,5-tetrahydro-4,1-benzoxazepine-3-propionic acid 8.5 g of 2-[N-benzyl-N-(4-ethoxycarbonyl-2-methanesulfonyloxy)butyryl]amino-4'-methoxybenzophenone obtained in (4) was subjected to substantially the same reaction as in Example 8 (5) to give a mixture product, which was purified by means of a silica gel column chromatography to give, as the first fraction, 2.0 g of ethyl ester of cis-1-benzyl-5-(4-methoxyphenyl)-2-oxo-1,2,3,5-tetrahydro-4,1-benzoxazepine-3-propionic acid as needles, m.p. 95°–96° C.

IRv$_{max}^{KBr}$cm$^{-1}$: 1730, 1670(C=O)

Elemental Analysis for C$_{28}$H$_{29}$NO$_5$: Calcd.: C 73.18; H 6.36; N 3.05 Found: C 73.09; H 6.42; N 3.19

As the second fraction, 0.88 g of ethyl ester of trans-1-benzyl-5-(4-methoxyphenyl)-2-oxo-1,2,3,5-tetrahydro-4,1-benzoxazepine-3-propionic acid was obtained as an oily product.

IRv$_{max}^{Neat}$cm$^{-1}$: 1730, 1670(C=O)

$^1$H-NMR spectrum (200 MHz,CDCl$_3$) δ: 1.17(3H,t,J=7.1 Hz), 2.1–2.4(2H,m), 2.47(2H,t,J=7.1 Hz), 3.82(1H,s), 3.95–4.2(3H,m), 4.87(1H,d,J=14.6 Hz), 5.42(1H,s), 6.58 (1H,d,J=7.2 Hz), 6.8–7.5(12H,m)

Example 12

Methyl ester of 1-benzyl-2-oxo-5-phenyl-1,2,3,5-tetrahydro-4,1-benzoxazepine-3-propionic acid (I) 2-[N-benzyl-N-(2-chloro-4-methoxycarbonyl) butyryl]aminobenzophenone A mixture of 7.6 g of 2-chloro-4-methoxycarbonyl valeric acid, 9.2 ml of thionyl chloride and 30 ml of toluene was stirred for 30 minutes at 80° C., followed by distilling off the solvent under reduced pressure to leave 2-chloro-4-methoxycarbonyl butyryl chloride. A mixture of this compound, 5.0 g of 2-benzylaminobenzophenone, 100 ml of ethyl acetate and 100 ml of a saturated aqueous solution of sodium hydrogencarbonate was stirred for 30 minutes at room temperature. The ethyl acetate layer was washed with water and dried over anhydrous magnesium sulfate, then the solvent was distilled off under reduced pressure. The residue was purified by means of a silica gel column chromatography (eluent, hexane:ethyl acetate=5:1) to give 1.2 g of 2-[N-benzyl-N-(2-chloro-4-methoxycarbonyl)butyryl] aminobenzophenone as an oily product.

IRv$_{max}^{Neat}$cm$^{-1}$: 1735, 1655(C=O)

Mass spectrum (m/e) : 449 (M$^+$)

$^1$H-NMR spectrum (200 MHz,CDCl$_3$) δ: 2.3–2.8(4H,m), 3.62(3H,s), 4.2–4.3(1H,m), 4.53(1H,d,J=14.4 Hz), 4.92(1H, d,J=14.4 Hz), 6.9–7.75(14H,m)

(2) 2-[N-benzyl-N-(2-chloro-4-methoxycarbonyl)butyryl] aminodiphenyl methanol

[Method A]

In 30 ml of methanol was dissolved 1.2 g of 2-[N-benzyl-N-(2-chloro-4-methoxycarbonyl)butyryl]amino benzophenone. To the solution was added, under ice-cooling, 0.135 g of sodium borohydride. The mixture was stirred for 30 minutes at room temperature, then the solvent was distilled off under reduced pressure. To the residue was added 100 ml of 1N hydrochloric acid to make the solution acid, which was subjected to extraction with 100 ml of ethyl acetate. The ethyl acetate layer was washed with an aqueous solution of sodium hydrogencarbonate and dried over anhydrous magnesium sulfate, then the solvent was distilled off. The residue was purified by means of a silica gel column chromatography (eluent, hexane: ethyl acetate=2:1) to give 1.1 g of 2-[N-benzyl-N-(2-chloro-4-methoxycarbonyl) butyryl] aminodiphenyl methanol.

IRv$_{max}^{Neat}$cm$^{-1}$: 3430(OH), 1735, 1660(C=O)

$^1$H-NMR spectrum (200 MHz,CDCl$_3$) δ: 1.95–2.65(4H, m), 3.24.–4.4(6H,m), 5.1–5.5(1H,m), 5.75–6.15(1H,m), 6.5–7.85(14H,m)

[Method B]

A mixture of 6.2 g of 2-chloro-4-methoxycarbonyl valeric acid and 12.6 ml of thionyl chloride was refluxed for 30 minutes, then the solvent was distilled off under reduced pressure to leave 2-chloro-4-methoxycarbonyl butyryl chloride. A mixture of this product, 5.0 g of 2-benzylaminodiphenyl methanol, 100 ml of ethyl acetate and 100 ml of a saturated aqueous solution of sodium hydrogencarbonate was stirred for one hour at room temperature. The ethyl acetate layer was washed with water and dried over anhydrous magnesium sulfate, then the solvent was distilled off under reduced pressure. The residue was purified by means of a silica gel column chromatography (eluent, hexane:ethyl acetate=2:1) to give 5.3 g of 2-[N-benzyl-N-(2-chloro-4-methoxycarbonyl)butyryl] aminodiphenyl methanol as an oily product.

(3) Methyl ester of cis-1-benzyl-2-oxo-5-phenyl-1,2,3,5-tetrahydro-4,1-benzoxazepine-3-propionic acid and methyl ester of trans-1-benzyl-2-oxo-5-phenyl-1,2,3,5-tetrahydro-4,1-benzoxazepine-3-propionic acid In 20 ml of tetrahydrofuran was dissolved 1.1 g of 2-[N-benzyl-N-(2-chloro-4-methoxycarbonyl)butyryl] aminodiphenyl methanol. To the solution was added 107 mg of sodium hydride (60% in oil), and the mixture was stirred for one hour at room temperature. To the reaction mixture was added 50 ml of 1N hydrochloric acid to make the solution acid, which was subjected to extraction with 100 ml of ethyl acetate. The ethyl acetate layer was washed with an aqueous solution of sodium hydrogencarbonate and dried over anhydrous magnesium sulfate, then the solvent was distilled off under reduced pressure. The residue was purified by means of a silica gel column chromatography (eluent, hexane:ethyl acetate=5:1). From the first fraction, 0.4 g of methyl ester of cis-1-benzyl-2-oxo-5-phenyl-1,2,3,5-tetrahydro-4,1-benzoxazepine-3-propionic acid as plates, m.p. 134°–136° C.

IRv$_{max}^{KBr}$cm$^{-1}$: 1740, 1670(C=O)

Elemental Analysis for C$_{25}$H$_{25}$NO$_4$: Calcd.: C 75.16; H 6.06; N 3.37 Found: C 74.74; H 5.97; N 3.38

From the second fraction, 0.18 g of of methyl ester of trans-1-benzyl-2-oxo-5-phenyl-1,2,3,5-tetrahydro-4,1-benzoxazepine- 3-propionic acid was obtained as needles, m.p. 116°–118° C.

IRv$_{max}^{KBr}$cm$^{-1}$: 1740, 1670(C=O)

Elemental Analysis for C$_{26}$H$_{25}$NO$_4$: Calcd.: C 75.16; H 6.06; N 3.73 Found: C 75.22; H 5.94; N 3.58

Example 13

Cis-1-benzyl-2-oxo-5-phenyl-1,2,3,5-tetrahydro-4,1-benzoxazepine-3-propionic acid In 20 ml of methanol was dissolved 0.5 g of ethyl ester of cis-1-benzyl-2-oxo-5-phenyl-1,2,3,5-tetrahydro-4,1-benzoxazepine-3-propionic acid obtained in Example 8. To the solution was added 7 ml of 1N sodium hydroxide, and the mixture was stirred for 30 minutes at room temperature. The reaction mixture was acidified with 100 ml of 1N hydrochloric acid, which was subjected to extraction with 150 ml of ethyl acetate. The ethyl acetate layer was washed with water and dried over anhydrous magnesium sulfate. Then the solvent was distilled off under reduced pressure to leave 0.46 g of cis-1-benzyl-2-oxo-5-phenyl-1,2,3,5-tetrahydro-4,1-benzoxazepine-3-propionic acid as plates, m.p. 112°–114° C.

IRv$_{max}^{KBr}$cm$^{-1}$: 1710, 1670(C=O)

Elemental Analysis for C$_{25}$H$_{23}$NO$_4$: Calcd.: C 74.80; H 5.77; N 3.49 Found: C 74.52; H 5.85; N 4.42

Example 14

Trans-1-benzyl-2-oxo-5-phenyl-1,2,3,5-tetrahydro-4,1-benzoxazepine-3-propionic acid In substantially the same manner as in Example 13, 1.0 g of ethyl ester of trans-1-benzyl-2-oxo-5-phenyl-1,2,3,5-tetrahydro-4,1-benzoxazepine-3-propionic acid obtained in Example 8 was subjected to hydrolysis to give 0.81 g of trans-1-benzyl-2-oxo-5-phenyl-1,2,3,5-tetrahydro-4,1-benzoxazepine-3-propionic acid as plates, m.p. 148°–150° C.

IRv$_{max}^{KBr}$cm$^{-1}$: 1735, 1650(C=O)

Elemental Analysis for C$_{25}$H$_{23}$NO$_4$: Calcd.: C 74.80; H 5.77; N 3.49 Found: C 74.66; H 5.78; N 3.55

In substantially the same manner as above, 0.9 g of methyl ester of trans-1-benzyl-2-oxo-5-phenyl-1,2,3,5-tetrahydro-4,1-benzoxazepine-3-propionic acid obtained in Example 12 was subjected to hydrolysis to give 0.86 g of trans-1-benzyl-2-oxo-5-phenyl-1,2,3,5-tetrahydro-4,1-benzoxazepine-3-propionic acid.

Example 15

Cis-1-benzyl-7-chloro-5-(2-chlorophenyl)-2-oxo-1,2,3,5-tetrahydro-4,1-benzoxazepine-3-propionic acid In substantially the same manner as in Example 13, 3.1 g of ethyl ester of cis-1-benzyl-7-chloro-5-(2-chlorophenyl)-2-oxo-1,2,3,5-tetrahydro-4,1-benzoxazepine-3-propionic acid obtained in Example 9 was subjected to hydrolysis to give 2.9 g of cis-1-benzyl- 7-chloro-5-(2-chlorophenyl)-2-oxo-1,2,3,5-tetrahydro-4,1-benzoxazepine-3-propionic acid as prisms, m.p. 135°–137° C.

IRv$_{max}^{KBr}$cm$^{-1}$: 1725, 1640(C=O)

Elemental Analysis for C$_{25}$H$_{21}$Cl$_2$NO$_4$: Calcd.: C 63.84; H 4.50; N 2.98 Found: C 64.02; H 4.76; N 2.88

Example 16

Trans-1-benzyl-7-chloro-5-(2-chlorophenyl)-2-oxo-1,2,3,5-tetrahydro-4,1-benzoxazepine-3-propionic acid In substantially the same manner as in Example 13, 2.7 g of ethyl ester of trans-1-benzyl-7-chloro-5-(2-chlorophenyl)-2-oxo-1,2,3,5-tetrahydro-4,1-benzoxazepine-3-propionic acid obtained in Example 9 was subjected to hydrolysis to give 2.5 g trans-1-benzyl-7-chloro-5-(2-chlorophenyl)-2-oxo-1,2,3,5-tetrahydro-4,1-benzoxazepine-3-propionic acid as prisms, m.p. 192°–194° C.

IRv$_{max}^{KBr}$cm$^{-1}$: 1730, 1640(C=O)

Elemental Analysis for C$_{25}$H$_{21}$Cl$_2$NO$_4$: Calcd.: C 63.84; H 4.50; N 2.98 Found: C 63.99; H 4.57; N 2.92

Example 17

7-Chloro-5-(2-chlorophenyl)-1-methyl-2-oxo-1,2,3,5-tetrahydro-4,1-benzoxazepine-3-propionic acid In substantially the same manner as in Example 13 4.1 g of ethyl ester of 7-chloro-5-(2-chlorophenyl)-1-methyl-2-oxo-1,2,3,5-tetrahydro-4,1-benzoxazepine-3-propionic acid obtained in Example 10 was subjected to hydrolysis to give 3.7 g of 7-chloro-5-(2-chlorophenyl)-1-methyl-2-oxo-1,2,3,5-tetrahydro-4,1-benzoxazepine-3-propionic acid as an oily product of the mixture of cis- and trans-compounds (1:1).

IRv$_{max}^{Neat}$cm$^{-1}$: 1705, 1670(C=O)

$^1$H-NMR spectrum (200 MHz,CDCl$_3$) δ: 2.0–2.4(4H,m), 2.45– 2.7(4H,m), 3.14(3H,s), 3.50(3H,s), 4.00(1H,dd,J=7.2×5.4 Hz), 4.35(1H,t,J=6.7 Hz), 5.99(1H,s), 6.16(1H,s), 6.50(1H,d,J=2.2 Hz), 7.0–7.81(13H,m)

Example 18

Cis-1-benzyl-5-(4-methoxyphenyl)-2-oxo-1,2,3,5-tetrahydro-4,1-benzoxazepine-3-propionic acid In substantially the same manner as in Example 13 1.7 g of ethyl ester of cis-1-benzyl-5-(4-methoxyphenyl)-2- oxo-1,2,3,5-tetrahydro-4,1-benzoxazepine-3-propionic acid obtained in Example 11 was subjected to hydrolysis to give 1.5 g of cis-1-benzyl-5-(4-methoxyphenyl)-2-oxo-1,2,3,5-tetrahydro-4,1 -benzoxazepine-3-propionic acid as prisms, m.p. 107° C.–109° C.

IRv$_{max}^{KBr}$cm$^{-1}$: 1715, 1670(C=O)

Elemental Analysis for C$_{26}$H$_{25}$NO$_5$: Calcd.: C 72.37; H 5.84; N 3.25 Found: C 72.26; H 5.90; N 3.10

Example 19

Trans-1-benzyl-5-(4-methoxyphenyl)-2-oxo-1,2,3,5-tetrahydro-4,1-benzoxazepine-3-propionic acid In substantially the same manner as in Example 13 0.85 g of ethyl ester of trans-1-benzyl-5-(4-methoxyphenyl)-2-oxo-1,2,3,5-tetrahydro-4,1-benzoxazepine-3-propionic acid was subjected to hydrolysis to give 0.78 g of trans-1-benzyl-5-(4-methoxyphenyl)-2-oxo-1,2,3,5-tetrahydro-4,1-benzoxazepine-3-propionic acid as an oily product.

IRv$_{max}^{Neat}$cm$^{-1}$: 1710, 1670(C=O)

$^1$H-NMR spectrum (200 MHz,CDCl$_3$) δ: 2.05–2.35(2H, m), 2.52(2H,t,J=7.1 Hz), 3.81(1H,s), 4.00(1H,dd,J=7.3×5.7 Hz), 4.39(1H,d,J=14.4 Hz), 5.40(1H,s), 5.49(1H,d,J=14.4 Hz), 6.57(1H,d,J=7.2 Hz), 6.8–7.5(12H,m)

Example 20

Trans-1-benzyl-3-(3-hydroxypropyl)-5-phenyl-1,5-dihydro-4,1-benzoxazepine-2(3H)-one The mixture of 0.4 g of methyl ester of trans-1-benzyl2-oxo-5-phenyl-1,2,3,5-tetrahydro-4,1-benzoxazepine-3-propionic acid obtained in Example 12, 0.16 g of sodium borohydride and 0.16 g of lithium chloride in 15 ml of tetrahydrofuran were stirred for 10 minutes at room temperature. To the resultant was added 30 ml of ethanol, which was stirred for 2 hours at 60° C. To the reaction mixture were added 100 ml of 1N hydrochloric acid and 150 ml of ethyl acetate. The ethyl acetate layer was washed with an aqueous solution of sodium hydrogencarbonate, which was dried over anhydrous magnesium sulfate, then the solvent was distilled off under reduced pressure. The residue was purified by means of a silica gel column chromatography (eluent, hexane:ethyl acetate=2:1) to give 0.19 g of trans-1-benzyl-3-(3-hydroxypropyl)-5-phenyl-1,5-dihydro-4,1-benzoxazepin-2(3H)-one as needles, m.p. 59°–62° C.

IRv$_{max}^{KBr}$cm$^{-1}$: 1645 (C=O)

Elemental Analysis for C$_{25}$H$_{25}$NO$_3$: Calcd.: C 77.49; H 6.50; N 3.61 Found: C 77.12; H 6.44; N 3.87

Example 21

Cis-1-benzyl-3-(3-3-hydroxypropyl)-5-phenyl-1,5-dihydro-4,1-benzoxazepin-2(3H)-one In substantially the same manner as in Example 20, 0.23 g of methyl ester of cis-1-benzyl-2-oxo-5-phenyl-1,2,3,5-tetrahydro-4,1-benzoxazepine-3-propionic acid obtained in Example 12 was subjected to reduction to give 0.09 g of cis-1-benzyl-3-(3-hydroxypropyl)-5-phenyl-1,5-dihydro-4,1-benzoxazepin-2(3H)-one as needles, m.p. 94°–95° C.

IRv$_{max}^{KBr}$cm$^{-1}$: 1675, 1660(C=O)

Elemental Analysis for C$_{25}$H$_{25}$NO$_3$: Calcd.: C 77.49; H 6.50; N 3.61 Found: C 77.44; H 6.49; N 3.76

Example 22

N-(cis-1-benzyl-2-oxo-5-phenyl-1,2,3,5-tetrahydro-4,1-benzoxazepine-3-propionyl)aminoethanol In 5 ml of N,N-dimethylformamide were dissolved 5 0.3 g of cis-1-benzyl-2-oxo-5-phenyl-1,2,3,5-tetrahydro-4,1-benzoxazepine-3-propionic acid obtained in Example 13 and 0.054 ml of ethanolamine. To the solution were added, under ice-cooling, 0.17 g of diethyl phosphorocyanidate and 0.14 ml of triethylamine. The mixture was stirred for 30 minutes at room temperature, to which was added 100 ml of wager. The mixture was subjected to extraction with ethyl acetate (100 ml×2). The ethyl acetate layer was washed with 1N hydrochloric acid and an aqueous solution of sodium hydrogencarbonate, successively, which was then dried over anhydrous magnesium sulfate. The solvent was distilled off under reduced pressure. The residue was purified by means of a silica gel column chromatography (eluent, hexane:methylene chloride:ethanol=5:5:1) to give 0.28 g of N-(cis-1-benzyl-2-oxo-5-phenyl-1,2,3,5-tetrahydro-4,1-benzoxazepine-3-propionyl)aminoethanol as needles, m.p. 117°–119° C.

IRv$_{max}^{KBr}$cm$^{-1}$: 1670, 1640(C=O)

Elemental Analysis for C$_{27}$H$_{28}$N$_2$O$_4$·0.5H$_2$O: Calcd.: C 71.50; H 6.44; N 6.18 Found: C 71.29; H 6.47; N 5.98

Example 23

N-(trans-1-benzyl-2-oxo-5-phenyl-1,2,3,5-tetrahydro-4,1-benzoxazepine-3-propionyl) aminoethanol In substantially the same manner as in Example 22 0.25 g of trans-1-benzyl-2-oxo-5-phenyl-1,2,3,5-tetrahydro-4,1-benzoxazepine-3-propionic acid obtained in Example 14 was subjected to condensation with ethanolamine to give 0.20 g of N-(trans-1-benzyl-2-oxo-5-phenyl-1,2,3,5-tetrahydro-4,1-benzoxazepine- 3-propionyl)aminoethanol as plates, m.p. 125° C.–127° C.

IRv$_{max}^{KBr}$cm$^{-1}$: 1675, 1645(C=O)

Elemental Analysis for C$_{27}$H$_{28}$N$_2$O$_4$: Calcd.: C 72.95; H 6.35; N 6.30 Found: C 72.70; H 6.36; N 6.19

Example 24

Methyl ester of N-(cis-1-benzyl-2-oxo-5-phenyl-1,2,3,5-tetrahydro-4,1-benzoxazepine-3-propionyl)-L-tryptophane In 10 ml of N,N-dimethylformamide were dissolved 0.35 g of cis-1-benzyl-2-oxo-5-phenyl-1,2,3,5-tetrahydro-4,1-benzoxazepine-3-propionic acid obtained in Example 13 and 0.23 g of L-tryptophane methyl ester hydrochloride. To the solution were added, under ice-cooling, 0.15 g of diethyl phosphorocyanidate and 0.24 ml of triethylamine. The mixture was stirred for 30 minutes at room temperature, which was subjected to extraction with the addition of 100 ml of water and 100 ml of ethyl acetate. The ethyl acetate layer was washed with 1N hydrochloric acid and an aqueous solution of sodium hydrogencarbonate, successively, which was then dried over anhydrous magnesium sulfate. The solvent was distilled off, and the residue was purified by means of a silica gel column chromatography (eluent, hexane:ethyl acetate=1:1) to give 0.50 g of methyl ester of N-(cis-1-benzyl-2-oxo-5-phenyl-1,2,3,5-tetrahydro-4,1-benzoxazepine-3-propionyl)-L-tryptophane as an oily product.

IRv$_{max}^{Neat}$cm$^{-1}$: 1740, 1665(C=O)

$^1$H-NMR spectrum (200 MHz,CDCl$_3$) δ: 2.15–2.5(4H, m), 3.27(2H,t,J=4.7 Hz), 3.62+3.63(3H,each s), 3.71(1H,d, J=16.0 Hz), 4.15–4.3(1H,m), 4.68(1H,d,J=16.0 Hz), 4.8–5.0 (1H,m), 5.85(1H,s), 6.15–6.35(1H,m), 6.9–7.6(19H,m), 8.13(1H,br)

Example 25

N-(cis-1-benzyl-2-oxo-5-phenyl-1,2,3,5-tetrahydro-4,1-benzoxazepine- 3-propionyl)-L-tryptophane In 10 ml of methanol was dissolved 0.5 g of methyl ester of N-(cis-1-benzyl-2-oxo-5-phenyl-1,2,3,5-tetrahydro-4,1-benzoxazepine-3-propionyl)-L-tryptophane obtained in Example 24. To the solution was added 5 ml of 1N sodium hydroxide, and the mixture was stirred for one hour at room temperature. The reaction mixture was made acid by the addition of 100 ml of 1N hydrochloric acid, which was subjected to extraction with 100 ml of ethyl acetate. The ethyl acetate layer was washed with water and dried over anhydrous magnesium sulfate. The solvent was then distilled off under reduced pressure to give 0.24 g of N-(cis-1-benzyl-2-oxo-5-phenyl-1,2,3,5-tetrahydro-4,1-benzoxazepine-3-propionyl)-L-tryptophane as a powdery product.

IRv$_{max}^{KBr}$cm$^{-1}$: 1730, 1660(C=O)

Elemental Analysis for C$_{36}$H$_{33}$N$_3$O$_5$ Calcd.: C 73.58; H 5.66; N 7.15 Found: C 73.56; H 6.07; N 6.79

Example 26

Methyl ester of N-(trans-1-benzyl-2-oxo-5-phenyl-1,2,3,5-tetrahydro-4,1-benzoxazepine-3-propionyl)-L-tryptophane In substantially the same manner as in Example 24, 0.2 g of trans-1-benzyl-2-oxo-5-phenyl-1,2,3,5-tetrahydro-4,1-benzoxazepine-3-propionic acid obtained in Example 14 was subjected to condensation with L-tryptophane methyl ester hydrochloride to give 0.28 g of methyl ester of N-(trans-1-benzyl-2-oxo-5-phenyl-1,2,3,5-tetrahydro-4,1-benzoxazepine-3-propionyl)-L-tryptophane as an oily product.

IRv$_{max}^{Neat}$cm$^{-1}$: 1740,1670(C=O)

$^1$H-NMR spectrum (200 MHz,CDCl$_3$) δ: 2.1–2.4(4H,m), 3.15–3.3(2H,m), 3.6–3.7(3H,m), 3.95–4.15(1H,m), 4.8–5.0 (2H,m), 5.45(1H,s), 5.49(1H,d,J=14.2 Hz), 6.05–6.2(1H,m), 6.45–6.6(1H,m), 6.9–7.6(18H,m), 8.03(1H,br)

Example 27

N-(trans-1-benzyl-2-oxo-5-phenyl-1,2,3,5-tetrahydro-4,1-benzoxazepine-3-propionyl)-L-tryptophane In substantially the same manner as in Example 25, 0.28 g of methyl ester of N-(trans-1-benzyl-2-oxo-5-phenyl-1,2, 3,5-tetrahydro-4,1-benzoxazepine-3-propionyl)-L-tryptophane obtained in Example 26 was subjected to hydrolysis to give 0.24 g of N-(trans-1-benzyl-2-oxo-5-phenyl-1,2,3,5-tetrahydro-4,1-benzoxazepine-3-propionyl)-L-tryptophane as a powdery product.

IRv$_{max}^{KBr}$cm$^{-1}$: 1730, 1660(C=O)

Elemental Analysis for C$_{36}$H$_{33}$N$_3$O$_5$·0.4H$_2$O: Calcd.: C 72.69; H 5.73; N 7.06 Found: C 72.82; H 5.84; N 6.79

Example 28

Methyl ester of N-[trans-1-benzyl-7-chloro-5-(2-chloro-phenyl)-2-oxo-1,2,3,5-tetrahydro-4,1-benzoxazepine-3-propionyl]-L-tryptophane In substantially the same manner as in Example 24, 0.3 g of trans-1-benzyl-7-chloro-5-(2-chlorophenyl)-2-oxo-1,2,3, 5-tetrahydro-4,1-benzoxazepine-2-propionic acid obtained in Example 16 was subjected to condensation with L-tryptophane methyl ester hydrochloride to give 0.41 g of methyl ester of N-[trans-1-benzyl-7-chloro-5-(2-chlorophenyl)-2-oxo-1,2,3,5-tetrahydro-4,1-benzoxazepine-3-propionyl]-L-tryptophane as an oily product.

IRv$_{max}^{Neat}$cm$^{-1}$: 1735, 1660(C=O)

$^1$H-NMR spectrum (200 MHz,CDCl$_3$) δ: 2.1–2.45(4H, m), 3.2–3.35(2H,m), 3.64+3.66(3H,each s), 3.95–4.15(1H, m), 4.65–4.8(1H,m), 4.8–5.0(1H,m), 5.5–5.65(1H,m), 5.76 (1H,s), 6.0–6.2(1H,m), 6.35–6.45(1H,m), 6.9–7.7(16H,m), 8.16(1H,br)

Example 29

N-[trans-1-benzyl-7-chloro-5-(2-chlorophenyl)-2-oxo- 1,2,3,5-tetrahydro-4,1-benzoxazepine-3-propionyl]-L-tryptophane In substantially the same manner as in Example 25, methyl ester of N-[trans-1-benzyl-7-chloro-5-(2- chlorophenyl)-2-oxo-1,2,3,5-tetrahydro-4,1-benzoxazepine-3-propionyl]-L-tryptophane (0.41 g) obtained in Example 28 was subjected to hydrolysis to give 0.31 g of N-[trans-1-benzyl-7-chloro-5-(2-chlorophenyl)-2-oxo-1,2,3,5-tetrahydro-4,1-benzoxazepine-3-propionyl]-L-tryptophane as a powdery product.

IR$v_{max}^{KBr}$cm$^{-1}$: 1730, 1660(C=O)

Elemental Analysis for $C_{36}H_{31}Cl_2N_3O_5$: Calcd.: C 65.86; H 4.76; N 6.40 Found: C 66.13; H 5.02; N 6.24

Example 30

Ethyl ester of N-[trans-1-benzyl-7-chloro-5-(2-chlorophenyl)-2-oxo-1,2,3,5-tetrahydro-4,1-benzoxazepine-3-propionyl]-D-tryptophane In substantially the same manner as in Example 24, 0.3 g of trans-1-benzyl-7-chloro-5-(2-chlorophenyl)-2-oxo-1,2,3,5-tetrahydro-4,1-benzoxazepine-3-propionic acid obtained in Example 16 was subjected to condensation with D-tryptophane ethyl ester hydrochloride to give 0.43 g of ethyl ester of N-[trans-1-benzyl-7-chloro-5-(2-chlorophenyl)-2-oxo-1,2,3,5-tetrahydro-4,1-benzoxazepine-3-propionyl]-D-tryptophane as an oily product.

IR$v_{max}^{Neat}$cm$^{-1}$: 1730, 1665(C=O)

$^1$H-NMR spectrum (200 MHz,CDCl$_3$) δ: 1.1–1.3(3H,m), 2.1–2.45(4H,m), 3.2–3.35(2H,m), 3.95–4.2(3H,m), 4.65–4,8(1H,m), 4.8–5.0(1H,m), 5.5–5.65(1H,m), 5.76(1H,s), 6.0–6.2(1H,m), 6.35–6.45(1H,m), 6.9–7.7(16H,m), 8.13 (1H,br)

Example 31

N-[trans-1-benzyl-7-chloro-5-(2-chlorophenyl)-2-oxo-1,2,3,5-tetrahydro-4,1-benzoxazepine-3-propionyl]-D-tryptophane In substantially the same manner as in Example 25, 0.43 g of ethyl ester of N-[trans-1-benzyl-7-chloro-5-(2-chlorophenyl)-2-oxo-1,2,3,5-tetrahydro-4,1-benzoxazepine-3-propionyl]-D-tryptophane obtained in Example 30 was subjected to hydrolysis to give 0.38 g of N-[trans-1-benzyl-7-chloro-5-(2-chlorophenyl)-2-oxo-1,2,3,5-tetrahydro-4,1-benzoxazepine-3-propionyl]-D-tryptophane as a powdery product.

IR$v_{max}^{Neat}$cm$^{-1}$: 1725, 1660(C=O)

Elemental Analysis for $C_{36}H_{31}Cl_2N_3O_5$: Calcd.: C 65.86; H 4.76; N 6.40 Found: C 65.90; H 5.15; N 6.03

Example 32

Methyl ester of N-[trans-7-chloro-5-(2-chlorophenyl)-1-methyl-2-oxo-1,2,3,5-tetrahydro-4,1-benzoxazepine-3-ylacetyl]-L-tryptophane To a mixture of 0.6 g of trans-7-chloro-5-(2-chlorophenyl)-1-methyl-2-oxo-1,2,3,5-tetrahydro-4,1-benzoxazepine-3-acetic acid obtained in Reference Example 4, 0.42 g of tryptophane methyl ester hydrochloride and 10 ml of dimethylformamide was added, while stirring under ice-cooling, 0.3 g of diethyl phosphorocyanidate. To the resultant was then added 0.55 ml of triethylamine. The reaction mixture was stirred for 40 minutes at room temperature, which was poured into ice-water, followed by subjecting the mixture to extraction with ethyl acetate. The organic layer was washed with a dilute aqueous solution of potassium hydrogensulfate, an aqueous solution of sodium hydrogencarbonate and water, successively, dried and concentrated under reduced pressure. The concentrate was purified by means of a silica gel column chromatography (eluent, hexane:ethyl acetate=1:1 to 1:3). From the first fraction of the eluate, 0.33 g of methyl ester of N-[trans-7-chloro-5-(2-chlorophenyl)- 1-methyl-2-oxo-1,2,3,5-tetrahydro-4,1-benzoxazepin-3-yl acetyl]tryptophane of a crystalline form was obtained, m.p. 236° C.–237° C.

Elemental Analysis for $C_{30}H_{27}Cl_2N_3O_5$: Calcd.: C 62.08; H 4.69; N 7.24 Found: C 61.82; H 4.71; N 6.95

From the subsequent fraction of the eluate, 0.28 g of the steric isomer of the above compound was obtained, m.p. 159° C.–160° C.

Elemental Analysis for $C_{30}H_{27}Cl_2N_3O_5$: Calcd.: C 62.08; H 4.69; N 7.24 Found: C 61.94; H 4.50; N 6.96

Example 33

In substantially the same manner as in Example 32, compounds shown in Table 24 through Table 28 were obtained by using the compounds in Reference Example 5 and Example 2.

TABLE 24

| compd. No. | R$_1$ | R$_2$ | m.p. (°C.) | Formula | Elemental Analysis (Found) C | H | N |
|---|---|---|---|---|---|---|---|
| 1 | —CH$_2$—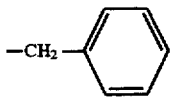 | —NHCH$_2$COOC$_2$H$_5$ | 153–155 | C$_{28}$H$_{26}$Cl$_2$N$_2$O$_5$ | 62.11 (62.05) | 4.84 (4.65) | 5.17 (4.98) |
| 2 | —CH$_2$—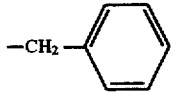 | —NH(CH$_2$)$_2$COOC$_2$H$_5$ | 130–131 | C$_{29}$H$_{28}$Cl$_2$N$_2$O$_5$ | 62.71 (63.00) | 5.08 (5.03) | 5.04 (4.99) |

TABLE 24-continued

| compd. No. | R₁ | R₂ | m.p. (°C.) | Formula | Elemental Analysis (Found) | | |
|---|---|---|---|---|---|---|---|
| | | | | | C | H | N |
| 3 | —CH₂—C₆H₅ | Trp.OMe (indole-CH₂-NH-CH-COOH₃) | amorphous solid | C₃₆H₃₁Cl₂N₃O₅ · H₂O | 64.10 (64.32) | 4.93 (4.78) | 6.23 (6.07) |
| 4 | —CH₂—C₆H₅ | Trp.OMe | amorphous solid | C₃₆H₃₁Cl₂N₃O₅ · 5/4H₂O | 63.67 (63.94) | 4.97 (4.84) | 6.19 (5.90) |
| 5 | —CH₂—C₆H₅ | D-Trp.OMe | amorphous solid | C₃₆H₃₁Cl₂N₃O₅ · 1/2C₄H₈O₂ · 1/2H₂O | 60.10 (60.11) | 4.88 (4.89) | 6.78 (6.69) |

TABLE 25

| compd. No. | R₁ | R₂ | m.p. (°C.) | Formula | Elemental Analysis (Found) | | |
|---|---|---|---|---|---|---|---|
| | | | | | C | H | N |
| 6 | —CH₂—C₆H₅ | D-Trp.OMe | amorphous solid | C₃₆H₃₁Cl₂N₃O₅ · 1/2C₄H₈O₂ · 1/4H₂O | 60.53 (60.44) | 4.84 (4.85) | 6.83 (6.83) |
| 7 | —CH₂—C₆H₅ | Phe.OEt (C₆H₅-CH₂-NH-CH-COOC₂H₅) | amorphous solid | C₃₅H₃₂Cl₂N₂O₅ · 1/4H₂O | 66.09 (66.10) | 5.15 (5.15) | 4.41 (4.17) |
| 8 | —CH₂—C₆H₅ | Phe.OEt | amorphous solid | C₃₅H₃₂Cl₂N₂O₅ · 1/4H₂O | 66.09 (66.20) | 5.15 (5.15) | 4.41 (4.17) |
| 9 | —CH₂—C₆H₅ | D-Phe.OMe | amorphous solid | C₃₄H₃₀Cl₂N₂O₅ · 1/4H₂O | 65.65 (65.62) | 4.94 (5.17) | 4.50 (4.51) |
| 10 | —CH₂—C₆H₅ | D-Phe.OMe | amorphous solid | C₃₄H₃₀Cl₂N₂O₅ · 1/4H₂O | 65.65 (65.48) | 4.94 (5.22) | 4.50 (4.31) |

TABLE 26

| compd. No. | R₁ | R₂ | m.p. (°C.) | Formula | Elemental Analysis (Found) C | H | N |
|---|---|---|---|---|---|---|---|
| 11 | —CH₂—C₆H₅ | C₆H₅—CH₂—N—CH₂COOEt | 164–165 | C₃₅H₃₂Cl₂N₂O₅ ·¼H₂O | 66.08 (66.18) | 5.17 (5.44) | 4.40 (4.13) |
| 12 | —CH₂—C₆H₅ | —NCH₂COOEt, CH₂-(indol-3-yl) | amorphous solid | C₃₇H₃₃Cl₂N₃O₅ ·2.5H₂O | 62.10 (62.32) | 5.35 (5.18) | 5.87 (5.63) |
| 13 | —C₂H₅ | —NHCH₂COOC₂H₅ | 175–176 | C₂₃H₂₄Cl₂N₂O₅ | 57.63 (57.29) | 5.05 (4.94) | 5.87 (5.90) |
| 14 | —(CH₂)₈CH₃ | —NHCH₂COOC₂H₅ | 160–161 | C₂₆H₃₄Cl₂N₂O₅ | 61.20 (61.47) | 6.24 (6.23) | 5.10 (5.39) |
| 15 | —CH₂CH(CH₃)₂ | —NHCH₂COOC₂H₅ | 168–170 | C₂₅H₂₈Cl₂N₂O₅ | 59.18 (58.97) | 5.56 (5.65) | 5.52 (5.40) |
| 16 | cyclopentyl | —NHCH₂COOC₂H₅ | 206–207 | C₂₆H₂₈Cl₂N₂O₅ | 60.12 (60.02) | 5.43 (5.51) | 5.39 (5.03) |
| 17 | —CH₂-(furan-2-yl) | —NHCH₂COOC₂H₅ | 164–165 | C₂₆H₂₄Cl₂N₂O₆ | 58.77 (58.79) | 4.55 (4.71) | 5.27 (5.19) |

TABLE 27

| Compd. No. | R₁ | R₂ | m.p. (°C.) | Formula | Elemental Analysis (Found) C | H | N |
|---|---|---|---|---|---|---|---|
| 18 | —CH₂CH(C₂H₅)₂ | —NHCH₂COOC₂H₅ | 142–143 | C₂₇H₃₂Cl₂N₂O₅ | 60.56 (60.80) | 6.02 (6.06) | 5.23 (5.24) |
| 19 | —CH₂C(CH₃)₃ | —NHCH₂COOC₂H₅ | 174–175 | C₂₆H₃₀Cl₂N₂O₅ | 59.89 (59.97) | 5.80 (5.91) | 5.37 (5.64) |
| 20 | —(CH₂)₂CH(CH₃)₂ | —NHCH₂COOC₂H₅ | 174–175 | C₂₆H₃₀Cl₂N₂O₅ | 59.89 (59.69) | 5.80 (5.64) | 5.37 (5.34) |
| 21 | —CH₂—CH=C(CH₃)₂ | —NHCH₂COOC₂H₅ | 174–175 | C₂₆H₂₈Cl₂N₂O₅ | 60.12 (60.14) | 5.43 (5.41) | 5.39 (5.31) |
| 22 | —CH₂—C(CH₃)=CH₂ | —NHCH₂COOC₂H₅ | 123–124 | C₂₅H₂₆Cl₂N₂O₅ | 59.41 (59.11) | 5.19 (5.12) | 5.54 (5.48) |
| 23 | —CH(C₂H₅)₂ | —NHCH₂COOC₂H₅ | 128–129 | C₂₆H₃₀Cl₂N₂O₅·¾H₂O | 58.37 (58.37) | 5.93 (5.85) | 5.24 (5.36) |
| 24 | —CH₂—CH=CH₂ | —NHCH₂COOC₂H₅ | 191–192 | C₂₂H₂₄Cl₂N₂O₅·½H₂O | 57.61 (57.54) | 5.07 (5.16) | 5.60 (5.58) |
| 25 | —CH₂C(CH₃)₃ | —NHCH₂CH₂COOC₂H₅ | 172–173 | C₂₇H₃₂Cl₂N₂O₅ | 60.56 (60.49) | 6.02 (6.15) | 5.23 (4.99) |

TABLE 28

| compd. No. | R₁ | R₂ | m.p. (°C.) | Formula | Elemental Analysis (Found) C | H | N |
|---|---|---|---|---|---|---|---|
| 26 | —CH₂C(CH₃)₃ | CH₂OH, NHCHCOOMe | amorphous solid | C₂₆H₃₀Cl₂N₂O₆ | 58.10 (57.79 | 5.63 5.62 | 5.21 5.37) |

TABLE 28-continued

| compd. No. | R₁ | R₂ | m.p. (°C.) | Formula | Elemental Analysis (Found) C | H | N |
|---|---|---|---|---|---|---|---|
| 27 | —CH₂C(CH₃)₃ | CH₂OH<br>\|<br>NHCHCOOMe | amorphous solid | $C_{26}H_{30}Cl_2N_2O_6$ | 58.10<br>(57.91 | 5.63<br>5.62 | 5.21<br>5.33) |
| 28 | —CH₂C(CH₃)₃ | CH₂COOMe<br>\|<br>NHCHCOOMe | amorphous solid | $C_{28}H_{32}Cl_2N_2O_7$ | 58.03<br>(58.19 | 5.57<br>5.64 | 4.83<br>4.69) |
| 29 | —CH₂C(CH₃)₃ | CH(CH₃)₂<br>\|<br>NHCHCOOMe | 190–192 | $C_{28}H_{34}Cl_2N_2O_5$ | 61.20<br>(61.25 | 6.21<br>6.28 | 5.10<br>5.18) |

Example 34

N-[trans-7-chloro-5-(2-chlorophenyl)-1-methyl-1,2,3,5-tetrahydro-2-oxo-4,1-benzoxazepine-3-ylacetyl]-L-tryptophane 0.2 g of ethyl ester of N-[trans-7-chloro-5-(2-chlorophenyl)-1-methyl-1,2,3,5-tetrahydro-2-oxo-4,1-benzoxazepin-3-ylacetyl]tryptophane obtained from the first fraction in Example 32 was dissolved in a mixture of 8 ml of methanol and 4 ml of tetrahydrofuran. To the solution were added 200 mg of potassium carbonate and 5 ml of water, and the mixture was stirred for 3 hours at 60° C. The reaction mixture was concentrated under reduced pressure. With 1N hydrochloric acid, the pH of the concentrate was adjusted to 3, followed by extraction with ethyl acetate. The organic layer was washed with water and dried, and the solvent was distilled off under reduced pressure. The residue was purified by means of a silica gel column chromatography (eluent, methylene chloride: methanol:water=100:15:1) to give 0.13 g of N-[trans-7-chloro-5-(2-chlorophenyl)-1-methyl-1,2,3,5-tetrahydro-2-oxo-4,1-benzoxazepin-3-ylacetyl]-L-tryptophane as a colorless powdery product.

$IRv_{max}^{KBr}cm^{-1}$: 3700–2200(COOH), 1,660 (CO), 1485, 1250, 1110, 740

$^1$H-NMR spectrum (200 MHz, CDCl₃) δ: 2.2–3.2(4H,m), 3.24(3H,s,N—CH₃), 4.2(1H,m,C₃—H), 4.63(1H,m), 5.73 (1H,s,C₅—H), 6.34(1H,d,C₆—H), 6.6–7.7(10H,m)

Elemental Analysis for $C_{29}H_{25}Cl_2N_3O_5 \cdot \frac{1}{2}H_2O$: Calcd.: C 60.10; H 4.88; N 6.78 Found: C 60.11; H 4.89; N 6.69

0.2 g of the compound subsequently eluted in the silica gel column chromatography was subjected to hydrolysis in substantially the same manner as described above to give 0.11 g of crystals of a steric isomer, m.p. 165° C.–167° C.

Elemental Analysis for $C_{29}H_{25}Cl_2N_3O_5 \cdot \frac{1}{2}C_4H_8O_2 \cdot \frac{1}{2}H_2O$: Calcd.: C 60.53; H 4.84; N 6.83 Found: C 60.44; H 4.88; N 6.83

Example 35

In substantially the same synthetic procedure as in Example 34, compounds shown in Table 29 through Table 33 were obtained.

TABLE 29

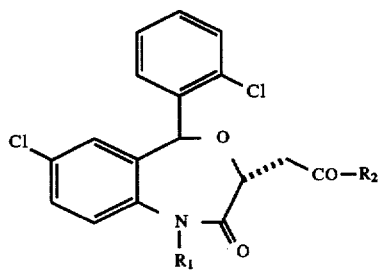

| compd. No. | R₁ | R₂ | m.p. (°C.) | Formula | Elemental Analysis (Found) C | H | N |
|---|---|---|---|---|---|---|---|
| 1 | —CH₂—⌬ | —NHCH₂COOH | 130–133 | $C_{26}H_{22}Cl_2N_2O_5$<br>$\cdot \frac{1}{2}H_2O$ | 59.78<br>(59.81) | 4.44<br>(4.78) | 5.36<br>(4.90) |
| 2 | —CH₂—⌬ | —NH(CH₂)₂COOH | 195–197 | $C_{27}H_{24}Cl_2N_2O_5$ | 61.49<br>(61.24) | 4.59<br>(4.35) | 5.31<br>(5.27) |

TABLE 29-continued

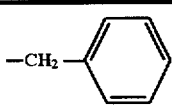

| compd. No. | R₁ | R₂ | m.p. (°C.) | Formula | Elemental Analysis (Found) C | H | N |
|---|---|---|---|---|---|---|---|
| 3 | —CH₂—C₆H₅ | Trp—OH (indole-CH₂-NH-CH-COOH) | 158–160 $[\alpha]_D^{25°} = -100.3°$ | $C_{35}H_{29}Cl_2N_3O_5$ ·1/4H₂O | 64.97 (64.99) | 4.60 (4.82) | 6.49 (6.14) |
| 4 | —CH₂—C₆H₅ | Trp—OH | amorphous solid $[\alpha]_D^{25°} = +120.7°$ | C}hd 35H₂₉Cl₂NO₅ ·1/4C₄H₈O₂ | 65.06 (65.09) | 4.70 (5.08) | 6.32 (6.00) |
| 5 | —CH₂—C₆H₅ | D-Trp—OH | 157–158 $[\alpha]_D^{25°} = +97.0°$ | $C_{35}H_{29}Cl_2N_3O_5$ ·3/2H₂O | 62.78 (62.77) | 4.81 (4.58) | 6.28 (6.04) |

TABLE 30

| compd. No. | R₁ | R₂ | m.p. (°C.) | Formula | Elemental Analysis (Found) C | H | N |
|---|---|---|---|---|---|---|---|
| 6 | —CH₂—C₆H₅ | D-Trp—OH | amorphous solid $[\alpha]_D^{25°} = -122.9°$ | $C_{35}H_{28}Cl_2N_3O_5$ ·3/2H₂O | 62.78 (62.51) | 4.81 (4.98) | 6.28 (6.02) |
| 7 | —CH₂—C₆H₅ | Phe—OH (C₆H₅-CH₂-NH-CH-COOH) | 120–125 $[\alpha]_D^{25°} = -109.2°$ | $C_{33}H_{28}Cl_2N_2O_5$ ·1/2H₂O | 64.71 (64.91) | 4.77 (4.70) | 4.57 (4.42) |
| 8 | —CH₂—C₆H₅ | Phe—OH | 119–122 $[\alpha]_D^{25°} = +142.0°$ | $C_{33}H_{28}Cl_2N_2O_5$ ·1/2H₂O | 64.71 (64.62) | 4.71 (4.69) | 4.57 (4.41) |
| 9 | —CH₂—C₆H₅ | D-Phe—OH | amorphous solid | $C_{33}H_{28}Cl_2N_2O_5$ ·3/2H₂O | 62.86 (62.71) | 4.96 (4.66) | 4.44 (4.30) |
| 10 | —CH₂—C₆H₅ | D-Phe—OH | amorphous solid | $C_{33}H_{28}Cl_2N_2O_5$ ·3/2H₂O | 62.86 (62.89) | 4.96 (4.72) | 4.44 (4.38) |

TABLE 30-continued

| compd. No. | R₁ | R₂ | m.p. (°C.) | Formula | Elemental Analysis (Found) | | |
|---|---|---|---|---|---|---|---|
| | | | | | C | H | N |
| 11 | $-CH_2-C_6H_5$ (benzyl) | benzyl-$N(CH_2)$-$CH_2COOH$ | 193–194 | $C_{33}H_{28}Cl_2N_2O_5$ | 65.68 (65.81) | 4.68 (4.91) | 4.44 (4.58) |
| 12 | $-CH_2-C_6H_5$ (benzyl) | $-NCH_2COOH$ with $CH_2$-indol-3-yl | amorphous solid | $C_{37}H_{33}Cl_2N_3O_5 \cdot 2.5H_2O$ | 62.10 (62.32) | 5.35 (5.18) | 5.87 (5.63) |

TABLE 31

| compd. No. | R₁ | R₂ | m.p. (°C.) | Formula | Elemental Analysis (Found) | | |
|---|---|---|---|---|---|---|---|
| | | | | | C | H | N |
| 13 | $-C_2H_5$ | $-NHCH_2COOH$ | 167–168 | $C_{21}H_{20}Cl_2N_2O_5 \cdot \frac{1}{2}H_2O$ | 54.79 (54.56) | 4.60 (4.57) | 6.09 (6.11) |
| 14 | $-(CH_2)_6CH_3$ | $-NHCH_2COOH$ | 185–186 | $C_{26}H_{30}Cl_2N_2O_5$ | 59.89 (59.84) | 5.80 (5.73) | 5.37 (5.53) |
| 15 | $-CH_2CH(CH_3)_2$ | $-NHCH_2COOH$ | 233–234 | $C_{23}H_{24}Cl_2N_2O_5$ | 57.63 (57.63) | 5.05 (5.23) | 5.84 (5.66) |
| 16 | cyclopentyl | $-NHCH_2COOH$ | 215–216 | $C_{24}H_{24}Cl_2N_2O_5$ | 58.67 (58.79) | 4.92 (5.00) | 5.70 (5.96) |
| 17 | $-CH_2$-(furan-2-yl) | $-NHCH_2COOH$ | 182–183 | $C_{24}H_{20}Cl_2N_2O_5$ | 57.27 (57.28) | 4.01 (4.03) | 5.57 (5.53) |
| 18 | $-CH_2CH(C_2H_5)_2$ | $-NHCH_2COOH$ | 110–115 | $C_{25}H_{28}Cl_2N_2O_5$ | 59.18 (58.32) | 5.56 (5.83) | 5.52 (5.47) |
| 19 | $-CH_2C(CH_3)_3$ | $-NHCH_2COOH$ | 235–236 | $C_{24}H_{26}Cl_2N_2O_5$ | 58.43 (58.57) | 5.31 (5.58) | 5.68 (5.60) |
| 20 | $-(CH_2)_2CH(CH_3)_2$ | $-NHCH_2COOH$ | 114–116 | $C_{24}H_{26}Cl_2N_2O_5 \cdot \frac{1}{2}H_2O$ | 57.59 (57.24) | 5.42 (5.44) | 5.58 (5.50) |

TABLE 32

| compd. No. | R₁ | R₂ | m.p. (°C.) | Formula | Elemental Analysis (Found) | | |
|---|---|---|---|---|---|---|---|
| | | | | | C | H | N |
| 21 | $-CH_2-CH=C(CH_3)_2$ | $-NHCH_2COOH$ | 146–147 | $C_{24}H_{24}Cl_2N_2O_5$ | 58.67 (58.92) | 4.92 (5.05) | 5.70 (5.77) |
| 22 | $-CH_2-C(CH_3)=CH_2$ | $-NHCH_2COOH$ | 200–201 | $C_{23}H_{22}Cl_2N_2O_5$ | 57.87 (57.87) | 4.65 (4.56) | 5.87 (6.17) |
| 23 | $-CH(C_2H_5)_2$ | $-NHCH_2COOH$ | 214–215 | $C_{24}H_{26}Cl_2N_2O_5$ | 58.43 (58.56) | 5.31 (5.39) | 5.68 (5.75) |
| 24 | $-CH_2-CH=CH_2$ | $-NHCH_2COOH$ | 128–130 | $C_{22}H_{20}Cl_2N_2O_5 \cdot \frac{1}{2}H_2O$ | 55.94 (56.09) | 4.48 (4.42) | 5.93 (5.87) |

TABLE 32-continued

| compd. No. | $R_1$ | $R_2$ | m.p. (°C.) | Formula | Elemental Analysis (Found) C | H | N |
|---|---|---|---|---|---|---|---|
| 25 | —$CH_2C(CH_3)_3$ | —$NHCH_2CH_2COOH$ | 213–214 | $C_{25}H_{28}Cl_2N_2O_5$ | 59.18 (59.12) | 5.56 (5.73) | 5.52 (5.27) |

TABLE 33

| compd. No. | $R_1$ | $R_2$ | m.p. (°C.) | Formula | Elemental Analysis (Found) C | H | N |
|---|---|---|---|---|---|---|---|
| 26 | —$CH_2C(CH_3)_3$ | $CH_2OH$<br>\|<br>NHCHCOOH | amorphous solid | $C_{25}H_{28}Cl_2N_2O_6$ | 57.37 (57.54 | 5.39 5.67 | 5.35 5.22) |
| 27 | —$CH_2C(CH_3)_3$ | $CH_2OH$<br>\|<br>NHCHCOOH | 143–146 | $C_{25}H_{28}Cl_2N_2O_6$ | 57.37 (57.34 | 5.39 5.47 | 5.35 5.34) |
| 28 | —$CH_2C(CH_3)_3$ | $CH_3$<br>\|<br>NHCHCOOH | 139–141 | $C_{25}H_{28}Cl_2N_2O_5$<br>$1/2H_2O$ | 58.14 (58.36 | 5.66 5.89 | 5.42 5.55) |
| 29 | —$CH_2C(CH_3)_3$ | $CH_2COOH$<br>\|<br>NHCHCOOH | 148–150 | $C_{26}H_{28}Cl_2N_2O_7$<br>$1/2CH_3COCH_3$ | 56.90 (56.88 | 5.38 5.66 | 4.83 4.77) |

Example 36

[Trans-1-benzyl-7-chloro-5-(2-chlorophenyl)-2-oxo-1,2,3,5-tetrahydro-4,1-benzoxazepine-3-yl] methylamine In 5 ml of dimethylformamide was dissolved 1.0 g of trans-1-benzyl-7-chloro-5-(2-chlorophenyl)-2-oxo-1,2,3,5-tetrahydro-4,1-benzoxazepine-3-acetic acid obtained in Reference Example 5. To the solution was added 0.3 ml of triethylamine, to which was added dropwise, while stirring under ice-cooling, 0.6 g of diphenylphosphoryl azide. The reaction mixture was stirred for one hour at room temperature, which was then poured into ice-water. The mixture was subjected to extraction with ether. The organic layer was washed with water and dried, which was then concentrated under reduced pressure. The concentrate was dissolved in 100 ml of benzene, which was heated for 30 minutes under reflux. The reaction mixture was concentrated under reduced pressure. To the concentrate was added 6 ml of conc. hydrochloric acid, and the mixture was heated for one hour under reflux. The reaction mixture was concentrated under reduced pressure. The concentrate was made alkaline by the addition of a 5% aqueous solution of potassium carbonate, followed by extraction with ethyl acetate. The organic layer was washed with water and dried, then the solvent was distilled off under reduced pressure. To the residue was added an ethanol solution of 4N hydrochloric acid to lead it to hydrochloride to give 0.85 g of [trans-1-benzyl-7-chloro-5-(2-chlorophenyl)-2-oxo-1,2,3,5-tetrahydro-4,1-benzoxazepine-3-yl]methylamine hydrochloride as crystals, m.p. 245°–250° C.

Elemental Analysis for $C_{23}H_{20}Cl_2N_2O_2 \cdot HCl \cdot \frac{1}{2}H_2O$: Calcd.: C 56.34; H 4.82; N 5.71 Found: C 56.65; H 4.44; N 6.09

Example 37

By substantially the same procedure as in Example 36, compounds shown in Table 34 were obtained.

TABLE 34

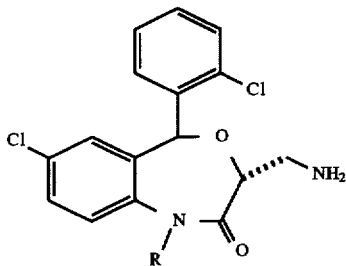

| Compd. No. | R | m.p. (°C.) | Formula | Elemental Analysis (Found) C | H | N |
|---|---|---|---|---|---|---|
| 1 | —CH₃ | 114–115 | C₁₇H₁₆Cl₂N₂O₂ | 58.13 (58.16) | 4.59 (4.79) | 7.98 (7.93) |
| 2 | —CH₂—⌬ | 250–253 | C₂₃H₂₆Cl₂N₂O₂·HCl ·1/4H₂O | 58.23 (58.08) | 5.52 (5.66) | 5.91 (5.68) |
| 3 | —CH(CH₃)₂ | 136–137 | C₁₉H₂₀Cl₂N₂O₂ | 60.17 (59.93) | 5.31 (5.38) | 7.39 (7.06) |

Example 38

Ethyl ester of N-[trans-1-benzyl-7-chloro-5-(2-chlorophenyl)-2-oxo-1,2,3,5-tetrahydro-4,1-benzoxazepin-3-yl-methylaminocarbonyl]glycine In 4 ml of dimethylformamide was dissolved 0.3 g of trans-1-benzyl-7-chloro-5-(2-chlorophenyl)-2-oxo-1,2,3,5-tetrahydro-4,1-benzoxazepine-3-acetic acid obtained in Reference Example 5. To the solution was added 0.15 ml of triethylamine. To the mixture was added, while stirring under ice-cooling, 0.18 g of diphenylphosphoryl azide. The reaction mixture was stirred for one hour at room temperature, to which was added ice-water, followed by extraction with ethyl acetate. The organic layer was washed with water, dried and concentrated under reduced pressure. To the concentrate was added 10 ml of benzene, and the mixture was heated for one hour under reflux while stirring. To the reaction mixture were added 0.14 g of glycine ethyl ester hydrochloric acid and 0.15 ml of triethylamine. The mixture was then heated for 3 hours under reflux. The reaction mixture was concentrated under reduced pressure. The concentrate was subjected to extraction with ethyl acetate. The organic layer was washed with water and dried, then the solvent was distilled off under reduced pressure. Crystals obtained from the residue were recrystallized from a mixture of ethyl acetate and hexane to give 0.33 g of the title compound as white crystals, m.p. 200°–201° C.

Elemental Analysis for C₂₈H₂₇Cl₂N₃O₅: Calcd.: C 60.44; H 4.89; N 7.55 Found: C 60.29; H 4.82; N 7.68

Example 39

In 8 ml of methanol was dissolved 0.2 g of ethyl ester of N-[trans-1-benzyl-7-chloro-5-(2-chlorophenyl)-2-oxo-1,2,3,5-tetrahydro-4,1-benzoxazepin-3-yl-methylaminocarbonyl]glycine. To the solution were added 0.2 g of potassium carbonate and 2 ml of water, and the mixture was stirred for 3 hours at 60° C. The reaction mixture was concentrated under acidified to pressure, to which was added water, followed by extraction with ether. The aqueous layer was acidified to pH 3 with dilute hydrochloric acid, which was subjected to extraction with ethyl acetate. The organic layer was washed with water and dried, then the solvent was distilled off under reduced pressure to leave crystalline residue. Recrystallization from ethyl acetate afforded 0.18 g of N-[trans-1-benzyl-7-chloro-5-(2-chlorophenyl)-2-oxo-1,2,3,5-tetrahydro-4,1-benzoxazepin-3-yl-methylaminocarbonyl]glycine as colorless needles, m.p. 153°–155° C.

Elemental Analysis for C₂₆H₂₃Cl₂N₀₅·1/4H₂O: Calcd.: C 58.60; H 4.45; N 7.88 Found: C 58.63; H 4.42; N 7.58

Example 40

Ethyl ester of N-[trans-1-benzyl-7-chloro-5-(2-chlorophenyl)-2-oxo-1,2,3,5-tetrahydro-4,1-benzoxazepin-3-ylmethyl]glycine In 10 ml of acetonitrile was dissolved 0.4 g of trans-1-benzyl-7-chloro-5-(2-chlorophenyl)-2-oxo-1,2,3,5-tetrahydro-4,1-benzoxazepine-3-methylamine obtained in Example 36. To the solution were added 0.15 g of ethyl chloroacetate and 0.5 g of potassium carbonate. The mixture was heated under reflux for 15 hours while stirring. The reaction mixture was concentrated under reduced pressure, and the concentrate was subjected to extraction with ethyl acetate. The organic layer was washed with water and dried, then the solvent was distilled under reduced pressure. The residue was purified by means of a silica gel column chromatography (eluent, hexane:ethyl acetate=3:2 to 1:2) to give 0.28 g of ethyl ester of N-[trans-1-benzyl-7-chloro-5-(2-chlorophenyl)- 2-oxo-1,2,3,5-tetrahydro-4,1-benzoxazepin-3-ylmethyl]glycine as an oily product. This product was made into hydrochloride salt to give white crystals, m.p. 182°–184° C.

Elemental Analysis for C₂₇H₂₆Cl₂N₂O₄·HCl: Calcd.: C 58.98; H 4.95; N 5.09 Found: C 58.70; H 4.98; N 5.07

Example 41

N-[trans-1-benzyl-7-chloro-5-(2-chlorophenyl)-2-oxo-1,2,3,5-tetrahydro-4,1-benzoxazepin-3-ylmethyl]glycine In 6 ml of methanol was dissolved 0.15 g of ethyl ester of N-[trans-1-benzyl-7-chloro-5-(2-chlorophenyl)-2-oxo-1,2, 3,5-tetrahydro-4,1-benzoxazepin-3-ylmethyl]glycine obtained in Example 40. To the solution were added 0.4 g of potassium carbonate and 2 ml of water. The mixture was stirred for 2 hours at 50° C. The reaction mixture was concentrated under reduced pressure, whose pH was adjusted to 3 with dilute hydrochloric acid, followed by extraction with methylene chloride. The organic layer was washed with water and dried, then the solvent was distilled off under reduced pressure. From the residue was obtained 0.13 g of N-[trans-1-benzyl-7-chloro-5-(2-chlorophenyl)-2-oxo-1,2,3,5-tetrahydro-4,1-benzoxazepin-3-ylmethyl]glycine as crystals, m.p. 224°–226° C.

Elemental Analysis for $C_{25}H_{22}Cl_2N_2O_4 \cdot \frac{1}{2}H_2O$: Calcd.: C 60.74; H 4.69; N 5.67 Found: C 60.74; H 4.48; N 5.70

Example 42

N-[trans-1-benzyl-7-chloro-5-(2-chlorophenyl)-2-oxo-1,2,3,5-tetrahydro-4,1-benzoxazepin-3-ylmethyl]-N-methylglycine To 0.13 g of ethyl ester of N-[trans-1-benzyl-7-chloro-5-(2-chlorophenyl)-2-oxo-1,2,3,5-tetrahydro-4,1-benzoxazepin-3-ylmethyl]glycine obtained in Example 40 were added 2 ml of formalin and 2 ml of oxalic acid: The mixture was heated at 80° C. for 2 hours. The reaction mixture was concentrated under reduced pressure, and the concentrate was subjected to 5 extraction with ethyl acetate. The organic layer was washed with an aqueous solution of sodium hydrogencarbonate, then with water, followed by drying. The solvent was distilled off under reduced pressure. The residue was dissolved in 6 ml of methanol. To the solution were added 0.2 g of potassium carbonate and 2 ml of water. The mixture was stirred for 2 hours at 60° C. The reaction mixture was concentrated under reduced pressure, to which was added water, followed by extraction with ether. The aqueous layer was acidified to pH 4 with dilute hydrochloric acid, followed by extraction with methylene chloride. The organic layer was washed with water and dried, then the solvent was distilled off under reduced pressure. From the residue was obtained 0.1 g of N-[trans-1-benzyl-7-chloro-5-(2-chlorophenyl)-2-oxo-1,2,3,5-tetrahydro-4,1-benzoxazepin-3-ylmethyl]-N-methylglycine as crystals, m.p. 195°–197° C.

Elemental Analysis for $C_{26}H_{24}Cl_2N_2O_4 \cdot \frac{1}{4}H_2O$: Calcd.: C 61.97; H 4.90; N 5.56 Found: C 61.90; H 4.73; N 5.67

Example 43

N-[trans-1-benzyl-7-chloro-5-(2-chlorophenyl)-2-oxo-1,2,3,5-tetrahydro-4,1-benzoxazepin-3-ylmethyl]-N-acetylglycine In 4 ml of methanol was dissolved 60 mg of ethyl ester of N-[trans-1-benzyl-7-chloro-5-(2-chlorophenyl)-2-oxo-1,2,3,5-tetrahydro-4,1-benzoxazepin-3-ylmethyl]glycine obtained in Example 40. To the solution were added 0.2 ml of acetic anhydride and 0.2 ml of triethylamine. The mixture was heated for one hour under reflux while stirring. The reaction mixture was concentrated under reduced pressure, which was subjected to extraction with ethyl acetate. The organic layer was washed with an aqueous solution of potassium hydrogensulfate, an aqueous solution of sodium hydrogencarbonate and water, which was then dried, followed by distilling off the solvent. The residue was dissolved in 4 ml of methanol, to which was added 2 ml of a 5% aqueous solution of potassium carbonate. The mixture was stirred for 30 minutes at 60° C. The reaction mixture was concentrated under reduced pressure, to which was added 1N hydrochloric acid to acidify the solution, followed by extraction with ethyl acetate. The organic layer was washed with water and dried, then the solvent was distilled off under reduced pressure. From the residue, 45 mg of N-[trans-1-benzyl-7-chloro-5-(2-chlorophenyl)-2-oxo-1,2,3,5-tetrahydro-4,1-benzoxazepin-3-ylmethyl]-N-acetyl glycine was obtained as crystals, m.p. 143°–145° C.

Elemental Analysis for $C_{27}H_{24}Cl_2N_2O_5 \cdot \frac{1}{4}H_2O$: Calcd.: C 60.96; H 4.64; N 5.27 Found: C 60.90; H 4.39; N 5.32

Example 44

N-[trans-1-benzyl-7-chloro-5-(2-chlorophenyl)-2-oxo-1,2,3,5-tetrahydro-4,1-benzoxazepin-3-ylmethyl]-N-benzoylglycine In 10 ml of methylene chloride was dissolved 0.15 g of ethyl ester of N-[trans-1-benzyl-7-chloro-5-(2-chlorophenyl)-2-oxo-1,2,3,5-tetrahydro-4,1-benzoxazepin-3-ylmethyl]glycine obtained in Example 40. To the solution were added 90 mg of benzoic anhydride, 0.1 ml of triethylamine and 10 mg of 4-dimethylaminopyridine. The mixture was stirred for 15 hours at room temperature. The reaction mixture was concentrated under reduced pressure, and the residue was subjected to extraction with ethyl acetate. The organic layer was washed with water and dried, then the solvent was distilled off under reduced pressure. The residue was purified by means of a silica gel column chromatography (eluent, hexane:ethyl acetate=3:2) to give an oily product. The oily product was dissolved in a mixture of 5 ml of methanol and 2 ml of tetrahydrofuran. To the solution were added 0.2 g of potassium carbonate and 2 ml of water. The mixture was then starred for 2 hours at 60° C. The reaction mixture was concentrated under reduced pressure. To the concentrate was added dilute hydrochloric acid to adjust the pH to 2, followed by extraction with ethyl acetate. The organic layer was washed with water and dried, then the solvent was distilled off under reduced pressure. From the residue was obtained 75 mg of N-[trans-1-benzyl-7-chloro-5-(2-chlorophenyl)-2-oxo-1,2,3,5-tetrahydro-4,1-benzoxazepin-3-ylmethyl]-N-benzoylglycine as amorphous solid matter.

IRv$_{max}^{KBr}$cm$^{-1}$: 3700–2200(COOH) 1740(CO), 1670 (CO), 1420, 1250, 1170, 1080, 750

$^1$H-NMR spectrum (200 MHz,CDCl$_3$) δ: 3.8–5.1(6H,m), 5.75(1H,s,C$_5$—H), 6.40(1H,s,C$_6$—H), 7.0–7.8(16H,m)

Elemental Analysis for $C_{32}H_{26}Cl_2N_2O_5 \cdot \frac{2}{3}H_2O$: Calcd.: C 62.34; H 4.74; N 4.54 Found: C 62.40; H 4.44; N 4.32

Example 45

Trans-1-benzyl-7-chloro-5-(2-chlorophenyl)-3-(3-methoxycarbonylmethylcarbamoyl)methyl-2-oxo-1,2,3,5-tetrahydro-4,1-benzoxazepine To a mixture of 0.25 g of [trans-1-benzyl-7-chloro-5-(2-chlorophenyl)-2-oxo-1,2,3,5-tetrahydro-4,1-benzoxazepine-3-yl]methylamine obtained in Example 36, 0.1 g of malonic acid half ester potassium salt and 4 ml of dimethylformamide were added, while stirring under ice-cooling, 0.13 g of diethyl phosphorocyanidate and 0.23 ml of triethylamine. The reaction mixture was stirred for 40 minutes at room temperature, to which was added ice-water, followed by extraction with ethyl acetate. The organic layer was washed with an aqueous solution of sodium hydrogensulfate, an aqueous solution of sodium hydrogen carbonate and water, successively, which was then dried. The solvent was distilled off, and the residue was purified by means of a silica gel column chromatography (eluent, hexane:ethyl acetate:ethanol=10:10:1) to give 0.22 g of trans-1-benzyl-7-chloro-5-(2-chlorophenyl)-3-(3-methoxycarbonylmethylcarbamoyl)methyl-2-oxo-1,2,3,5-tetrahydro-4,1-benzoxazepine as a white powdery product.

IRv$_{max}^{KBr}$cm$^{-1}$: 3370(NH), 2950, 1745(CO), 1670(CO), 1480, 1420, 1250

$^1$H-NMR spectrum (200 MHz,CDCl$_3$) δ: 3.31(2H,s,CO CH$_2$CO$_2$), 3.74(3H,s,OCH$_3$), 3.7–4.2(3H,m), 4.8(1H,d), 5.6 (1H,d), 5.8(1H,s,C$_5$—H), 6.42(1H,d,C$_6$—H), 7.2–7.8(1H, m)

Elemental Analysis for C$_2$H$_{24}$Cl$_2$N$_2$O$_5$·½H$_2$O: Calcd.: C 60.46; H 4.70; N 5.22 Found: C 60.27; H 4.85; N 4.95

In 5 ml of methanol was dissolved 0.15 g of the white powdery product obtained above. To the solution were added 0.2 g of potassium carbonate and 1.5 ml of water, then the mixture was stirred for 2 hours at 50° C. The reaction mixture concentrated under reduced pressure. The concentrate was neutralized with dilute hydrochloric acid, followed by extraction with ethyl acetate. The organic layer was washed with water and dried, then the solvent was distilled off under reduced pressure. From the residue was obtained 0.14 g of Trans-1-benzyl-7-chloro-5-(2-chlorophenyl)-3-(3-hydroxycarbonylmethylcarbamoyl)methyl-2-oxo-1,2,3,5-tetrahydro-4,1-benzoxazepine as a white powdery product.

IRv$_{max}^{KBr}$cm$^{-1}$: 3700–2200(COOH), 1730(CO), 1670 (CO), 1480, 1240

$^1$H-NMR spectrum (200 MHz,CDCl$_3$) δ: 3.31(2H,s,—CO CH$_2$COOH), 3.7–4.2(3H,m), 4.75(1H,d), 5.62(1H,d), 5.77 (1H,s,C$_5$—H), 6.44(1H,d,C$_6$—H), 7.04(1H,t,NH), 7.2–7.7 (11H,m)

Elemental Analysis for C$_{26}$H$_{22}$Cl$_2$N$_2$O$_5$·½H$_2$O: Calcd.: C 59.78; H 4.44; N 5.36 Found: C 59.47; H 4.69; N 5.13

Example 46

Trans-1-benzyl-7-chloro-5-(2-chlorophenyl)-2-oxo-1,2,3,5-tetrahydro-4,1-benzoxazepine-3-methanol and 3,5-trans-7-chloro-3-chloromethyl-5-(2-chlorophenyl)-2-oxo-1,2,3,5-tetrahydro-4,1-benzoxazepine In mixture of 12 ml of glacial acetic acid and 10 ml of water was suspended 2.0 g of [trans-1-benzyl-7-chloro-5-(2-chlorophenyl)-2-oxo-1,2,3,5-tetrahydro-4,1-benzoxazepine-3-yl]methylamine hydrochloride obtained in Example 36. To the suspension was added dropwise, while stirring under ice-cooling, 1 ml of an aqueous solution of 1.0 g of sodium nitrite, in the course of 10 minutes. The reaction mixture was stirred for one hour at room temperature, which was added to ice-water, followed by extraction with ethyl acetate. The organic layer was washed with an aqueous solution of sodium hydrogencarbonate and water, successively, which was then dried, followed by distilling off the solvent under reduced pressure. The residue was dissolved in 50 ml of methanol, to which was added 5 ml of a 10% aqueous solution of potassium carbonate. The mixture was stirred for 15 minutes at 60° C. The reaction mixture was concentrated under reduced pressure. The concentrate was subjected to extraction with ethyl acetate. The organic layer was washed with water and dried, then the solvent was distilled off under reduced pressure. The residue was purified by means of a silica gel column chromatography (eluent, hexane:ethyl acetate=4:1 to 1:1). From the preceding portion of the eluate, 0.2 g of trans-7-chloro-3-chloromethyl-5-(2-chlorophenyl)-2-oxo-1,2,3,5-tetrahydro-4,1-benzoxazepine as colorless prisms, m.p. 177°–179° C.

Mass spectrum (m/e) : 445 (M$^+$)

Elemental Analysis for C$_{23}$H$_{18}$Cl$_3$NO$_2$: Calcd.: C 61.83; H 4.06; N 3.14 Found: C 62.11; H 4.01; N 3.38

From the subsequent portion of the eluate, 1.05 g of trans-1-benzyl-7-chloro-5-(2-chlorophenyl)-2-oxo-1,2,3,5-tetrahydro-4,1-benzoxazepine-3-methanol as Colorless needles, m.p. 158°–159° C.

Mass spectrum (m/e) : 427, 429 (M$^+$)

Elemental Analysis for C$_{23}$H$_{19}$Cl$_2$NO$_3$: Calcd.: C 64.49; H 4.47; N 3.27 Found: C 64.36; H 4.39; N 3.34

Example 47

By substantially the same procedure as in Example 46, compounds shown in Table 35 were obtained.

TABLE 35

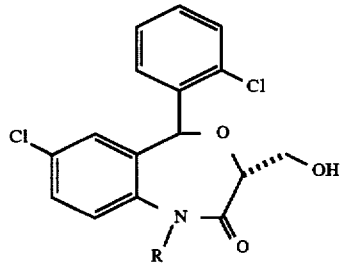

| compd. No. | R | m.p. (°C.) | Formula | Elemental Analysis (Found) | | |
|---|---|---|---|---|---|---|
| | | | | C | H | N |
| 1 | —CH$_3$ | 208–209 | C$_{17}$H$_{15}$Cl$_2$NO$_3$ | 57.97 (58.18) | 4.29 (4.46) | 3.98 (3.79) |

TABLE 35-continued

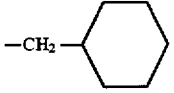

| compd. No. | R | m.p. (°C.) | Formula | Elemental Analysis (Found) C | H | N |
|---|---|---|---|---|---|---|
| 2 | —CH₂—C₆H₁₁ (cyclohexyl) | 171–172 | C₂₃H₂₅Cl₂NO₃ | 63.60 (63.60) | 5.80 (5.89) | 3.22 (3.02) |
| 3 | —CH(CH₃)₂ | 154–155 | C₁₉H₁₉Cl₂NO₃ | 60.01 (59.83) | 5.04 (4.91) | 3.68 (3.79) |

Example 48

Trans-1-benzyl-7-chloro-5-(2-chlorophenyl)-2-oxo-1,2,3,5-tetrahydro-4,1-benzoxazepine-3-carboxylic acid In 20 ml of acetone was dissolved 0.5 g of trans-1-benzyl-7-chloro-5-(2-chlorophenyl)-2-oxo-1,2,3,5-tetrahydro-4,1-benzoxazepine-3-methanol obtained in Example 46. To the solution was added dropwise, while stirring at room temperature, 0.5 ml of a Jones reagent. The reaction mixture was stirred for one hour at room temperature, which was then concentrated under reduced pressure. The concentrate was subjected to extraction with ethyl acetate. The organic layer was washed with water and dried, then the solvent was distilled off under reduced pressure. From the residue was obtained 0.23 g of trans-1-benzyl-7-chloro-5-(2-chlorophenyl)-2-oxo-1,2,3,5-tetrahydro-4,1-benzoxazepine-3-carboxylic acid as white crystals, m.p.177°–178 C.

Elemental Analysis for C₂₃H₁₇Cl₂NO₄: Calcd.: C 62.46; H 3.87; N 3.17 Found: C 62.24; H 3.93; N 3.30

Example 49

By substantially the same synthetic procedure as in Example 48, compounds listed in Table 36 were obtained.

TABLE 36

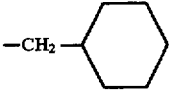

| compd. No. | R | m.p. (°C.) | Formula | Elemental Analysis (Found) C | H | N |
|---|---|---|---|---|---|---|
| 1 | —CH₃ | 167–168 | C₁₇H₁₃Cl₂NO₄ ·¼C₄H₁₀O·¼H₂O | 55.54 (55.72) | 4.14 (4.34) | 3.60 (3.34) |
| 2 | —CH₂—C₆H₁₁ (cyclohexyl) | 189–190 | C₂₃H₂₃Cl₂NO₄ | 57.88 (57.76) | 4.35 (4.55) | 3.55 (3.43) |
| 3 | —CH(CH₃)₂ | 181–182 | C₁₉H₁₇Cl₂NO₄ | 61.62 (61.69) | 5.17 (5.39) | 3.12 (3.39) |

Example 50

Ethyl ester of 3-[trans-1-benzyl-7-chloro-5-(2-chlorophenyl)-2-oxo-1,2,3,5-tetrahydro-4,1-benzoxazepin-3-ylmethyl]thioglycolic acid In 6 ml of acetonitrile was dissolved 0.2 g of trans-1-benzyl-7-chloro-5-(2-chlorophenyl)-3-chloromethyl-2-oxo-1,2,3,5-tetrahydro-4,1-benzoxazepine. To the solution were added 0.08 g of ethyl thioglycolate and 0.1 g of cesium fluoride. The mixture was heated under reflux for 40 minutes while stirring. The reaction mixture was concentrated under reduced pressure. The concentrate was subjected to extraction with ethyl acetate. The organic layer was washed with water and dried, then the solvent was distilled off under reduced pressure. The residue was purified by means of a silica gel column chromatography (eluent, hexane:ethyl acetate=4:1) to afford 0.16 g of ethyl 3-[trans-1-benzyl-7-chloro-5-(2-chlorophenyl)-2-oxo-1,2,3,5-tetrahydro-4,1-benzoxazepin-3-ylmethyl] thioglycolate as colorless needles, m.p.153°–154° C.

Elemental Analysis for $C_{27}H_{25}Cl_2NO_4S$: Calcd.: C 61.13; H 4.75; N 2.64 Found: C 61.04; H 4.72; N 2.54

Example 51

3-[Trans-1-benzyl-7-chloro-5-(2-chlorophenyl)-2-oxo-1,2,3,5-tetrahydro-4,1-benzoxazepin-3-ylmethyl]glycolic acid In a mixture of 4 ml of methanol and 2 ml of tetrahydrofuran was dissolved 0.11 g of 3-[trans-1-benzyl-7-chloro-5-(2-chlorophenyl)-2-oxo-1,2,3,5-tetrahydro-4,1-benzoxazepin-3-ylmethyl]thioglycolic acid ester. To the solution were added 0.2 g of potassium carbonate and 2 ml of water, then the mixture was stirred for one hour at 60° C. The reaction mixture was concentrated under reduced pressure. The concentrate was rendered acid with dilute hydrochloric acid, which was then subjected to extraction with ethyl acetate. The organic layer was washed with water and dried, then the solvent was distilled off under reduced pressure. From the residue was obtained 90 mg of 3-[trans-1-benzyl-7-chloro-5-(2-chlorophenyl)-2-oxo-1,2,3,5-tetrahydro-4,1-benzoxazepin-3-ylmethyl]thioglycolic acid as white crystals, m.p.148°–149° C.

Elemental Analysis for $C_{25}H_{21}Cl_2NO_4S$: Calcd.: C 59.77; H 4.21; N 2.79 Found: C 59.89; H 4.31; N 2.77

Example 52

3-[Trans-1-benzyl-7-chloro-5-(2-chlorophenyl)-2-oxo-1,2,3,5-tetrahydro-4,1-benzoxazepin-3-ylmethyl]glycolic acid To a suspension of 50 mg of sodium hydride in 4 ml of dimethylformamide was added 0.2 g of trans-1-benzyl-7-chloro-5-(2-chlorophenyl)-2-oxo-1,2,3,5-tetrahydro-4,1-benzoxazepine3-methanol, while stirring under ice-cooling. The mixture was stirred for 10 minutes at the same temperature, to which was then added 0.1 g of ethyl chloroacetate, followed by stirring for 30 minutes at room temperature. The reaction mixture was poured into ice-water, which was subjected to extraction with ethyl acetate. The organic layer was washed with an aqueous solution of potassium hydrogensulfate, an aqueous solution of sodium hydrogencarbonate and water, successively and dried, then the solvent was distilled off under reduced pressure. The residue was purified by means of a silica gel column chromatography (eluent, hexane:ethyl acetate=5:1) to give crystals. The crystals were dissolved in 5 ml of methanol. To the solution were added 0.2 g of potassium carbonate and 2 ml of water. The mixture was stirred for 5 hours at 60° C. The reaction mixture was concentrated under reduced pressure. The concentrate was rendered acid with dilute hydrochloric acid, followed by extraction with ethyl acetate. The organic layer was washed with water and dried, then the solvent was distilled off under reduced pressure. From the residue was obtained 50 mg of 3-[trans-1-benzyl-7-chloro-5-(2-chlorophenyl)-2-oxo-1,2,3,5-tetrahydro-4,1-benzoxazepin-3-ylmethyl]glycolic acid as white crystals, m.p.92°–94° C.

Elemental Analysis for $C_{25}H_{21}Cl_2NO_5 \cdot \frac{1}{2}C_4H_{10}O \cdot \frac{1}{2}H_2O$: Calcd.: C 60.91; H 5.11; N 2.63 Found: C 60.95; H 4.99; N 2.77

Example 53

Methyl ester of N-[trans-1-benzyl-7-chloro-5-(2-chlorophenyl)-2-oxo-1,2,3,5-tetrahydro-4,1-benzoxazepin-3-ylcarbonyl]tryptophane By substantially the same procedure as in Example 32, 0.4 g of 3,5-trans-1-benzyl-7-chloro-5-(2-chlorophenyl)-2-oxo-1,2,3,5-tetrahydro-4,1-benzoxazepine-3-carboxylic acid obtained in Example 48 was subjected to the reaction to give a crude product, which was purified by means of a silica gel column chromatography (eluent, hexane:ethyl acetate:methylene chloride=9:3:1). From the preceding portion of the eluate, 0.25 g of the product was obtained as a white powdery product.

IR$v_{max}^{KBr}$cm$^{-1}$: 3400(NH) 1740(CO), 1690(CO), 1655 (CO)

$^1$H-NMR spectrum (200 MHz,CDCl$_3$) δ: 3.44(2H,d), 3.64 (3H,s,OCH$_3$), 4.55(1H,s,C$_3$—H), 4.70(1H,d,PhCH$_2$), 5.03 (1H,m), 5.69(1H,d,PhCH$_2$), 5.79(1H,s,C$_5$—H), 6.37(1H,d, C$_6$—H), 6.9–8.2(15H,m)

From the subsequent portion of the eluate, 0.22 g of the title compound as an amorphous solid product.

IR$v_{max}^{KBr}$cm$^{-1}$: 3400(NH) 1740(CO), 1695(CO), 1660 (CO), 1520, 1480, 1240

$^1$H-NMR spectrum (200 MHz,CDCl$_3$) δ: 3.2–3.55(2H, m), 3.70(3H,s,OCH$_3$), 4.53(1H,s,C$_3$—H), 4.62(1H,d), 5.06 (1H,m), 5.63(1H,d), 5.76(1H,s,C$_5$—H), 6.33(1H,d,C$_6$—H), 6.8–8.4(15H,m)

Example 54

N-[trans-1-benzyl-7-chloro-5-(2-chlorophenyl)-2-oxo-1,2,3,5-tetrahydro-4,1-benzoxazepin-3-ylcarbonyl]tryptophane N-[trans-1-benzyl-7-chloro-5-(2-chlorophenyl)-2-oxo-1,2,3,5-tetrahydro-4,1-benzoxazepin-3-ylcarbonyl] tryptophane ethyl ester obtained in Example 53 was subjected to substantially the same procedure as in Example 34. From 0.25 g of the compound obtained as the preceding eluate, 70 mg of a colorless crystalline product was obtained, m.p.250°–155° C. (decomp.).

Elemental Analysis for $C_{34}H_{27}Cl_2N_3O_5 \cdot H_2O$: Calcd.: C 63.16; H 4.52; N 6.50 Found: C 63.34; H 4.63; N 6.42

From 0.22 g of the compound eluted subsequently, 0.11 g of a colorless amorphous solid product was obtained IR$v_{max}^{KBr}$cm$^{-1}$: 3700–2200(NH,COOH), 1740(CO), 1680(CO), 1660(CO), 1525, 1240

$^1$H-NMR spectrum (200 MHz,CDCl$_3$) δ: 3.40(2H,m), 4.54(1H,s), 4.63(1H,d), 5.05(1H,m), 5.63(1H,d), 5.70(1H,s, C$_5$—H), 6.31(1H,d,C$_6$—H), 6.8–8.4(15H,m)

Example 55

N-(cis-7-chloro-1-isopropyl-5-phenyl-2-oxo-1,2,3,5-tetrahydro-4,1-benzoxazepin-3-ylacetyl)glycine ethyl ester In 5 ml of methanol was dissolved 0.3 g of ethyl ester of 3,5-cis-7-chloro-1-isopropyl-5-phenyl-1,2,3,5-tetrahydro-2-oxo-4,1-benzoxazepine-3-acetic acid ethyl ester disclosed in JPA S57(1982)-35576. To the solution were added 0.3 g of potassium carbonate and 2 ml of water. The mixture was stirred for 8 hours at room temperature. The reaction mixture was concentrated under reduced pressure. To the concentrate was added water, which was subjected to extraction with ether. The aqueous layer was separated, to which was added dilute hydrochloric acid to adjust its pH to 3. The organic layer was washed with water and dried, then the solvent was distilled off under reduced pressure. From the residue was obtained 0.15 g of a powdery product. The product and 0.07 g of glycine ethyl ester hydrochloride were dissolved in 4 ml of dimethylformamide. To the solution were added, while stirring under ice-cooling, 0.1 g of diethyl phosphorocyanidate and, then, 0.2 ml of triethylamine. The reaction mixture was stirred for one hour at room temperature, which was poured into ice-water, followed by extraction with ethyl acetate. The organic layer was washed with an aqueous solution of potassium hydrogensulfate, an aqueous solution of hydrogencarbonate and water, successively, which was then dried. The solvent was distilled off under reduced pressure. The residue was purified by means of a silica gel column chromatography (eluent, hexane:ethyl acetate=2:1 to 3:2) to afford 0.11 g of N-[cis-7-chloro-1-isopropyl-5-phenyl-2-oxo-1,2,3,5-tetrahydro-4,1-benzoxazepin-3-ylacetyl]glycine ethyl ester as a crystalline product, m.p.188° C.–190° C.

Elemental Analysis for $C_{24}H_{27}ClN_2O_5$: Calcd.: C 62.81; H 5.93; N 6.10 Found: C 62.52; H 6.10; N 6.04

Example 56

N-[cis-7-chloro-1-isopropyl-5-phenyl)-1,2,3,5-tetrahydro-2-oxo-4,1-benzoxazepin-3-ylacetyl] glycine In a mixture of 2 ml of methanol and 1 ml of water was suspended 48 mg of N-(trans-7-chloro-1-isopropyl-5-phenyl- 1,2,3,5-tetrahydro-2-oxo-4,1-benzoxazepin-3-ylacetyl)glycine ethyl ester obtained in Example 55. To the suspension was added 0.1 g of potassium carbonate. The mixture was stirred for 6 hours at room temperature. The reaction mixture was adjusted to pH 4 with dilute hydrochloric acid, which was subjected to extraction with ethyl acetate. The organic layer was washed with water and dried, then the solvent was distilled off under reduced pressure. Crystals obtained form the residue were recrystallized from ether and hexane to afford 29 mg of N-(cis-7-chloro-1-isopropyl-5-phenyl-1,2,3,5-tetrahydro-2-oxo-4,1-benzoxazepin-3-ylacetyl)glycine as white needles.

$IRv_{max}^{KBr}cm^{-1}$: 3700–2200(COOH), 1710(CO), 1680 (CO), 1480, 1250, 700

$^1$H-NMR spectrum (200 MHz,CDCl$_3$) δ: 2.7–3.4(2H,m), 4.4(1H,dd,C$_3$—H), 4.75(1H,d), 5.34(1H,s,C$_5$—H), 5.5(1H, d), 6.48(1H,s,C$_6$—H), 6.9–7.6(12H,m)

Elemental Analysis for $C_{24}H_{20}ClNO_4 \cdot \frac{3}{4}H_2O$: Calcd.: C 66.20; H 4.98; N 3.22 Found: C 66.12; H 5.19; N 2.97

Elemental Analysis for $C_{34}H_{27}Cl_2N_3O_5$: Calcd.: C 64.97; H, 4.33; N 6.67 Found: C 64.70; H, 4.58; N 6.49

Example 57

Trans-7-chloro-5-(2-chlorophenyl)-1-isopropyl-2-oxo-1,2,3,5-tetrahydro-4,1-benzoxazepine-3-butyric acid ethyl ester (1) A solution of oxalyl chloride (0.72 ml) in methylene chloride (10 ml) was cooled to –65° C., to which was added dropwise a solution of dimethyl sulfoxide (0.63 ml) in methylene chloride (2 ml) taking 5 minutes, followed by stirring for 5 minutes. To the mixture was added dropwise, taking 15 minutes, a solution of trans-7-chloro-5-(2-chlorophenyl)-1-isopropyl-2-oxo-1,2,3,5-tetrahydro-4,1-benzoxazepine-3-ethanol (2.5 g) obtained in Example 47 in methylene chloride (15 ml), which was stirred for 10 minutes. To the resultant mixture was added triethylamine (3.45 ml) taking 5 minutes, then the cooling bath was removed. The mixture was stirred for 10 minutes at room temperature, to which was then added 1N hydrochloric acid (50 ml), followed by stirring. The methylene chloride layer was dried over anhydrous magnesium sulfate, then the solvent was distilled off under reduced pressure to leave trans-7-chloro-5-(2-chlorophenyl)-1-isopropyl-2-oxo-1,2,3,5-tetrahydro-4, 1-benzoxazepine-3-acetaldehyde (2.3 g) as an oily product.

$IRv_{max}^{Neat}cm^{-1}$: 1720, 1670(C=O)

$^1$H-NMR spectrum (200 MHz, CDCl$_3$) δ:1.29(3H,t,J=7.1 Hz), 1.29(3H,d,J=7.0 Hz), 1.56(3H,d,J=6.8 Hz), 2.7–2.85 (2H,m) 3.91(1H,t,J=6.5 Hz), 4.19(2H,q,J=7.1 Hz), 4.75–5.0 (1H,m), 5.90(1H,dt,J=15.6, 1.5 Hz), 6.01(1H,s), 6.51(1H,d, J=2.4 Hz), 6.97(1H,dt,J=15.6, 7.2 Hz), 7.2–7.8(6H,m), 9.83 (1H,s)

(2) In toluene (20 ml) was dissolved trans-7-chloro-5-(2-chlorophenyl)-1-isopropyl-2-oxo-1,2,3,5-tetrahydro-4,1-benzoxazepine-3-acetaldehyde (1.5 g). To the solution was added (ethoxycarbonylmethylene)-triphenylphosphorane (2.0 g), and the mixture was stirred for 3 hours at 90° C. The solvent was distilled off, and the residue was purified by means of a silica gel column chromatography (hexane:ethyl acetate=10:1) to give ethyl ester of trans-7-chloro-5-(2-chlorophenyl)-1-isopropyl-2-oxo-1,2,3,5-tetrahydro-4,1-benzoxazepine-3-crotonic acid (1.28 g) as prisms, m.p.126°–127° C.

$IRv_{max}^{KBr}cm^{-1}$: 1715(C=O) 1670(C=C)

Elemental Analysis for $C_{24}H_{25}Cl_2NO_4$: Calcd.: C 62.34; H 5.45; N 3.03 Found: C 62.47; H 5.28; N 3.08

(3) In ethyl acetate (20 ml) was dissolved ethyl ester of trans-7-chloro-5-(2-chlorophenyl)-1-isopropyl-2-oxo-1,2,3, 5-tetrahydro-4,1-benzoxazepine-3-crotonic acid (0.45 g). To the solution was added 10% palladium carbon (0.1 g), and the mixture was subjected to catalytic reduction at room temperatures under atmospheric pressure. The theoretical amount of hydrogen was allowed to be absorbed, then the catalyst was removed, followed by distilling off ethyl acetate under reduced pressure. The residue was crystallized from a small volume of hexane to give ethyl ester of trans-7-chloro-5-(2-chlorophenyl)-1-isopropyl-2-oxo-1,2,3,5-tetrahydro-4, 1-benzoxazepine-3-butyric acid (0.37 g) as prisms, m.p.100°–101° C.

$IRv_{max}^{KBr}cm^{-1}$: 1730, 1670(C=O)

Elemental Analysis for $C_{24}H_{27}Cl_2NO_4$: Calcd.: C 62.07; H 5.86; N 3.02 Found: C 62.35; H 5.93; N 2.95

Example 58

Trans-7-chloro-5-(2-chlorophenyl)-1-isopropyl-2-oxo-1,2,3,5-tetrahydro-4,1-benzoxazepine-3-butyric acid In ethanol (5 ml) was dissolved ethyl ester of trans-7-chloro-5-(2-chlorophenyl)-1-isopropyl-2-oxo-1,2,3,5- tetrahydro-4,1-benzoxazepine-3-butyric acid (0.25 g). To the solution was added 1N sodium hydroxide (4 ml), then the mixture was stirred for 30 minutes at room temperatures. The mixture was acidified with 1N aqueous solution of hydrochloric acid (50 ml), followed by extraction with ethyl acetate (100 ml). The ethyl acetate layer was washed with water and dried over anhydrous magnesium sulfate. The solvent was distilled off under reduced pressure to leave trans-7-chloro-5-(2-chlorophenyl)-1-isopropyl-2-oxo-1,2,3, 5-tetrahydro-4,1-benzoxazepine-3-butyric acid (0.20 g) as prisms, m.p.158°–160° C.

IR$v_{max}^{KBr}$cm$^{-1}$: 1710 1670(C=O)

Elemental Analysis for $C_{22}H_{23}Cl_2NO_4$: Calcd.: C 60.56; H 5.31; N 3.21 Found: C 60.62; H 5.18; N 3.23

Example 59

Ethyl ester of N-[trans-1-isobutyl-2-oxo-5-(o-tolyl)-1,2,3,5-tetrahydro-4,1-benzoxazepine-3-acetyl] aminoacetic acid Trans-1-isobutyl-2-oxo-5-(o-tolyl)-1,2,3,5-tetrahydro-4, 1-benzoxazepine-3-acetic acid (0.4 g) obtained in Example 5 and glycine ethyl ester hydrochloride were subjected to substantially the same procedure as in Example 24 to give ethyl ester of N-[trans-1-isobutyl-2-oxo-5-(o-tolyl)-1,2,3,5-tetrahydro-4,1-benzoxazepine-3-acetyl]aminoacetic acid (0.47 g) as needles, m.p. 137°–138° C.

IR$v_{max}^{KBr}$cm$^{-1}$: 3360(NH), 1745, 1655(C=O)

Elemental Analysis for $C_{26}H_{32}N_2O_5$: Calcd.: C 69.01; H 7.13; N 6.19 Found: C 69.01; H 7.18; N 6.26

Example 60

N-[trans-1-isobutyl-2-oxo-5-(o-tolyl)-1,2,3,5-tetrahydro-4,1-benzoxazepine-3-acetyl]aminoacetic acid Ethyl ester of N-[trans-1-isobutyl-2-oxo-5-(o-tolyl)-1,2,3, 5-tetrahydro-4,1-benzoxazepine-3-acetyl]aminoacetic acid (0.3 g) obtained in Example 59 was subjected to hydrolysis in substantially the same manner as in Example 35 to afford N-[trans-1-isobutyl-2-oxo-5-(o-tolyl)-1,2,3,5-tetrahydro-4, 1-benzoxazepine-3-acetyl]aminoacetic acid (0.26 g) as prisms, m.p.220°–223° C.

IR$v_{max}^{KBr}$cm$^{-1}$: 1755, 1670, 1630(C=O)

Elemental Analysis for $C_{24}H_{26}N_2O_5$: Calcd.: C 67.91; H 6.65; N 6.60 Found: C 67.96; H 6.86; N 6.69

Example 61

Ethyl ester of N-[trans-5-(2-fluorophenyl)-1-isobutyl-2-oxo-1,2,3,5-tetrahydro-4,1-benzoxazepine-3-acetyl] aminoacetic acid Trans-5-(2-fluorophenyl)-1-isobutyl-2-oxo-1,2,3,5-tetrahydro- 4,1-benzoxazepine-3-acetic acid (0.4 g) obtained in Example 6 was allowed to react with glycine ethyl ester hydrochloride in substantially the same manner as in Example 24 to afford ethyl ester of N-[trans-5-(2-fluorophenyl)-isobutyl-2-oxo-1,2,3,5-tetrahydro-4,1-benzoxazepine-3-acetyl]aminoacetic acid (0.45 g) as needles, m.p.166°–168° C.

IR$v_{max}^{KBr}$cm$^{-1}$: 3370(NH) 1750, 1660(C=O)

Elemental Analysis for $C_{25}H_{29}FN_2O_5$: Calcd.: C 65.78; H 6.40; N 6.14 Found: C 65.89; H 6.34; N 6.15

Example 62

N-[trans-5-(2-fluorophenyl)-1-isobutyl-2-oxo-1,2,3, 5-tetrahydro-4,1-benzoxazepine-3-acetyl] aminoacetic acid Ethyl ester of N-[trans-5-(2-fluorophenyl)-1-isobutyl-2-oxo-1,2,3,5-tetrahydro-4,1-benzoxazepine-3-acetyl] aminoacetic acid (0.3 g) obtained in Example 61 was subjected to hydrolysis in substantially the same manner as in Example 25 to afford N-[trans-5-(2-fluorophenyl)-1-isobutyl-2-oxo-1,2,3,5-tetrahydro-4,1-benzoxazepine-3-acetyl]aminoacetic acid (0.27 g) as prisms, m.p.201°–203° C.

IR$v_{max}^{KBr}$cm$^{-1}$: 1755, 1670, 1630(C=O)

Elemental Analysis for $C_{25}H_{25}FN_2O_5$: Calcd.: C 64.48; H 5.88; N 6.54 Found: C 64.54; H 5.95; N 6.51

Example 63

Ethyl ester of N-[trans-1-isobutyl-5-(2-methoxyphenyl)-2-oxo-1,2,3,5-tetrahydro-4,1-benzoxazepine-3-acetyl] aminoacetic acid In N,N-dimethylformamide (10 ml) were dissolved trans-1-isobutyl-5-(2-methoxyphenyl)-2-oxo-1,2,3,5-tetrahydro-4,1-benzoxazepine-3-acetic acid (0.4 g) obtained in Example 6 and glycine ethyl ester hydrochloride (0.18 g). To the solution were added, under ice-cooling, diethyl phosphorocyanidate (0.22 g) and triethylamine (0.35 ml). The mixture was stirred for 30 minutes at room temperature, to which were then added water (100 ml) and ethyl acetate (100 ml), followed by extraction. The ethyl acetate layer was washed with 1N hydrochloric acid and an aqueous solution of sodium hydrogencarbonate, which was then dried on anhydrous magnesium sulfate, followed by distilling off the solvent under reduced pressure. The residue was purified by means of a silica gel column chromatography (hexane:ethyl acetate=1:1) to give ethyl ester of N-[trans-1-isobutyl-5-(2-methoxyphenyl)-2-oxo-1,2,3,5-tetrahydro-4,1-benzoxazepine-3-acetyl] aminoacetic acid (0.45 g) as needles, m.p.135°–137° C.

IR$v_{max}^{KBr}$cm$^{-1}$: 1750, 1670(C=O)

Elemental Analysis for $C_{26}H_{32}N_2O_6$: Calcd.: C 66.65; H 6.88; N 5.98 Found: C 66.72; H 6.91; N 5.98

Example 64

N-[trans-1-isobutyl-5-(2-methoxyphenyl)-2-oxo-1,2, 3,5-tetrahydro-4,1-benzoxazepine-3-acetyl] aminoacetic acid In ethanol (5 ml) was dissolved ethyl ester of N-[trans-1-isobutyl-5-(2-methoxyphenyl)-2-oxo-1,2,3,5-tetrahydro-4,1- benzoxazepine-3-acetyl]aminoacetic acid (0.3 g) obtained in Example 63. To the solution was added 1N sodium hydroxide, and the mixture was stirred for 15 minutes, which was acidified by the addition of 1N aqueous solution of hydrochloric acid (50 ml), followed by extraction with ethyl acetate (100 ml). The ethyl acetate layer was washed with water, which was then dried over anhydrous magnesium sulfate. The solvent was distilled off under reduced pressure to leave N-[trans-1-isobutyl-5-(2-methoxyphenyl)-2-oxo-1,2,3,5-tetrahydro-4,1-benzoxazepine-3-acetyl]aminoacetic acid (0.27 g) as prisms, m.p.210°–211° C.

IR$v_{max}^{KBr}$cm$^{-1}$: 1760 1670, 1630(C=O)

Elemental Analysis for $C_{24}H_{28}N_2O_6$: Calcd.: C 65.44; H 6.41; N 6.36 Found: C 65.32; H 6.38; N 6.33

Example 65

Trans-7-chloro-5-(2-chlorophenyl)-1-isopropyl-2-oxo-1,2,3,5-tetrahydro-4,1-benzoxazepine-3-ethanol In tetrahydrofuran (7 ml) were dissolved trans-7-chloro-5-(2-chlorophenyl)-1-isopropyl-2-oxo-1,2,3,5-tetrahydro-4, 1-benzoxazepine-3-acetic acid (0.5 g) obtained in Reference Example 5, and N-methylmorpholine (0.15 ml). To the solution was added ethyl chlorocarbonate (0.13 ml) at −10° C., and the mixture was stirred for 10 minutes. To the mixture was added sodium borohydride (0.15 g), to which was then added dropwise methanol taking 5 minutes, followed by stirring for 30 minutes at 0° C. The reaction mixture was poured into 1N hydrochloric acid (50 ml), followed by extraction with ethyl acetate (100 ml). The ethyl acetate layer was washed with an aqueous solution of sodium hydrogencarbonate, then dried over anhydrous magnesium sulfate, followed by distilling off the solvent under reduced pressure. The residue was purified by means of a silica gel column chromatography to afford trans-7-chloro-5-(2-chlorophenyl)-1-isopropyl-2-oxo-1,2,3,5-tetrahydro-4,1-benzoxazepine-3-ethanol (0.41 g) as prisms, m.p.188°–189° C.

IR$v_{max}^{KBr}$cm$^{-1}$: 3430(OH), 1650(C=O)

Elemental Analysis for $C_{20}H_{21}Cl_2NO_3$: Calcd.: C 60.92; H 5.37; N 3.55 Found: C 61.12; H 5.39; N 3.72

Example 66

Ethyl ester of N-[trans-7-chloro-5-(2-chlorophenyl)-1-isopropyl-2-oxo-1,2,3,5-tetrahydro-4,1-benzoxazepine-3-acetyl]aminoacetic acid In N,N-dimethylformamide (10 ml) were dissolved trans-7-chloro-5-(2-chlorophenyl)-1-isopropyl-2-oxo- 1,2,3,5-tetrahydro-4,1-benzoxazepine-3-acetic acid (0.3 g) and glycine ethyl ester hydrochloride (0.12 g). To the solution were added, under ice-cooling, diethyl phosphorocyanidate (0.15 g) and triethylamine (0.24 ml). The mixture was stirred for 30 minutes at room temperature, to which were added water (100 ml) and ethyl acetate (100 ml), followed by extraction. The ethyl acetate layer was washed with 1N hydrochloric acid and an aqueous solution of sodium hydrogencarbonate, which was then dried over anhydrous magnesium sulfate, followed by distilling off the solvent under reduced pressure. The residue was purified by means of a silica gel column chromatography (hexane:ethyl acetate=1:1) to afford ethyl ester of N-[trans-7-chloro-5-(2-chlorophenyl)-1-isopropyl-2-oxo-1,2,3,5-tetrahydro-4,1-benzoxazepine-3-acetyl] aminoacetic acid (0.31 g) as needles, m.p.197°–1990° C.

IR$v_{max}^{KBr}$cm$^{-1}$: 1755, 1670, 1655(C=O) Elemental Analysis for $C_{24}H_{26}Cl_2N_2O_5$: Calcd.: C 58.43; H 5.31; N 5.68 Found: C 58.73; H 5.33; N 5.80

Example 67

N-[trans-7-chloro-5-(2-chlorophenyl)-1-isopropyl-2-oxo-1,2,3,5-tetrahydro-4,1-benzoxazepine-3-acetyl] aminoacetic acid In ethanol (10 ml) was dissolved ethyl ester of N-[trans-7-chloro-5-(2-chlorophenyl)-1-isopropyl-2-oxo-1,2,3,5-tetrahydro-4,1-benzoxazepine-3-acetyl]aminoacetic acid (0.2 g) obtained in Example 66. To the solution was added 1N sodium hydroxide (2 ml), and the mixture was stirred for 15 minutes. To the reaction mixture was added 1N aqueous solution of hydrochloric acid (100 ml) to make the solution acid, followed by extraction with ethyl acetate (100 ml). The ethyl acetate layer was washed with water, which was then dried over anhydrous magnesium sulfate, followed by distilling off the solvent to leave N-[trans-7-chloro-5-(2-chlorophenyl)-1-isopropyl-2-oxo-1,2,3,5- tetrahydro-4,1-benzoxazepine-3-acetyl]aminoacetic acid (0.18 g) as crystals, m.p.134°–135° C.

IR$v_{max}^{KBr}$cm$^{-1}$: 1725, 1650(C=O)

Elemental Analysis for $C_{22}H_{22}Cl_2N_2O_5 \cdot \frac{1}{2}Et_2O$: Calcd.: C 57.38; H 5.42; N 5.58 Found: C 57.48; H 5.59; N 5.58

Example 68

By substantially the same synthetic method as in Example 66, compounds listed in Table 37 and Table 38 were obtained as crystalline or oily products.

TABLE 37

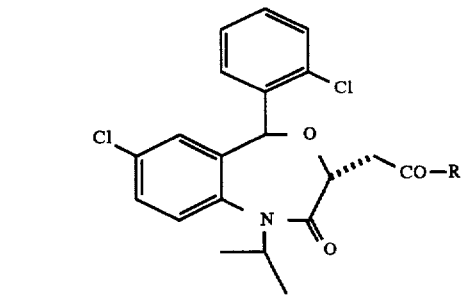

| compd. No | R | m.p. (°C.) | Formula | Elemental Analysis (Found) C | H | N |
|---|---|---|---|---|---|---|
| 1 | NHCH$_2$CH$_2$COOEt | 182–183 | C$_{26}$H$_{28}$Cl$_2$N$_2$O$_5$ | 59.18 (59.13) | 5.56 (5.56) | 5.52 (5.45) |
| 2 | —NH—CH—COOCH$_3$ with phenyl (D,L) | 160–164 | C$_{29}$H$_{28}$Cl$_2$N$_2$O$_5$ | 62.71 (62.55) | 5.08 (5.11) | 5.04 (4.86) |

TABLE 37-continued

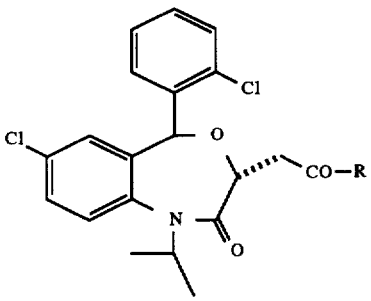

| compd. No | R | m.p. (°C.) | Formula | Elemental Analysis (Found) | | |
|---|---|---|---|---|---|---|
| | | | | C | H | N |
| 3 | 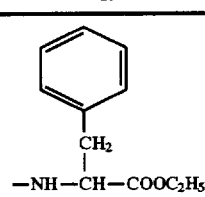—NH—CH—COOC₂H₅ | 187–188 | C₃₁H₃₂Cl₂N₂O₅ | 63.81 (63.97) | 5.53 (5.59) | 4.80 (4.98) |

TABLE 38

| compd. No. | R | IRν_max^neat cm⁻¹ | ¹H-NMR spectrum (200 MHZ, CDCl₃) |
|---|---|---|---|
| 4 | L-Ser—OMe<br>OH<br>\|<br>CH₂<br>\|<br>NH—CH—COOCH₃ | 1745, 1660 (C=O) | 1.29(3H, d, J=7.0Hz), 1.54, 1.56(3H, both d, J=6.6Hz), 2.6–3.05 (2H, m), 3.76, 3.77(3H, both s, OMe), 3.85–4.2(3H, m), 4.25–4.45(1H, 4.55–4.7(1H, m), 4.7–4.95(1H, m), 5.99, 6.01(1H, both s), 6.45–6.55(1H, m), 6.84, 6.92(1H, both brd, J=7.0Hz), 7.2–7.8(6H, m) |
| 5 | CH₃OOC<br>\|<br>CH₂<br>\|<br>NH—CH—COOCH₃ | 1740, 1670 (C=O) | 1.29(3H, d, J=7.0Hz), 1.55, 1.56(3H, both d, J=6.8Hz), 2.65–3.1(4H, m), 3.6–3.8(6H, m, CH₃×2), 4.25–4.4(1H, m), 4.7–5.0(2H, m), 6.00(1H, s), 6.45–6.55(1H, m), 6.8–7.0(1H, m), 7.2–7.8(6H, m) |
| 6 | COOC₂H₅<br>\|<br>CH₂<br>\|<br>CH₂<br>\|<br>NH—CH—COOC₂H₅ | 1735, 1670 (C=O) | 1.15–1.4(9H, m), 1.55, 1.56(3H, both d, J=6.8Hz), 1.9–2.5(4H, m), 2.70(1H, dd, J=14.4, 6.2Hz), 2.85–3.05(1H, m), 4.05–4.4 (5H, m), 4.5–4.7(1H, m), 4.7–5.0(1H, m), 6.00, 6.01(1H, s), 6.50 (1H, d, J=2.4Hz), 6.55, 6.64 (1H, both brd), 7.2–7.8(6H, m) |

Example 69

By substantially the same synthetic method as in Example 67, compounds listed in Table 39 and Table 40 were obtained.

TABLE 39

[Structure: 2,5-dichloro diphenylmethyl compound with N-isopropyl amide and -O-CH-C(=O)-R side chain]

| compd. No. | R | m.p. (°C.) | Formula | Elemental Analysis(Found) | | |
|---|---|---|---|---|---|---|
| | | | | C | H | N |
| 1 | NHCH₂CH₂COOH | 182–184 | C₂₃H₂₄Cl₂N₂O₅ | 57.63 (57.36) | 5.05 (5.08) | 5.84 (5.67) |
| 2 | (phenyl)-NH—CH—COOH | amorphous solid | C₂₈H₂₆Cl₂N₂O₅ | 62.11 (62.09) | 4.84 (5.02) | 5.17 (5.24) |
| 3 | (phenyl)-CH₂-NH—CH—COOH | 213–215 | C₂₉H₂₈Cl₂N₂O₅ | 62.71 (62.61) | 5.08 (4.96) | 5.04 (5.13) |

TABLE 40

| Compd. No. | R | m.p. (°C.) | Formula | Elemental Analysis(Found) | | |
|---|---|---|---|---|---|---|
| | | | | C | H | N |
| 4 | L-Ser—OH<br>HO<br>\|<br>CH₂<br>\|<br>NH—CH—COOH | amorphous solid | C₂₃H₂₄Cl₂N₂O₆ | 55.77 (55.88) | 4.88 (5.27) | 5.66 (5.84) |
| 5 | COOH<br>\|<br>CH₂<br>\|<br>NH—CH—COOH (L) | amorphous solid | C₂₄H₂₄Cl₂N₂O₇ | 55.07 (54.65) | 4.62 (4.98) | 5.35 (5.22) |
| 6 | COOH<br>\|<br>(CH₂)₂<br>\|<br>NH—CH—COOH (L) | 198–199 | C₂₅H₂₆Cl₂N₂O₇ | 55.8 (55.97) | 4.88 (5.16) | 5.21 (5.16) |

Example 70

By substantially the same synthetic method as in Reference Example 2, a compound listed in Table 41 was obtained.

TABLE 41

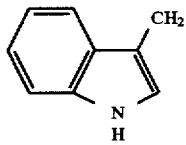

| R₁ | R₂ | m.p. (°C.) | Formula | Elemental Analysis(Found) C | H | N |
|---|---|---|---|---|---|---|
| 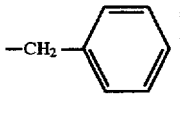 | —CH₂— ⌬ | amorphous solid | C₃₃H₂₆Cl₂N₂O₄ | IRν_max^neat cm⁻¹: 3400(NH), 1740(CO), 1670(CO) ¹H-NMR(CDCl₃) δ: (1H, dd), 3.2(1H, dd), 4.47(1H, dd, C₃—H), 5.54(1H, s, C₅—H) | | |

Also, Physicochemical properties of an intermediate are shown in Table 42.

TABLE 42

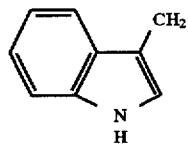

| R₁ | R₂ | m.p. (°C.) | Formula | Elemental Analysis(Found) C | H | N |
|---|---|---|---|---|---|---|
| 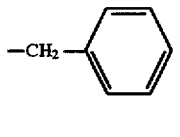 | —CH₂— ⌬ | amorphous solid | C₃₃H₂₆Cl₂N₂O₄ | ¹H-NMR(CDCl₃) δ: 4.7 (1H, d), 5.03(2H, s, CH₂Ph), 5.657(1H, d), 6.0– 8.3(20H, m) | | |

Example 71

Ethyl ester of trans-7-chloro-5-(2,4,6-trimethoxyphenyl)-1-neopentyl-2-oxo-1,2,3,5-tetrahydro-4,1-benzoxazepine-3-acetic acid (1) 2-acetylamino-5-chloro-2',4',6'-trimethoxybenzophenone A solution of 2.41 g of 1,3,5-trimethoxybenzene in 10 ml of dry tetrahydrofuran was cooled to −78° C. and 9.1 ml of n-butyl lithium (1.58M solution in hexane) was added dropwise over a period of 10 minutes. This solution was added dropwise to a solution of 2.0 g of 6-chloro-4-methyl-4H-3,1-benzoxazin-4-one in 20 ml of dry tetrahydrofuran. After mixture stirring at 0° C. for 1 hour, the solvent was removed, after which the residue was acidified with dilute hydrochloric acid and then extracted with ethyl acetate. After the extract was washed with dilute hydrochloric acid and an aqueous solution of sodium hydrogen carbonate, the solvent was removed, and the residue was subjected to silica gel column chromatography to yield 1.28 g of a crystal.

Melting point: 159°–160° C.

Elemental analysis (for C₁₈H₁₈ClNO₅) Calcd.: C 59.43; H 4.99; N 3.85 Found: C 59.39; H 4.94; N 3.86

(2) 2-amino-5-chloro-2',4',-6'-trimethoxybenzophenone

A mixture of 4.7 g of 2-acetylamino-5-chloro-2',4',6'-trimethoxybenzophenone, 50 ml of 6N hydrochloric acid and 50 ml of ethanol was refluxed for 1 hour while heating. After the solvent was distilled off, the residue was basefied with an aqueous solution of sodium hydrogen carbonate and then extracted with ethyl acetate. After the extract was washed with water and dried, the solvent was removed, and the residue was subjected to silica gel column chromatography to yield 3.75 g of a crystal.

(3) 2-amino-5-chloro-α-(2,4,6-trimethoxyphenyl)benzyl alcohol

To a solution of 3.0 g of 2-amino-5-chloro-2',4',6'-trimethoxybenzophenone in 50 ml of tetrahydrofuran, 0.43 g of lithium aluminum hydride was added, followed by stirring for 1 hour. After water was added, the solution was extracted with ethyl acetate and dried over anhydrous sodium sulfate, after which the solvent was removed and the residue was subjected to silica gel column chromatography to yield 2.9 g of a crystal.

(4) 5-chloro-α-(2,4,6-trimethoxyphenyl)-2-(neopentylamino)benzyl alcohol

After a solution of 2.5 g of 2-amino-5-chloro-α-(2,4,6-trimethoxyphenyl)benzyl alcohol, 1.01 ml of trimethylacetaldehyde and 0.56 g of acetic acid in 30 ml of ethanol was stirred at room temperature for 1.5 hours, 0.81 g of sodium cyanoborohydride was added, followed by stirring overnight. After concentration and subsequent dilution with water, the solution was extracted with ethyl acetate. After solvent removal, the residue was subjected to silica gel column chromatography to yield 2.2 g of a crystal.

(5) Ethyl ester of 3-[N-(4-chloro-2-(α-hydroxy-2,4,6-trimethoxybenzyl)phenyl]-N-neopentylcarbamoyl]acrylic acid 2.0 g of 5-chloro-α-(2,4,6-trimethoxyphenyl)-2-(neopentylamino)benzyl alcohol, 0.99 g of monoethyl ester of chlorofumaric acid and 0.85 g of sodium hydrogen carbonate were added to 30 ml of dichloromethane, and this mixture was stirred for 30 minutes. To the reaction mixture was added water, and the organic layer was dried, after which the solvent was removed and the residue was subjected to silica gel column chromatography to yield 2.5 g of an oily compound.

(6) Ethyl ester of trans-7-chloro-5-(2,4,6-trimethoxyphenyl)-1-neopentyl-2-oxo-1,2,3,5-tetrahydro-4,1-benzoxazepine-3-acetic acid.

2.5 g of ethyl ester of 3-[N-(4-chloro-2-(α-hydroxy-2,4,6-trimethoxybenzyl)phenyl]-N-neopentylcarbamoyl]acrylic acid and 1.33 g of potassium carbonate were added to 30 ml of ethanol, and this mixture was stirred at room temperature overnight. After ethyl acetate was added, the mixture was washed with water and dried, after which the solvent was removed and the residue was subjected to silica gel column chromatography to yield 2.0 g of a crystal.

Melting point: 154°–155° C.

Elemental analysis (for $C_{27}H_{34}ClNO_7$) Calcd.: C 62.36; H 6.59; N 2.69 Found: C 62.51; H 6.32; N 2.67

Example 72

By the same procedure as in Example 71, the compounds listed in Tables 43 and 44 were obtained.

TABLE 43

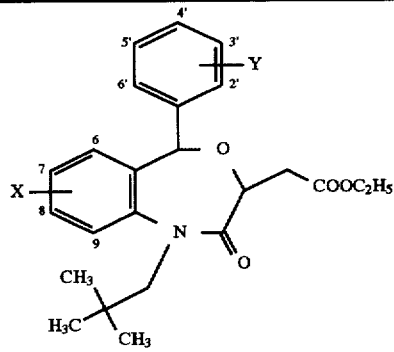

| Compd. No. | X | Y | m.p. (°C.) | Formula | Elemental Analysis(Found) | | |
|---|---|---|---|---|---|---|---|
| | | | | | C | H | N |
| 1 | 7-Cl | 2',4'-OCH₃ | 117–119 | $C_{26}H_{32}ClNO_6$ | 63.73 (63.63 | 6.58 6.81 | 2.86 2.83) |
| 2 | 7-Cl | 2',6'-OCH₃ | 175–177 | $C_{26}H_{32}ClNO_6$ | 63.73 (63.54 | 6.58 6.49 | 2.86 2.89) |
| 3 | 7-Cl | 2',5'-OCH₃ | 165–166 | $C_{26}H_{32}ClNO_6$ | 63.73 (63.63 | 6.58 6.59 | 2.86 2.82) |
| 4 | 7-Cl | 2',3'-OCH₂O— | 164–167 | $C_{25}H_{28}ClNO_6$ | 63.35 (63.31 | 5.95 5.88 | 2.96 2.92) |
| 5 | 7-Cl | 3',4'-OCH₂O— | 133–134 | $C_{25}H_{28}ClNO_6$ | 63.36 (63.13 | 5.95 5.96 | 2.96 2.79) |

TABLE 44

| Compd. No. | X | Y | m.p. (°C.) | Formula | Elemental Analysis (Found) | | |
|---|---|---|---|---|---|---|---|
| | | | | | C | H | N |
| 6 | 8-Cl | 2'-Cl | 142–143 | $C_{24}H_{27}Cl_2NO_4$ | 62.07 (61.87 | 5.86 6.01 | 3.02 2.89) |
| 7 | 7,9-Cl | 2'-OCH₃ | 167–169 | $C_{25}H_{29}Cl_2NO_5$ | 60.73 (60.73 | 5.91 5.97 | 2.83 2.74) |
| 8 | 7-Cl | 2'-OCH³ | 173–174 | $C_{25}H_{30}ClNO_5$ | 65.28 | 6.57 | 3.05 |

TABLE 44-continued

| Compd. No. | X | Y | m.p. (°C.) | Formula | Elemental Analysis (Found) | | |
|---|---|---|---|---|---|---|---|
| | | | | | C | H | N |
| | | | | | (65.32 | 6.64 | 3.11) |
| 9 | 7-Cl | 2'-Br | 128–129 | C$_{24}$H$_{27}$BrClNO$_4$ | 56.65 | 5.35 | 2.75 |
| | | | | | (56.77 | 5.42 | 2.76) |
| 10 | 7-Br | 2'-Cl | 143–146 | C$_{24}$H$_{27}$BrClNO$_4$ | 56.65 | 5.35 | 2.75 |
| | | | | | (56.50 | 5.23 | 2.58) |
| 11 | 7-Cl | 2',3'-OCH$_3$ | 184–185 | C$_{26}$H$_{32}$ClNO$_6$ | 63.73 | 6.58 | 2.86 |
| | | | | | (63.75 | 6.82 | 2.67) |

Example 73

By the same procedure as in Example 71 except that isobutyl aldehyde was used in place of trimethylacetaldehyde, the compounds listed in Tables 45 through 47 were obtained.

TABLE 45

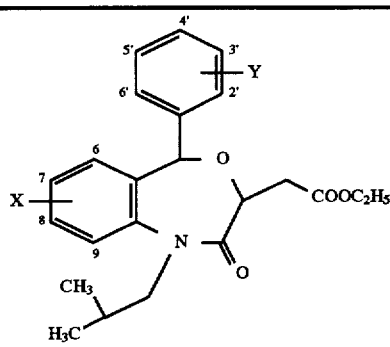

| Compd. No. | X | Y | m.p. (°C.) | Formula | Elemental Analysis(Found) | | |
|---|---|---|---|---|---|---|---|
| | | | | | C | H | N |
| 1 | 7-F | 2'-Cl | oil | C$_{23}$H$_{25}$ClFNO$_4$ | $^1$H-NMR(CDCl$_3$) δ: 0.93 and 1.03(each 3H, d, J=6.6Hz), 1.25(3H, t, J=7.2Hz), 1.86–2.10(1H, m), 2.80(1H, dd, J=16.5, 6.2Hz), 3.06(1H, dd, J=16.5, 7.4Hz), 3.44 (1H, dd, J=13.8, 5.4Hz), 4.14(2H, q, J=7.2Hz), 4.32(1H, dd, J=13.8, 8.4Hz), 4.43(1H, dd, J=7.4, 6.2Hz), 6.15(1H, s), 6.26(1H, dd, J=9.0, 2.9Hz), 7.12(1H, ddd, J=8.8, 7.6, 2.9Hz), 7.29–7.47(4H, m), 7.66–7.75(1H, m) | | |
| 2 | 7-OCH$_3$ | 2'-Cl | oil | C$_{24}$H$_{28}$ClNO$_5$ | $^1$H-NMR(CDCl$_3$) δ: | | |

TABLE 45-continued

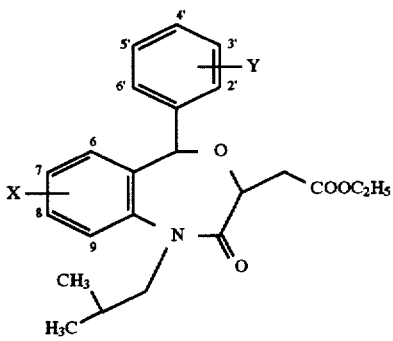

| Compd. No. | X | Y | m.p. (°C.) | Formula | Elemental Analysis(Found) | | |
|---|---|---|---|---|---|---|---|
| | | | | | C | H | N |
| | | | | | 0.93(3H, d, J=6.8Hz), 1.03(3H, d, J=6.6Hz), 1.25(3H, J=7.2Hz), 1.98(1H, m), 2.80(1H, dd, J=6.2, 16.4Hz), 3.04(1H, dd, J=7.2, 16.4Hz), 3.43(1H, dd, J=5.4, 13.6Hz), 3.6(3H, s), 4.13(2H, q, J=7.2Hz), 4.30(1H, dd, J=8.4, 13.6Hz), 4.44(1H, dd, J=6.2, 7.2Hz), 6.06 (1H, d, J=3.0Hz), 6.16(1H, s), 6.93(1H, dd, J=3.0, 8.6Hz), 7.25–7.74(5H, m) | | |

TABLE 46

| Compd. No. | X | Y | m.p. (°C.) | Formula | Elemental Analysis (Found) C | H | N |
|---|---|---|---|---|---|---|---|
| 3 | 7-Cl | 2',4'-Cl | amorphous solid | $C_{23}H_{24}Cl_3NO_4$ | 56.98 (56.92 | 4.99 5.00 | 2.89 2.95) |
| 4 | 7-Cl | 2'-CF$_3$ | 120–122 | $C_{24}H_{25}ClF_3NO_4$ | 59.57 (59.57 | 5.21 5.18 | 2.89 2.84( |
| 5 | 7-Cl | 2-OCH$_3$ | 124–125 | $C_{24}H_{28}ClNO_5$ | 64.64 (64.54 | 6.33 6.34 | 3.14 3.07) |
| 6 | 7-Cl | 2'-Br | oil | $C_{23}H_{25}BrClNO_4$ | $^1$H-NMR(CDCl$_3$) δ: 0.95(3H, d, J=6.8Hz), 1.06 (3H, d, J=6.6Hz), 1.25(3H, t, J=7.1Hz), 1.85–2.09(1H, m), 2.80(1H, dd, J=16.6, 6.2Hz), 3.05(1H, dd, J=16.6, 7.4Hz), 3.48(1H, dd, J=13.8, 5.2Hz), 4.14(2H, q, J=7.1Hz), 4.29 (1H, dd, J=13.8, 8.8Hz), 4.43(1H, dd, J=7.4, 6.2Hz), 6.07(1H, s), 6.50(1H, d, J=2.2Hz), 7.22–7.75(6H, m) | | |
| 7 | 7-Br | 2'-Cl | oil | $C_{23}H_{25}BrClNO_4$ | $^1$H-NMR(CDCl$_3$) δ: 0.93 and 1.02(each 3H, d, J=6.6Hz), 1.25(3H, t, J=7.2Hz), 1.86–2.08 (1H, m), 2.79(1H, dd, J=16.6, 6.2Hz), 3.06(1H, dd, J=16.6, 7.4Hz), 3.44(1H, dd, J=13.8, 5.6Hz), 4.13(2H, q, J=7.2Hz), 4.31(1H, dd, J=13.8, 8.4Hz), 4.43(1H, dd, J=7.4, 6.2Hz), 6.13(1H, s), 6.65(1H, d, J=2.4Hz), 7.20–7.75(6H, m) | | |

TABLE 47

| Compd. No. | X | Y | m.p. (°C.) | Formula | Elemental Analysis (Found) C | H | N |
|---|---|---|---|---|---|---|---|
| 8 | 7-Cl | 4'-Cl | oil | $C_{23}H_{25}Cl_2NO_4$ | $^1$H-NMR(CDCl$_3$) δ: 0.91 and 0.98(each 3H, d, J=6.6Hz), 1.24(3H, t, J=7.1Hz), 1.93–2.20(1H, m), 2.76(1H, dd, J=16.6, 6.0Hz), 3.05(1H, dd, J=16.6, 7.6Hz), 3.44 (1H, dd, J=13.6, 7.6Hz), 4.12(2H, q, J=7.1Hz), 4.26(1H, dd, J=13.6, 7.6Hz), 4.41(1H, dd, J=7.6, 6.0Hz), 5.84(1H, s), 6.57(1H, s), 7.20–7.50(6H, m) | | |
| 9 | H | 2'-CH$_3$ | 88–90 | $C_{24}H_{29}NO_4$ | 72.89 (73.18 | 7.39 7.25 | 3.54 3.54) |
| 10 | 7-Cl | 3'-Cl | oil | $C_{23}H_{25}Cl_2NO_4$ | $^1$H-NMR(CDCl$_3$) δ: 0.91(3H, d, J=20Hz), 0.98(3H, d, J=6.6Hz), 1.25(3H, t, J=7.1Hz), 1.95–2.18 (1H, m), 2.78(1H, dd, J=16.4, 6.0Hz), 3.05(1H, dd, J=16.4, 7.6Hz), 3.44(1H, dd, J=13.6, 6.4Hz), 4.13(2H, q, J=7.1Hz), 4.26(1H, dd, J=13.6, 7.6Hz), 4.40(1H, dd, J=7.6, 6.0Hz), 5.84(1H, s), 6.59(1H, d, J=2.0Hz), 7.14–7.50(6H, m) | | |
| 11 | 7-CF$_3$ | H | 100–102 | $C_{24}H_{26}F_3NO_4$ | 64.13 (64.44 | 5.83 5.85 | 3.12 2.98) |
| 12 | 7-Cl | H | oil | $C_{23}H_{26}ClNO_4$ | $^1$H-NMR(CDCl$_3$) δ: 0.91 and 0.99(each 3H, d, J=6.6Hz), 1.24(3H, t, J=7.2Hz), 1.95–2.20(1H, m), 2.78(1H, dd, J=16.6, 5.8Hz), 3.07(1H, dd, J=16.6, 7.8Hz), 3.44 (1H, dd, J=14.8, 6.4Hz), 4.13(2H, q, J=7.2Hz), 4.27(1H, dd, J=13.8, 7.6Hz), 4.43(1H, d, J=7.8, 5.8Hz), 5.88(1H, s), 6.61(1H, d, J=2.4 Hz), 7.24–7.49(7H, m) | | |

Example 74

The compounds obtained in Examples 71 and 72 were hydrolyzed by the same procedure as in Reference Examples 5 and Example 2 to yield the compounds listed in Tables 48 and 49.

TABLE 48

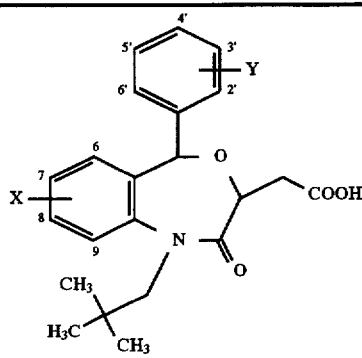

| Compd. No. | X | Y | m.p. (°C.) | Formula | Elemental Analysis(Found) C | H | N |
|---|---|---|---|---|---|---|---|
| 1 | 7-Cl | 2',4'-OCH3 | 260–263 | $C_{24}H_{28}ClNO_6$ | 62.40 (62.27 | 6.11 6.26 | 3.03 2.97) |
| 2 | 7-Cl | 2', —6'OCH$_3$ | 263–270 (decomp) | $C_{24}H_{28}ClNO_8$ +0.3H$_2$O | 61.68 (61.72 | 6.17 6.15 | 3.00 2.90) |
| 3 | 7-Cl | 2',5'-OCH$_3$ | 230–232 | $C_{24}H_{28}ClNO_6$ | 62.40 (62.31 | 6;11 6.13 | 3.03 3.03) |
| 4 | 7-Cl | 2',4',6' | 260–263 (decomp) | $C_{25}H_{30}ClNO_7$ | 61.04 (60.97 | 6.15 6.12 | 2.85 2.71) |
| 5 | 7-Cl | 2',3'-OCH$_2$O— | 215–218 | $C_{23}H_{24}ClNO_6$ | 61.95 (61.78 | 5.42 5.56 | 3.14 3.31) |

TABLE 49

| Compd. No. | X | Y | m.p. (°C.) | Formula | Elemental Analsis (Found) C | H | N |
|---|---|---|---|---|---|---|---|
| 6 | 7-Cl | 3',4'-OCH$_2$O— | 211–212 | $C_{23}H_{24}ClNO_6$ | 61.95 (61.79 | 5.43 5.37 | 3.14 2.94) |
| 7 | 8-Cl | 2'-Cl | 186–187 | $C_{22}H_{23}Cl_2NO_4$ | 60.56 (60.23 | 5.31 5.58 | 3.21 3.06) |
| 8 | 7,9-Cl | 2'-OCH$_3$ | 265–267 | $C_{23}H_{25}Cl_2NO_5$+0.5H$_2$O | 58.12 (58.18 | 5.51 5.27 | 2.94 2.69) |
| 9 | 7-Cl | 2'-OCH$_3$ | 167–168 | $C_{23}H_{26}ClNO_5$ | 63.96 (63.56 | 6.07 6.14 | 3.24 3.07) |
| 10 | 7-Cl | 2'-Br | 251–253 | $C_{22}H_{23}BrClNO_4$ | 54.96 (54.97 | 4.82 4.85 | 2.91 2.87) |
| 11 | 7-Br | 2'-Cl | 247–250 | $C_{22}H_{23}BrClNO_4$ | 54.96 (54.73 | 4.82 5.12 | 2.91 2.82) |
| 12 | 7-Cl | 2',3'-OCH$_3$ | 244–247 | $C_{24}H_{28}ClNO_6$+0.3H$_2$O | 61.68 (61.65 | 6.17 6.16 | 3.00 2.89) |

Example 75

The compounds obtained in Example 73 were hydrolyzed by the same procedure as in Reference Example 5 and Example 2 to yield the compounds listed in Tables 50 and 51.

TABLE 50

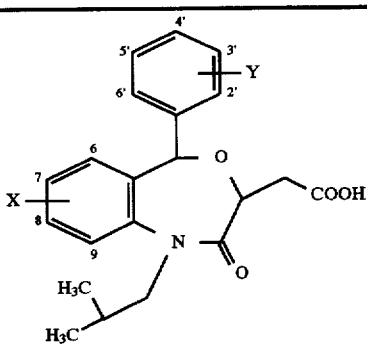

| Compd. No. | X | Y | m.p. (°C.) | Formula | Elemental Analysis (Found) | | |
|---|---|---|---|---|---|---|---|
| | | | | | C | H | N |
| 1 | 7-F | 2'-Cl | 204–206 | $C_{21}H_{21}ClFN_4$ | 62.15 (61.96 | 5.22 5.18 | 3.45 3.66) |
| 2 | 7-OCH$_3$ | 2'-Cl | 92–94 | $C_{22}H_{24}ClNO_5$ +0.4H$_2$O | 62.16 (62.14 | 5.88 5.93 | 3.30 3.28) |
| 3 | 7-Cl | 2',4'-Cl | 236–238 | $C_{21}H_{20}Cl_3NO_4$ | 55.22 (55.12 | 4.41 4.45 | 3.07 3.00) |
| 4 | 7-Cl | 2'-CF3 | 212–225 | $C_{22}H_{21}ClF_3NO_4$ | 57.97 (57.72 | 4.64 4.67 | 3.07 3.05) |

TABLE 51

| Compd. No. | X | Y | m.p. (°C.) | Formula | Elemental Analysis (Found) | | |
|---|---|---|---|---|---|---|---|
| | | | | | C | H | N |
| 5 | 7-Cl | 2'-OCH$_3$ | 219–222 | $C_{22}H_{24}ClNO_5$ | 63.23 (62.88 | 5.79 6.09 | 3.35 3.16) |
| 6 | 7-Cl | 2'-Br | 212–216 | $C_{21}H_{21}BrClNO_4$ | 54.04 (53.68 | 4.53 4.56 | 3.00 3.10) |
| 7 | 7-Br | 2'-Cl | 194–196 | $C_{21}H_{21}BrClNO_4$+0.2H$_2$O | (53.44 (53.44 | 4.49 4.49 | 2.91) 2.91) |
| 8 | 7-Cl | 4'-Cl | 223–225 | $C_{21}H_{21}Cl_2NO_4$ | 59.73 (59.58 | 5.01 5.01 | 3.32 3.23) |
| 9 | H | 2'-CH$_3$ | 192–195 | $C_{22}H_{25}NO_4$ | 71.91 (71.86 | 6.86 6.78 | 3.81 3.80) |
| 10 | 7-Cl | 3'-Cl | 158–160 | $C_{21}H_{21}Cl_2NO_4$+0.2H$_2$O | 59.22 (59.00 | 5.06 5.00 | 3.29 3.23) |
| 11 | 7-CF$_3$ | H | 149–151 | $C_{22}H_{22}F_3NO_4$ | 62.70 (62.51 | 5.26 5.50 | 3.32 3.14) |
| 12 | 7-Cl | H | 190–192 | $C_{21}H_{22}ClNO_4$ | 65.03 (64.94 | 5.72 5.61 | 3.61 3.48) |

Example 76 n-butyl ester of trans-7-chloro-5-(2-chlorophenyl)-1-neopentyl-2-oxo-1,2,3,5-tetrahydro-4,1-benzoxazepine-3-acetic acid A solution of 0.4 g of trans-7-chloro-5-(2-chlorophenyl)-1-neopentyl-2-oxo-1,2,3,5-tetrahydro-4,1-benzoxazepine-3-acetic acid as obtained in Example 2, 0.21 ml of n-butyl iodide and 0.21 ml of triethylamine in 5 ml of dimethylformamide was stirred overnight at room temperature. After ethyl acetate was added, the mixture was washed with dilute hydrochloric acid, an aqueous solution of sodium hydrogen carbonate and water. After the solution was dried, the solvent was removed and the residue was subjected to silica gel column chromatography to yield 0.25 g of a crystal.

Melting point: 106°–109° C.

Elemental analysis (for $C_{26}H_{31}Cl_2NO_4$) Calcd.: C 63.42; H 6.35; N 2.84 Found: C 63.42; H 6.39; N 2.71

Example 77

By the same procedure as in Example 76, the compounds listed in Tables 52 through 54 were synthesized.

TABLE 52

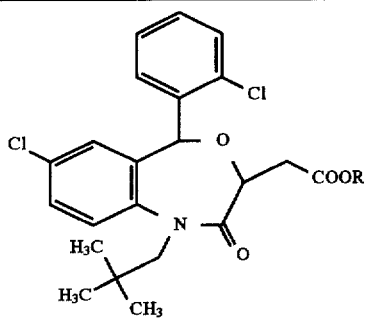

| Compd. No. | R | m.p. (°C.) | Formula | Elemental Analysis(Found) C | H | N |
|---|---|---|---|---|---|---|
| 1 | —CH₂OC(=O)C(CH₃)₃ | oil | C₂₉H₃₄Cl₂NO₆ | ¹H-NMR(CDCl₃) δ: 0.93(9H, s, Buᵗ), 1.19(9H, s, Buᵗ), 2.86(1H, dd, J=16.8, 6.4H), 3.09(1H, dd, J=16.6, 7.0Hz), 4.27(1H, t, J=6.8Hz), 4.50(1H, d, J=14.0Hz), 5.73(1H, d, J=15.0Hz), 5.79(1H, d, J=15.0Hz), 6.26(1H, s, C₅—H), 6.5–6.6(1H, m), 7.3–7.8(6H, m, aromatic) | | |
| 2 | —CH(CH₃)OCO-cyclohexyl | oil | C₃₁H₃₇Cl₂NO₇ | ¹H-NMR(CDCl₃) δ: 0.93(9H, s, Buᵗ), 1.1–1.6(6H, m), 1.65–2.0(4H, m), 2.75–3.2(2H, m), 3.3–3.5(1H, m), 4.35–4.7(3H, m), 6.25 and 6.28(1H, each s, C₅—H), 6.52(1H, s, aromatic), 6.7–6.85(1H, m), 7.3–7.8(6H, m, aromatic) | | |

TABLE 53

| Compd. No. | R | m.p (°C.) | Formula | Elemental Analysis(Found) C | H | N |
|---|---|---|---|---|---|---|
| 3 | —CH₂C(=CHC₂H₅)COCH₂CH(CH₃)₂ | oil | C₃₂H₃₉Cl₂NO₆ | ¹H-NMR(CDCl₃) δ: 0.93(6H, d, J=6.8Hz), 0.94 (9H, s, Buᵗ), 1.06(3H, t, J=7.6Hz), 1.85–2.1 (1H, m), 2.2–2.4(2H, m), 2.81(1H, dd, J=16.6, 6.8H), 3.02(1H, dd, J=16.6, 6.8Hz), 3.39(1H, d, J=14.0Hz), 3.92(2H, d, J=6.6 Hz), 4.42(1H, t, J=6.7Hz), 4.50(1H, d, J=14.0Hz), 4.81(1H, d, J=11.6Hz), 4.93(1H, d, J=11.6Hz), 6.25(1H, s, C₅—H), 6.52(1H, s), 7.04(1H, t, J=7.8Hz), 7.3–7.8(6H, m) | | |
| 4 | —CH₂CN(CH₃)₂ (C=O) | 167–168 | C₂₆H₃₀Cl₂N₂O₅ | 59.89 (59.92 | 5.80 5.82 | 5.37 5.15) |
| 5 | —CH₂CN(CH(CH₃)₂)₂ (C=O) | oil | C₃₀H₃₈Cl₂N₂O₅ | ¹H-NMR(CDCl₃) δ: 0.94(9H, s, Buᵗ), 1.1–1.5 (12H, m), 2.99(1H, dd, J=16.8, 6.1Hz), 3.20(1H, dd, J= 16.8, 7.2Hz), 3.39(1H, d, J=14.0Hz), 3.3–3.8(2H, m), 4.4–4.65 (3H, m), 4.78(1H, d, J=14.0Hz), 6.27(1H, s), 6.52(1H, s), 7.3–7.8(6H, m) | | |
| 6 | —CH₂-(5-methyl-2-oxo-1,3-dioxol-4-yl) | 165–166 | C₂₇H₂₁Cl₂NO₇ | 59.13 (59.21 | 4.96 5.28 | 2.55 2.46) |
| 7 | —CH₂-(3-oxo-1(3H)-isobenzofuranyl) | 191–193 | C₃₂H₂₉Cl₂NO₆ | 64.65 (64.67 | 4.92 5.27 | 2.36 2.14) |

TABLE 54

| Compd. No. | R | m.p (°C.) | Formula | Elemental Analysis(Found) C | H | N |
|---|---|---|---|---|---|---|
| 8 | —CH$_3$ | 158–159 | C$_{23}$H$_{25}$Cl$_2$NO$_4$ | 61.34 (61.48 | 5.60 5.78 | 3.11 2.84) |
| 9 | —CH$_2$—C$_6$H$_5$ | 122–123 | C$_{29}$H$_{29}$Cl$_2$NO$_4$ · 1/2H$_2$O | 65.54 (65.49 | 5.69 5.70 | 2.64 2.43) |
| 10 | —CH$_2$COOCH$_3$ | 137–138 | C$_{25}$H$_{27}$Cl$_2$NO$_6$ | 59.06 (59.11 | 5.35 5.34 | 2.76 2.60) |
| 11 | —CH$_2$CH=CH$_2$ | 108–109 | C$_{25}$H$_{27}$Cl$_2$NO$_4$ | 63.03 (63.12 | 5.71 5.86 | 2.94 2.77) |
| 12 | —CH$_2$—C$_6$H$_{11}$ | 89–90 | C$_{29}$H$_{35}$Cl$_2$NO$_4$ | 65.41 (65.62 | 6.62 6.51 | 2.63 2.42) |
| 13 | —CH$_2$COO—C(CH$_3$)$_3$ | 140 | C$_{28}$H$_{33}$Cl$_2$NO$_6$ | 61.09 (60.87 | 6.04 6.14 | 2.54 2.48) |

Example 78

Phenyl ester of trans-7-chloro-5-(2-chlorophenyl)-1-neopentyl-2-oxo-1,2,3,5-tetrahydro-4,1-benzoxazepine-3-acetic acid 0.3 g of trans-7-chloro-5-(2-chlorophenyl)-1-neopentyl-2-oxo-1,2,3,5-tetrahydro-4,1-benzoxazepine-3-acetic acid as obtained in Example 2 and 0.072 g of phenol were dissolved in 12 ml of dichloromethane, and 10 ml of 1-ethyl-3-(3-dimethylaminopropyl)carbodiimide hydrochloride was added, followed by stirring at room temperature for 1.5 hours. The reaction mixture was concentrated, ethyl acetate was added and the mixture was washed with water, after which the organic layer was dried and the solvent was distilled off. The residue was subjected to silica gel column chromatography to yield 0.28 g of a crystal.

Melting point: 147°–148° C.

Elemental analysis (for C$_{28}$H$_{27}$Cl$_2$NO$_4$) Calcd.: C 65.63; H 5.31; N 2.73 Found: C 65.55; H 5.45; N 2.46

Example 79

The compounds obtained in Example 2 were subjected to the same procedure as in Example 78 to yield the compounds listed in Table 55.

TABLE 55

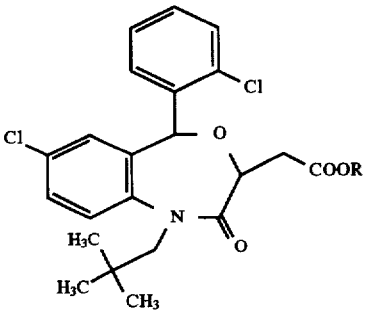

| Compd. No. | R | m.p (°C.) | Formula | Elemental Analysis(Found) C | H | N |
|---|---|---|---|---|---|---|
| 1 | —C$_6$H$_4$—COOC$_2$H$_5$ | 199–200 | C$_{31}$H$_{31}$Cl$_2$NO$_6$ | 63.70 (63.71 | 5.35 5.63 | 2.10 2.11) |
| 2 | —CH(CH$_3$)$_2$ | 100–101 | C$_{25}$H$_{29}$Cl$_2$NO$_4$ | 62.76 (62.91 | 6.11 6.32 | 2.93 2.72) |

Example 80

Cyclohexylthio ester of trans-7-chloro-5-(2-chlorophenyl)-1-neopentyl-2-oxo-1,2,3,5-tetrahydro-4,1-benzoxazepine-3-acetic acid 0.3 g of trans-7-chloro-5-(2-chlorophenyl)-1-neopentyl-2-oxo-1,2,3,5-tetrahydro-4,1-benzoxazepine-3-acetic acid as obtained in Example 2 and 0.09 g of cyclohexylmercaptan were subjected to the same procedure as in Example 78 to yield 0.19 g of a crystalline compound.

Melting point: 157°–158° C.

Elemental analysis (for $C_{28}H_{33}Cl_2NO_3S$) Calcd.: C 62.91; H 6.22; N 2.62 Found: C 62.94; H 6.08; N 2.40

Example 81 t-butyl ester of trans-7-chloro-5-(2-chlorophenyl)-1-neopentyl-2-oxo-1,2,3,5-tetrahydro-4,1-benzoxazepine-3-acetic acid.

To a solution of 1.2 g of trans-7-chloro-5-(2-chlorophenyl)-1-neopentyl-2-oxo-1,2,3,5-tetrahydro-4,1-benzoxazepine-3-acetic acid as obtained in Example 2 in 40 ml of dichloromethane, 10 ml of isobutene and 0.1 ml of concentrate sulfuric acid were added, and the mixture was kept standing at room temperature for 3 days. After reaction mixture concentration, ethyl acetate and an aqueous solution of sodium hydrogen carbonate were added, and the organic layer was washed with water and dried, after which the solvent was removed and the residue was subjected to silica gel column chromatography to yield 1.07 g of a crystal.

Melting point: 141°–142° C.

Elemental analysis (for $C_{26}H_{31}ClNO_4$) Calcd.: C 63.42; H 6.35; N 2.84 Found: C 63.52; H 6.37; N 2.80

Example 82

Carboxymethyl ester of trans-7-chloro-5-(2-chlorophenyl)-1-neopentyl-2-oxo-1,2,3,5-tetrahydro-4,1-benzoxazepine-3-acetic acid 0.3 g of t-butoxycarbonylmethyl ester of trans-7-chloro-5-(2-chlorophenyl)-1-neopentyl-2-oxo-1,2,3,5-tetrahydro-4,1-benzoxazepine-3-acetic acid as obtained in Example 77 was dissolved in 3 ml of trifluoroacetic acid, and this solution was kept standing at room temperature for 30 minutes. After the solution was concentrated, ethyl acetate was added, followed by washing with water and subsequent drying, after which the solvent was removed and the residue was recrystallized from petroleum ether to yield 0.24 g of a crystal.

Melting point: 186°–190° C.

Elemental analysis (for $C_{24}H_{25}Cl_2NO_6 \cdot \frac{1}{2}H_2O$) Calcd.: C 57.27; H 5.21; N 2.78 Found: C 57.38; H 5.05; N 2.78

Example 83

Methyl ester of 2-[trans-7-chloro-5-(2-chlorophenyl)-1-isopropyl-2-oxo-1,2,3,5-tetrahydro-4,1-benzoxazepine-3-acetyl]aminobenzoic acid 0.35 g of trans-7-chloro-5-(2-chlorophenyl)-1-isopropyl-2-oxo-1,2,3,5-tetrahydro-4,1-benzoxazepine-3-acetic acid as obtained in Reference Example 5 was dissolved in 10 ml of toluene, and 0.63 ml of thionyl chloride was added, followed by stirring for 30 minutes while heating at 90° C. The solution was concentrated and the residue was dissolved in 10 ml of dichloromethane, and 0.13 ml of methyl ester of 2-aminobenzoic acid and 0.14 ml of triethylamine were added, followed by stirring at room temperature for 30 minutes. After the solution was concentrated, ethyl acetate was added, and the mixture was washed with dilute hydrochloric acid, an aqueous solution of sodium hydrogen carbonate and water. The solvent was removed and the residue was subjected to silica gel column chromatography to yield 0.25 g of a crystal.

Melting point: 188°–190° C.

Elemental analysis (for $C_{28}H_{26}Cl_2N_2O_5$) Calcd.: C 62.11; H 4.91; N 5.24 Found: C 61.94; H 4.91; N 5.24

Example 84

By the same procedure as in Example 83, the compounds listed in Tables 56 and 57 were obtained.

TABLE 56
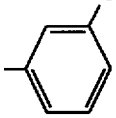
| Compd. No. | R | m.p (°C.) | Formula | Elemental Analysis (Found) | | |
|---|---|---|---|---|---|---|
| | | | | C | H | N |
| 1 | 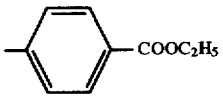 (COOC₂H₅, meta) | 161–163 | $C_{29}H_{28}Cl_2N_2O_5$ | 62.71 (62.62 | 5.08 4.96 | 5.04 5.15) |
| 2 | 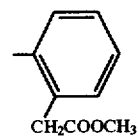 —COOC₂H₅ | 236–238 | $C_{29}H_{28}Cl_2N_2O_5$ | 62.71 (62.67 | 5.08 5.26 | 5.04 5.09) |
| 3 | 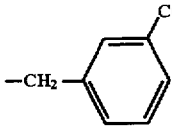 CH₂COOCH₃ | 172–174 | $C_{29}H_{28}Cl_2N_2O_5$ | 62.71 (62.63 | 5.08 5.00 | 5.04 5.28) |
| 4 | —CH₂—  COOCH₃ | 92–94 | $C_{29}H_{28}Cl_2N_2O_5$ ·1/2H₂O | 61.71 (61.85 | 5.18 5.33 | 1.96 5.10) |
TABLE 57
| Compd. No. | R | m.p (°C.) | Formula | Elemental Analysis (Found) | | |
|---|---|---|---|---|---|---|
| | | | | C | H | N |
| 5 | —CH₂— 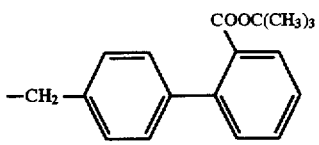 —COOCH₃ | 139–142 | $C_{29}H_{28}Cl_2N_2O_5$ | 62.71 (62.62 | 5.08 5.12 | 5.04 4.96) |
| 6 | —CH₂— (biphenyl-COOC(CH₃)₃) | oil | $C_{38}H_{38}Cl_2N_2O_5$ | ¹H-NMR(CDCl₃) δ: 1.27(9H, s, Buᵗ), 1.29(3H, d, J=6.8Hz),1.54(3H, d, J= 6.8Hz), 2.71(1H, dd, J=14.2, 6.0Hz), 2.95(1H, dd, J=14.2, 7.4Hz), 4.38(1H, t, J= 6.6Hz), 4.45–4.6(1H, m), 4.7–4.9(2H, m), 6.00(1H, s), 6.3–6.45(1H, m, NH), 6.50(1H, d, J=2.4Hz), 7.2–7.85(14H, m) | | | |

Example 85

2-[trans-7-chloro-5-(2-chlorophenyl)-1-isopropyl-2-oxo-1,2,3,5-tetrahydro-4,1-benzoxazepine-3-acetyl]aminobenzoic acid 0.15 g of methyl ester of 2-[trans-7-chloro-5-(2-chlorophenyl)-1-isopropyl-2-oxo-1,2,3,5-tetrahydro-4,1-benzoxazepine-3-acetyl]aminobenzoic acid as obtained in Example 83 was subjected to the same procedure of ester hydrolysis as in Example 34 to yield 0.11 g of a crystal.

Melting point: 208°–211° C.

Elemental analysis (for $C_{27}H_{24}Cl_2N_2O_5$) Calcd.: C 61.49; H 4.59; N 5.31 Found: C 61.22; H 4.68; N 5.35

Example 86

The compounds obtained in Example 84 were subjected to the same procedure of ester hydrolysis as in Example 34 to yield the compounds listed in Table 58.

TABLE 58

| Compd. No. | R | m.p (°C.) | Formula | Elemental Analysis (Found) C | H | N |
|---|---|---|---|---|---|---|
| 1 | ![-C6H4-COOH (meta)] | 149–152 | $C_{27}H_{24}Cl_2N_2O_5$ | 61.49 (61.81 | 4.59 4.79 | 5.31 5.45) |
| 2 | ![-C6H4-COOH (para)] | >300 | $C_{27}H_{24}Cl_2N_2O_5 \cdot 1/4H_2O$ | 60.97 (60.97 | 4.64 4.76 | 5.27 5.39) |
| 3 | ![-C6H4-CH2COOH (ortho)] | 223–225 | $C_{28}H_{26}Cl_2N_2O_5$ | 62.11 (61.96 | 4.84 4.82 | 5.17 5.35) |
| 4 | $-CH_2-$C6H4-COOH (meta) | 240–244 | $C_{28}H_{26}Cl_2N_2O_5$ | 62.11 (62.13 | 4.84 5.00 | 5.17 5.17) |
| 5 | $-CH_2-$C6H4-COOH (para) | 242–244 (decomp) | $C_{28}H_{26}Cl_2N_2O_5$ | 62.11 (61.96 | 4.84 4.85 | 5.17 5.25) |

Example 87

Ethyl ester of 4-[trans-7-chloro-5-(2-chlorophenyl)-1-neopentyl-2-oxo-1,2,3,5-tetrahydro-4,1-benzoxazepine-3-acetyl]aminobenzoic acid 0.6 g of trans-7-chloro-5-(2-chlorophenyl)-1-neopentyl-2-oxo-1,2,3,5-tetrahydro-4,1-benzoxazepine-3-acetic acid as obtained in Example 2 and 0.27 g of ethyl ester of 4-aminobenzoic acid were subjected to the same procedure as in Example 83 to yield 0.43 g of a crystal.

Melting point: 218°–210° C.

Elemental analysis (for $C_{31}H_{32}Cl_2N_2O_5$) Calcd.: C 63.81; H 5.53; N 4.80 Found: C 63.79; H 5.38; N 4.70

Example 88

By the same procedure as in Example 83, the compounds listed in Tables 59 and 60 were synthesized.

TABLE 59

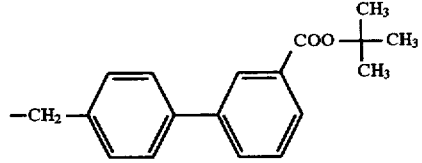

| Compd. No. | R | m.p (°C.) | Formula | Elemental Analysis(Found) C | H | N |
|---|---|---|---|---|---|---|
| 1 | —CH₂—C₆H₄—COOCH₃ | 181–182 | $C_{31}H_{32}Cl_2N_2O_5$ | 63.81 (63.85 | 5.53 5.41 | 4.80 4.66) |
| 2 | —CH₂—C₆H₄—COOCH₃ | 208–209 | $C_{31}H_{32}Cl_2N_2O_5$ | 63.81 (63.62 | 5.53 5.53 | 4.80 4.79) |
| 3 | —C₆H₄—CH₂COOCH₃ | 224–225 | $C_{31}H_{32}Cl_2N_2O_5$ | 63.81 (63.69 | 5.53 5.60 | 4.80 4.54) |
| 4 | —CH₂CH₂—C₆H₄—COOCH₃ | 114–115 | $C_{32}H_{34}Cl_2N_2O_5$ | 64.32 (61.22 | 5.74 5.97 | 4.69 4.43) |

TABLE 60

| Compd. No. | R | m.p (°C.) | Formula C | Elemental Analysis(Found) H | N |
|---|---|---|---|---|---|
| 5 | —CH₂—(biphenyl)—COO—C(CH₃)₃ | oil | ¹H-NMR(CDCl₃) δ: 0.94(9H, s, Buᵗ), 1.27(9H, s, Buᵗ), 2.72(1H, dd, J=14.2, 6.0Hz), 2.92(1H, dd, J=14.2, 7.2Hz), 3.40(1H, d, J=14.0Hz), 4.30–4.7(4H, m), 6.27(1H, s), 5.52(1H, d, J=1.6Hz), 7.1–7.9(14H, m) | | |

Example 89

The compounds synthesized in Examples 87 and 88 were subjected to the same procedure as in Examples 24 and 82 to yield the compounds listed in Tables 61 and 62.

TABLE 61

| Compd. No. | R | m.p (°C.) | Formula | Elemental Analysis(Found) | | |
|---|---|---|---|---|---|---|
| | | | | C | H | N |
| 1 | —⟨phenyl⟩—COOH | 283–286 | $C_{29}H_{28}Cl_2N_2O_5$ | 62.71 (62.95 | 5.08 5.39 | 5.04 5.01) |
| 2 | —$CH_2$—⟨phenyl⟩-COOH (ortho) | 220–223 | $C_{30}H_{30}Cl_2N_2O_5$ | 63.27 (63.24 | 5.31 5.23 | 4.92 4.78) |
| 3 | —$CH_2$—⟨phenyl⟩—COOH | 251–253 | $C_{30}H_{30}Cl_2N_2O_5$ | 63.27 (62.98 | 5.31 5.43 | 4.92 4.61) |
| 4 | —⟨phenyl⟩—$CH_2COOH$ | 156–158 | $C_{30}H_{30}Cl_2N_2O_5$ | 63.27 (63.39 | 5.31 5.21 | 4.92 4.76) |

TABLE 62

| Compd. No. | R | m.p (°C.) | Formula | Elemental Analysis(Found) | | |
|---|---|---|---|---|---|---|
| | | | | C | H | N |
| 5 | —$CH_2CH_2$—⟨phenyl⟩—COOH | 143–145 | $C_{31}H_{32}Cl_2N_2O_5$ 1/2$H_2O$ | 62.28 (62.32 | 5.61 5.78 | 4.73 4.49) |
| 6 | —$CH_2$—⟨biphenyl⟩—COOH | 158–161 | $C_{38}H_{38}Cl_2N_2O_5$ | 66.77 (66.76 | 5.60 5.80 | 4.33 4.39) |

Example 90

Trans-7-chloro-5-(2-chlorophenyl)-1-isobutyl-2-oxo-1,2,3,5-tetrahydro-4,1-benzoxazepine-3-acetamide 1.0 g of trans-7-chloro-5-(2-chlorophenyl)-1-isobutyl-2-oxo-1,2,3,5-tetrahydro-4,1-benzoxazepine-3-acetic acid and 0.5 g of ammonium chloride were dissolved in 8 ml of dimethylformamide, and 0.46 g of 1-ethyl-3-(3-dimethylaminopropyl)carbodiimide hydrochloride and 0.7 ml of triethylamine were added, followed by stirring at room temperature for 30 minutes. After water was added, the solution was extracted with ethyl acetate, followed by washing with water, after which the solvent was removed and the residue was recrystallized to yield 0.75 g of a crystal.

Melting point: 271°–272° C.

Elemental analysis (for $C_{21}H_{22}Cl_2N_2O_3$) Calcd.: C 59.87; H 5.26; N 6.65 Found: C 59.91; H 5.33; N 6.91

Example 91

The compound obtained in Example 2 and Reference Example 5 and various amines were subjected to the same procedure as in Example 90 to yield the compounds listed in Tables 63 through 67.

TABLE 63

| Compd. No. | $R^1$ | $R^2$ | m.p (°C.) | Formula | Elemental Analysis(Found) | | |
|---|---|---|---|---|---|---|---|
| | | | | | C | H | N |
| 1 | $CH(CH_3)_2$ | $NH_2$ | 226–227 | $C_{20}H_{20}Cl_2N_2O_3$ | 58.98 (58.93 | 4.95 4.85 | 6.88 6.75) |
| 2 | $CH_3$ | $NH_2$ | 187–189 | $C_{18}H_{16}Cl_2N_2O_3$ | 56.34 (56.53 | 4.33 4.55 | 7.30 6.94) |
| 3 | $-CH_2-$cyclohexyl | $NH_2$ | 246–248 | $C_{24}H_{26}Cl_2N_2O_3$ | 62.48 (62.28 | 5.68 5.87 | 6.07 5.86) |
| 4 | $-CH_2-$phenyl | $NH_2$ | 185–187 | $C_{24}H_{20}Cl_2N_2O_3$ | 63.31 (63.23 | 4.43 4.49 | 6.15 6.10) |

TABLE 64

| Compd. No. | $R_1$ | $R_2$ | m.p. (°C.) | Formula | Elemental Analysis (Found) | | |
|---|---|---|---|---|---|---|---|
| | | | | | C | H | N |
| 5 | $-CH_2-$phenyl | $NHCH_3$ | 189–190 | $C_{25}H_{22}Cl_2N_2O_3$ | 63.97 (64.01 | 4.72 4.53 | 5.97 5.90) |
| 6 | $-CH_2-$phenyl | $N(CH_3)_2$ | 183–184 | $C_{26}H_{24}Cl_2N_2O_3$ ·1/4$H_2O$ | 64.00 (63.97 | 5.06 5.03 | 5.74 5.81) |
| 7 | $-CH_2-$phenyl-$OCH_3$ | $NHCH_3$ | 104–107 | $C_{26}H_{24}Cl_2N_2O_4$ ·1/2$H_2O$ | 61.42 (61.65 | 4.96 5.05 | 5.51 5.40) |
| 8 | $-CH_2CH_2-$phenyl | $NHCH_3$ | 193–195 | $C_{26}H_{24}Cl_2N_2O_3$ | 64.60 (64.42 | 5.00 4.99 | 5.80 5.73) |
| 9 | $-CH_2-$phenyl-$OCH_3$ | $NHCH_3$ | 171–172 | $C_{26}H_{24}Cl_2N_2O_4$ | 62.53 (62.24 | 4.84 5.05 | 5.61 5.34) |

TABLE 64-continued

| Compd. No. | $R_1$ | $R_2$ | m.p. (°C.) | Formula | C | H | N |
|---|---|---|---|---|---|---|---|
| 10 | —CH$_2$-(1-naphthyl) | NHCH$_3$ | 190–191 | C$_{20}$H$_{24}$Cl$_2$N$_2$O$_3$ | 67.06 (66.78 | 4.66 4.56 | 5.39 5.26) |
| 11 | CH$_2$CH(CH$_3$)$_2$ | N(CH$_3$)$_2$ | 134–135 | C$_{23}$H$_{26}$Cl$_2$N$_2$O$_3$ | 61.47 (61.33 | 5.83 5.76 | 6.23 6.18) |

TABLE 65

| Compd. No. | $R_1$ | $R_2$ | m.p. (°C.) | Formula | C | H | N |
|---|---|---|---|---|---|---|---|
| 12 | CH$_2$CH(CH$_3$)$_2$ | H, N(CH$_2$)$_3$CH$_3$ | 135–136 | C$_{25}$H$_{30}$Cl$_2$N$_2$O$_3$ | 62.89 (63.15 | 6.33 6.38 | 5.87 5.87) |
| 13 | CH$_2$CH(CH$_3$)$_2$ | H, NCH$_2$-Ph | 168–169 | C$_{28}$H$_{28}$Cl$_2$N$_2$O$_3$ | 65.76 (65.89 | 5.52 5.67 | 5.48 5.57) |
| 14 | —CH$_2$-Ph | 1,2,3,4-tetrahydroisoquinolin-2-yl | 141–142 | C$_{33}$H$_{28}$Cl$_2$N$_2$O$_3$ ·1/2H$_2$O | 68.28 (68.33 | 5.04 5.12 | 4.83 4.65) |
| 15 | —CH$_2$-Ph | H, NCH$_2$-(2-OCH$_3$-C$_6$H$_4$) | 177–178 | C$_{33}$H$_{28}$Cl$_2$N$_2$O$_4$ | 66.79 (66.97 | 4.90 4.91 | 4.87 4.83) |
| 16 | —CH$_2$-Ph | 4-phenylpiperazin-1-yl | 177–179 | C$_{35}$H$_{33}$Cl$_2$N$_3$O$_3$ | 68.40 (68.35 | 5.41 5.57 | 6.84 6.82) |
| 17 | CH$_2$C(CH$_3$)$_3$ | NHNH$_2$ | 248–250 | C$_{22}$H$_{25}$Cl$_2$N$_3$O$_3$ | 58.67 (58.76 | 5.60 5.90 | 9.33 8.93) |
| 18 | CH$_2$C(CH$_3$)$_3$ | NHN(CH$_3$)$_2$ | 232–235 | C$_{24}$H$_{29}$Cl$_2$N$_3$O$_3$ | 60.25 (60.14 | 6.11 6.20 | 8.78 8.51) |

TABLE 66

| Compd. No. | $R_1$ | $R_2$ | m.p. (°C.) | Formula | C | H | N |
|---|---|---|---|---|---|---|---|
| 19 | CH$_2$CH(CH$_3$)$_2$ | 3-amino-1,2,4-triazol-yl (HN–C(=N)–NH–N=) | 270–271 | C$_{22}$H$_{22}$Cl$_2$N$_6$O$_3$ | 53.50 (53.63 | 4.59 4.43 | 17.02 16.88) |
| 20 | CH(CH$_3$)$_2$ | H, N(CH$_2$)$_2$C(O)NH$_2$ | 247–248 | C$_{22}$H$_{23}$Cl$_2$N$_3$O$_4$ | 56.91 (56.69 | 4.99 4.90 | 9.05 8.96) |
| 21 | CH$_2$CH(CH$_3$)$_2$ | NH$_2$ | 271–272 | C$_{21}$H$_{22}$Cl$_2$N$_2$O$_3$ | 59.87 (59.91 | 5.26 5.33 | 6.65 6.91) |

TABLE 67

| Compd. No. | R$_1$ | R$_2$ | m.p. (°C.) | Formula | Elemental Analysis (Found) C | H | N |
|---|---|---|---|---|---|---|---|
| 22 | CH$_2$C(CH$_3$)$_3$ | H-NCH$_2$-C$_6$H$_4$-N(CH$_3$)$_2$ | 198–199 | C$_{31}$H$_{35}$Cl$_2$N$_3$O$_3$ | 65.49 (65.91 | 6.20 6.50 | 7.39 7.28) |
| 23 | CH$_2$C(CH$_3$)$_3$ | piperazinyl-C$_6$H$_4$-F | 132–133 | C$_{32}$H$_{34}$Cl$_2$FN$_3$O$_3$ | 64.21 (64.45 | 5.73 5.83 | 7.02 7.13) |
| 24 | CH$_2$C(CH$_3$)$_3$ | H—N(CH$_2$)$_3$N(CH$_3$)$_2$ | 118–121 | C$_{27}$H$_{35}$Cl$_2$N$_3$O$_3$ (COOH)$_2$.1/2H$_2$O | 56.22 (56.37 | 6.18 6.35 | 6.78 6.56) |
| 25 | CH$_2$C(CH$_3$)$_3$ | H—N(CH$_2$)$_2$N(pyrrolidinyl) | 179–180 | C$_{28}$H$_{35}$Cl$_2$N$_3$O$_3$ .1/4H$_2$O | 62.62 (62.66 | 6.66 6.54 | 7.83 7.85) |

Example 92

Ethyl ester of 7-chloro-5-(2-chlorophenyl)-1-isobutyl-5-methyl-1,2,3,5-tetrahydro-2-oxo-4,1-benzoxazepine-3-acetic acid (1) 4-chloro-2-[α-hydroxy-α-methyl-(2-chlorophenyl) methyl]aniline A tetrahydrofuran solution of a Grignard reagent synthesized from 0.45 g of magnesium and 1.2 g of methyl iodide was added dropwise to a solution of 2.0 g of 2-amino-5-chloro-2'-chlorobenzophenone in 20 ml of tetrahydrofuran. After refluxing with heating for 10 minutes, the mixture was cooled with water, and a saturated aqueous solution of ammonium chloride was added, and the mixture was extracted with ethyl acetate. The solvent was distilled off, and the residue was subjected to silica gel column chromatography to yield 1.5 g of an oily compound.

$^1$H-NMR (CDCl$_3$) δ: 8:2.04 (3H, s, CH$_3$), 7.0–7.8 (7H, m)

(2) N-isobutyl-4-chloro-2-[α-hydroxy-α-methyl-(2-chlorophenyl)methyl]aniline

To a solution of 1.2 g of 4-chloro-2-[α-hydroxy-α-methyl-(2-chlorophenyl)methyl]aniline and 0.32 g of isobutylaldehyde in 8 ml of acetic acid, 0.25 g of sodium borohydride was added, followed by stirring at room temperature for 40 minutes. After water was added, the reaction mixture was extracted with ethyl acetate, after which the solvent was removed and the residue was subjected to silica gel column chromatography to yield 1.4 g of an oily compound $^1$H-NMR (CDCl$_3$) δ: 0.75, 0.80 (6H, each, d, CH$_3$), 1.67 (1H, m), 1.99 (3H, s, CH$_3$), 2.74 (2H, d), 7.05–7.8 (7H, m)

(3) Ethyl ester of 3-[N-[4-chloro-2-[α-hydroxy-α-methyl-(2-chlorophenylmethyl)phenyl]-N-isobutylcarbamoyl]acrylic acid 1.4 g of N-isobutyl-4-chloro-2-[α-hydroxy-α-methyl-(2-chlorophenyl)methyl]aniline was dissolved in 15 ml of dichloromethane, and 0.7 g of sodium hydrogen carbonate was added, after which a solution of 0.68 g of monomethyl ester of chlorofumaric acid in 4 ml of dichloromethane was added dropwise over a period of 20 minutes. After the mixture was washed with water and dried, the solvent was removed and the residue was subjected to silica gel column chromatography to yield 0.65 g of a crystal.

Melting point: 153°–154° C.
Elemental analysis (for C$_{24}$H$^{27}$Cl$_2$NO$_4$) Calcd.: C 62.07; H 5.86; N 3.02 Found: C 62.19; H 5.86; N 2.90

(4) Ethyl ester of 7-chloro-5-(2-chlorophenyl)-1-isobutyl-5-methyl-1,2,3,5-tetrahydro-2-oxo-4,1-benzoxazepine-3-acetic acid 1.0 g of ethyl ester of 3-[N-[4-chloro-2-[α-hydroxy-α-methyl-(2-chlorophenylmethyl)phenyl]-N-isobutylcarbamoyl]acrylic acid was dissolved in 10 ml of ethanol, and 0.35 g of potassium carbonate was added, followed by stirring for 12 hours. After water was added, the reaction mixture was extracted with ethyl acetate and dried, after which the solvent was removed and the residue was subjected to silica gel column chromatography to yield 0.8 g of a crystal. Melting point: 119°–120° C.

Elemental analysis (for C$_{24}$ H$_{27}$Cl$_2$NO$_4$) Calcd.: C 62.07; H 5.86; N 3.02 Found: C 62.08; H 5.93; N 2.98

Example 93

7-chloro-5-(2-chlorophenyl)-1-isobutyl-5-methyl-1,2,3,5-tetrahydro-2-oxo-4,1-benzoxazepine-3-acetic acid 0.3 g of ethyl ester of 7-chloro-5-(2-chlorophenyl)-1-isobutyl-5-methyl-1,2,3,5-tetrahydro-2-oxo-4,1-benzoxazepine-3-acetic acid was dissolved in 10 ml of methanol, and 2 ml of a 10% aqueous solution of potassium carbonate was added, followed by stirring for 40 minutes with heating at 70° C. After acidification with dilute hydrochloric acid, the reaction mixture was 5 extracted with ethyl acetate. After the extract was dried, the solvent was removed and the residue was recrystallized from ethyl acetate-hexane to yield 0.16 g of a crystal.

Melting point: 153°–154° C.
Elemental analysis (for C$_{22}$H$_{23}$Cl$_2$NO$_4$) Calcd.: C 60.56; H 5.31; N 3.21 Found: C 60.59; H 5.32; N 2.92

Reference Example 9

Ethyl ester of trans-7-chloro-5-(2-chlorophenyl)-1-(2,2,2-trifluoroethyl)-1,2,3,5-tetrahydro-2-oxo-4,1-benzoxazepine-3-acetic acid (1) 5-chloro-α-(2-chlorophenyl)-2-(trifluoroacetylamino) benzyl alcohol To a solution of 1.0 g of 2-amino-5-chloro-α-(2-chlorophenyl)benzyl alcohol in 12 ml of dichloromethane, a solution of 0.8 g of anhydrous trifluoroacetic acid in 2 ml of dichloromethane was added. After reaction, an aqueous solution of sodium hydrogen carbonate was added, and the organic layer was dried, after which the solvent was removed and the residue was recrystallized from hexane to yield 1.3 g of a crystal.

(2) 5-chloro-α-(2-chlorophenyl)-2-(2,2,2-trifluoroethylamino)benzyl alcohol

To a suspension of 0.25 g of lithium aluminum hydride in 20 ml of absolute ethyl ether, a solution of 1.2 g of 5-chloro-α-(2-chlorophenyl)-2-(trifluoroacetylamino) benzyl alcohol in 5 ml of tetrahydrofuran was added dropwise. After mixture stirring at room temperature for 1 hour, water was added, and the organic layer was dried, after which the solvent was removed and the residue was subjected to silica gel column chromatography to yield 1.0 g of an oily compound.

(3) Ethyl ester of 3-[N-[4-chloro-2-(α-hydroxy-2-chlorophenylmethyl)phenyl]-N-(2,2,2-trifluoroethyl)carbamoyl]acrylic acid 5-chloro-α-(2-chlorophenyl)-2-(2,2,2-trifluoroethylamino)benzyl alcohol and monomethyl ester of chlorofumaric acid were subjected to the same procedure as in Reference Example 1 to yield an oily compound.

(4) Ethyl ester of trans-7-chloro-5-(2-chlorophenyl)-1-(2,2,2-trifluoroethyl)-1,2,3,5-tetrahydro-2-oxo-4,1-benzoxazepine-3-acetic acid Ethyl ester of 3-[N-[4-chloro-2-(α-hydroxy-2-chlorophenylmethyl)phenyl]-N-(2,2,2-trifluoroethyl)carbamoyl]acrylic acid was subjected to the same procedure as in Reference Example 2 to yield a crystal.

Melting point: 163°–164° C.

Elemental analysis (for $C_{21}H_{21}Cl_2F_3NO_4$) Calcd.: C 52.96; H 3.81; N 2.94 Found: C 52.93; H 3.88; N 2.91

Reference Example 10

By the same procedure as in Reference Examples 2 and 9, the compounds listed in Table 68 were synthesized.

TABLE 68

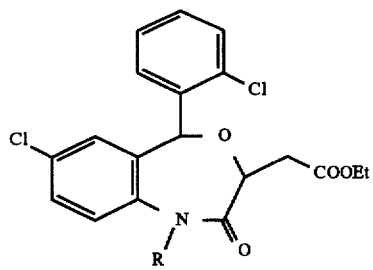

| Compd. No. | R | m.p. (°C.) | Formula | C | H | N |
|---|---|---|---|---|---|---|
| 1 | $CH_2CF_2CF_3$ | oil | $^1$H-NMR(CDCl$_3$) δ: 1.25(3H, t), 2.8, 3.1(2H, δdd), 4.0–4.3 (3H, m), 4.48(1H, dd), 5.1–5.35(1H, m), 6.18(1H, s), 6.56 (1H, d), 7.2–7.8(6H, m) | | | |
| 2 | CH$_2$—◁ | 106–107 | $C_{23}H_{23}Cl_2NO_4$ | 61.62 (61.66 | 5.17 5.31 | 3.12 3.16) |

Example 94

By the same procedure as in Reference Examples 2 and 9, the compounds listed in Table 69 were synthesized.

TABLE 69

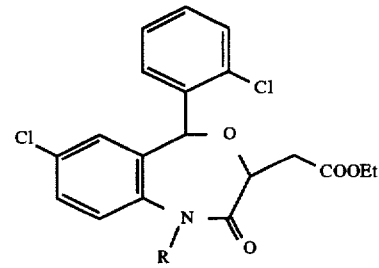

| Compd. No. | R | m.p. (°C.) | Formula | C | H | N |
|---|---|---|---|---|---|---|
| 1 | $CH_2CH_2C(CH_3)_3$ | oil | $^1$H-NMR(CDCl$_3$) δ: 0.94(9H, s), 1.25(3H, t), 1.3–1.8(2H, m), 2.8, 3.08(2H, δdd), 3.54(1H, dt), 4.13 (2H, dq), 4.35–4.6(2H, m), 6.0(1H, s), 6.52(1H, d), 7.1–7.8(6H, m) | | | |

Reference Example 11

The compounds obtained in Reference Examples 9 and 10 were subjected to the same procedure as in Reference Example 4 to Field the compounds listed in Table 70.

TABLE 70

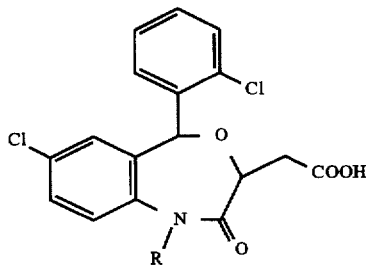

| Compd. No. | R | m.p. (°C.) | Formula | Elemental Analysis (Found) | | |
|---|---|---|---|---|---|---|
| | | | | C | H | N |
| 1 | $CH_2CF_2CF_3$ | 186–187 | $C_{20}H_{14}Cl_2F_5NO_4$ | 48.21 (47.91 | 2.83 2.82 | 2.81 2.95) |
| 2 | $CH_2$-◁ | 230–232 | $C_{21}H_{19}Cl_2NO_4$ | 60.01 (59.74 | 4.56 1.55 | 3.33 3.29) |
| 3 | $CH_2CF_3$ | 213–215 | $C_{19}H_{14}Cl_2F_3NO_4$ | 50.91 (50.97 | 3.15 3.26 | 3.12 3.05) |

Example 95

The compounds obtained in Example 94 were subjected to the same procedure as in Reference Example 4 to yield the compounds listed in Table 71.

TABLE 71

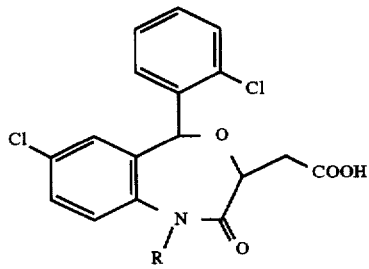

| Compd. No. | R | m.p. (°C.) | Formula | Elemental Analysis (Found) | | |
|---|---|---|---|---|---|---|
| | | | | C | H | N |
| 1 | $CH_2CH_2C(CH_3)_3$ | 176–177 | $C_{23}H_{25}Cl_2NO_4$ | 61.34 (61.45 | 5.60 5.68 | 3.11 3.25) |

Also, physicochemical properties of intermediates of compounds obtained in Reference Examples 9 and 10 and Example 94 are shown in Tables 72 and 73.

TABLE 72

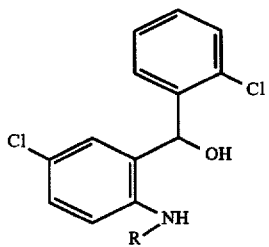

| R | m.p. (°C.) | Formula | Elemental Analysis (Found) C H N |
|---|---|---|---|
| CH₂CF₂CF₃ | oil | C₁₆H₁₂Cl₂F₅NO | ¹NMR(CDCl₃) δ: 3.82 (2H, dt), 6.17(1H, s), 6.69 (1H, d), 6.84(1H, d), 7.1–7.5(5H, m) |
| CH₂–⟨▷⟩ | oil | C₁₇H₁₇Cl₂NO | ¹NMR(CDCl₃) δ: 0.1–0.6(4H, m), 1.0–1.2 (1H, m), 2.92(2H, d), 6.16(1H, s), 6.57(1H, d), 6.91(1H, d), 7.1–7.6(5H, m) |

TABLE 72-continued

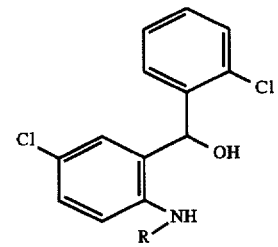

| R | m.p. (°C.) | Formula | Elemental Analysis (Found) C H N |
|---|---|---|---|
| CH₂CH₂C(CH₃)₃ | oil | C₁₉H₂₃Cl₂NO | ¹NMR(CDCl₃) δ: 0.94 (9H, s), 1.4–1.6(2H, m), 3.1(2H, m), 6.10(1H, s), 6.62(1H, d), 6.83(1H, d), 7.1–7.5(5H, m) |
| CH₂CF₃ | oil | C₁₅H₁₂Cl₂F₃NO | ¹H-NMR(CDCl₃) δ: 2.68(2H, d), 5.23(1H, m) 6.15(1H, d), 6.7(1H, d), 6.83(1H, d), 7.1–7.6 (5H, m) |

TABLE 73

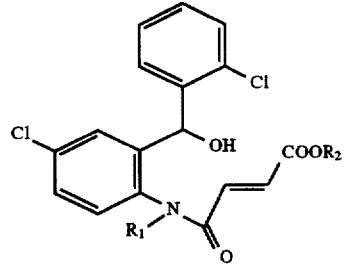

| R | R | m.p. (°C.) | Formula | ElementalAnalysis (Found) C H N |
|---|---|---|---|---|
| CH₂CF₂CF₃ | —C₂H₅ | oil | C₂₂H₁₉Cl₂F₅NO₄ | ¹NMR(CDCl₃) δ: 1.15–1.4(3H, m), 3.2–5.45(4H, m), 6.0–7.6(10H, m) |
| CH₂–⟨▷⟩ | —C₂H₅ | oil | C₂₃H₂₃Cl₂NO₄ | ¹H-NMR(CDCl₃) δ: 0.1–0.55(4H, m), 0.9–1.4(4H, m), 2.4–4.4(4H, m), 6.0–7.7(10H, m) |
| CH₂CH₂CH(CH₃)₃ | —C₂H₅ | oil | C₂₅H₃₀Cl₂NO₄ | ¹H-NMR(CDCl₃) δ: 0.76, 0.91(9H, both s), 1.1–1.8(2H, m), 2.6–4.5(4H, m), 5.95–7.7(10H, m) |
| CH₂CF₃ | —C₂H₅ | oil | C₂₁H₁₈Cl₂F₃NO₄ | ¹H-NMR(CDCl₃) δ: 1.17–1.4(3H, m), 3.2–5.3(4H, m), 6.0–7.6(10H, m) |

Example 96

Ethyl ester of trans-7-chloro-5-(2-chlorophenyl)-1-neopentyl-1,2,3,5-tetrahydro-2-oxo-4,1-benzoxazepine-3-propionic acid.

(1) Trans-7-chloro-5-(2-chlorophenyl)-3-(2-cyanoethyl)-1-neopentyl-1,2,3,5-tetrahydro-2-oxo-4,1-benzoxazepine 0.3 g of 7-chloro-3-(2-chloroethyl)-5-(2-chlorophenyl)-1-neopentyl-1,2,3,5-tetrahydro-2-oxo-4,1-benzoxazepine and 0.1 g of sodium cyanide were suspended in 6 ml of dimethylsulfoxide, followed by stirring at 100° C. for 1 hour. Water was added and the suspension was extracted with ethyl acetate, after which the solvent was removal and the residue was subjected to silica gel column chromatography to yield 0.25 g of a crystal.

Melting point: 194°–195° C.

Elemental analysis (for $C_{23}H_{24}Cl_2N_2O_2$) Calcd.: C 64.04; H 5.61; N 6.49 Found: C 63.96; H 5.56; N 6.66

(2) Ethyl ester of trans-7-chloro-5-(2-chlorophenyl)-1-neopentyl-1,2,3,5-tetrahydro-2-oxo-4,1-benzoxazepine-3-propionic acid To 0.2 g of trans-7-chloro-5-(2-chlorophenyl)-3-(2-cyanoethyl)-1-neopentyl-1,2,3,5-tetrahydro-2-oxo-4,1-benzoxazepine, 6 ml of an ethanol solution of 6N hydrogen chloride was added, followed by refluxing with heating for 6 hours. After solvent removal, ethyl acetate and water were added, the organic layer was dried, the solvent was removed, and the residue was subjected to silica gel column chromatography to yield 0.18 g of a crystal.

Melting point: 130°–131° C.

Elemental analysis (for $C_{25}H_{29}Cl_2NO_4$) Calcd.: C 62.76; H 6.11; N 2.93 Found: C 62.78; H 6.12; N 2.68

Example 97

Trans-7-chloro-5-(2-chlorophenyl)-1-neopentyl-1,2,3,5-tetrahydro-2-oxo-4,1-benzoxazepine-3-propionic acid 90 mg of ethyl ester of trans-7-chloro-5-(2-chlorophenyl)-1-neopentyl-1,2,3,5-tetrahydro-2-oxo-4,1-benzoxazepine-3-propionic acid as obtained in Example 96 was subjected to the same procedure as in Reference Example 4 to yield 80 mg of a crystal.

Melting point: 225°–227° C.

Elemental analysis (for $C_{23}H_{25}Cl_2NO_4$) Calcd.: C 61.34; H 5.60; N 3.11 Found: C 61.34; H 5.65; N 2.89

Example 98

Trans-7-chloro-5-(2-chlorophenyl)-1-isobutyl-1,2,3,5-tetrahydro-2-oxo-4,1-benzoxazepine-3-ethanol Trans-7-chloro-5-(2-chlorophenyl)-1-isobutyl-1,2,3,5-tetrahydro-2-oxo-4,1-benzoxazepine-3-acetic acid as obtained in Example 2 was subjected to the same procedure as in Example 65 to yield 1.5 g of a crystal.

Example 99

Ethyl ester of 3-[trans-7-chloro-5-(2-chlorophenyl)-1-isobutyl-2-oxo-1,2,3,5-tetrahydro-4,1-benzoxazepine-3-ylethyl]thioglycolic acid (1) Trans-7-chloro-3-(2-chloroethyl)-5-(2-chlorophenyl)-1-isobutyl-1,2,3,5-tetrahydro-2-oxo-4,1-benzoxazepine 1.0 g of trans-7-chloro-5-(2-chlorophenyl)-1-isobutyl-1,2,3,5-tetrahydro-2-oxo-4,1-benzoxazepine-3-ethanol as obtained in Example 98 was dissolved in 25 ml of toluene, and 0.1 ml of pyridine and 0.4 ml of thionyl chloride were added, followed by stirring for 30 minutes with heating at 100° C. After solvent removal under reduced pressure, the residue was dissolved in ethyl acetate and washed with a saturated aqueous solution of sodium hydrogen carbonate and dried, after which the solvent was removed and the residue was subjected to silica gel column chromatography to yield 0.8 g of a crystal.

Melting point: 138°–140° C.

Elemental analysis (for $C_{21}H_{22}Cl_3NO_2$) Calcd.: C 59.10; H 5.20; N 3.28 Found: C 59.17; H 5.22; N 2.25

(2) Ethyl ester of 3-[trans-7-chloro-5-(2-chlorophenyl)-1-isobutyl-2-oxo-1,2,3,5-tetrahydro-4,1-benzoxazepine-3-ylethyl]thioglycolic acid 0.15 g of trans-7-chloro-3-(2-chloroethyl)-5-(2-chlorophenyl)-1-isobutyl-1,2,3,5-tetrahydro-2-oxo-4,1-benzoxazepine, 0.08 g of ethyl ester of thioglycolic acid and 0.1 g of cesium fluoride were added to 5 ml of acetonitrile, followed by refluxing with heating for 40 minutes. After ice water was added and the mixture was extracted with ethyl acetate, the organic layer was dried, after which the solvent was removed and the residue was subjected to silica gel column chromatography to yield 0.17 g of an oily compounds.

$^1$H-NMR (CDCl$_3$) δ: 0.93, 1.03 (6H, each, d), 1.26 (3H, t), 1.8–2.4 (3H, m), 2.8 (2H, m), 3.19 (2H, s), 3.42 (1H, dd), 4.0–4.4 (4H, m), 6.12 (1H, s), 6.51 (1H, d), 7.2–7.8 (6H, m)

Example 100

3-[trans-7-chloro-5-(2-chlorophenyl)-1-isobutyl-2-oxo-1,2,3,5-tetrahydro-4,1-benzoxazepine-3-ylethyl]thioglycolic acid 0.17 g of ethyl ester of 3-[trans-7-chloro-5-(2-chlorophenyl)-1-isobutyl-2-oxo-1,2,3,5-tetrahydro-4,1-benzoxazepine-3-ylethyl]thioglycolic acid as obtained in Example 99 was subjected to the same procedure as in Example 51 to yield 0.18 g of a crystal.

Melting point: 194°–195° C.

Elemental analysis (for $C_{25}H_{25}Cl_2NO_4S$) Calcd.: C 57.26; H 5.22; N 2.90 Found: C 57.27; H 5.20; N 2.96

Example 101

3-[trans-7-chloro-5-(2-chlorophenyl)-1-isobutyl-2-oxo-1,2,3,5-tetrahydro-4,1-benzoxazepine-3-ylethyl] sulfonylacetic acid 0.18 g of ethyl ester of 3-[trans-7-chloro-5-(2-chlorophenyl)-1-isobutyl-2-oxo-1,2,3,5-tetrahydro-4,1-benzoxazepine-3-ylethyl]thioglycolic acid as obtained in Example 99 was dissolved in 8 ml of dichloromethane, and 0.25 g of m-chloroperbenzoic acid was added, followed by stirring for 1 hour. To the reaction mixture was added an aqueous solution of sodium hydrogen carbonate, followed by washing and the organic layer was dried and the solvent was removed, after which the residue was subjected to silica gel column chromatography to yield 0.18 g of an oily compound, which was then subjected to the same procedure of ethyl ester hydrolysis as in Example 51 to yield 0.13 g of a crystal.

Melting point: 171°–172° C.

Elemental analysis (for $C_{23}H_{25}Cl_2NO_6S$) Calcd.: C 53.70; H 4.90; N 2.72 Found: C 53.62; H 4.95; N 2.68

Example 102

Trans-7-chloro-5-(2-chlorophenyl)-1-neopentyl-3-[3-(tetrazol-5-yl)phenylaminocarbonylmethyl]-2-oxo-1,2,3,5-tetrahydro-4,1-benzoxazepine (1) Trans-7-chloro-5-(2-chlorophenyl)-3-(3-cyanophenylaminocarbonylmethyl)-1-neopentyl-2-oxo-1,2,3,5-tetrahydro-4,1-benzoxazepine To a solution of 0.5 g of trans-7-chloro-5-(2-chlorophenyl)-1-isobutyl-2-oxo-1,2,3,5-tetrahydro-4,1-benzoxazepine-3-acetic acid as obtained in Example 2 and 0.15 g of m-cyanoaniline in 10 ml of dichloromethane, 0.35 g of 1-ethyl-3-(dimethylaminopropyl)carbodiimide hydrochloride and 20 mg of dimethylaminopyridine were added, followed by stirring at room temperature for 4 hours. The solution was concentrated, and the residue was dissolved in ethyl acetate, followed by washing with water, after which the solvent was removed and the residue was subjected to silica gel column chromatography to yield 0.48 g of a crystal.

Melting point: 213°–214° C.

Elemental analysis (for $C_{29}H_{27}Cl_2N_3O_3$) Calcd.: C 64.93; H 5.07; N 7.83 Found: C 64.68; H 4.96; N 7.90

(2) Trans-7-chloro-5-(2-chlorophenyl)-1-neopentyl-3-[3-(tetrazol-5-yl)phenylaminocarbonylmethyl]-2-oxo-1,2,3,5-tetrahydro-4,1-benzoxazepine A solution of 0.2 g of trans-7-chloro-5-(2-chlorophenyl)-3-(3-cyanophenylaminocarbonylmethyl)-1-neopentyl-2-oxo-1,2,3,5-tetrahydro-4,1-benzoxazepine and 80 mg of sodium azide in 5 ml of dimethylformamide was stirred at 90° C. for 60 hours. After water was added, the mixture was washed with water, after which the solvent was removed and the residue was subjected to silica gel column chromatography to yield 0.11 g of a crystal.

Melting point: 218°–220° C.

Elemental analysis (for $C_{29}H_{28}Cl_2N_6O_3$) Calcd.: C 59.64; H 4.92; N 14.39 Found: C 59.44; H 4.87; N 14.30

Example 103

Trans-7-chloro-5-(2-chlorophenyl)-1-neopentyl-3-[4-(tetrazol-5-yl)phenylaminocarbonylmethyl]-2-oxo-1,2,3,5-tetrahydro-4,1-benzoxazepine. The title compound was synthesized by the same procedure as in Example 102.

(1) Trans-7-chloro-5-(2-chlorophenyl)-3-(4-cyanophenylaminocarbonylmethyl)-1-neopentyl-2-oxo-1,2,3,5-tetrahydro-4,1-benzoxazepine Melting point: 257°–259° C.

Elemental analysis (for $C_{29}H_{29}Cl_2N_3O_3 \cdot \frac{1}{4}H_2O$) Calcd.: C 64.39; H 5.12; N 7.77 Found: C 64.33; H 5.13; N 7.64

(2) Trans-7-chloro-5-(2-chlorophenyl)-1-neopentyl-3-[4-(tetrazol-5-yl)phenylaminocarbonylmethyl]-2-oxo-1,2,3,5-tetrahydro-4,1-benzoxazepine Melting point: 206°–210° C.

Elemental analysis (for $C_{29}H_{28}Cl_2N_6O_3 \cdot \frac{1}{4}H_2O$) Calcd.: C 59.64; H 4.92; N 14.39 Found: C 59.71; H 4.96; N 14.34

Example 104

Trans-7-chloro-5-(2-chlorophenyl)-1-isopropyl-3-[(tetrazol-5-yl)methylaminocarbonylmethyl]-2-oxo-1,2,3,5-tetrahydro-4,1-benzoxazepine (1) Trans-7-chloro-5-(2-chlorophenyl)-3-(cyanomethylaminocarbonylmethyl)-1-isopropyl-2-oxo-1,2,3,5-tetrahydro-4,1-benzoxazepine 0.3 g of trans-7-chloro-5-(2-chlorophenyl)-1-isopropyl-2-oxo-1,2,3,5-tetrahydro-4,1-benzoxazepine-3-acetic acid as obtained in Reference Example 5 and 0.1 g of aminoacetonitrile sulfuric acid salt were dissolved in 5 ml of dimethylformaldehyde, and 0.18 g of diethyl phosphorocyanidate and 0.17 ml of triethylamine were added, followed by stirring at room temperature for 1 hour. After water was added, the mixture was extracted with ethyl acetate, washed with water and then dried. After solvent removal, the residue was subjected to silica gel column chromatography to yield 0.31 g of a crystal.

Melting point: 216°–217° C.

Elemental analysis (for $C_{22}H_{21}Cl_2N_3O_3$) Calcd.: C 59.20; H 4.74; N 9.41 Found: C 58.92; H 4.68; N 9.12

(2) Trans-7-chloro-5-(2-chlorophenyl)-1-isopropyl-3-[(tetrazol-5-yl)methylaminocarbonylmethyl]-2-oxo-1,2,3,5-tetrahydro-4,1-benzoxazepine Trans-7-chloro-5-(2-chlorophenyl)-3-(cyanomethylaminocarbonylmethyl)-1-isopropyl-2-oxo-1,2,3,5-tetrahydro-4,1-benzoxazepine and sodium azide were subjected to the same procedure as in Example 102 to yield a crystal.

Melting point: 253°–254° C.

Elemental analysis (for $C_{22}H_{22}Cl_2N_6O_3$) Calcd.: C 54.00; H 4.53; N 17.17 Found: C 53.85; H 4.68; N 17.02

Example 105

Trans-7-chloro-5-(2-chlorophenyl)-1-isobutyl-3-[(tetrazol-5-yl)methylaminocarbonylmethyl]-2-oxo-1,2,3,5-tetrahydro-4,1-benzoxazepine Trans-7-chloro-5-(2-chlorophenyl)-1-isobutyl-2-oxo-1,2,3,5-tetrahydro-4,1-benzoxazepine-3-acetic acid as obtained in Example 2 was subjected to the same procedure as in Examples 102 and 104 to yield a crystalline compound.

(1) Trans-7-chloro-5-(2-chlorophenyl)-3-(cyanomethylaminocarbonylmethyl)-1-isobutyl-2-oxo-1,2,3,5-tetrahydro-4,1-benzoxazepine Melting point: 168°–169° C.

Elemental analysis (for $C_{23}H_{23}Cl_2N_3O_3$) Calcd.: C 60.01; H 5.04; N 9.13 Found: C 60.11; H 5.28; N 9.15

(2) Trans-7-chloro-5-(2-chlorophenyl)-1-isobutyl-3-[(tetrazol-5-yl)methylaminocarbonylmethyl]-2-oxo-1,2,3,5-tetrahydro-4,1-benzoxazepine Melting point: 234°–235° C.

Elemental analysis (for $C_{23}H_{24}Cl_2N_6O_3$) Calcd.: C 54.88; H 4.81; N 16.69 Found: C 55.07; H 4.84; N 16.92

Example 106

Trans-7-chloro-5-(2-chlorophenyl)-1-isobutyl-3-[(tetrazol-5-yl)methyl]-2-oxo-1,2,3,5-tetrahydro-4,1-benzoxazepine (1) Trans-7-chloro-5-(2-chlorophenyl)-3-cyanomethyl-1-isobutyl-2-oxo-1,2,3,5-tetrahydro-4,1-benzoxazepine 0.5 g of Trans-7-chloro-5-(2-chlorophenyl)-1-isobutyl-2-oxo-1,2,3,5-tetrahydro-4,1-benzoxazepine-3-acetamide as obtained in Example 91, 0.38 g of carbonyldiimidazole and 1.14 g of allyl bromide were dissolved in 10 ml of acetonitrile, followed by refluxing with heating for 4 hours. The solution was concentrated and ethyl acetate was added, followed by washing with water, after which the solvent was removed and the residue was subjected to silica gel column chromatography to yield 0.44 g of a crystal.

Melting point: 158°–159° C.

Elemental analysis (for $C_{21}H_{20}Cl_2N_2O_2$) Calcd.: C 62.54; H 5.00; N 6.95 Found: C 62.68; H 5.13; N 7.22

(2) Trans-7-chloro-5-(2-chlorophenyl)-1-isobutyl-3-[(tetrazol-5-yl)methyl]-2-oxo-1,2,3,5-tetrahydro-4,1-benzoxazepine 0.2 g of trans-7-chloro-5-(2-chlorophenyl)-3-cyanomethyl-1-isobutyl-2-oxo-1,2,3,5-tetrahydro-4,1-benzoxazepine was subjected to the same procedure as in Example 102 and to yield 90 mg of a crystal.

Melting point: 202°–203° C.

Elemental analysis (for $C_{21}H_{21}Cl_2N_5O_2$) Calcd.: C 56.51; H 4.74; N 15.69 Found: C 56.29; H 4.70; N 15.67

Example 107

Trans-7-chloro-5-(2-chlorophenyl)-1-isobutyl-3-[2-(tetrazol-5-yl)ethyl]-2-oxo-1,2,3,5-tetrahydro-4,1-benzoxazepine (1) Trans-7-chloro-5-(2-chlorophenyl)-1-isobutyl-3-(2-cyanoethyl)-1-isobutyl-2-oxo-1,2,3,5-tetrahydro-4,1-benzoxazepine 0.5 g of trans-7-chloro-3-(2-chloroethyl)-5-(2-chlorophenyl)-1-isobutyl-2-oxo-1,2,3,5-tetrahydro-4,1-benzoxazepine as obtained in Example 99 and 0.4 g of sodium cyanide were added to 8 ml of dimethylsulfoxide, followed by stirring at 100° C. for 40 minutes. After water was added, the reaction mixture was extracted with ethyl acetate, and the organic layer was washed with water and dried, after which the solvent was removed and the residue was subjected to silica gel column chromatography to yield 0.45 g of an oily substance.

$^1$H-NMR (CDCl$_3$) δ: 0.93, 1.03 (6H, each, d), 1.85–2.4 (3H, m), 2.59 (2H, t), 3.43 (1H, dd), 4.05 (1H, dd), 4.3 (1H, dd), 6.14 (1H, s), 6.53 (1H, d), 7.3–7.8 (6H, m)

(2) Trans-7-chloro-5-(2-chlorophenyl)-1-isobutyl-3-[2-(tetrazol-5-yl)ethyl]-2-oxo-1,2,3,5-tetrahydro-4,1-benzoxazepine Trans-7-chloro-5-(2-chlorophenyl)-3-(2-cyanoethyl)-1-isobutyl-2-oxo-1,2,3,5-tetrahydro-4,1-benzoxazepine was subjected to the same procedure as in Example 102 to yield 0.22 g of a crystal.

Melting point: 125°–127° C.

Elemental analysis (for C$_{22}$H$_{23}$Cl$_2$N$_5$O$_2$) Calcd.: C 57.40; H 5.04; N 15.21 Found: C 57.15; H 5.26; N 14.97

Example 108

Trans-7-chloro-5-(2-chlorophenyl)-3-[2-(4,5-dihydro-5-oxo-1,2,4-oxadiazol-3-yl)ethyl]-1-isobutyl-2-oxo-1,2,3,5-tetrahydro-4,1-benzoxazepine 0.25 g of trans-7-chloro-5-(2-chlorophenyl)-3-(2-cyanoethyl)-1-isobutyl-1,2,3,5-tetrahydro-2-oxo-4,1-benzoxazepine as obtained in Example 107, 120 mg of hydroxylamine hydrochloride and 0.23 g of sodium carbonate were added to 5 ml of ethanol, followed by refluxing with heating for 18 hours. After solvent removal, ethyl acetate was added, and the mixture was washed with water an dried, after which the solvent was removed and the residue was recrystallized from ethyl acetate.

Melting point: 212°–214° C.

Elemental analysis (for C$_{22}$H$_{25}$Cl$_2$N$_3$O$_3$) Calcd.: C 58.67; H 5.60; N 9.33 Found: C 58.84; H 5.68; N 9.24

0.1 g of this amidoxime, 0.1 g of carbonyldiimidazole and 0.05 ml of triethylamine were added to 5 ml of ethyl acetate, followed by refluxing with heating for 24 hours. The solution was concentrated and the residue was dissolved in ethyl acetate, washed with water and dried, after which the solvent was removed and the residue was recrystallized from ethyl acetate to yield 85 mg of a crystal.

Melting point: 241°–242° C.

Elemental analysis (for C$_{22}$H$_{23}$Cl$_2$N$_3$O$_4$) Calcd.: C 57.99; H 4.87; N 8.82 Found: C 57.79; H 5.07; N 9.00

Example 109

Tert-butyl ester of N-[(3S,5R)-7-chloro-5-(2-chlorophenyl)-1-isobutyl-2-oxo-1,2,3,5-tetrahydro-4,1-benzoxazepine-3-acetyl]-L-alanine; and tert-butyl ester of N-[(3R,5S)-7-chloro-5-(2-chlorophenyl)-1-isobutyl-2-oxo-1,2,3,5-tetrahydro-4,1-benzoxazepine-3-acetyl]-L- alanine In 20 ml of N,N-dimethylformamide were dissolved 0.5 g of trans-7-chloro-5-(2-chlorophenyl)-1-isobutyl-2-oxo-1,2, 3,5-tetrahydro-4,1-benzoxazepine-3-acetic acid, as obtained in Example 2, and 0.26 g of L-alanine tert-butyl ester hydrochloride; under ice-cooling, to this solution were added 0.26 g of diethyl phosphorocyanidate and 0.41 ml of triethylamine. After stirring for 30 minutes at room temperature, extraction was conducted with the addition of 100 ml of water and 150 ml of ethyl acetate. The ethyl acetate layer was washed with 5% aqueous solutions of potassium hydrogen sulfate and sodium bicarbonate, and after drying over anhydrous magnesium sulfate, it was distilled off under reduced pressure. The residue was then purified by silica gel column chromatography (eluent, hexane:ethyl acetate=2:1) to obtain, as the first fraction, 0.17 g of tert-butyl ester of N-[(3S, 5R)-7-chloro-5-(2-chlorophenyl)-1-isobutyl-2-oxo-1,2,3,5-tetrahydro-4,1-benzoxazepine-3-acetyl]-L-alanine as plate crystals, m.p. 146° to 147° C.

Elemental Analysis for C$_{28}$H$_{34}$Cl$_2$N$_2$O$_5$: Calcd.: C 61.20; H 6.24; N 5.10 Found: C 61.20; H 6.33; N 5.15

Also, as the second fraction, 0.22 g of tert-butyl ester of N-[(3R,5S)-7-chloro-5-(2-chlorophenyl)-1-isobutyl-2-oxo-1,2,3,5-tetrahydro-4,1-benzoxazepine-3-acetyl]-L-alanine was obtained as an oily product.

IRv$_{max}^{neat}$cm$^{-1}$: 3330 (NH); 1730, 1670 (C=O)

$^1$H-NMR (200 MHz, CDCl$_3$) δ: 0.93 (3H, d, J=6.8 Hz), 1.03 (3H, d, J=6.8 Hz), 1.34 (3H, t, J=7.0 Hz), 1.46 (9H, s, Bu$^t$), 1.85–2.1 (1H, m), 2.71 (1H, dd, J=14.6, 6.2 Hz), 2.89 (1H dd, J=14.6, 7.2 Hz), 3.43 (1H, dd, J=14.0, 5.4 Hz), 4.25–4.55 (3H, m), 6.13 (1H, s), 6.31 (1H, brd, NH), 6.51 (1H, d, J=2.2 Hz), 7.2–7.85 (6H, m)

Example 110

N-[(3S,5R)-7-chloro-5-(2-chlorophenyl)-1-isobutyl-2-oxo-1,2,3,5-tetrahydro-4,1-benzoxazepine-3-acetyl]-L-alanine In 10 ml of a 4N solution of hydrochloric acid in dioxane was dissolved 0.16 g of tert-butyl ester of N-[(3S,5R)-7-chloro-5-(2-chlorophenyl)-1-isobutyl- 2-oxo-1,2,3,5-tetrahydro-4,1-benzoxazepine-3-acetyl]-L-alanine, as obtained in Example 109, and the solution was stirred overnight at room temperature. After distillation under reduced pressure, it was crystallized with hexanediethylether to form 0.12 g of N-[(3S,5R)-7-chloro-5-(2-chlorophenyl)-1-isobutyl-2-oxo-1,2,3,5-tetrahydro-4,1-benzoxazepine-3-acetyl]-L-alanine as a powdery product.

Elemental Analysis for C$_{24}$H$_{26}$Cl$_2$N$_2$O$_5$: Calcd.: C 58.43; H 5.31; N 5.68 Found: C 58.43; H 5.65; N 5.54

$^1$NH-NMR spectrum (200 MHz, d$_6$-DMSO) δ: 0.89 (3H, d, J=6.8 Hz), 0.94 (3H, d, J=6.6 Hz), 1.25 (3H, d, J =7.2 Hz), 1.7–1.9 (1H, m), 2.4–2.55 (2H, m), 3.58 (1H, dd, J=14.0, 5.0 Hz), 4.1–4.4 (3H, m), 5.99 (1H, s), 6.30 (1H, d, J=2.4 Hz), 7.45–7.8 (4H, m), 8.33 (1H, d, J=7.6 Hz), 12.53 (1H, br, NH)

Example 111

N-[(3R,5S)-7-chloro-5-(2-chlorophenyl)-1-isobutyl-2-oxo-1,2,3,5-tetrahydro-4,1-benzoxazepine-3-acetyl]-L-alanine In 10 ml of a 4N solution of hydrochloric acid in dioxane was dissolved 0.2 g of tert-butyl ester of N-[(3R,5S)-7-chloro-5-(2-chlorophenyl)-1-isobutyl-2-oxo-1,2,3,5-tetrahydro-4,1-benzoxazepine-3-acetyl]-L-alanine, as obtained in Example 109, and the mixture was stirred for 4 hours at room temperature. After distillation under reduced pressure, it was crystallized from hexane-diethylether to form 0.17 g of N-[(3R,5S)-7-chloro-5-(2-chlorophenyl)-1-isobutyl-2-oxo-1,2,3,5-tetrahydro-4,1-benzoxazepine-3-acetyl]-L-alanine as plate crystals, m.p. 120° to 124° C.

Elemental Analysis for $C_{24}H_{26}Cl_2N_2O_5 \cdot \frac{1}{2}H_2O$: Calcd.: C 57.37; H 5.42; N 5.57 Found: C 57.37; H 5.69; N 5.48

Example 112

Methyl ester of (R)-O-[(3R,5S)-7-chloro-5-(2-chlorophenyl)-1-isobutyl-2-oxo-1,2,3,5-tetrahydro-4,1-benzoxazepine-3-acetyl]lactic acid; and methyl ester of (R)—O-[(3S,5R)-7-chloro-5-(2-chlorophenyl)-1-isobutyl-2-oxo-1,2,3,5-tetrahydro-4,1-benzoxazepine-3-acetyl]lactic acid and methyl ester of (R)—O-[(3S,5R)-7-chloro-5-(2-chlorophenyl)-1-isobutyl-2-oxo-1,2,3,5-tetrahydro-4,1-benzoxazepine-3-acetyl]lactic acid In 50 ml of methylene chloride were dissolved 2.0 g of trans-7-chloro-5-(2-chlorophenyl)-1-isobutyl-2-oxo-1,2,3,5-tetrahydro-4,1-benzoxazepine-3-acetic acid, as obtained in Example 2, and 0.59 g of methyl ester of (R)-lactic acid; to this solution were added 1.09 g of 1-ethyl-3-(3-dimethylaminopropyl) carbodiimide hydrochloride and 0.2 g of 4-dimethylaminopyridine; the mixture was stirred for 1.5 hours at room temperature. The reaction mixture was washed with 1N aqueous solutions of hydrochloric acid and sodium bicarbonate, and after drying over anhydrous magnesium sulfate, the solvent was distilled off under reduced pressure. The residue was separated and purified by means of silica gel column chromatography (eluent, hexane:diethyl ether=3: 1) to yield, as the first fraction, 0.46 g of methyl ester of (R)-O-[(3S,5R)-7-chloro-5-(2-chlorophenyl)-1-isobutyl-2-oxo-1,2,3,5-tetrahydro-4,1-benzoxazepine-3-acetyl]lactic acid as an oily product.

IR$v_{max}^{neat}$cm$^{-1}$: 1740, 1675 (C=O)

$^1$H-NMR (200 MHz, CDCl$_3$) δ:0.93 (3H, d, J=6.8 Hz), 1.02 (3H, d, J=6.6 Hz), 1.49 (3H, d, J=7.2 Hz), 1.85–2.1 (1H, m), 2.91 (1H, dd, J=17.0, 5.4 Hz), 3.19 (1H, dd, J=17.0, 8.0 Hz), 3.44 (1H, dd, J=13.8, 5.4 Hz), 3.72 (3H, s), 4.31 (1H, dd, J=13.8, 8.4 Hz), 4.44 (1H dd, J=8.0, 5.4 Hz), 5.07 (1H, q, J=7.2 Hz), 6.14 (1H, s), 6.52 (1H, d, J=2.2 Hz), 7.2–7.8 (6H, m)

As the second fraction, 0.63 g of methyl ester of (R)—O-[(3R,5S)-7-chloro-5-(2-chlorophenyl)-1-isobutyl-2-oxo-1,2,3,5-tetrahydro-4,1-benzoxazepine-3-acetyl]lactic acid was obtained as an oily product. IR$v_{max}^{neat}$ cm$^{-1}$. 1740, 1675 (C=O) $^1$H-NMR (200 MHz, CDCl$_3$) δ:0.93 (3H, d, J=6.8 Hz), 1.03 (3H, d, J=6.6 Hz), 1.48 (3H, d, J=7.0 Hz), 1.85–2.1 (1H, m), 2.93 (1H, dd, J=16.8, 7.2 Hz), 3.10 (1H, dd, J=16.8, 6.2 Hz), 3.43 (1H, dd, J=13.8, 5.4 Hz), 3.28 (3H, s), 4.34 (1H dd, J=13.8, 5.4 Hz), 4.45 (1H, t, J=6.6 Hz), 5.12 (1H, q, J=7.0 Hz), 6.16 (1H, s), 6.52 (1H, d, J=2.2 Hz), 7.2–7.8 (6H, m)

Example 113

(3S,5R)-7-chloro-5-(2-chlorophenyl)-1-isobutyl-2-oxo-1,2,3,5-tetrahydro-4,1-benzoxazepine-3-acetic acid In 20 ml of methanol was dissolved 0.45 g of methyl ester of (R)—O-[(3S,5R)-7-chloro-5-(2-chlorophenyl)-1-isobutyl-2-oxo-1,2,3,5-tetrahydro-4,1-benzoxazepine-3-acetyl]lactic acid, as obtained in Example 112, to which was added 10 ml of an aqueous solution containing 0.37 g of potassium carbonate; this mixture was stirred for 40 minutes at 60° C. The mixture was concentrated under reduced pressure, and the concentrate subjected to extraction with the addition of 50 ml of 1N hydrochloric acid and 100 ml of ethyl acetate. The ethyl acetate layer was washed with water, dried over anhydrous magnesium sulfate, and distilled off under reduced pressure. The residue was purified by means of silica gel column chromatography (eluent, hexane:ethyl acetate=3:1; eluent, hexane:methylene chloride:ethanol= 5:5:1) to yield 53 mg of (3S, 5R)-7-chloro-5-(2-chlorophenyl)-1-isobutyl-2-oxo-1,2,3,5-tetrahydro-4,1-benzoxazepine-3-acetic acid as prism crystals, m.p. 183° to 186° C.

$[α]_D^{20}$+223.7° (c=0.47, methanol)

Elemental Analysis for $C_{21}H_{21}Cl_2NO_4$: Calcd.: C 59.73; H 5.01; N 3.32 Found: C 59.36; H 5.09; N 3.19

Example 114

(3R,5S)-7-chloro-5-(2-chlorophenyl)-1-isobutyl-2-oxo-1,2,3,5-tetrahydro-4,1-benzoxazepine-3-acetic acid In 20 ml of methanol was dissolved 0.6 g of methyl ester of (R)—O-[(3S,5R)-7-chloro-5-(2-chlorophenyl)-1-isobutyl-2-oxo-1,2,3,5-tetrahydro-4,1-benzoxazepine-3-acetyl]lactic acid, as obtained in Example 112, to which was added 10 ml of an aqueous solution containing 0.49 g of potassium carbonate; this mixture was stirred for 40 minutes at 60° C. The mixture was concentrated under reduced pressure, and the concentrate subjected to extraction with the addition of 50 ml of 1N hydrochloric arid and 100 ml of ethyl acetate. The ethyl acetate layer was washed with water, dried over anhydrous magnesium sulfate, and distilled off under reduced pressure. The residue was purified by silica gel column chromatography (eluent, hexane:ethyl acetate= 3:1; eluent, hexane:methylene chloride:ethanol=5:5:1) to yield 54 mg of (3S,5R)-7-chloro-5-(2-chlorophenyl)-1-isobutyl-2-oxo-1,2,3,5-tetrahydro-4,1-benzoxazepine-3-acetic acid as prism crystals, m.p. 182° to 185° C.

$[α]_D^{20}$-215.3°(c=0.43, methanol)

Elemental Analysis for $C_{21}H_{21}Cl_2NO_4 \cdot \frac{1}{4}H_2O$: Calcd.: C 59.10; H 5.08; N 3.28 Found: C 59.05; H 5.07; N 3.53

Example 115

Methyl ester of(R)—O-[(3R,5S)-7-chloro-5-(2-chlorophenyl)-1-neopentyl-2-oxo-1,2,3,5-tetrahydro-4,1-benzoxazepine-3-acetyl]lactic acid; and methyl ester of (R)—O-[(3S,5R)-7-chloro-5-(2-chlorophenyl)-1-neopentyl-2-oxo-1,2,3,5-tetrahydro-4,1-benzoxazepine-3-acetyl]lactic acid In 50 ml of methylene chloride were dissolved 2.0 g of trans-7-chloro-5-(2-chlorophenyl)-1-neopentyl-2-oxo-1,2,3,5-tetrahydro-4,1-benzoxazepine-3-acetic acid, as obtained in Example 2, and 0.57 g of methyl ester of (R)-lactic acid. To the solution were added 1.05 g of 1-ethyl-3-(3-dimethylaminopropyl) carbodiimide hydrochloride and 0.2 g of 4-dimethylaminopyridine; the mixture was stirred for 3 hours at room temperature. The reaction mixture was washed with 1N solutions of hydrochloric acid and sodium bicarbonate and dried over anhydrous magnesium sulfate; then the solvent was distilled off under reduced pressure. The residue was separated and purified by silica gel column chromatography (eluent, hexane:diethylether=3:1) to yield, as the first fraction, 0.48 g of methyl ester of (R)—O-[(3S, 5R)-7-chloro-5-(2-chlorophenyl)-1-neopentyl-2-oxo-1,2,3,5-tetrahydro-4,1-benzoxazepine-3-acetyl]lactic acid as prism crystals, m.p. 155° to 157° C.

$[\alpha]_D^{20}$+222.6°(c=1.0, methanol)

Elemental Analysis for $C_{26}H_{29}Cl_2NO_6$: Calcd.: C 59.78; H 5.60; N 2.68 Found: C 59.87; H 5.75; N 2.41

As the second fraction, 0.6 g of methyl ester of (R)—O-[(3R,5S)-7-chloro-5-(2-chlorophenyl)-1-neopentyl-2-oxo-1,2,3,5-tetrahydro-4,1-benzoxazepine-3-acetyl]lactic acid was recovered as an oily product.

$IRv_{max}^{neat}cm^{-1}$: 1745, 1675 (C=O)

$^1$H-NMR (200 MHz, CDCl$_3$) δ: 0.94 (9H, s, Bu$^t$), 1.47 (3H, d, J=7.0 Hz 2.92 (1H, dd, J=16.8, 7.2 Hz), 3.08 (1H, dd, J=16.8, 6.0 Hz), 3.39 (1H, d, J=14.0 Hz), 3.72 (3H, s), 4.45 (1H, dd, J=7.2, 6.0 Hz), 4.52 (1H, d, J=14.0 Hz), 5.11 (1H, q, J=7.0 Hz), 6.28 (1H, s), 6.52 (1H, s), 7.3–7.8 (6H, m

Example 116

Methyl ester of (S)-O-[(3R,5S)-7-chloro-5-(2-chlorophenyl)-1-neopentyl-2-oxo-1,2,3,5-tetrahydro-4,1-benzoxazepine-3-acetyl]lactic acid; and methyl ester of (S)-O-[(3S,5R)-7-chloro-5-(2-chlorophenyl)-1-neopentyl-2-oxo-1,2,3,5-tetrahydro-4,1-benzoxazepine-3-acetyl]lactic acid In 150 ml of methylene chloride were dissolved 10 g of trans-7-chloro-5-(2-chlorophenyl)-1-neopentyl-2-oxo-1,2,3,5-tetrahydro-4,1-benzoxazepine-3-acetic acid, as obtained in Example 2, and 4.77 g of methyl ester of (S)-lactic acid. To the solution were added, under ice-cooling, 5.27 g of 1-ethyl-3-(3-dimethylaminopropyl) carbodiimide hydrochloride and 0.3 g of 4-dimethylaminopyridine. The mixture was stirred for 2 hours at room temperature, followed by washing with 1N aqueous solutions of hydrochloric acid and sodium bicarbonate, drying over magnesium sulfate. The solvent was then distilled off under reduced pressure. The residue was separated and purified by means of silica gel column chromatography (eluent, hexane:diethylether=3:1) to yield, as the first fraction, 2.7 g of methyl ester of (S)-O-[(3R,5S)-7-chloro-5-(2-chlorophenyl)-1-neopentyl-2-oxo-1,2,3,5- tetrahydro-4,1-benzoxazepine-3-acetyl]lactic acid as prism crystals, m.p. 155° to 157° C.

$[\alpha]_D^{20}$-227.1° (c=0.94, methanol)

Elemental Analysis for $C_{26}H_{29}Cl_2NO_6$: Calcd.: C 59.78; H 5.60; N 2.68 Found: C 59.82; H 5.69; N 2.51

As the second fraction, 2.8 g of methyl ester of (S)-O-[(3S,5R)-7-chloro-5-(2-chlorophenyl)-1-neopentyl-2-oxo-1, 2,3,5-tetrahydro-4, 1-benzoxazepine-3-acetyl]lactic acid was recovered as prism crystals, m.p. 119° to 120° C.

$[\alpha]_D^{20}$+160.1° (c=0.7, methanol)

Elemental Analysis for $C_{26}H_{29}Cl_2NO_6$: Calcd.: C 59.78; H 5.60; N 2.68 Found: C 59.69; H 5.63; N 2.67

Example 117

(3S,5R)-7-chloro-5-(2-chlorophenyl)-1-neopentyl-2-oxo-1,2,3,5-tetrahydro-4,1-benzoxazepine-3-acetic acid In 20 ml of methanol was dissolved 0.4 g of methyl ester of (R)—O-[(3S,5R)-7-chloro-5-(2-chlorophenyl)-1-neopentyl-2-oxo-1,2,3,5-tetrahydro-4,1-benzoxazepine-3-acetyl]lactic acid, as obtained in Example 115. To the solution was added 10 ml of an aqueous solution containing 0.32 g of potassium carbonate; the reaction mixture was then stirred for 2 hours at 60° C. and concentrated under reduced pressure, followed by extraction by the addition of 50 ml of 1N hydrochloric acid and 50 ml of ethyl acetate. The ethyl acetate layer was washed with water, dried over anhydrous magnesium sulfate, then distilled off under reduced pressure. The residue was purified by means of silica gel column chromatography (eluent, hexane:ethyl acetate=2:1; methylene chloride:methanol=3:1) to yield 0.15 g of (3S,5R)-7-chloro-5-(2-chlorophenyl)-1-neopentyl-2-oxo-1,2,3,5-tetrahydro-4,1-benzoxazepine-3-acetic acid as needles, m.p. 241° to 245° C.

$[\alpha]_D^{20}$+244.8°(c=0.52, methanol)

Elemental Analysis for $C_{22}H_{23}Cl_2NO_4\cdot\frac{1}{4}H_2O$: Calcd.:. C 59.94; H 5.37; N 3.18 Found: C 60.19; H 5.47; N 2.97

Example 118

(3S,5R)-7-chloro-5-(2-chlorophenyl)-1-neopentyl-2-oxo-1,2,3,5-tetrahydro-4,1-benzoxazepine-3-acetic acid (1); and ethyl ester of (3R,5S)-7-chloro-5-(2-chlorophenyl)-1-neopentyl-2-oxo-1,2,3,5-tetrahydro-4,1-benzoxazepine-3-acetic acid (2)

In 45 ml of methanol was dissolved 2.2 g of methyl ester of (S)-O-[(3S,5R)-7-chloro-5-(2-chlorophenyl)-1-neopentyl-2-oxo-1,2,3,5-tetrahydro-4,1-benzoxazepine-3-acetyl]lactic acid, as obtained in Example 116, to which was added 15 ml of an aqueous solution containing 1.75 g of potassium carbonate; the mixture was then stirred for 2 hours at 60° C., concentrated under reduced pressure and subjected to extraction with the addition of 100 ml of 1N hydrochloric acid and 100 ml of ethyl acetate. The ethyl acetate layer was washed with water, dried over anhydrous magnesium sulfate, then distilled off under reduced pressure. The residue was purified by silica gel column chromatography (eluent, hexane:ethyl acetate=2:1; methylene chloride:methanol=3:1) to yield crystals. Recrystallization from hexane-ethanol yielded 0.85 g of (3S,5R)-7-chloro-5-(2-chlorophenyl)-1-neopentyl-2-oxo-1,2,3,5-tetrahydro-4,1-benzoxazepine-3-acetic acid as needles, m.p. 250° to 252° C.

$[\alpha]_D^{20}$-252.0° (c=0.5, methanol)

Elemental Analysis for $C_{22}H_{23}Cl_2NO_4$: Calcd.: C 59.94; H 5.37; N 3.28 Found: C 59.84; H 5.28; N 3.31

The filtrate was distilled off under reduced pressure; the residue was then dissolved in 30 ml of ethanol, to which 0.3 ml of concentrated sulfuric acid was added; the mixture was then stirred for 2 days. Distillation under reduced pressure was followed by extraction with the addition of 100 ml of water and 100 ml of ethyl acetate. The ethyl acetate layer was washed with aqueous sodium bicarbonate and with water, dried over anhydrous magnesium sulfate, and distilled off under reduced pressure. The residue was purified by means of silica gel column chromatography (eluent, hexane:ethyl acetate=5:1) to yield 0.63 g of ethyl ester of (3R,5S)-7-chloro-5-(2-chlorophenyl)-1-neopentyl-2-oxo-1, 2,3,5-tetrahydro-4,1-benzoxazepine-3-acetic acid as prim crystals, m.p. 120°to 121° C.

$[\alpha]_D^{20}$ -235.5° (c=0.51, methanol)

Elemental Analysis for $C_{24}H_{27}Cl_2NO_4$: Calcd.: C 62.07; H 5.86; N 3.02 Found: C 62.10; H 5.95; N 2.93

Also, in substantially the same manner as above, the hydrolysis of 0.6 g of methyl ester of (R)—O-[(3R, 5S)-7-chloro-5-(2-chlorophenyl)-1-neopentyl-2-oxo-1,2,3,5-tetrahydro-4,1-benzoxazepine-3-acetyl]lactic acid yielded 0.37 g of (3R,5S)-7-chloro-5-(2-chlorophenyl)-1-neopentyl-2-oxo-1,2,3,5-tetrahydro-4,1-benzoxazepine-3-acetic acid.

Example 119

Ethyl ester of N-[(3R,5S)-7-chloro-5-(2-chlorophenyl)-1-neopentyl-2-oxo-1,2,3,5-tetrahydro-4,1-benzoxazepine-8-acetyl]aminoacetic acid In 5 ml of N,N-dimethylformamide were dissolved 0.15 g of (3R,5S)-7-chloro-5-(2-chlorophenyl)-1-neopentyl-2-oxo- 1,2,3,5-tetrahydro-4,1-benzoxazepine-3-acetic acid, as obtained in Example 118, and 58 mg of glycine ethylester hydrochloride. To the solution were added, under ice-cooling, 71 mg of diethyl phosphorocyanidate and 0.12 ml of triethylamine. After the reaction mixture was stirred for 30 minutes at room temperature, it was subjected to extraction with the addition of 50 ml of water and 50 ml of ethyl acetate. The ethyl acetate layer was washed with 1N hydrochloric acid and an aqueous solution of sodium bicarbonate, dried over anhydrous magnesium sulfate, and distilled off under reduced pressure. The residue was purified by means of silica gel column chromatography (eluent, hexane:ethyl acetate=1:1) to yield 0.16 g of ethyl ester of N-[(3R,5S)-7-chloro-5-(2-chlorophenyl)-1-neopentyl-2-oxo-1,2,3,5-tetrahydro-4,1-benzoxazepine-3-acetyl]aminoacetic acid as plate crystals, m.p. 138° to 189° C.

$[\alpha]_D^{20}$ −220.8° (c=0.45, methanol)

Elemental Analysis for $C_{26}H_{30}Cl_2N_2O_5$: Calcd.: C 59.89; H 5.80; N 5.37 Found: C 59.86; H 5.94; N 5.12

Example 120

N-[(3R,5S)-7-chloro-5-(2-chlorophenyl)-1-neopentyl-2-oxo-1,2,3,5-tetrahydro-4,1-benzoxazepine-3-acetyl]aminoacetic acid In 5 ml of ethanol was dissolved 0.12 g of ethyl ester of N-[(3R,5S)-7-chloro-5-(2-chlorophenyl)-1-neopentyl-2-oxo-1,2,3,5-tetrahydro-4,1-benzoxazepine-3-acetyl]aminoacetic acid, as obtained in Example 119, to which was added 2 ml of 1N sodium hydroxide. The reaction mixture was stirred for 15 minutes at room temperature, after which was subjected to extraction with the addition of 50 ml of 1N hydrochloric acid and 50 ml of ethyl acetate. The ethyl acetate layer was washed with water, dried over anhydrous magnesium sulfate, and distilled off under reduced pressure to leave 0.10 g of N-[(3R,5S)-7-chloro-5-(2-chlorophenyl)-1-neopentyl-2-oxo-1,2,3,5-tetrahydro-4,1-benzoxazepine-3-acetyl]aminoacetic acid as a powdery product.

$[\alpha]_D^{20}$ −229.8° (c=0.46, methanol)

Elemental Analysis for $C_{24}H_{26}Cl_2N_2O_5$: Calcd.: C 58.43; H 5.31; N 5.68 Found: C 58.56; H 5.63; N 5.57

Example 121

(3S,5R)-7-chloro-5-(2-chlorophenyl)-1-neopentyl-2-oxo-1,2,3,5-tetrahydro-4,1-benzoxazepine-3-acetic acid; and (3R,5S)-7-chloro-5-(2-chlorophenyl)-1-neopentyl-2-oxo-1,2,3,5-tetrahydro-4,1-benzoxazepine-3-acetic acid In ethanol were dissolved 10 g of 7-chloro-5-(2-chlorophenyl)-1-neopentyl-2-oxo-1,2,3,5-tetrahydro-4,1-benzoxazepine-3-acetic acid, as obtained in Example 2, and quinine of equal molarity. After this mixture was concentrated, 150 ml of ethyl ether was added, and crystallization was allowed to occur under ice-cooling. The crystals thus obtained were dissolved in a mixture of ethanol and ethyl ether and allowed to recrystallize. The mother liquor was removed from the crystals thus formed, and was concentrated, leaving a residue. This residue underwent recrystallization using hexane, and the crystals thus formed were dissolved in ethyl acetate. The quinine in this solution was removed with dilute hydrochloric acid. The residue after removal of the solvent underwent recrystallization using hexane, resulting in (3S,5R)-7-chloro-5-(2-chlorophenyl)-1-neopentyl-2-oxo-1,2,3,5-tetrahydro-4,1-benzoxazepine-3-acetic acid as crystals. The solvent was then removed from the mother liquor remaining from the very first crystallization. The residue was dissolved in ethyl acetate, and the quinine was removed with dilute hydrochloric acid. The solvent was removed, leaving a residue which was recrystallized using a mixture solvent of ethanol and ethyl ether. After removal of the crystals thus formed, the mother liquor was concentrated, and the residue recrystallized using hexane, resulting in (3R,5S)-7-chloro-5-(2-chlorophenyl)-1-neopentyl-2-oxo-1,2,3,5-tetrahydro-4,1-benzoxazepine-3-acetic acid as crystals.

Example 122

Ethyl ester of (3S,5R)-7-chloro-5-(2-chlorophenyl)-1-neopentyl-2-oxo-1,2,3,5-tetrahydro-4,1-benzoxazepine-3-acetic acid; and ethyl ester of (3R,5S)-7-chloro-5-(2-chlorophenyl)-1-neopentyl-2-oxo-1,2,3,5-tetrahydro-4,1-benzoxazepine-3-acetic acid To ethyl iodide in dimethyl formamide as a solvent, and under the presence of potassium carbonate, were added, as separate reactions, (3S,5R)-7-chloro-5-(2-chlorophenyl)-1-neopentyl-2-oxo-1,2,3,5-tetrahydro-4,1-benzoxazepine-3-acetic acid and (3R,5S)-7-chloro-5-(2-chlorophenyl)-1-neopentyl-2-oxo-1,2,3,5-tetrahydro-4,1-benzoxazepine-3-acetic acid, as obtained in Example 121, resulting in the above compounds. Ethyl ester of (3S,5R)-7-chloro-5-(2-chlorophenyl)-1-neopentyl-2-oxo-1,2,3,5-tetrahydro-4,1-benzoxazepine-3-acetic acid, m.p. 117° to 118° C.

$[\alpha]_D^{20}$ +224.6° (c=0.5, MeOH)

Elemental Analysis for $C_{24}H_{27}Cl_2NO_4$: Calcd.: C 62.07; H 5.86; N 3.02 Found: C 62.01; H 5.88; N 2.97

Example 123

Ethyl ester of trans-7-chloro-5-(2-ethoxyphenyl)-1-isobutyl-2-oxo-1,2,3,5-tetrahydro-4,1-benzoxazepine-3-acetic acid (1) 2-amino-5-chloro-2'-hydroxybenzophenone A mixture of 2.15 g of 2-amino-5-chloro-2'-methoxybenzophenone and 20 ml of 47% hydrogen bromide was heated for 1 hour under reflux. The solution was rendered neutral with sodium bicarbonate, and subjected to extraction with 100 ml of ethyl acetate. The extract solution was washed with water and dried over anhydrous magnesium sulfate; the solvent was then distilled off under reduced pressure. The residue was purified by means of silica gel column chromatography (eluent, hexane:ethyl acetate=10:1) to yield 1.9 g of 2-amino-5-chloro-2'-hydroxybenzophenone as needles, m.p. 51° to 52° C.

Elemental Analysis for $C_{13}H_{10}ClNO_2$: Calcd.: C 63.04; H 4.07; N 5.66 Found: C 62.90; H 4.04; N 5.61

A mixture of 10 g of 2-acetylamino-5-chloro-2'-methoxybenzophenone and 100 ml of 47% hydrogen bromide was heated for 2 hours under reflux. The solution was rendered neutral with sodium hydroxide, and was subjected to extraction with 200 ml of ethyl acetate. The extract solution was washed with water and dried over anhydrous magnesium sulfate; the solvent was then distilled off under reduced pressure. The residue was purified by means of silica gel column chromatography (eluent, hexane:ethyl acetate=5:1) to yield 8.0 g of 2-amino-5-chloro-2'-hydroxybenzophenone as needles.

(2) 2-amino-5-chloro-2'-ethoxybenzophenone

In 10 ml of N,N-dimethylformamide was dissolved 1.5 g of 2-amino-5-chloro-2'-hydroxybenzophenone, as obtained in (1), to which were added 1.26 g of potassium carbonate and 0.63 ml of ethyl iodide. The reaction mixture was stirred for 3 hours at room temperature, after which it was subjected to extraction with 100 ml of water and 100 ml of ethyl acetate. The ethyl acetate layer was washed with water, dried over anhydrous magnesium sulfate, and distilled off under reduced pressure. The residue was purified by means of silica gel column chromatography (eluent, hexane:ethyl acetate=5:1) to yield 1.6 g of 2-amino-5-chloro-2'-ethoxybenzophenone as an oily product.

IR $\nu_{max}^{neat}$ cm$^{-1}$: 3460, 3340 (NH); 1610 (C=O)

$^1$H-NMR spectrum (200 MHz, CDCl$_3$) δ: 1.21 (3H, t, J=7.0 Hz), 4.04 (2H, q, J=7.0 Hz), 6.1–6.5 (2H, br, NH$_2$), 6.65 (1H, d, J=8.8 Hz), 6.9–7.1 (2H, m), 7.15–7.35 (3H, m), 7.35–7.5 (1H, m)

(3) 2-amino-5-chloro-α-(2-ethoxyphenyl)benzyl alcohol

In 30 ml of ethanol was dissolved 1.5 g of 2-amino-5-chloro-2'-ethoxybenzophenone, as obtained in (2), to which was added 0.34 g of sodium borohydride. The reaction mixture was stirred overnight at room temperature. After the ethanol was distilled off under reduced pressure and after dissociation by the addition of an aqueous solution of hydrochloric acid, 50 ml of 1N sodium hydroxide was added to render the solution neutral, and extraction was carried out with 100 ml of ethyl acetate. The ethyl acetate layer was washed with water, dried over anhydrous magnesium sulfate, and distilled off under reduced pressure. The residue was purified by means of silica gel column chromatography (eluent, hexane:ethyl acetate=3:1) to yield 1.35 g of 2-amino-5-chloro-α-(2-ethoxyphenyl)benzyl alcohol as prism crystals, m.p. 80° to 81° C.

Elemental Analysis of C$_{15}$H$_{16}$ClNO$_2$: Calcd.: C 64.87; H 5.81; N 5.04 Found: C 64.77; H 5.81; N 4.85

(4) 5-chloro-α-(2-ethoxyphenyl)-2-isobutylaminobenzyl alcohol

In 10 ml of acetic acid were dissolved 1.3 g of 2-amino-5-chloro-α-(2-ethoxyphenyl)benzyl alcohol, as obtained in (3), and 0.47 ml of isobutylaldehyde, to which was added, under ice-cooling, 0.24 g of sodium borohydride. The reaction mixture was stirred for 30 minutes at room temperature, after which it was subjected to extraction with the addition of 100 ml of water and 100 ml of ethyl acetate. The ethyl acetate layer was washed with 1N sodium hydroxide, dried over anhydrous magnesium sulfate, and then distilled off under reduced pressure. The residue was purified by means of silica gel column chromatography (eluent, hexane:ethyl acetate=20:1 to 5:1) to yield 1.5 g of 5-chloro-α-(2-ethoxyphenyl)-2-isobutylaminobenzyl alcohol as an oily product.

IR $\nu_{max}^{neat}$ cm$^{-1}$: 3520, 3410 (NH, OH)

$^1$H-NMR spectrum (200 MHz, CDCl$_3$) δ: 0.90 (3H, d, J=6.8 Hz), 0.91 (3H, d, J=6.6 Hz), 1.41 (3H, t, J=7.0 Hz), 1.7–2.0 (1H, m), 2.89 (2H, d, J=6.8 Hz), 3.2–3.6 (1H, br), 4.13 (2H, q, J=7.0 Hz), 4.7–5.1 (1H, br), 5.97 (1H, s), 6.55 (1H, d, J=8.6 Hz), 6.85–7.4 (6H, m)

(5) Ethyl ester of 3-[N-[4-chloro-2-[2-ethoxy-α-hydroxybenzyl]phenyl]-N-isobutylcarbamoyl]acrylic acid A solution containing 0.84 g of monoethyl ester of fumaric acid and 1.28 ml of thionyl chloride in 10 ml of toluene was stirred for 30 minutes at 90° C. The solvent was distilled off under reduced pressure, leaving monoethyl ester acid chloride of fumaric acid. This product and 1.5 g of 5-chloro-α-(2-methoxyphenyl)-2-isobutylaminobenzyl alcohol, as obtained in (4), were then dissolved in 30 ml of methylene chloride, to which 0.75 g of sodium bicarbonate was added; the mixture was then stirred for 30 minutes at room temperature. The reaction mixture was washed with water and dried over anhydrous magnesium sulfate; the solvent was then distilled off under reduced pressure. The residue was purified by means of silica gel column chromatography (eluent, hexane:ethyl acetate=4:1) to yield 1.95 g of ethyl ester of 3-[N-[4-chloro-2-[2-ethoxy-α-hydroxybenzyl]phenyl]-N-isobutylcarbamoyl]acrylic acid as an oily product.

IR $\nu_{max}^{neat}$ cm$^{-1}$: 3400 (OH); 1720, 1660, 1630 (C=C, C=O)

$^1$H-NMR spectrum (200 MHz, CDCl$_3$) δ: 0.65–1.0 (6H, m), 1.15–1.4 (6H, m), 1.6–2.0 (1H, m), 2.3–3.0 (2H, m), 3.9–4.4 (5H, m), 5.8–6.3 (3H, m), 6.6–8.05 (7H, m)

(6) Ethyl ester of trans-7-chloro-5-(2-ethoxyphenyl)-1-isobutyl-2-oxo-1,2,3,5-tetrahydro-4,1-benzoxazepine-3-acetic acid In 30 ml of ethanol was dissolved 1.95 g of ethyl ester of 3-[N-[4-chloro-2-[2-ethoxy-α-hydroxybenzyl]phenyl]-N-isobutylcarbamoyl]acrylic acid, as obtained in (5), to which was added 1.17 g of potassium carbonate, and the mixture was stirred overnight. The reaction mixture was subjected to extraction with 100 ml of water and 100 ml of ethyl acetate. The ethyl acetate layer was washed with water, dried over anhydrous magnesium sulfate, and distilled off under reduced pressure. The residue was purified by means of silica gel column chromatography (eluent, hexane:ethyl acetate=5:1) to yield 1.55 g of ethyl ester of trans-7-chloro-5-(2-ethoxyphenyl)-1-isobutyl-2-oxo-1,2,3,5-tetrahydro-4,1-benzoxazepine-3-acetic acid as prism crystals, m.p. 129° to 130° C.

Elemental Analysis for C$_{25}$H$_{30}$ClNO$_5$: Calcd.: C 65.28; H 6.57; N 3.05 Found: C 65.38; H 6.44; N 2.91

Example 124

Trans-7-chloro-5-(2-ethoxyphenyl)-1-isobutyl-2-oxo-1,2,3,5-tetrahydro-4,1-benzoxazepine-3-acetic acid In 30 ml of methanol was dissolved 1.25 g of ethyl ester of trans-7-chloro-5-(2-ethoxyphenyl)-1-isobutyl-2-oxo-1,2,3,5-tetrahydro-4,1-benzoxazepine-3-acetic acid, as obtained in Example 123, to which was added 10 ml of an aqueous solution containing 0.75 g of potassium carbonate; the mixture was then stirred for 3 hours at 60° C. After the reaction mixture was concentrated under reduced pressure, it was rendered acid by the addition of 50 ml of 1N hydrochloric acid, and subjected to extraction with 100 ml of ethyl acetate. The extract solution was washed with water and dried over anhydrous magnesium sulfate; the solvent was then distilled off under reduced pressure. The residue was purified by means of silica gel column chromatography (eluent, hexane:ethyl acetate=2:1; eluent, hexane:dichloromethane:ethanol=5:5:1) to yield 0.66 g of trans-7-chloro-5-(2-ethoxyphenyl)-1-isobutyl-2-oxo-1,2,3,5-tetrahydro-4,1-benzoxazepine-3-acetic acid as prism crystals, m.p. 190° to 192° C.

Elemental Analysis for C$_{23}$H$_{26}$ClNO$_5$: Calcd.: C 63.96; H 6.07; N 3.24 Found: C 63.64; H 5.96; N 3.58

Example 125

Ethyl ester of trans-5-(2-benzyloxyphenyl)-7-chloro-1-isobutyl-2-oxo-1,2,3,5-tetrahydro-4,1-benzoxazepine-3-acetic acid (1) 2-amino-2'-benzyloxy-5-chlorobenzophenone In 30 ml of N,N-dimethylformamide was dissolved 5.0 g of 2-amino-5-chloro-2'-hydroxybenzophenone, as obtained in Example 123 (1), to which were added 4.2 g of potassium carbonate and 2.9 ml of benzyl bromide; the mixture was then stirred for 2 hours at room temperature. The mixture was subjected to extraction with 150 ml of water and 200 ml of ethyl acetate, and the ethyl acetate layer was washed with water, dried over anhydrous magnesium sulfate, and distilled off under reduced pressure. The residue was purified by means of silica gel column chromatography (eluent, hexane:ethyl acetate=10:1 to 5:1) to yield 6.4 g of 2-amino-2'-benzyloxy-5-chlorobenzophenone as prism crystals, m.p. 110° to 111° C.

Elemental Analysis for $C_{20}H_{16}ClNO_2$: Calcd.: C 71.11; H 4.77; N 4.15 Found: C 71.34; H 4.80; N 4.23

(2) 2-amino-α-(2-benzyloxyphenyl)-5-chlorobenzyl alcohol

In 50 ml of methanol was dissolved 6.0 g of 2-amino-2'-benzyloxy-5-chlorobenzophenone, as obtained in (1), to which was added 1.12 g of sodium borohydride; the mixture was then stirred for 4 hours at room temperature. After ethanol was distilled off under reduced pressure, with dissociation by the addition of an aqueous solution of hydrochloric acid, the reaction mixture was rendered neutral by the addition of 50 ml of 1N sodium hydroxide and subjected to extraction with 200 ml of ethyl acetate. The ethyl acetate layer was washed with water, dried over anhydrous magnesium sulfate, then distilled off under reduced pressure to leave 5.9 g of 2-amino-α-(2-benzyloxyphenyl)-5-chlorobenzyl alcohol as plate crystals, m.p. 120° to 121° C.

Elemental Analysis for $C_{20}H_{18}ClNO_2$: Calcd.: C 70.69; H 5.34; N 4.12 Found: C 70.85; H 5.16; N 4.24

(3) α-(2-benzyloxyphenyl)-5-chloro-2-isobutylaminobenzyl alcohol

In 50 ml of acetic acid were dissolved 5.0 g of 2-amino-α-(2-benzyloxyphenyl)-5-chlorobenzyl alcohol, as obtained in (2), and 1.47 ml of isobutylaldehyde. To the solution was added, under ice-cooling, 0.74 g of sodium borohydride. The reaction mixture was stirred for 30 minutes at room temperature, and, after addition of 150 ml of water, was subjected to extraction with 200 ml of ethyl acetate. The extract solution was washed with 1N sodium hydroxide and dried over anhydrous magnesium sulfate; then the solvent was distilled off under reduced pressure. The residue was purified by means of silica gel column chromatography (eluent, hexane:ethyl acetate=20:1 to 5:1) to yield 5.6 g of α-(2-benzyloxyphenyl)-5-chloro-2-isobutylaminobenzyl alcohol as prism crystals, m.p. 79° to 80° C.

Elemental Analysis for $C_{24}H_{26}ClNO_2$: Calcd.: C 72.81; H 6.62; N 3.54 Found: C 72.95; H 6.62; N 3.62

(4) Ethyl ester of 3-[N-[4-chloro-2-[2-benzyloxy-α-hydroxybenzyl]phenyl]-N-isobutylcarbamoyl]acrylic acid A solution comprised of 2.65 g of monoethyl ester of fumaric acid and 4.0 ml of thionyl chloride in 30 ml of toluene was stirred for 1 hour at 90° C. It was then distilled under reduced pressure, leaving monoethyl ester acid chloride of fumaric acid. This product and 5.6 g of α-(2-benzyloxyphenyl)-5-chloro-2-isobutylaminobenzyl alcohol, as obtained in (3), were dissolved in 100 ml of methylene chloride; after the addition of 2.38 g of sodium bicarbonate, the mixture was stirred for 30 minutes at room temperature. The reaction mixture was washed with water and dried over anhydrous magnesium sulfate; then the solvent was distilled off under reduced pressure to yield 6.4 g ethyl ester of 3-[N-[4-chloro-2-[2-benzyloxy-α-hydroxybenzyl]phenyl]-N-isobutylcarbamoyl]acrylic acid as prism crystals, m.p. 169° to 171° C.

Elemental Analysis for $C_{30}H_{32}ClNO_5$: Calcd.: C 69.02; H 6.18; N 2.68 Found: C 69.24; H 6.04; N 2.71

(5) Ethyl ester of trans-5-(2-benzyloxyphenyl)-7-chloro-1-isobutyl-2-oxo-1,2,3,5-tetrahydro-4,1-benzoxazepine-3-acetic acid In 150 ml of ethanol was dissolved 6.0 g of ethyl ester of 3-[N-[4-chloro-2-[2-benzyloxy-α-hydroxybenzyl]phenyl]-N-isobutylcarbamoyl]acrylic acid, as obtained in (4), to which was added 3.18 g of potassium carbonate; the mixture was then stirred overnight. The solvent was distilled off under reduced pressure, and the residue was subjected to extraction with 150 ml of water and 200 ml of ethyl acetate. The ethyl acetate layer was washed with water and dried over anhydrous magnesium sulfate, then distilled off under reduced pressure. The residue was purified by means of silica gel column chromatography (eluent, hexane:ethyl acetate=5:1) to yield 5.8 g of ethyl ester of trans-5-(2-benzyloxyphenyl)-7-chloro-1-isobutyl-2-oxo-1,2,3,5-tetrahydro-4,1-benzoxazepine-3-acetic acid as prism crystals, m.p. 146° to 147° C.

Elemental Analysis for $C_{30}H_{32}ClNO_5$: Calcd.: C 69.02; H 6.18; N 2.68 Found: C 69.20; H 6.21; N 2.95

Example 126

Trans-5-(2-benzyloxyphenyl)-7-chloro-1-isobutyl-2-oxo-1,2,3,5-tetrahydro-4,1-benzoxazepine-3-acetic acid In a mixture of 20 ml of methanol and 10 ml of tetrahydrofuran was dissolved 0.5 g of ethyl ester of trans-5-(2-benzyloxyphenyl)-7-chloro-1-isobutyl-2-oxo-1,2,3,5-tetrahydro-4,1-benzoxazepine-3-acetic acid, as obtained in Example 125. To this solution was added 10 ml of an aqueous solution containing 0.66 g of potassium carbonate, and the mixture was stirred for 6 hours at 60° C. The reaction mixture was concentrated under reduced pressure, rendered acid by the addition of 50 ml of 1N hydrochloric acid, and subjected to extraction with 100 ml of ethyl acetate. The extract solution was washed with water and dried over anhydrous magnesium sulfate; then the solvent was distilled off under reduced pressure. The residue was purified by means of silica gel column chromatography (eluent, hexane:ethyl acetate=3:1; eluent, hexane:dichloromethane:ethanol=5:5:1) to yield 0.21 g of trans-5-(2-benzyloxyphenyl)-7-chloro-1-isobutyl-2-oxo-1,2,3,5-tetrahydro-4,1-benzoxazepine-3-acetic acid as prism crystals, m.p. 194° to 197° C.

Elemental Analysis for $C_{28}H_{28}ClNO_5$: Calcd.: C 68.08; H 5.71; N 2.84 Found: C 68.07; H 5.75; N 2.85

Example 127

Ethyl ester of trans-7-chloro-5-(2-hydroxyphenyl)-1-isobutyl-2-oxo-1,2,3,5-tetrahydro-4,1-benzoxazepine-3-acetic acid In 50 ml of ethyl acetate was dissolved 3.5 g of ethyl ester of trans-5-(2-benzyloxyphenyl)-7-chloro-1-isobutyl-2-oxo-1,2,3,5-tetrahydro-4,1-benzoxazepine-3-acetic acid, as obtained in Example 125. To this solution was added 1.0 g of 10% palladium carbon and hydrogenolysis was then allowed to occur at normal temperature and pressure. After the calculated amount of hydrogen was absorbed, the catalyst was removed, and the ethyl acetate was distilled off under reduced pressure. The residue was purified by means of silica gel column chromatography (eluent, hexane:ethyl acetate=3:1) to yield 2.8 g of ethyl ester of trans-7-chloro-5-(2-hydroxyphenyl)-1-isobutyl-2-oxo-1,2,3,5-tetrahydro-4,1-benzoxazepine-3-acetic acid as an oily product.

IR $v_{max}^{neat}$ cm$^{-1}$: 3380 (OH); 1730, 1670, 1650 (C=O)
$^1$H-NMR spectrum (200 MHz, CDCl$_3$) δ: 0.90 (3H, d, J=6.6 Hz), 0.99 (3H, d, J=6.6 Hz), 1.24 (3H, t, J=7.2 Hz), 1.9–2.2 (1H, m), 2.85 (1H, dd, J=17.8, 5.0 Hz), 2.97 (1H, d, J=17.8, 8.2 Hz), 3.41 (1H, dd, J=13.8, 6.4 Hz), 4.16 (2H, q, J=7.2 Hz), 4.30 (1H, dd, J=13.8, 7.8 Hz), 4.49 (1H, dd, J=8.2, 4.8 Hz), 5.97 (1H, s), 6.85 (1H, d, J=2.4 Hz), 6.85–7.5 (6H, m), 7.54 (1H, br OH)

Example 128

Trans-7-chloro-5-(2-hydroxyphenyl)-1-isobutyl-2-oxo-1,2,3,5-tetrahydro-4,1-benzoxazepine-3-acetic acid In 10 ml of methanol was dissolved 0.4 g of ethyl ester of trans-7-chloro-5-(2-hydroxyphenyl)-1-isobutyl-2-oxo-1,2,3,5-tetrahydro-4,1-benzoxazepine-3-acetic acid, as obtained in Example 127, to which was added 5 ml of an aqueous solution containing 0.51 g of potassium carbonate; the mixture was then stirred for 1 hour at 60° C. The reaction mixture was condensed under reduced pressure, rendered acid by the addition of 50 ml of 1N hydrochloric acid, and subjected to extraction with 100 ml of ethyl acetate. The extract solution was washed with water and dried over anhydrous magnesium sulfate; the solvent was then distilled off under reduced pressure. The residue was purified by means of silica gel column chromatography (eluent, hexane:ethyl acetate=2:1; eluent, hexane:dichloromethane:ethanol=5:5:2) to yield 0.11 g of trans-7-chloro-5-(2-hydroxyphenyl)-1-isobutyl-2-oxo-1,2,3,5-tetrahydro-4,1-benzoxazepine-3-acetic acid as prism crystals, m.p. 238° to 242° C. (decomposition).

Elemental Analysis for $C_{21}H_{22}ClNO_5$: Calcd.: C 62.45; H 5.49; N 3.47 Found: C 62.55; H 5.68; N 3.41

Example 129

Ethyl ester of trans-7-chloro-1-isobutyl-5-(2-isopropyloxyphenyl)-2-oxo-1,2,3,5-tetrahydro-4,1-benzoxazepine-3-acetic acid In 10 ml of N,N-dimethylformamide was dissolved 0.7 g of ethyl ester of trans-7-chloro-5-(2-hydroxyphenyl)-1-isobutyl-2-oxo-1,2,3,5-tetrahydro-4,1-benzoxazepine-3-acetic acid, as obtained in Example 127, to which was added 0.34 g of potassium carbonate and 0.24 ml of isopropyl iodide; the mixture was then stirred overnight at room temperature. The mixture was subjected to extraction with 100 ml of water and 150 ml of ethyl acetate, after which the ethyl acetate layer was washed with 1N hydrochloric acid and sodium bicarbonate, dried over anhydrous magnesium sulfate, and distilled off under reduced pressure. The residue was purified by means of silica gel column chromatography (eluent, hexane:ethyl acetate=3:1) to yield 0.55 g of ethyl ester of trans-7-chloro-1-isobutyl-5-(2-isopropyloxyphenyl)-2-oxo-1,2,3,5-tetrahydro-4,1-benzoxazepine-3-acetic acid as needles, m.p. 135° to 137° C.

Elemental Analysis for $C_{26}H_{32}ClNO_5$: Calcd.: C 65.88; H 6.80; N 2.96 Found: C 66.09; H 6.83; N 3.24

Example 130

Trans-7-chloro-1-isobutyl-5-(2-isopropyloxyphenyl)-2-oxo-1,2,3,5-tetrahydro-4,1-benzoxazepine-3-acetic acid In 20 ml of methanol was dissolved 0.4 g of ethyl ester of trans-7-chloro-5-(2-isopropyloxyphenyl)-1-isobutyl-2-oxo-1,2,3,5-tetrahydro-4,1-benzoxazepine-3-acetic acid, as obtained in Example 129. To this solution was added 10 ml of an aqueous solution containing 0.23 g of potassium carbonate; the mixture was then stirred for 3 hours at 80° C. The reaction mixture was concentrated under reduced pressure, rendered acid by the addition of 50 ml of 1N hydrochloric acid, and subjected to extraction with 100 ml of ethyl acetate. The extract solution was washed with water and dried over anhydrous magnesium sulfate, the solvent was then distilled off under reduced pressure. The residue was purified by means of silica gel column chromatography (eluent, hexane:ethyl acetate=3:1; eluent, hexane:dichloromethane:ethanol=5:5:1) to yield 0.24 g of trans-7-chloro-1-isobutyl-5-(2-isopropyloxyphenyl)-2-oxo-1,2,3,5-tetrahydro-4,1-benzoxazepine-3-acetic acid as prism crystals, m.p. 146° to 149° C.

Elemental Analysis for $C_{24}H_{28}ClNO_5 \cdot 0.2H_2O$: Calcd.: C 64.12; H 6.37; N 3.11 Found: C 64.18; H 6.37; N 3.28

Example 131

Ethyl trans-7-bromo-1-neopentyl-2-oxo-5-(2-pyridyl)-1,2,3,5-tetrahydro-4,1-benzoxazepine-3-acetate (1) 2-Amino-5-bromo-α-(2-pyridyl)benzyl alcohol In 100 ml of methanol was dissolved 10 g of 2-amino-5-bromophenyl-2-pyridylketone. To the solution was added 1.7 g of sodium borohydride and stirred for 30 minutes. The solvent methanol was evaporated off under reduced pressure. The residue was treated with an aqueous solution of hydrochloric acid. The decomposed residue was then neutralized with 200 ml of a sodium bicarbonate aqueous solution, and extracted with ethyl acetate. The ethyl acetate layer was washed with water, dried over anhydrous magnesium sulfate and concentrated under reduced pressure. The residue was purified by silica gel column chromatography (eluent, hexane:ethyl acetate=2:1) to give 2-amino-5-bromo-α-(2-pyridyl)benzyl alcohol (9.0 g) as prisms, m.p. 104°–105° C.

Elementary analysis for $C_{12}H_{11}BrN_2O$ Calcd.: C 51.64; H 3.97; N 10.04 Found: C 51.61; H 3.93; N 10.04

(2) 5-Bromo-2-neopentylamino-α-(2-pyridyl)benzyl alcohol

In 20 ml of acetic acid was dissolved 2.0 g of 2-amino-5-bromo-α-(2-pyridyl)benzyl alcohol obtained in (1) together with 0.86 ml of trimethylacetoaldehyde. To the solution was added 0.36 g of sodium borohydride under ice-cooling. The reaction mixture was stirred for 30 minutes at room temperature and then subjected to extraction with a mixture of 100 ml of water and 150 ml of ethyl acetate. The ethyl acetate layer was washed with 1N sodium hydroxide, dried over anhydrous magnesium sulfate, and concentrated to dryness under reduced pressure. The residue was purified by silica gel column chromatography (eluent, hexane:ethyl acetate=5:1) to afford 5-bromo-2-neopentylamino-α-(2-pyridyl)benzyl alcohol (2.4 g) as an oily product.

IR $\nu_{Max}^{Neat}$ cm$^{-1}$: 3390, 3280 (NH,OH)

$^1$H-NMR spectrum (200 MHz, CDCl$_3$) δ: 0.80 (9H, s, But), 2.68 (2H; s), 5.69 (1H, s), 6.48 (1H, d, J=8.4 Hz), 7.1–7.35 '(4H, m), 7.55–7.7 (1H, m), 8.5–8.6 (1H, m).

(3) Ethyl 3-[N-[4-bromo-2-[α-(2-pyridyl)hydroxymethyl]phenyl]-N-neopentylcarbamoyl]acrylate In 50 ml of dichloromethane was dissolved 2.4 g of 5-bromo-2-neopentylamino-α-(2-pyridyl)benzyl alcohol obtained in (2). To the solution were added 1.15 g of sodium borohydride and 1.23 g of monomethyl fumarate acid chloride. After stirring for 2 hours at room temperature, the reaction mixture was washed with water and dried over anhydrous magnesium sulfate. The solvent was evaporated off under reduced pressure. The residue was purified by column chromatography using silica gel (eluent, hexane:ethyl acetate=2:1) to give ethyl 3-[N-[4-bromo-2-[α-(2-pyridyl) hydroxymethyl]phenyl]-N-neopentylcarbamoyl] acrylate as prisms, m.p. 165°–166° C.

Elementary analysis for $C_{23}H_{27}BrN_2O_4$: Calcd.: C 58.11; H 5.72; N 5.89 Found: C 58.21; H 5.65; N 6.14

(4) Ethyl trans-7-bromo-1-neopentyl-5-(2-pyridyl)-2-oxo-1,2,3,5-tetrahydro-4,1-benzoxazepine-3-acetate In 30 ml of ethanol was dissolved 2.0 g of ethyl 3-[N-[4-bromo-2-[α-(2-pyridyl)hydroxymethyl]phenyl]-N-neopentylcarbamoyl]acrylate obtained in (3). To the solution was added 1.16 g of potassium carbonate and the mixture was stirred overnight at room temperature. The solvent was evaporated off under reduced pressure. The residue was then extracted with 100 ml of water and 100 ml of ethyl acetate. The organic layer was washed with water, dried over anhydrous magnesium sulfate, and concentrated under reduced pressure. The residue was purified on a silica gel column (eluent, hexane:ethyl acetate=3:1) to give 1.9 g of ethyl trans-7-bromo-1-neopentyl-5-(2-pyridyl)-2-oxo-1,2,3,5-tetrahydro-4,1-benzoxazepine-3-acetate as an oily product.

IR $v_{Max}^{Neat}$ cm$^{-1}$: 1730, 1675 (C=O)

$^1$H-NMR (CDCl$_3$) δ: 0.94(9H,s,Bu$^t$), 1.25(3H,t,J=7.2 Hz), 2.80(1H,dd,J=16.6,5.8 Hz), 3.07(1H,dd,J=16.6,7.8 Hz), 3.31(1H,d,J=13.8 Hz), 4.13(2H,q, J=7.2 Hz), '4.44(1H, dd,J=7.8,5.8 Hz), 4.49(1H,d,J=13.8 Hz), 6.07 (1H,s), 6.59 (1H,d,J=2.2 Hz), 7.2–7.9 (5H,m), 8.6–8.7(1H,m)

Example 132

Trans-7-bromo-1-neopentyl-5-(2-pyridyl)-2-oxo-1,2,3,5-tetrahydro-4,1-benzoxazepine-3-acetic acid In 20 ml of methanol was dissolved 1.9 g of ethyl trans-7-bromo-1-neopentyl-5-(2-pyridyl)-2-oxo-1,2,3,5-tetrahydro-4,1-benzoxazepine-3-acetate obtained in Example 131. To the solution was added 10 ml of an aqueous solution containing 1.1 g of potassium carbonate. The mixture was heated and refluxed for 30 minutes, and then concentrated under reduced pressure. The concentrate was crystallized by the addition of 30 ml of a hydrochloric acid aqueous solution. The product was collected by filteration and recrystallized from hexane and ethanol to give 1.25 g of trans-7-bromo-1-neopentyl-5-(2-pyridyl)-2-oxo-1,2,3,5-tetrahydro-4,1-benzoxazepine-3-acetic acid as prisms, m.p.>263° C. (decomp.)

Elementary analysis for $C_{21}H_{23}BrN_2O_4$ Calcd.: C 56.39; H, 5.18; N 6.26 Found: C 56.39; H, 5.18; N 6.10

Example 133

Ethyl N-benzyl-N-[trans-7-chloro-5-(2-chlorophenyl)-1-neopentyl-2-oxo-1,2,3,5-tetrahydro-4,1-benzoxazepine-3-acetyl]aminoacetate In 10 ml of dimethylformamide were dissolved 0.3 g of trans-7-chloro-5-(2-chlorophenyl)-1-neopentyl-2-oxo-1,2,3,5-tetrahydro-4,1-benzoxazepine-3-acetic acid obtained in Example 2 and 0.27 g of N-benzylglycine ethyl ester. To the solution was added 0.24 g of diethyl phosphorocyanidate together with 0.19 ml of triethylamine under ice-cooling. The mixture was stirred for 30 minutes at room temperature and then subjected to extraction with a mixture of 100 ml of water and 100 ml of ethyl acetate. The ethyl acetate layer was washed with 1N hydrochloric acid and with a sodium bicarbonate aqueous solution, dried over anhydrous magnesium sulfate, and concentrated under reduced pressure. The residue was purified by silica gel column chromatography (eluent, hexane:ethyl acetate=3:1) to afford ethyl N-benzyl-N-[trans-7-chloro-5-(2-chlorophenyl)-1-neopentyl-2-oxo-1,2,3,5-tetrahydro-4,1-benzoxazepine-3-acetyl]amino acetate (0.56 g) as prisms, m.p. 195°–197° C.

Elementary Analysis for $C_{33}H_{36}Cl_2N_2O_5$ Calcd.: C 64.81; H 5.93; N,4.58 Found: C 64.84; H 5.97; N 4.45

Example 134

N-Benzyl-N-[trans-7-chloro-5-(2-chlorophenyl)-1-neopentyl-2-oxo-1,2,3,5-tetrahydro-4,1-benzoxazepine-3-acetyl]amino acetic acid In 15 ml of methanol was dissolved 0.3 g of ethyl N-benzyl-N-[trans-7-chloro-5-(2-chlorophenyl)-1-neopentyl-2-oxo-1,2,3,5-tetrahydro-4,1-benzoxazepine-3-acetyl]amino acetate obtained in Example 133. To the solution was added 4 ml of sodium hydroxide and the mixture was stirred for 20 minutes. The reaction mixture, after acidified with 50 ml of 1N HCl, was subjected to extraction with 100 ml of ethyl acetate. The ethyl acetate layer was washed with water and dried over anhydrous magnesium sulfate. The solvent was 'evaporated under reduced pressure to yield N-benzyl-N-[trans-7-chloro-5-(2-chlorophenyl)-1-neopentyl-2-oxo-1,2,3,5-tetrahydro-4,1-benzoxazepine-3-acetyl]amino acetic acid as prisms, m.p. 190°–192° C.

Elementary Analysis for $C_{31}H_{32}Cl_2N_2O_5$: Calcd.: C 63.81; H 5.53; N 4.80 Found: C 64.02; H 5.85; N 4.81

Example 135

Methyl N-[trans-7-chloro-5-(2-chlorophenyl)-1-neopentyl-2-oxo-1,2,3,5-tetrahydro-4,1-benzoxazepine-3-acetyl]-N-phenyl aminoacetate A mixture of 0.6 g of trans-7-chloro-5-(2-chlorophenyl)-1-neopentyl-2-oxo-1,2,3,5-tetrahydro-4,1-benzoxazepine-3-acetic acid obtained in Example 2,10 ml of thionyl chloride and 10 ml of toluene was stirred for 30 minutes at 90° C., and then concentrated under reduced pressure. The concentrate trans-7-chloro-5-(2-chlorophenyl)-1-neopentyl-2-oxo-1,2,3,5-tetrahydro-4,1-benzoxazepine-3-acetyl chloride was dissolved in 10 ml of methylene chloride. To the solution were added 0.27 g of N-phenylglycine methyl ester and 0.23 ml of triethylamine. The mixture was stirred for one hour at room temperature, and then subjected to extraction with 100 ml of ethyl acetate. The organic layer was washed with 1N HCl and with a sodium bicarbonate aqueous solution, dried over anhydrous magnesium sulfate and concentrated under reduced pressure.

The residue was purified on a silica gel column (eluent, hexane:ethyl acetate=3:1) to give methyl N-[trans-7-chloro-5-(2-chlorophenyl)-1-neopentyl-2-oxo-1,2,3,5-tetrahydro-4,1-benzoxazepine-3-acetyl]-N-phenyl amino acetate (0.35 g) as prisms, m.p. 226°–228° C.

Elementary Analysis for $C_{31}H_{32}Cl_2N_2O_5$: Calcd.: C 63.81; H 5.53; N 4.80 Found: C 63.78; H 5.59; N 4.60

Example 136

N-[trans-7-chloro-5-(2-chlorophenyl)-1-neopentyl-2-oxo-1,2,3,5-tetrahydro-4,1-benzoxazepine-3-acetyl]-N-phenylamino acetic acid In 3 ml of methanol was dissolved 0.25 g of methyl N-[trans-7-chloro-5-(2-chlorophenyl)-1-neopentyl-2-oxo-1,2,3,5-tetrahydro-4,1-benzoxazepine-3-acetyl]-N-phenyl amino acetate obtained in Example 135. To the solution was added 2 ml of 1N sodium hydroxide. The mixture was stirred for 1.5 hours at 60° C. and then acidified with 50 ml of 1N HCl for extraction with ethyl acetate. The ethyl acetate layer was washed with water, dried over anhydrous magnesium sulfate, and concentrated under reduced pressure to give 0.23 g of N-[trans-7-chloro-5-(2-chlorophenyl)-1-neopentyl-2-oxo-1,2,3,5-tetrahydro-4,1-benzoxazepine-3-acetyl]-N-phenylaminoacetic acid 0.23 g) as prisms, m.p. 238°–240° C.

Elementary Analysis for $C_{30}H_{30}Cl_2N_2O_5$: Calcd.: C 63.27; H 5.31; N 4.92 Found: C 63.46; H 5.54; N 4.70

Example 137

Ethyl N-[trans-7-chloro-5-(2-methoxyphenyl)-1-neopentyl-2-oxo-1,2,3,5-tetrahydro-4,1-benzoxazepine-3-acetyl]amino acetate In 10 ml of dimethylformamide were dissolved 0.3 g of trans-7-chloro-5-(2-methoxyphenyl)-1-neopentyl-2-oxo-1, 2,3,5-tetrahydro-4,1-benzoxazepine-3-acetic acid obtained in Example 74 and 0.12 g of glycine ethyl ester hydrochloride. To the solution were added 0.14 g of diethyl phosphorocyanidate and 0.24 ml of triethylamine under ice-cooling. The mixture was stirred for 30 minutes at room temperature and then subjected to extraction with 100 ml of water and 100 ml of ethyl acetate. The ethyl acetate layer was washed with 1N HCl and with a sodium bicarbonate aqueous solution and dried over anhydrous magnesium sulfate. Ethyl acetate was evaporated off under reduced pressure. The residue was purified by silica gel column chromatography (eluent, hexane:ethyl acetate=1:1) to yield ethyl N-[trans-7-chloro-5-(2-methoxyphenyl)-1-neopentyl-2-oxo-1,2,3,5-tetrahydro-4,1-benzoxazepine-3-acetyl]amino acetate (0.33 g) as needles, m.p. 233°–236° C.

Elementary Analysis for $C_{27}H_{33}ClN_2O_6$ Calcd.: C 62.72; H 6.43; N 5.42 Found: C 62.54; H 6.47; N 5.28

Example 138

N-[Trans-7-chloro-5-(2-methoxyphenyl)-1-neopentyl-2-oxo-1,2,3,5-tetrahydro-4,1-benzoxazepine-3-acetyl]aminoacetic acid In 5 ml of ethanol was dissolved 0.25 g of ethyl N-[trans-7-chloro-5-(2-methoxyphenyl)-1-neopentyl-2-oxo-1,2,3,5-tetrahydro-4,1-benzoxazepine-3-acetyl]aminoacetate obtained in Example 137. To the solution was added 2 ml of 1N NaOH. After stirring for 15 minutes, the reaction mixture was acidified with 100 ml of 1N HCl and subjected to extraction with ethyl acetate. The organic layer was washed with water and dried over anhydrous magnesium sulfate. Ethyl acetate was evaporated off under reduced pressure to afford N-[trans-7-chloro-5-(2-methoxyphenyl)-1-neopentyl-2-oxo-1,2,3,5-tetrahydro-4,1-benzoxazepine-3-acetyl] amino acetic acid as prisms, m.p. 239°–242° C.

Elementary Analysis for $C_{25}H_{29}ClN_2O_5$ Calcd.: C 61.41; H 5.98; N 5.73 Found: C 61.38; H 5.91; N 5.83

Example 139

Trans-7-chloro-5-(2-chlorophenyl)-1-neopentyl-2-oxo-1,2,3,5-tetrahydro-4,1-benzoxazepine-3-methylamine hydrochloride In the same manner as done in Example 36 was treated 1.0 g of trans-7-chloro-5-(2-chlorophenyl)-1-neopentyl-2-oxo-1,2,3,5-tetrahydro-4,1-benzoxazepine-3-acetic acid obtained in Example 2. The product was 0.90 g of trans-7-chloro-5-(2-chlorophenyl)-1-neopentyl-2-oxo-1,2,3,5-tetrahydro-4,1-benzoxazepine-3-methylamine hydrochloride as plate crystals, m.p. 173°–175° C.

Elementary Analysis for $C_{21}H_{24}Cl_2N_2O_2 \cdot HCl \cdot H_2O$ Calcd.: C 54.62; H 5.89; N 6.06 Found: C 54.77; H 5.95; N 5.83

Example 140

Methyl N-[trans-7-chloro-5-(2-chlorophenyl)-1-neopentyl-2-oxo-1,2,3,5-tetrahydro-4,1-benzoxazepine-3-methyl]carbamoyl acetate In 10 ml of N,N-dimethylformamide were dissolved 0.3 g of trans-7-chloro-5-(2-chlorophenyl)-1-neopentyl-2-oxo-1, 2,3,5-tetrahydro-4,1-benzoxazepine- 3-methylamine hydrochloride obtained in Example 139 and 0.12 g of monomethyl malonate potassium salt. To the solution was added 0.13 g of diethyl phosphorocyanate together with 0.11 ml of triethylamine under ice-cooling. After stirring for 30 minutes at room temperature, the reaction mixture was subjected to extraction with 100 ml of water and 100 ml of ethyl acetate. The ethyl acetate layer was washed with 1N HCl and with a sodium bicarbonate aqueous solution, and dried over anhydrous magnesium sulfate. The solvent ethyl acetate was then evaporated off under reduced pressure. The residue was purified by silica-gel column chromatography (eluent, hexane:ethyl acetate=1:1) to give 0.28 g of methyl N-[trans-7-chloro-5-(2-chlorophenyl)-1-neopentyl-2-oxo-1,2,3,5-tetrahydro-4,1-benzoxazepine-3-methyl]carbamoyl acetate as an oily product.

IR $\nu_{Max}^{Neat}$ cm$^{-1}$: 3330(NH); 1740, 1670 (C=O)

$^1$H-NMR (200 MHz, CDCl$_3$) δ: 0.94 (9H,s,Bu$^t$), 3.28 (2H,s), 3.38 (1H,d,J=13.9 Hz), 3.74(3H,s), 3.7–3.85(2H,m), 3.99(1H,t,J=6.1 Hz), 4.54(1H,d,J=13.9 Hz), 6.25(1H,s), 6.52(1H,d,J=1.9 Hz), 7.2–7.9(7H,m,NH).

Example 141

N-[Trans-7-chloro-5-(2-chlorophenyl)-1-neopentyl-2-oxo-1,2,3,5-tetrahydro-4,1-benzoxazepine-3-methyl]carbamoyl acetic acid In 5 ml of ethanol was dissolved 0.28 g of methyl N-[trans-7-chloro-5-(2-chlorophenyl)-1-neopentyl-2-oxo-1, 2,3,5-tetrahydro-4,1-benzoxazepine-3-methyl]carbamoyl acetate obtained in Example 140. To the solution was added 2 ml of 1N sodium hydroxide and the mixture was stirred for 10 minutes at room temperature. The reaction mixture was acidified with 50 ml of 1N hydrochloric acid and then subjected to extraction with 50 ml of ethyl acetate. The ethyl acetate layer was washed with water, dried over anhydrous magnesium sulfate, and concentrated under reduced pressure to afford 0.23 g of N-[trans-7-chloro-5-(2-chlorophenyl)-1-neopentyl-2-oxo-1,2,3,5-tetrahydro-4,1-benzoxazepine-3-methyl]carbamoyl acetic acid as plate crystals, m.p. 135°–138° C.

Elementary analysis for $C_{24}H_{26}Cl_2N_2O_5$: Calcd.: C 58.43; H 5.31; N 5.68 Found: C 58.48; H 5.42; N 5.52

Example 142

Tert-butyl N-[trans-7-chloro-5-(2-chlorophenyl)-1-neopentyl-2-oxo-1,2,3,5-tetrahydro-4,1-benzoxazepine 3-methyl]aminoacetate A mixture of 2.5 g of trans-7-chloro-5-(2-chlorophenyl)-1-neopentyl-2-oxo-1,2,3,5-tetrahydro-4,1-benzoxazepine-3-methylamine hydrochloride obtained in Example 139, 0.93 ml of ethyl chloroacetate, 1.87 g of potassium carbonate, and 50 ml of acetonitrile was heated and refluxed overnight. The reaction mixture was concentrated under reduced pressure and the concentrate was extracted with 100 ml of water and 150 ml of ethyl acetate. The organic layer was washed with water and dried over anhydrous magnesium sulfate. Ethyl acetate was evaporated under reduced pressure to give 1.95 g of tert-butyl N-[trans-7-chloro-5-(2-chlorophenyl)-1-neopentyl-2-oxo-1,2,3,5-tetrahydro-4,1-benzoxazepine-3-methyl]aminoacetate as an oily product.

IR $v_{Max.}^{Neat}$ cm$^{-1}$:3330 (NH); 1735, 1675 (C=O)

$^1$H-NMR (200 MHz, CDCl$_3$) δ: 0.94 (9H,s,Bu$^t$), 1.44 (9H,s, Bu$^t$), 3.00 (1H,dd,J=12.2,6.4 Hz), 3.11 (1H,dd,J=12.2,6.2 Hz), 3.33(2H,s), 3.36(1H,d,J=14.0 Hz), 4.04(1H,t, J=6.3 Hz), 4.52(1H,d,J=14.0 Hz), 6.26(1H,s), 6.52(1H,d,J= 1.8 Hz), 7.2–7.85(6H,m)

Example 143

N-[Trans-7-chloro-5-(2-chlorophenyl)-1-neopentyl-2-oxo-1,2,3,5-tetrahydro-4,1-benzoxazepine-3-methyl]aminoacetic acid hydrochloride In 15 ml of 4N HCl-dioxane solution was dissolved 0.3 mg of tert-butyl N-[trans-7-chloro-5-(2-chlorophenyl)-1-neopentyl-2-oxo-1,2,3,5-tetrahydro-4,1-benzoxazepine-3-methyl]aminoacetate obtained in Example 142. After stirring for 8 hours at room temperature, the reaction mixture was concentrated under reduced pressure. The addition of hexane and ethyl acetate to the residue yielded 0.23 g of powdered 'N-[trans-7-chloro-5-(2-chlorophenyl)-1-neopentyl-2-oxo-1,2,3,5-tetrahydro-4,1-benzoxazepine-3-methyl]aminoacetic acid hydrochloride.

Elementary analysis for $C_{23}H_{26}Cl_2N_2O_4 \cdot HCl$ Calcd.: C 55.05; H 5.42; N 5.58 Found: C 55.38; H 5.77; N 5.39

$^1$H-NMR spectrum (200 MHz, d$_6$-DMSO) δ: 0.89(9H,s, Bu$^t$), 3.2–3.55(2H,m), 3.68(1H,d,J=14.0 Hz), 3.88(2H,s), 4.32(1H,d,J=14.0 Hz), 4.3–4.5(1H,m), 6.19(1H, s), 6.39(1H, d,J=2.4 Hz), 7.5–8.1(6H,m).

Example 144

Tert-butyl N-[trans-7-chloro-5-(2-chlorophenyl)-1-neopentyl-2-oxo-1,2,3,5-tetrahydro-4,1-benzoxazepine-3-methyl]-N-methansulfonylaminoacetate In 5 ml of N,N-dimethylformamide was dissolved 0.44 g of tert-butyl N-[trans-7-chloro-5-(2-chlorophenyl)-1-neopentyl-2-oxo-1,2,3,5-tetrahydro-4,1-benzoxazepine-3-methyl]aminoacetate obtained in Example 142. To the solution was added 0.072 ml of methanesulfonyl chloride 'and 0.14 ml of triethylamine under ice-cooling. After stirring for 30 minutes at room temperature, the reaction mixture was subjected to extraction with 100 ml of water and 100 ml of ethyl acetate. The ethyl acetate layer was washed with 5% potassium bisulfate solution and with a sodium bicarbonate aqueous solution and dried over anhydrous magnesium sulfate. Ethyl acetate was evaporated off under reduced pressure. The residue was purified by silica gel column chromatography (hexane:acetate=3:1) to afford 0.37 g of tert-butyl N-[trans-7-chloro-5-(2-chlorophenyl)-1-neopentyl-2-oxo-1,2,3,5-tetrahydro-4,1-benzoxazepine-3-methyl]-N-methanesulfonylaminoacetate as prisms, m.p. 178°–180° C.

Elementary analysis for $C_{28}H_{36}Cl_2N_2O_6S$ Calcd.: C 56.09; H 6.05; N 4.67 Found: C 55.92; H 6.06; N 4.47

Example 145

N-[Trans-7-chloro-5-(2-chlorophenyl)-1-neopentyl-2-oxo-1,2,3,5-tetrahydro-4,1-benzoxazepine-3-methyl]-N-methanesulfonylaminoacetic acid In 20 ml of 4N HCl-dioxane solution was dissolved 0.25 g of tert-butyl N-[trans-7-chloro-5-(2-chlorophenyl)-1-neopentyl-2-oxo-1,2,3,5-tetrahydro-4,1-benzoxazepine-3-methyl]-N-methanesulfonylaminoacetate obtained in Example 144. After stirring for 8 hours at room temperature, the reaction mixture was concentrated under reduced pressure. The residue was treated with hexane and ethyl acetate to give 0.21 g of N-[trans-7-chloro-5-(2-chlorophenyl)-1-neopentyl-2-oxo-1,2,3,5-tetrahydro-4,1-benzoxazepine-3-methyl]N-methanesulfonylaminoacetic acid as prisms, m.p. 236°–238° C.

Elementary analysis for $C_{24}H_{28}Cl_2N_2O_6S$ Calcd.: C 53.04; H 5.19; N 5.15 Found: C 53.32; H 5.42; N 5.02

Example 146

Tert-butyl N-[trans-7-chloro-5-(2-chlorophenyl)-1-neopentyl-2-oxo-1,2,3,5-tetrahydro-4,1-benzoxazepine-3-methyl]-N-(p-toluenesulfonyl)aminoacetate In 10 ml of N,N-dimethylformamide was dissolved 0.5 g of tert-butyl N-[trans-7-chloro-5-(2-chlorophenyl)-1-neopentyl-2-oxo-1,2,3,5-tetrahydro-4,1-benzoxazepine-3-methyl]aminoacetate obtained in Example 142. To the solution was added 0.22 g of p-toluenesulfonyl chloride together with 0.16 ml of triethylamine under ice-cooling.

The mixture was stirred for one hour at room temperature and then subjected to extraction with 100 ml of water and 100 ml of ethyl acetate. The ethyl acetate layer was washed with 5% potassium bisulfate solution and with sodium bicarbonate aqueous solution, dried over anhydrous magnesium sulfate. The solvent was evaporated off under reduced pressure. The residue was purified by column chromatography using silica gel (eluent, hexane:ethyl acetate=5:1) to afford tert-butyl N-[trans-7-chloro-5-(2-chlorophenyl)-1-neopentyl-2-oxo-1,2,3,5-tetrahydro-4,1-benzoxazepine-3-methyl]-N-(p-toluenesulfonyl)aminoacetate as an oily product.

IR $v_{Max}^{Neat}$ cm$^{-1}$: 1740, 1670 (C=O)

$^1$H-NMR (200 MHz, CDCl$_3$) δ: 0.92 (9H,s,Bu$^t$), 2.39(3H, s), 3.36(1H,d,J=14.0 Hz), 3.66(1H,dd,J=15.6,6.4 Hz), 3.84 (1H,dd, J=15.6,5.9 Hz), 3.98(1H,d,J=18.4 Hz), 4.2–4.3(1H, m), 4.29(1H, d,J=18.4 Hz), 4.45(1H,d,J=14.0 Hz), 6.20(1H, s), 6.46(1H,s, J=2.1 Hz), 7.15–7.7(10H,m).

Example 147

N-[Trans-7-chloro-5-(2-chlorophenyl)-1-neopentyl-2-oxo-1,2,3,5-tetrahydro-4,1-benzoxazepine-3-methyl]-N-(p-toluenesulfonyl)aminoacetic acid In 15 ml of 4N HCl-dioxane solution was dissolved 0.5 g of tert-butyl N-[trans-7-chloro-5-(2-chlorophenyl)-1-neopentyl-2-oxo-1,2,3,5-tetrahydro-4,1-benzoxazepine-3-methyl]-N-(p-toluenesulfonyl)aminoacetate obtained in Example 146. After stirring for 4 hours at room temperature, the reaction solution was concentrated under reduced pressure. The residue was treated with hexane and diethyl ether to afford 0.41 g of N-[trans-7-chloro-5-(2-chlorophenyl)-1-neopentyl-2-oxo-1,2,3,5-tetrahydro-4,1-benzoxazepine-3-methyl]-N-(p-toluenesulfonyl)aminoacetic acid as needles, m.p. 132°–134° C.

Elementary analysis for $C_{30}H_{32}Cl_2N_2O_6S$: Calcd.: C 58.16; H 5.21; N 4.52 Found: C 58.01; H 5.32; N 4.55

Example 148

Tert-butyl N-acetyl-N-[trans-7-chloro-5-(2-chlorophenyl)-1-neopentyl-2-oxo-1,2,3,5-tetrahydro-4,1-benzoxazepine-3-methyl]aminoacetate.

In 10 ml of N,N-dimethylformamide was dissolved 0.5 g of tert-butyl N-[trans-7-chloro-5-(2-chlorophenyl)-1- neopentyl-2-oxo-1,2,3,5-tetrahydro-4,1-benzoxazepine-3-methyl]aminoacetate obtained in Example 142. To the solution was added 0.082 ml of acetyl chloride and 0.16 ml of triethylamine under ice-cooling.

The mixture was stirred for 80 minutes at room temperature and then subjected to extraction with 100 ml of water and 100 ml of ethyl acetate. The ethyl acetate layer was washed with 5% potassium bisulfate solution and with a sodium bicarbonate aqueous solution, dried over anhydrous magnesium sulfate, and concentrated under reduced pressure. The residue was purified on a silica gel column (eluent, hexane:ethyl acetate=1:1) to give 0.5 g of tert-butyl N-acetyl-N-[trans-7-chloro-5-(2-chlorophenyl)-1-neopentyl-2-oxo-1,2,3,5-tetrahydro-4,1-benzoxazepine-3-methyl]aminoacetate as an oily product.

IR $v_{Max}^{Neat}$ cm$^{-1}$: 1740, 1670 (C=O)

$^1$H-NMR (200 MHz, CDCl$_3$) δ: 0.92 and 0.94 (9H,each s,Bu$^t$), 1.95 and 2.15 (3H,each s,Bu$^t$), 3.35 and 3.38 (1H, each d,J=14.0 Hz), 3.7–4.3 (5H,m), 4.45 and 4.48 (1H,each d,J=14.0 Hz), 6.23 and 6.28 (1H, each s), 6.45–6.55 (1H, m), 7.3–7.8 (6H, m).

Example 149

N-Acetyl-N-[trans-7-chloro-5-(2-chlorophenyl)-1-neopentyl-2-oxo-1,2,3,5-tetrahydro-4,1-benzoxazepine-3-methyl]aminoacetic acid In 20 ml of 4N HCl-dioxane solution was dissolved 0.5 g of tert-butyl N-acetyl-N-[trans-7-chloro-5-(2-chlorophenyl)-1-neopentyl-2-oxo-1,2,3,5-tetrahydro-4,1-benzoxazepine-3-methyl]aminoacetate obtained in Example 148. After stirring overnight at room temperature, the mixture was concentrated under reduced pressure. The concentrate was treated with hexane and diethylether to afford 0.37 g of powdery N-acetyl-N-[trans-7-chloro-5-(2-chlorophenyl)-1-neopentyl-2-oxo-1,2,3,5-tetrahydro-4,1-benzoxazepine-3-methyl]aminoacetic acid.

Elementary analysis for C$_{25}$H$_{28}$Cl$_2$N$_2$O$_5$: Calcd.: C 59.18; H 5.56; N 5.52 Found: C 59.36; H 5.70; N 5.50

$^1$H-NMR spectrum (200 MHz, CDCl$_3$) δ: 0.92 and 0.94 (9H, each s, Bu$^t$), 2.00 and 2.20 (3H, each s), 3.3–3.5 (1H, m), 3.7–4.5 (6H, m), 6.22 and 6.28 (1H, each s), 6.45–6.55 (1H, m), 7.3–7.8 (6H, m)

Example 150

Methyl ester of 4-N-[trans-7-chloro-5-(2-chlorophenyl)-1-neopentyl-2-oxo-1,2,3,5-tetrahydro-4,1-benzoxazepine-3-methyl]aminomethylbenzoic acid (A) In 30 ml of acetonitrile was mixed 1.0 g of trans-7-chloro-5-(2-chlorophenyl)-1-neopentyl-2-oxo-1,2,3,5-tetrahydro-4,1-benzoxazepine-3-methylamine hydrochloride obtained in Example 139 with 0.6 g of methyl 4-bromomethylbenzoate and 0.75 g of potassium carbonate. The mixture was refluxed by heating for 2 hours. After the addition of 0.2 g of methyl 4-bromomethylbenzoate, reflux was confined by heating for 5 hours, followed by concentration under reduced pressure. The concentrate was extracted with 100 ml of water and 150 ml of ethyl acetate. The ethyl acetate layer was washed with water and dried over anhydrous magnesium sulfate. The solvent was evaporated off under reduced pressure and the residue was purified by silica gel column chromatography (eluent, hexane:ethyl acetate=10:1-1:2) to yield 0.15 g of methyl ester of 4-N-[trans-7-chloro-5-(2-chlorophenyl)-1-neopentyl-2-oxo-1,2,3,5-tetrahydro-4,1-benzoxazepine-3-methyl] aminomethylbenzoic acid as prisms, m.p. 171° to 173° C.

Elementary analysis for C$_{30}$H$_{32}$Cl$_2$N$_2$O$_4$: Calcd.: C 64.87; H 5.81; N 5.04 Found: C 64.88; H 5.97; N 4.76

(B) In 20 ml of ethanol was dissolved 0.45 g of trans-7-chloro-5-(2-chlorophenyl)-1-neopentyl-2-oxo-1,2,3,5-tetrahydro-4,1-benzoxazepine-3-methylamine hydrochloride obtained in Example 139. To the solution was added 0.19 g of terephthalaldehydic acid methyl ester together with 0.5 ml of acetic acid. After stirring for 30 minutes at room temperature, 82 mg of sodium cyanoborohydride was added to the mixture. After further stirring for 2 hours at room temperature, the mixture was concentrated under reduced pressure and the concentrate was extracted with 100 ml of water and 100 ml of ethyl acetate. The organic layer was washed with water and dried over anhydrous magnesium sulfate. The organic solvent was evaporated off under reduced pressure and the residue was purified by column chromatography using silica gel (eluent, hexane:ethyl acetate=1:1) to yield 0.31 g of methyl ester of 4-N-[trans-7-chloro-5-(2-chlorophenyl)-1-neopentyl-2-oxo-1,2,3,5-tetrahydro-4,1-benzoxazepine-3-methyl] aminomethylbenzoic acid.

Example 151

Methyl ester of 4-[N-[trans-7-chloro-5-(2-chlorophenyl)-1-neopentyl-2-oxo-1,2,3,5-tetrahydro-4,1-benzoxazepine-3-methyl]-N-methanesulfonyl] aminomethylbenzoic acid In 5 ml of N,N-dimethylformamide was dissolved 0.3 g of methyl ester of 4-N-[trans-7-chloro-5-(2-chlorophenyl)-1-neopentyl-2-oxo-1,2,3,5-tetrahydro-4,1-benzoxazepine-3-methyl]aminomethylbenzoic acid obtained in Example 150. To the solution were added 0.05 ml of methanesulfonyl chloride and 0.09 ml of triethylamine. After stirring for one hour at room temperature, the reaction mixture was subjected to extraction with 100 ml of water and 100 ml of ethyl acetate. The ethyl acetate layer was washed with 1N hydrochloric acid and with a sodium bicarbonate aqueous solution, dried over anhydrous magnesium sulfate, and concentrated under reduced pressure. The residue was purified by silica gel column chromatography (eluent, hexane-:ethyl acetate=2:1) to afford 0.27 g of methyl ester of 4-[N-[trans-7-chloro-5-(2-chlorophenyl)-1-neopentyl-2-oxo-1,2,3,5-tetrahydro-4,1-benzoxazepine-3-methyl]-N-methanesulfonyl]aminomethylbenzoic acid as needles, m.p. 173° to 174° C.

Elementary analysis for C$_{31}$H$_{34}$Cl$_2$N$_2$O$_6$S: Calcd.: C 58.77; H 5.41; N 4.42 Found: C 58.59; H 5.68; N 4.19

Example 152

4-[N-[trans-7-chloro-5-(2-chlorophenyl)-1-neopentyl-2-oxo-1,2,3,5-tetrahydro-4,1-benzoxazepine-3-methyl]-N-methanesulfonyl] aminomethylbenzoic acid In 10 ml of methanol was dissolved 0.17 g of methyl ester of 4-[N-[trans-7-chloro-5-(2-chlorophenyl)-1-neopentyl-2-oxo-1,2,3,5-tetrahydro-4,1-benzoxazepine-3-methyl]-N-methanesulfonyl]aminomethylbenzoic acid obtained in Example 151. After the addition of 4 ml of 1N sodium hydroxide the solution was stirred for one hour at 60° C. The reaction mixture was then acidified with 50 ml of 1N hydrochloric acid and subjected to extraction with 50 ml of ethyl acetate. The ethyl acetate layer was washed with water, dried over anhydrous magnesium sulfate and concentrated under reduced pressure to give 0.16 g of 4-[N-[trans-7-chloro-5-(2-chlorophenyl)-1-neopentyl-2-oxo- 1,2,3,5-tetrahydro-4,1-benzoxazepine-3-methyl]-N-methanesulfonyl]aminomethylbenzoic acid as prisms, m.p. 235° to 237° C.

Elementary analysis for $C_{30}H_{32}Cl_2N_2O_6S$: Calcd.: C 58.16; H 5.21; N 4.52 Found: C 58.25; H 5.49; N 4.29

Example 153

Trans-7-chloro-5-(2-chlorophenyl)-1-neopentyl-2-oxo-1,2,3,5-tetrahydro-4,1-benzoxazepine-3-ethanol In 200 ml of tetrahydrofuran was dissolved 14.7 g of trans-7-chloro-5-(2-chlorophenyl)-1-neopentyl-2-oxo-1,2,3,5-tetrahydro-4,1-benzoxazepine-3-acetic acid obtained in Example 2 and 4.51 ml of N-methylmorpholine. To the solution was added 3.92 ml of ethyl chlorocarbonate at −10° C.; the mixture was then stirred for 15 minutes. After the addition of 3.86 g of sodium borohydride, 200 ml of methanol was added dropwise to the solution. The mixture was stirred for one hour at room temperature and then concentrated. After the addition of 200 ml of 1N hydrochloric acid, the concentrate was extracted with 200 ml of ethyl acetate. The organic layer was washed with a saturated sodium bicarbonate aqueous solution and dried over anhydrous magnesium sulfate. The solvent was evaporated off under reduced pressure. The residue was purified by silica gel column chromatography (eluent, hexane:ethyl acetate= 1:1) to yield 14.2 g of trans-7-chloro-5-(2-chlorophenyl)-1-neopentyl-2-oxo-1,2,3,5-tetrahydro-4,1-benzoxazepine-3-ethanol as colorless crystals, m.p. 157° to 159° C.

Elementary analysis for $C_{22}H_{25}Cl_2NO_3$: Calcd.: C 62.56; H 5.97; N 3.32 Found: C 62.30; H 6.02; N 3.17

Example 154

Ethyl ester of N-[trans-7-chloro-5-(2-chlorophenyl)-1-neopentyl-2-oxo-1,2,3,5-tetrahydro-4,1-benzoxazepine-3-ethyl]aminoacetic acid (1) Trans-7-chloro-5-(2-chlorophenyl)-1-neopentyl-2-oxo-1,2,3,5-tetrahydro-4,1-benzoxazepine-3-acetaldehyde To 25 ml of dichloromethane solution containing 0.70 ml of oxalyl chloride was added 5 ml of dichloromethane solution containing 0.71 ml of dimethylsulfoxide at −78° C., followed by stirring for 5 minutes. To the solution was slowly added 10 ml of dichloromethane solution containing 1.69 g of trans-7-chloro-5-(2-chlorophenyl)-1-neopentyl-2-oxo-1,2,3,5-tetrahydro-4,1-benzoxazepine- 3-ethanol obtained in Example 160, followed by stirring for 15 minutes at −78° C. To the reaction mixture was added 2.79 ml of triethylamine and the mixture was further stirred for one hour at 0° C. and for 1.5 hours at room temperature. After the addition of 100 ml of water, extraction was performed with 100 ml of dichloromethane. The dichloromethane layer was washed with saturated saline and dried over anhydrous magnesium sulfate. The solvent was evaporated off under reduced pressure. The residue was purified by column chromatography using silica gel (eluent, hexane:ethyl acetate=1:1) to give 1.08 g of trans-7-chloro-5-(2-chlorophenyl)-1-neopentyl-2-oxo-1,2,3,5-tetrahydro-4,1-benzoxazepine-3-acetaldehyde as light-yellow crystals, m.p. 173° to 176° C.

Elementary analysis for $C_{22}H_{23}Cl_2NO_3 \cdot 0.5H_2O$: Calcd.: C 61.55; H 5.63; N 3.26 Found: C 61.27; H 5.49; N 3.17

(2) Ethyl ester of N-[trans-7-chloro-5-(2-chlorophenyl)-1-neopentyl-2-oxo-1,2,3,5-tetrahydro-4,1-benzoxazepine-3-ethyl]aminoacetic acid To 40 ml of ethanol containing 1.12 g of trans-7-chloro-5-(2-chlorophenyl)-1-neopentyl-2-oxo-1,2,3,5-tetrahydro-4,1-benzoxazepine-3-acetaldehyde obtained in Example 161 (1) and 0.56 g of glycine ethyl ester hydrochloride was added 10 ml of ethanol containing 0.13 g of sodium cyanoborohydride dropwise over 1.5 hours. After additional 3-hour stirring, the reaction mixture was subjected to extraction with 200 ml of water and 200 ml of ethyl acetate. The ethyl acetate layer was washed with saturated saline and dried over anhydrous magnesium sulfate. The solvent was evaporated off under reduced pressure and the residue was purified by silica gel column chromatography (eluent, ethyl acetate) to afford 0.75 g of amorphous solid ethyl ester of N-[trans-7-chloro-5-(2-chlorophenyl)-1-neopentyl-2-oxo-1, 2,3,5-tetrahydro-4,1-benzoxazepine-3-ethyl]aminoacetic acid.

Elementary analysis for $C_{26}H_{32}Cl_2N_2O_4$: Calcd.: C 61.54; H 6.36; N 5.52 Found: C 61.16; H 6.29; N 5.56

$^1$H-NMR (CDCl$_3$) δ: 0.93 (9H, s, Bu$^t$), 1.26 (3H, t, J=7.2 Hz), 1.90–2.15 (3H, m), 2.76 (2H, dd, J=7.2, 6.6 Hz), 3.38 (1H, d, J=13.9 Hz), 3.38 (2H, s), 4.03 (1H, dd, J=6.6, 6.2 Hz), 4.17 (2H, q, J=7.2 Hz), 4.51 (1H, d, J=13.9 Hz), 6.24 (1H, s), 6.51 (1H, d, J=1.6 Hz), 7.30–7.50 (5H, m), 7.70–7.80 (1H, m).

Example 155

Ethyl ester of N-acetyl-N-[trans-7-chloro-5-(2-chlorophenyl)-1-neopentyl-2-oxo-1,2,3,5-tetrahydro-4,1-benzoxazepine-3-ethyl]aminoacetic acid In 5 ml of N,N-dimethylformamide was dissolved 0.15 g of ethyl ester of N-[trans-7-chloro-5-(2-chlorophenyl)-1-neopentyl-2-oxo-1,2,3,5-tetrahydro-4,1-benzoxazepine-3-ethyl]aminoacetate obtained in Example 154. To the solution were added 0.031 ml of acetyl chloride and 0.050 ml of triethylamine under ice-cooling. After stirring for 30 minutes under ice-cooling, the reaction mixture was subjected to extraction with 40 ml of water and 40 ml of ethyl acetate. The ethyl acetate layer was washed with saturated saline and dried over anhydrous magnesium sulfate. The solvent was evaporated off under reduced pressure. The residue was purified by column, chromatography using silica gel (eluent, hexane:ethyl acetate=1:3) to give 0.15 g of amorphous solid ethyl ester of N-acetyl-N-[trans-7-chloro-5-(2-chlorophenyl)-1-neopentyl-2-oxo-1,2,3,5-tetrahydro-4,1-benzoxazepine-3-ethyl]aminoacetic acid.

Elementary analysis for $C_{28}H_{34}Cl_2N_2O_5 \cdot 0.4H_2O$: Calcd.: C 60.41; H 6.30; N 5.03 Found: C 60.44; H 6.43; N 4.96

$^1$H-NMR (CDCl$_3$) δ: 0.93 and 0.94 (9H, each s, Bu$^t$), 1.20–1.32 (3H, m), 1.95–2.20 (2H, m), 1.95 and 2.13 (total 3H, each s), 3.32–3.68 (3H, m), 3.90–4.27 (5H, m), 4.48 and 4.50 (total 1H, each d, J=13.8 Hz), 6.22 and 6.24 (total 1H, each s), 6.50 and 6.53 (total 1H, each d, J=2.0 Hz), 7.29–7.50 (5H, m), 7.65–7.80 (1H, m)

Example 156

N-acetyl-N-[trans-7-chloro-5-(2-chlorophenyl)-1-neopentyl-2-oxo-1,2,3,5-tetrahydro-4,1-benzoxazepine-3-ethyl]aminoacetic acid To 5 ml of methanol containing 0.11 g of ethyl ester of N-acetyl-N-[trans-7-chloro-5-(2-chlorophenyl)-1-neopentyl-2-oxo-1,2,3,5-tetrahydro-4,1-benzoxazepine-3-ethyl]aminoacetate obtained in Example 155 was added 1 ml of 0.5M potassium carbonate aqueous solution. After stirring for 30 minutes at 60° C., the reaction mixture was acidified with 0.5 ml of 1N hydrochloric acid and subjected to extraction with 20 ml of water and 20 ml of ethyl acetate. The ethyl acetate layer was washed with saturated saline and dried over anhydrous magnesium sulfate. The solvent was evaporated off under reduced pressure. The residue was treated with ether to yield 0.07 g of white powdery N-acetyl-N-[trans-7-chloro-5-(2-chlorophenyl)-1-neopentyl-2-oxo-1, 2,3,5-tetrahydro-4,1-benzoxazepine-3-ethyl]aminoacetic acid, m.p. 210° to 212° C.

Elementary analysis for $C_{26}H_{30}Cl_2N_2O_5$: Calcd.: C 59.89; H 5.80; N 5.37 Found: C 59.78; H 5.85; N 5.13

Example 157

Ethyl ester of N-[trans-7-chloro-5-(2-chlorophenyl)-1-neopentyl-2-oxo-1,2,3,5-tetrahydro-4,1-benzoxazepine-3-ethyl]-N-methanesulfonylaminoacetic acid In 5 ml of N,N-dimethylformamide was dissolved 0.15 g of ethyl ester of N-[trans-7-chloro-5-(2-chlorophenyl)-1-neopentyl-2-oxo-1,2,3,5-tetrahydro-4,1-benzoxazepine-3-ethyl]aminoacetate obtained in Example 154. To the solution were added 0.028 ml of methanesulfonyl chloride and 0.050 ml of triethylamine under ice-cooling. After stirring for 30 minutes under ice-cooling, extraction was performed with 40 ml of water and 40 ml of ethyl acetate. The ethyl acetate layer was washed with saturated saline and dried over anhydrous magnesium sulfate. The solvent was evaporated off under reduced pressure, and the residue was purified on a silica gel column chromatography (eluent, hexane:ethyl acetate=2:1) to afford 0.12 g of ethyl ester of N-trans-7-chloro-5-(2-chlorophenyl)-1-neopentyl-2-oxo-1,2,3,5-tetrahydro-4,1-benzoxazepine-3-ethyl]-N-methanesulphonylaminoacetic acid as a white powdery product, m.p. 134° to 135° C.

Elementary analysis for $C_{27}H_{34}Cl_2N_2O_6S$: Calcd.: C 55.38; H 5.85; N 4.78 Found: C 55.66; H 5.98; N 4.61

Example 158

N-[trans-7-chloro-5-(2-chlorophenyl)-1-neopentyl-2-oxo-1,2,3,5-tetrahydro-4,1-benzoxazepine-3-ethyl]-N-methanesulfonylaminoacetic acid In the same manner as in Example 156 was hydrolyzed 0.12 g of ethyl ester of N-[trans-7-chloro-5-(2-chlorophenyl)-1-neopentyl-2-oxo-1,2,3,5-tetrahydro-4,1-benzoxazepine-3-ethyl]-N-methanesulfonylaminoacetic acid obtained in Example 157 to give 0.10 g of white powdery N-[trans-7-chloro-5-(2-chlorophenyl)-1-neopentyl-2-oxo-1,2,3,5-tetrahydro-4,1-benzoxazepine-3-ethyl]-N-methanesulfonylaminoacetic acid, m.p. 135° to 137° C.

Elementary analysis for $C_{25}H_{30}Cl_2N_2O_6S \cdot 0.5H_2O$: Calcd.: C 53.00; H 5.52; N 4.94 Found: C 53.25; H 5.78; N 4.71

Example 159

Ethyl ester of N-[trans-7-chloro-5-(2-chlorophenyl)-1-neopentyl-2-oxo-1,2,3,5-tetrahydro-4,1-benzoxazepine-3-ethyl]-N-(p-toluenesulfonyl) aminoacetic acid In 5 ml of N,N-dimethylformamide was dissolved 0.15 g of ethyl ester of N-[trans-7-chloro-5-(2-chlorophenyl)-1-neopentyl-2-oxo-1,2,3,5-tetrahydro-4,1-benzoxazepine-3-ethyl]aminoacetic acid obtained in Example 154. To the solution was added 0.069 g of p-toluenesulfonyl chloride together with 0.050 ml of triethylamine under ice-cooling. After stirring for 30 minutes under ice-cooling, the reaction mixture was subjected to extraction with 40 ml of water and 40 ml of ethyl acetate. The ethyl acetate layer was washed with saturated saline and dried over anhydrous magnesium sulfate. Ethyl acetate was evaporated off under reduced pressure. The residue was purified by column chromatography using silica gel (eluent, hexane:ethyl acetate=3:1) to yield 0.17 g of amorphous ethyl ester of N-[trans-7-chloro-5-(2-chlorophenyl)-1-neopentyl-2-oxo-1,2,3,5-tetrahydro-4, 1-benzoxazepine-3-ethyl]-N-p-toluenesulfonylaminoacetic acid.

Elementary analysis for $C_{33}H_{38}Cl_2N_2O_6S$: Calcd.: C 59.91; H 5.79; N 4.23 Found: C 60.25; H 6.01; N 4.04

$^1$H-NMR (CDCl$_3$) δ: 0.94 (9H, s, Bu$^t$), 1.15 (3H, t, J=7.2 Hz), 1.90–2.30 (2H, m), 2.41 (3H, s), 3.20–3.60 (2H, m), 3.41 (1H, d, J=140 Hz), 3.97–4.18 (5H, m), 4.50 (1H, d, J=14.0 Hz), 6.23 (1H, s), 6.52 (1H, s), 7.21–7.50 (7H, m), 7.62–7.80 (3H, m)

Example 160

N-[trans-7-chloro-5-(2-chlorophenyl)-1-neopentyl-2-oxo-1,2,3,5-tetrahydro-4,1-benzoxazepine-3-ethyl]-N-p-toluenesulfonylaminoacetic acid In the same manner as in Example 156, 0.15 g of ethyl ester of N-[trans-7-chloro-5-(2-chlorophenyl)-1-neopentyl-2-oxo-1,2,3,5-tetrahydro-4,1-benzoxazepine-3-ethyl]-N-p-toluenesulfonylaminoacetic acid was hydrolyzed to yield 0.11 g of N-[trans-7-chloro-5-(2-chlorophenyl)-1-neopentyl-2-oxo-1,2,3,5-tetrahydro-4,1-benzoxazepine-3-ethyl]-N-p-toluenesulfonylaminoacetic acid as white powder, m.p. 274° to 277° C.

Elementary analysis for $C_{31}H_{34}Cl_2N_2O_6S$: Calcd.: C 58.77; H 5.41; N 4.42 Found: C 58.70; H 5.59; N 4.13

Example 161

Methyl ester of 4-N-[trans-7-chloro-5-(2-chlorophenyl)-1-neopentyl-2-oxo-1,2,3,5-tetrahydro-4,1-benzoxazepine-3-ethyl]aminomethylbenzoic acid A mixture of 0.42 g of trans-7-chloro-5-(2-chlorophenyl)-1-neopentyl-2-oxo-1,2,3,5-tetrahydro-4,1-benzoxazepine-3-acetaldehyde obtained in Example 154 (1), 0.30 g of 4-aminomethylbenzoic acid methyl ester hydrochloric acid salt, and 30 ml of ethanol was stirred for 2 hours at room temperature. Subsequently 5 ml of ethanol containing 0.06 g of sodium cyanoborohydride was slowly added dropwise to the mixture. After stirring for 2 hours, the reaction mixture was subjected to extraction with 100 ml of water and 100 ml of ethyl acetate. The ethyl acetate layer was washed with saturated saline and dried over anhydrous magnesium sulfate. The organic solvent was evaporated off under reduced pressure. The residue was purified by column chromatography using silica gel (eluent, ethyl acetate) to give amorphous methyl ester of 4-N-[trans-7-chloro-5-(2-chlorophenyl)-1-neopentyl-2-oxo-1,2,3,5-tetrahydro-4,1-benzoxazepine-3-ethyl]aminomethylbenzoic acid.

Elementary analysis for $C_{31}H_{34}Cl_2N_2O_4$: Calcd.: C 65.38; H 6.02; N 4.92 Found: C 64.99; H 6.11; N 5.19

$^1$H-NMR(CDCl$_3$) δ: 0.94 (9H, s, Bu$^t$), 1.98–2.26 (3H, m), 2.65–2.90 (2H, m), 3.38 (1H, d, J=14.0 Hz), 3.83 (2H, s), 3.91 (3H, s), 4.06 (1H, t, J=6.2 Hz), 4.49 (1H, d, J=14.0 Hz), 6.21 (1H, s), 5.51 (1H, d, J=2.0 Hz), 7.26–7.62 (8H, m), 7.92–8.02 (2H, m)

Example 162

Methyl ester of 4-[N-acetyl-N-[trans-7-chloro-5-(2-chlorophenyl)-1-neopentyl-2-oxo-1,2,3,5-tetrahydro-4,1-benzoxazepine-3-ethyl]]aminomethylbenzoic acid In the same manner as in Example 155, 0.13 g of methyl ester of 4-N-[trans-7-chloro-5-(2-chlorophenyl)-1- neopentyl-2-oxo-1,2,3,5-tetrahydro-4,1-benzoxazepine-3-ethyl]aminomethylbenzoic acid obtained in Example 161 was treated to yield 0.13 g of amorphous methyl ester of 4-[N-acetyl-N-[trans-7-chloro-5-(2-chlorophenyl)-1-neopentyl-2-oxo-1,2,3,5-tetrahydro-4,1-benzoxazepine-3-ethyl]]aminomethylbenzoic acid.

Elementary analysis for $C_{33}H_{36}Cl_2N_2O_5$: Calcd.: C 64.81; H 5.93; N 4.58 Found: C 65.14; H 6.12; N 4.11

$^1$H-NMR (CDCl$_3$) δ: 0.93 (9H, s, Bu$^t$), 2.00–2.20 (2H, m), 2.02 and 2.18 (total 3H, each s), 3.20–3.60 (3H, m), 3.78–4.00 (1H, m), 3.91 and 3.93 (total 3H, each s), 4.42–4.76 (3H, m), 6.21 (1H, s), 6.50 (1H, d, J=1.8 Hz), 7.17–7.70 (8H, m), 7.95 (1H, d, J=8.0 Hz), 8.02 (1H, d, J=8.2 Hz)

Example 163

4-[N-acetyl-N-[trans-7-chloro-5-(2-chlorophenyl)-1-neopentyl-2-oxo-1,2,3,5-tetrahydro-4,1-benzoxazepine-3-ethyl]]aminomethylbenzoic acid In the same manner as in Example 156, 0.10 g of methyl ester of 4-[N-acetyl-N-[trans-7-chloro-5-(2-chlorophenyl)-1-neopentyl-2-oxo-1,2,3,5-tetrahydro-4,1-benzoxazepine-3-ethyl]]aminomethylbenzoic acid obtained in Example 162 was hydrolyzed to afford 0.08 g of white powdery 4[N-acetyl-N-[trans-7-chloro-5-(2-chlorophenyl)-1-neopentyl-2-oxo-1,2,3,5-tetrahydro-4,1-benzoxazepine-3-ethyl]] aminomethylbenzoic acid, m.p. 242° to 244° C.

Elementary analysis for $C_{32}H_{34}Cl_2N_2O_5$: Calcd.: C 64.32; H 5.74; N 4.69 Found: C 64.34; H 5.87; N 4.66

Example 164

Methyl ester of 4-[N-[trans-7-chloro-5-(2-chlorophenyl)-1-neopentyl-2-oxo-1,2,3,5-tetrahydro-4,1-benzoxazepine-3-ethyl]-N-methanesulfonyl] aminomethylbenzoic acid In the same manner as in Example 157, 0.13 g of methyl ester of 4-N-[trans-7-chloro-5-(2-chlorophenyl)-1-neopentyl-2-oxo-1,2,3,5-tetrahydro-4,1-benzoxazepine-3-ethyl]aminomethylbenzoic acid obtained in Example 161 was treated to give 0.12 g of methyl ester of 4-[N-[trans-7-chloro-5-(2-chlorophenyl)-1-neopentyl-2-oxo-1,2,3,5-tetrahydro-4,1-benzoxazepine-3-ethyl]-N-methanesulfonyl] aminomethylbenzoic acid as colorless crystals, m.p. 172° to 174° C.

Elementary analysis for $C_{32}H_{36}Cl_2N_2O_6S$: Calcd.: C 59.35; H 5.60; N 4.33 Found: C 59.15; H 5.79; N 4.16

Example 165

4-[N-[trans-7-chloro-5-(2-chlorophenyl)-1-neopentyl-2-oxo-1,2,3,5-tetrahydro-4,1-benzoxazepine-3-ethyl]-N-methanesulfonyl] aminomethylbenzoic acid In the same manner as in Example 156, 0.09 g of methyl ester of 4-[N-[trans-7-chloro-5-(2-chlorophenyl)-1-neopentyl-2-oxo-1,2,3,5-tetrahydro-4,1-benzoxazepine-3-ethyl]-N-methanesulfonyl]aminomethylbenzoic acid obtained in Example 164 was hydrolyzed to afford 0.06 g of 4-[N-[trans-7-chloro-5-(2-chlorophenyl)-1-neopentyl-2-oxo-1,2,3,5-tetrahydro-4,1-benzoxazepine-3-ethyl]-N-methanesulfonyl]aminomethylbenzoic acid as colorless crystals, m.p. 185° to 187° C.

Elementary analysis for $C_{31}H_{34}Cl_2N_2O_6S \cdot 0.5H_2O$: Calcd.: C 57.95; H 5.49; N 4.36 Found: C 58.30; H 5.83; N 4.19

Example 166

Methyl ester of 4-[N-[trans-7-chloro-5-(2-chlorophenyl)-1-neopentyl-2-oxo-1,2,3,5-tetrahydro-4,1-benzoxazepine-3-ethyl]-N-p-toluenesulfonyl] aminomethylbenzoic acid In the same manner as in Example 159, 0.13 g of methyl ester of 4-N-[trans-7-chloro-5-(2-chlorophenyl)-1-neopentyl-2-oxo-1,2,3,5-tetrahydro-4,1-benzoxazepine-3-ethyl]aminomethylbenzoic acid obtained in Example 161 was treated to give 0.14 g of methyl ester of 4-[N-[trans-7-chloro-5-(2-chlorophenyl)-1-neopentyl-2-oxo-1,2,3,5-tetrahydro-4,1-benzoxazepine-3-ethyl]-N-p-toluenesulfonyl]aminomethylbenzoic acid as colorless crystals, m.p. 145° to 147° C.

Elementary analysis for $C_{38}H_{40}Cl_2N_2O_6S$: Calcd.: C 63.07; H 5.57; N 3.87 Found: C 63.09; H 5.50; N 3.93

Example 167

4-[N-[trans-7-chloro-5-(2-chlorophenyl)-1-neopentyl-2-oxo-1,2,3,5-tetrahydro-4,1-benzoxazepine-3-ethyl]-N-p-toluenesulfonyl] aminomethylbenzoic acid In the same manner as in Example 156, 0.12 g of methyl ester of 4-[N-[trans-7-chloro-5-(2-chlorophenyl)-1-neopentyl-2-oxo-1,2,3,5-tetrahydro-4,1-benzoxazepine-3-ethyl]-N-p-toluenesulfonyl]aminomethylbenzoic acid obtained in Example 166 was hydrolyzed to afford 0.09 g of 4-[N-[trans-7-chloro-5-(2-chlorophenyl)-1-neopentyl-2-oxo-1,2,3,5-tetrahydro-4,1-benzoxazepine- 3-ethyl]-N-p-toluenesulfonyl]aminomethylbenzoic acid as colorless powder, m.p. 265° to 268° C.

Elementary analysis for $C_{37}H_{38}Cl_2N_2O_6S$: Calcd.: C 62.62; H 5.40; N 3.95 Found: C 62.67; H 5.36; N 3.96

Example 168

Trans-7-chloro-5-(2-chlorophenyl)-1-neopentyl-3-[(tetrazol-5-yl)methylaminocarbonylmethyl]-2-oxo-1,2,3,5-oxo-4,1-benzoxazepine In the same manner as in Examples 104, trans-7-chloro-5-(2-chlorophenyl)-1-neopentyl-2-oxo-1,2,3,5-tetrahydro-4,1-benzoxazepine-3-acetic acid obtained in Example 2 was treated to afford the following crystalline compounds:

(1) Trans-7-chloro-5-(2-chlorophenyl)-3-(cyanomethylaminocarbonylmethyl)-1-neopentyl-2-oxo-1,2,3,5-tetrahydro-4,1-benzoxazepine, m.p. 171° to 172° C.

Elementary analysis for $C_{24}H_{25}Cl_2N_3O_3$: Calcd.: C 60.77; H 5.31; N 8.86 Found: C 60.68; H 5.24; N 8.62

(2) Trans-7-chloro-5-(2-chlorophenyl)-1-neopentyl-3-[(tetrazol-5-yl)methylaminocarbonylmethyl]-2-oxo-1,2,3,5-tetrahydro-4,1-benzoxazepine, m.p. 251° to 252° C.

Elementary analysis for $C_{24}H_{26}Cl_2N_6O_3$: Calcd.: C 55.71; H 5.06; N 16.24 Found: C 55.38; H 5.22; N 16.03

Materials and intermediate compounds included in Examples are listed in Tables 74 to 88.

2-aminobenzophenones as the starting material can be synthesized by, or in accordance with, the method described in D. A. Walsh, Synthesis, 677 (1980) or the method cited in said reference.

Example 169

(3S,5R)-7-chloro-5-(2-methoxyphenyl)-1-neopentyl-2-oxo-1,2,3,5-tetrahydro-4,1-benzoxazepine-3-acetic acid (I) and (3R,5S)-7-Chloro-5-(2-methoxyphenyl) -1-neopentyl-2-oxo-1,2,3,5-tetrahydro-4,1-benzoxazepine-3-acetic acid (II)

(1) N-[(3S,5R)-7-chloro-5-(2-methoxyphenyl)-1-neopentyl-2-oxo-1,2,3,5-tetrahydro-4,1-benzoxazepine-3-acetyl]-L- alanine tert-butyl ester and N-[(3R,5S)-7-chloro-5-(2-methoxyphenyl)-1-neopentyl-2-oxo-1,2,3,5-tetrahydro-4,1-benzoxazepine-3-acetyl]-L-alanine tert-butyl ester To a solution of trans-7-chloro-5-(2-methoxyphenyl)-1-neopentyl-2-oxo-1,2,3,5-tetrahydro-4,1-benzoxazepine-3-acetic acid (3.0 g) and L-alanine tert-butyl ester hydrochloride (1.51 g) in N,N-dimethylformamide (20 ml) were added to diethylphosphorocyanidate (1.43 g) and triethylamine (2.42 ml) at 0° C. After being stirred for 30 min. at room temperature, the mixture was diluted with water and extracted with ethyl acetate (50 ml). The mixture was washed with 1N hydrochloric acid (20 ml×2) and aqueous sodium bicarbonate (20 ml×2), dried over magnesium sulfate and concentrated in vacuo. The residue was purified by silica gel column chromatography (hexane:ethyl acetate= 3:1-1:1) to give firstly N-[(3S,5R)-7-chloro-5-(2-methoxyphenyl)-1-neopentyl-2-oxo-1,2,3,5-tetrahydro-4,1-benzoxazepine-3-acetyl]-L-alanine tert-butyl ester (1.55 g) as colorless crystals (mp 74°–79° C.).

Anal. Calcd. for $C_{30}H_{39}ClN_2O_6$ Calcd: C, 64.55; H, 7.03; N, 5.01 Found: C, 64.05; H, 7.27; N, 4.72.

From the second fraction was obtained N-[(3R,5S)-7-chloro-5-(2-methoxyphenyl)-1-neopentyl-2-oxo-1,2,3,5-tetrahydro-4,1-benzoxazepine-3-acetyl]-L-alanine tert-butyl ester (1.8 g) as an oil.

$^1$H-NMR(CDCl$_3$) δ: 0.93(9H, s), 1.35(3H, d, J=7.0 Hz), 1.45(9H, s), 2.69(1H, dd, J=14.6, 5.7 Hz), 2.87(1H, dd, J=14.6, 7.2 Hz), 3.34(1H, d, J=14.0 Hz), 3.62(3H, s), 4.3–4.5 (2H, m), 4.49(1H, d, J=14.0 Hz), 6.27(1H, s), 6.3–6.4(1H, brd), 6.6–6.7(1H, m), 6.8–7.7(6H, m).

(2) N-[(3S,5R)-7-chloro-5-(2-methoxyphenyl)-1-neopentyl-2-oxo-1,2,3,5-tetrahydro-4,1-benzoxazepine-3-acetyl]-L-alanine A solution of N-[(3S,5R)-7-chloro-5-(2-methoxyphenyl)-1-neopentyl-2-oxo-1,2,3,5-tetrahydro-4,1-benzoxazepine-3-acetyl]-L-alanine tert-butyl ester (1.4 g) in 4N hydrogen chloride/dioxane solution (20 ml) was stirred for 5 h. The mixture was diluted with water (50 ml) and extracted with ethyl acetate (50 ml). The mixture was washed with water, dried over magnesium sulfate and concentrated in vacuo to give N-[(3S,5R)-7-chloro-5-(2-methoxyphenyl)-1-neopentyl-2-oxo-1,2,3,5-tetrahydro-4,1-benzoxazepine-3-acetyl]-L-alanine (1.20 g) as an amorphous powder.

Anal. Calcd. for $C_{26}H_{31}ClN_2O_6$ Calcd: C, 62.09; H, 6.21; N, 5.57 Found: C, 62.38; H, 6.51; N, 5.34.

$^1$H-NMR(CDCl$_3$) δ: 0.93(9H, s), 1.44(3H, d, J=7.2 Hz), 2.71(1H, dd, J=14.4, 5.5 Hz), 2.93(1H, dd, J=14.4, 7.6 Hz), 3.35(1H, d, J=13.9 Hz), 3.63(3H, s), 4.3–4.4(1H, m), 4.4–4.6(2H, m), 6.27(1H, s), 6.63(1H, d, J=1.9 Hz), 6.71 (1H, brd, J=6.8 Hz), 6.8–7.7(6H, m).

(3) N-[(3R,5S)-7-chloro-5-(2-methoxyphenyl)-1-neopentyl-2-oxo-1,2,3,5-tetrahydro-4,1-benzoxazepine-3-acetyl]-L-alanine N-[(3R,5S)-7-chloro-5-(2-methoxyphenyl)-1-neopentyl-2-oxo-1,2,3,5-tetrahydro-4,1-benzoxazepine-3-acetyl]-L-alanine tert-butyl ester (1.8 g) was converted to N-[(3R,5S)-7-chloro-5-(2-methoxyphenyl)-1-neopentyl-2-oxo-1,2,3,5-tetrahydro-4,1-benzoxazepine-3-acetyl]-L-alanine (1.35 g, an amorphous powder) in a similar manner to that described in example 169 (2).

Anal. Calcd. for $C_{26}H_{31}ClN_2O_6$ Calcd: C, 62.09; H, 6.21; N, 5.57 Found: C, 61.69; H, 6.23; N, 5.38.

$^1$H-NMR(CDCl$_3$) δ: 0.93(9H, s), 1.43(3H, d, J=7.2 Hz), 2.73(1H, dd, J=14.6, 5.8 Hz), 2.89(1H, dd, J=14.6, 5.8 Hz), 3.35(1H, d, J=14.0 Hz), 3.63(3H, s), 4.38(1H, t, J=7.4 Hz), 4.45–4.6(2H, m), 6.28(1H, s), 6.55(1H, brd, J=6.8 Hz), 6.64(1H, d, J=2.0 Hz), 6.8–7.7(6H, m).

(4) (3S,5R)-7-chloro-5-(2-methoxyphenyl)-1-neopentyl-2-oxo-1,2,3,5-tetrahydro-4,1-benzoxazepine-3-acetic acid (I)

A mixture of N-[(3S,5R)-7-chloro-5-(2-methoxyphenyl)-1-neopentyl-2-oxo-1,2,3,5-tetrahydro-4,1-benzoxazepine-3-acetyl]-L-alanine (1.0 g), concentrated hydrochloric acid (10 ml) and methanol (10 ml) was refluxed for 24 h. After cooling, the mixture was diluted with water and extracted with ethyl acetate (50 ml). The extract was washed with water, dried over magnesium sulfate and concentrated in vacuo. A mixture of the residue, methyl iodide (0.19 ml), potassium carbonate (0.55 g) and N,N-dimethylformamide (20 ml) was stirred for 1 h. The mixture was diluted with water and extracted with ethyl acetate (50 ml). The extract was washed with 1N hydrochloric acid (20 ml×2) and aqueous sodium bicarbonate, dried over magnesium sulfate and concentrated in vacuo. The residue was purified by silica gel column chromatography (hexane:ethyl acetate=3:1) to give methyl (3S,5R)-7-chloro-5-(2-methoxyphenyl)-1-neopentyl-2-oxo-1,2,3,5-tetrahydro-4,1-benzoxazepine-3-acetate (0.51 g). A mixture of the methyl ester (0.51 g), potassium carbonate (0.32 g), methanol (10 ml) and water (10 ml) was refluxed for 2.5 h. The mixture was acidified with 1N hydrochloric acid (20 ml) and extracted with ethyl acetate (50 ml). The extract was washed with water, dried over magnesium sulfate and concentrated in vacuo. The residue was purified by silica gel column chromatography (hexane:ethyl acetate=2:1-dichloromethane:methanol=2:1) to give (3S,5R)-7-chloro-5-(2-methoxyphenyl)-1-neopentyl-2-oxo-1,2,3,5-tetrahydro-4,1-benzoxazepine-3-acetic acid (0.46 g) as crystals (mp 179°–183° C.).

$[\alpha]_D^{25}$+248.7° (c=0.45, MeOH)

Anal. Calcd. for $C_{23}H_{26}ClNO_5 \cdot H_2O$ Calcd: C, 61.40; H, 6.27; N, 3.11 Found: C, 61.12; H, 5.99; N, 3.28.

(5) (3R,5S)-7-chloro-5-(2-methoxyphenyl)-1-neopentyl-2-oxo-1,2,3,5-tetrahydro-4,1-benzoxazepine-3-acetic acid (II)

N-[(3R,5S)-7-chloro-5-(2-methoxyphenyl)-1-neopentyl-2-oxo-1,2,3,5-tetrahydro-4,1-benzoxazepine-3-acetyl]-L-alanine (1.0g) was converted to (3R,5S)-7-chloro-5-(2-methoxyphenyl)-1-neopentyl-2-oxo-1,2,3,5-tetrahydro-4,1-benzoxazepine-3-acetic acid (0.32 g) in a similar manner to that described in example 169 (4).

mp 176°–180° C.

Anal. Calcd. for $C_{23}H_{26}ClNO_5 \cdot 5H_2O$ Calcd: C, 60.19; H, 6.37; N, 3.05 Found: C, 60.05; H, 5.88; N, 3.22.

$[\alpha]_D^{25}$−246.2° (c=0.45, MeOH)

Example 170

(3S,5R)-7-chloro-5-(2,3-dimethoxyphenyl)-1-neopentyl-2-oxo-1,2,3,5-tetrahydro-4,1-benzoxazepine-3-acetic acid (I) and (3R,5S)-7-chloro-5-(2,3-dimethoxyphenyl)-1-neopentyl-2-oxo-1,2,3,5-tetrahydro-4,1-benzoxazepine-3-acetic acid (II)

These compounds were prepared from trans-7-chloro-5-(2,3-dimethoxyphenyl)-1-neopentyl-2-oxo-1,2,3,5-tetrahydro-4,1-benzoxazepine-3-acetic acid in a similar manner to that described in example 169.

(1) N-[(3S,5R)-7-chloro-5-(2,3-dimethoxyphenyl)-1-neopentyl-2-oxo-1,2,3,5-tetrahydro-4,1-benzoxazepine-3-acetyl]-L-alanine tert-butyl ester colorless crystals (mp 120°–122° C.)

Anal. Calcd. for $C_{31}H_{41}ClN_2O_7 \cdot 0.5H_2O$ Calcd: C, 62.25; H, 7.08; N, 4.68 Found: C, 62.45; H, 6.89; N, 4.68.

(2) N-[(3R,5S)-7-chloro-5-(2,3-dimethoxyphenyl)-1-neopentyl-2-oxo-1,2,3,5-tetrahydro-4,1-benzoxazepine-3-acetyl]-L-alanine tert-butyl ester colorless crystals (mp 136°–137° C.)

Anal. Calcd. for $C_{31}H_{41}ClN_2O_7.0.8H_2O$ Calcd: C, 61.69; H, 7.11; N, 4.64 Found: C, 61.60; H, 7.45; N, 4.58.

(3) N-[(3S,5R)-7-chloro-5-(2,3-dimethoxyphenyl)-1-neopentyl-2-oxo-1,2,3,5-tetrahydro-4,1-benzoxazepine-3-acetyl]-L-alanine colorless crystals (mp 182°–185° C.)

Anal. Calcd. for $C_{27}H_{33}ClN_2O_7$ Calcd: C, 60.84; H, 6.24; N, 5.26 Found: C, 60.78; H, 6.09; N, 4.99.

(4) N-[(3R,5S)-7-chloro-5-(2,3-dimethoxyphenyl)-1-neopentyl-2-oxo-1,2,3,5-tetrahydro-4,1-benzoxazepine-3-acetyl]-L-alanine colorless crystals (mp 137°–140° C.)

Anal. Calcd. for $C_{27}H_{33}ClN_2O_7.0.3C_6H_{14}.0.3H_2O$ Calcd: C, 61.11; H, 6.77; N, 4.95 Found: C, 61.21; H, 6.91; N, 5.05.

(5) (3S,5R)-7-chloro-5-(2,3-dimethoxyphenyl)-1-neopentyl-2-oxo-1,2,3,5-tetrahydro-4,1-benzoxazepine-3-acetic acid (I) colorless crystals (mp 227°–230° C.)

Anal. Calcd. for $C_{24}H_{28}ClNO_6.0.5H_2O$ Calcd: C, 61.21; H, 6.21; N, 2.97 Found: C, 61.20; H, 6.07; N, 2.91.

$[\alpha]_D^{24}$+242.7° (c=0.41, MeOH)

(6) (3R,5S)-7-chloro-5-(2,3-dimethoxyphenyl)-1-neopentyl-2-oxo-1,2,3,5-tetrahydro-4,1-benzoxazepine-3-acetic acid (II) colorless crystals (mp 218°–222° C.)

Anal. Calcd. for $C_{24}H_{28}ClNO_6.0.75H_2O$ Calcd: C, 60.63; H, 6.25; N, 2.95 Found: C, 60.58; H, 6.05; N, 2.95.

$[\alpha]_D^{24}$–246.8° (c=0.43, MeOH)

Example 171

(3S,5R)-7-chloro-5-(2,4-dimethoxyphenyl)-1-neopentyl-2-oxo-1,2,3,5-tetrahydro-4,1-benzoxazepine-3-acetic acid (I) and (3R,5S)-7-chloro-5-(2,4-dimethoxyphenyl)-1-neopentyl-2-oxo-1,2,3,5-tetrahydro-4,1-benzoxazepine-3-acetic acid (II)

(1) N-[(3S,5R)-7-chloro-5-(2,4-dimethoxyphenyl)-1-neopentyl-2-oxo-1,2,3,5-tetrahydro-4,1-benzoxazepine-3-acetyl]-L-leucine methyl ester and N-[(3R,5S)-7-chloro-5-(2,4-dimethoxyphenyl)-1-neopentyl-2-oxo-1,2,3,5-tetrahydro-4,1-benzoxazepine-3-acetyl]-L-leucine methyl ester To a solution of trans-7-chloro-5-(2,4-dimethoxyphenyl)-1-neopentyl-2-oxo-1,2,3,5-tetrahydro-4,1-benzoxazepine-3-acetic acid (11.0 g) and L-leucine methyl ester hydrochloride (5.2 g) in N,N-dimethylformamide (50 ml) were added diethyl phosphorocyanidate (4.9 g) and triethylamine (8.3 ml) at 0° C. After being stirred for 30 min. at room temperature, the mixture was diluted with water (200 ml) and extracted with ethyl acetate (300 ml). The extract was washed with 1N hydrochloric acid (100 ml×2) and aqueous sodium bicarbonate (100 ml×2), dried over magnesium sulfate and concentrated in vacuo. The residue was purified by silica gel column chromatography (hexane:ethyl acetate= 2:1–1:1) to give firstly N-[(3R,5S)-7-chloro-5-(2,4-dimethoxyphenyl)-1-neopentyl-2-oxo-1,2,3,5-tetrahydro-4,1-benzoxazepine-3-acetyl]-L-leucine methyl ester (6.7 g) as colorless crystals (mp 93°–96° C.).

Anal. Calcd. for $C_{31}H_{41}ClN_2O_7.0.5H_2O$ Calcd: C, 62.25; H, 7.08; N, 4.68 Found: C, 62.38; H, 7.42; N, 4.43.

From the second fraction was obtained N-(3S,5R)-7-chloro-5-(2,4-dimethoxyphenyl)-1-neopentyl-2-oxo-1,2,3,5-tetrahydro-4,1-benzoxazepine-3-acetyl]-L-leucine methyl ester (6.5 g) as an oil.

$^1$H-NMR(CDCl$_3$) δ: 0.8–1.1(15H, m), 1.5–1.75(1H, m), 2.70(1H, dd, J=14.4, 6.0 Hz), 2.88(1H, dd, J=14.4, 6.6 Hz), 3.35(1H, d, J=14.0 Hz), 3.60(3H, s), 3.71(3H, s), 3.86(3H, s), 4.33(1H, t, J=6.2 Hz), 4.51(1H, d, J=14.0 Hz), 4.5–4.7 (1H, m), 6.21(1H, m), 6.45–6.7(4H, m), 7.2–7.6(3H, m).

(2) (3S,5R)-7-chloro-5-(2,4-dimethoxyphenyl)-1-neopentyl-2-oxo-1,2,3,5-tetrahydro-4,1-benzoxazepine-3-acetic acid (I)

A mixture of N-[(3S,5R)-7-chloro-5-(2,4-dimethoxyphenyl)-1-neopentyl-2-oxo-1,2,3,5-tetrahydro-4,1-benzoxazepine-3-acetyl]-L-leucine methyl ester (1.0 g), concentrated sulfuric acid (4 ml) and methanol (20 ml) was refluxed for 24 h. After cooling, the mixture was diluted with water and extracted with ethyl acetate (50 ml). The extract was washed with 1N hydrochloric acid (20 ml×2) and sodium bicarbonate (20 ml×2), dried over magnesium sulfate and concentrated in vacuo. The residue was purified by silica gel column chromatography (hexane:ethyl acetate= 5:1) to give methyl (3S,5R)-7-chloro-5-(2,4-dimethoxyphenyl)-1-neopentyl-2-oxo-1,2,3,5-tetrahydro-4,1-benzoxazepine-3-acetate (0.22 g). A mixture of the methyl ester (0.22 g), potassium carbonate (0.13 g), methanol (10 ml), tetrahydrofuran (5 ml) and water (10 ml) was refluxed for 2 h. The mixture was acidified with 1N hydrochloric acid and extracted with ethyl acetate. The extract was washed with water, dried over magnesium sulfate and concentrated in vacuo to give (3S,5R)-7-chloro-5-(2,4-dimethoxyphenyl) -1-neopentyl-2-oxo-1,2,3,5-tetrahydro-4,1-benzoxazepine-3-acetic acid (0.20 g) as colorless crystals (mp 233°–234° C.).

Anal. Calcd. for $C_{24}H_{28}ClNO_6$ Calcd: C, 62.40; H, 6.11; N, 3.03 Found: C, 62.28; H, 6.41; N, 2.89.

$[\alpha]_D^{22}$+228.1° (c=0.51, MeOH)

(3) (3R,5S)-7-chloro-5-(2,4-dimethoxyphenyl)-1-neopentyl-2-oxo-1,2,3,5-tetrahydro-4,1-benzoxazepine-3-acetic acid (II)

N-[(3R,5S)-7-chloro-5-(2,4-dimethoxyphenyl)-1-neopentyl-2-oxo-1,2,3,5-tetrahydro-4,1-benzoxazepine-3-acetyl]-L-leucine methyl ester (6.0 g) was converted to (3R,5S)-7-chloro-5-(2,4-dimethoxyphenyl)-1-neopentyl-2-oxo-1,2,3,5-tetrahydro-4,1-benzoxazepine-3-acetic acid (0.74 g) in a similar manner to that described in example 171 (2).

Anal. Calcd. for $C_{24}H_{28}ClNO_6$ Calcd: C, 62.40; H, 6.11; N, 3.03 Found: C, 62.39; H, 6.20; N, 2.81.

$[\alpha]_D^{22}$–232.5° (c=0.41, MeOH)

Example 172 sodium (3R,5S)-7-chloro-5-(2-methoxyphenyl)-1-neopentyl-2-oxo-1,2,3,5-tetrahydro-4,1-benzoxazepine-3-acetate To a suspension of (3R,5S)-7-chloro-5-(2-methoxyphenyl)-1-neopentyl-2-oxo-1,2,3,5-tetrahydro-4,1-benzoxazepine-3-acetic acid (12 g) in methanol (200 ml) was added 1N aqueous sodium hydroxide (27.7 ml). After the acid was dissolved completely, the mixture was concentrated in vacuo. To the residue was added ethyl acetate (200 ml) and the mixture was concentrated in vacuo. The deposited crystals were collected to give sodium (3R,5S)-7-chloro-5-(2-methoxyphenyl)-1-neopentyl-2-oxo-1,2,3,5-tetrahydro-4,1-benzoxazepine-3-acetate (11.8 g) as colorless crystals (mp>300° C.).

Anal. Calcd. for $C_{23}H_{25}ClNO_5Na.0.75H_2O$ Calcd: C, 59.10; H, 5.71; N, 3.00 Found: C, 59.27; H, 5.97; N, 2.75.

$[\alpha]_D^{22}$–263.6° (c=0.64, MeOH)

Example 173 sodium (3R,5S)-7-chloro-5-(2-chlorophenyl)-1-neopentyl-2-oxo-1,2,3,5-tetrahydro-4,1-benzoxazepine-3-acetate (3R,5S)-7-chloro-5-(2-chlorophenyl)-1-neopentyl-2-oxo-1,2,3,5-tetrahydro-4,1-benzoxazepine-3-acetic acid (1.2 g)

was converted to sodium (3R,5S)-7-chloro-5-(2-chlorophenyl)-1-neopentyl-2-oxo-1,2,3,5-tetrahydro-4,1-benzoxazepine-3-acetate (1.1 g) in a similar manner to that described in Example 172. mp>300° C.

Anal. Calcd. for $C_{22}H_{22}Cl_2NO_4Na \cdot H_2O$ Calcd: C, 55.47; H, 5.08; N, 2.94 Found: C, 55.41; H, 5.26; N, 2.83.

$[\alpha]_D^{22}$ -37.1° (C=0.57, MeOH)

Example 174 sodium (3R,5S)-7-chloro-5-(2,3-dimethoxyphenyl)-1-neopentyl-2-oxo-1,2,3,5-tetrahydro-4,1-benzoxazepine-3-acetate (3R,5S)-7-chloro-5-(2,3-dimethoxyphenyl)-1-neopentyl-2-oxo-1,2,3,5-tetrahydro-4,1-benzoxazepine-3-acetic acid (30 g) was converted to sodium (3R,5S)-7-chloro-5-(2,3-dimethoxyphenyl)-1-neopentyl-2-oxo-1,2,3,5-tetrahydro-4,1-benzoxazepine-3-acetate (31.9 g) in a similar manner to that described in Example 172. mp>300° C.

Anal. Calcd. for $C_{24}H_{23}ClNO_6Na \cdot 1.5H_2O$ Calcd: C, 56.42; H, 5.92; N, 2.74 Found: C, 56.49; H, 6.02; N, 2.75.

$[\alpha]_D^{23}$ -235.1° (c=0.60, MeOH)

Example 175 sodium (3R,5S)-7-chloro-5-(2,4-dimethoxyphenyl)-1-neopentyl-2-oxo-1,2,3,5-tetrahydro-4,1-benzoxazepine-3-acetate (3R,5S)-7-chloro-5-(2,4-dimethoxyphenyl)-1-neopentyl-2-oxo-1,2,3,5-tetrahydro-4,1-benzoxazepine-3-acetic acid (24 g) was converted to sodium (3R,5S)-7-chloro-5-(2,4-dimethoxyphenyl)-1-neopentyl-2-oxo-1,2,3,5-tetrahydro-4,1-benzoxazepine-3-acetate (24.7 g) in a similar manner to that described in example 172. mp>300° C.

Anal. Calcd. for $C_{24}H_{27}ClNO_6Na \cdot 0.75H_2O$ Calcd: C, 57.95; H, 5.78; N, 2.82 Found: C, 57.86; H, 6.08; N, 2.81.

$[\alpha]_D^{23}$ -231.1° (c=0.70, MeOH)

Example 176 trans-7-chloro-5-(4-ethoxy-2-methoxyphenyl)-1-neopentyl-2-oxo-1,2,3,5-tetrahydro-4,1-benzoxazepine-3-acetic acid (1) 2-amino-4'-benzyloxy-5-chloro-2'-methoxybenzophenone A mixture of 4-bromo-3-methoxyphenol (21 g), benzyl bromide (13.5 ml), potassium carbonate (21.4 g) and acetone (200 ml) was stirred at room temperature for 24 h. The insoluble materials were removed by filtration and the filtrate was concentrated in vacuo. The residue was purified by silica gel column chromatography (hexane:ethyl acetate= 20:1) to give 4-benzyloxy-2-methoxybromobenzene (25 g) as an oil.

$^1$H-NMR(CDCl$_3$) δ: 3.85(3H, s), 5.04(2H, s), 6.47(1H, dd, J=8.6, 2.6 Hz), 6.57(1H, d, J=2.6 Hz), 7.3–7.5(8H, m).

2-amino-4'-benzyloxy-5-chloro-2'-methoxybenzophenone (20.4 g) was prepared from 4-benzyloxy-2-methoxybromobenzene according to the literature (L. H. Sternbach et al., *J. Org. Chem.*, 27, 378 (1962)). mp=97°–98° C.

Anal. Calcd. for $C_{21}H_{18}ClNO_4$ Calcd: C, 68.57; H, 4.93; N, 3.81 Found: C, 68.62; H, 5.09; N, 3.65.

(2) 2-amino-α-(4-benzyloxy-2-methoxyphenyl)-5-chlorobenzyl alcohol

To a solution of 2-amino-4'-benzyloxy-5-chloro-2'-methoxybenzophenone (10 g) in methanol (100 ml) was added sodium borohydride (1.4 g). After being stirred for 24 h, the mixture was concentrated in vacuo. The residue was diluted with water (200 ml) and extracted with ethyl acetate (300 ml). The extract was washed with water, dried over magnesium sulfate and concentrated in vacuo. The residue was purified by silica gel column chromatography (hexane:ethyl acetate=4:1-2:1) to give 2-amino-α-(4-benzyloxy-2-methoxyphenyl)-5-chlorobenzyl alcohol (9.5 g) as colorless crystals (mp=101°–103° C.).

Anal. Calcd. for $C_{21}H_{20}ClNO_3$ Calcd: C, 68.20; H, 5.41; N, 3.79 Found: C, 67.97; H, 5.42; N, 3.58.

(3) α-(4-benzyloxy-2-methoxyphenyl)-2-neopentylamino-5-chlorobenzyl alcohol

A mixture of 2-amino-α-(4-benzyloxy-2-methoxyphenyl)-5-chlorobenzyl alcohol (9.5 g), pivalaldehyde (3.35 ml), acetic acid (1.85 g) and ethanol (200 ml) was stirred for 30 min. To the mixture was added sodium cyanoborohydride (2.33 g) and the mixture was stirred for 24 h. After the mixture was concentrated in vacuo, the residue was diluted with water (200 ml) and extracted with ethyl acetate (200 ml). The extract was washed with water, dried over magnesium sulfate and concentrated in vacuo. The residue was purified by silica gel column chromatography (hexane:ethyl acetate=5:1) to give α-(4-benzyloxy-2-methoxyphenyl)-2-neopentylamino-5-chlorobenzyl alcohol (10.0 g) as a colorless oil.

$^1$H-NMR(CDCl$_3$) δ: 0.91(9H, s), 2.82(2H, s), 3.10(1H, br), 3.85(3H, s), 4.75(1H, br), 5.06(2H, s), 5.94(1H, s), 6.45–6.7(3H, m), 6.95–7.5(7H, m).

(4)-ethyl 3-[N-[4-chloro-2-(4-benzyloxy-α-hydroxy-2-methoxybenzyl)phenyl]-N-neopentylcarbamoyl]acrylate A mixture of α-(4-benzyloxy-2-methoxyphenyl)-2-neopentylamino-5-chlorobenzyl alcohol (10 g), fumaric acid chloride monomethyl ester (4.43 g), sodium bicarbonate (6.28 g) and dichloromethane (200 ml) was stirred for 30 min. The mixture was washed with water, dried over magnesium sulfate and concentrated in vacuo. The residue was purified by silica gel column chromatography (hexane:ethyl acetate=5:1-2:1) to give ethyl 3-[N-[4-chloro-2-(4-benzyloxy-α-hydroxy-2-methoxybenzyl)phenyl]-N-neopentylcarbamoyl]acrylate (12.0 g) as a colorless oil.

$^1$H-NMR(CDCl$_3$) δ: 0.7–1.0(9H, m), 1.1–1.3(3H, m), 2.5–3.15(2H, m), 3.69, 3.77(3H, each s), 3.9–4.5(3H, m), 4.95, 5.07(2H, each s), 5.9–6.85(5H, m), 6.95–7.9(10H, m).

(5) ethyl trans-5-(4-benzyloxy-2-methoxyphenyl)-7-chloro-1-neopentyl-2-oxo-1,2,3,5-tetrahydro-4,1-benzoxazepine-3-acetate To a mixture of ethyl 3-[N-[4-chloro-2-(4-benzyloxy-α-hydroxy-2-methoxybenzyl)-phenyl]-N-neopentylcarbamoyl]acrylate (12 g), potassium carbonate (5.9 g) and ethanol (150 ml) was stirred for 24 h. After the mixture was concentrated in vacuo, the residue was diluted with water (200 ml) and extracted with ethyl acetate (200 ml). The extract was washed with water, dried over magnesium sulfate and concentrated in vacuo. The residue was purified by silica gel column chromatography (hexane:ethyl acetate=3:1) to give ethyl trans-5-(4-benzyloxy-2-methoxyphenyl)-7-chloro-1-neopentyl-2-oxo-1,2,3,5-tetrahydro-4,1-benzoxazepine-3-acetate (9.8 g) as needles (mp=130°–131° C.).

Anal. Calcd. for $C_{32}H_{36}ClNO_6$ Calcd: C, 67.90; H, 6.41; N, 2.47 Found: C, 67.73; H, 6.35; N, 2.33.

(6) ethyl trans-7-chloro-5-(4-hydroxy-2-methoxyphenyl)-1-neopentyl-2-oxo-1,2,3,5-tetrahydro-4,1-benzoxazepine-3-acetate A solution of ethyl trans-5-(4-benzyloxy-2-methoxyphenyl)-7-chloro-1-neopentyl-2-oxo-1,2,3,5- tetrahydro-4,1-benzoxazepine-3-acetate (7.0 g) and 1N hydrochloric acid (0.1 ml) in ethyl acetate (150 ml) was hydrogenated over 10% Pd-C (50% wet, 1.0 g) under atmospheric pressure until the absorption of hydrogen stopped. The catalyst was removed by filtration and the filtrate was concentrated in vacuo to give ethyl trans-7-chloro-5-(4-hydroxy-2-methoxyphenyl)-1-neopentyl-2-oxo-1,2,3,5-tetrahydro-4,1-benzoxazepine-3-acetate (5.6 g) as colorless crystals (mp=197°–199° C.).

Anal. Calcd. for $C_{25}H_{30}ClNO_6$ Calcd: C, 63.09; H, 6.35; N, 2.94 Found: C, 62.97; H, 6.57; N, 2.81.

(7) ethyl trans-7-chloro-5-(4-ethoxy-2-methoxyphenyl)-1-neopentyl-2-oxo-1,2,3,5-tetrahydro-4,1-benzoxazepine-3-acetate A mixture of ethyl trans-7-chloro-5-(4-hydroxy-2-methoxyphenyl)-1-neopentyl-2-oxo-1,2,3,5-tetrahydro-4,1-benzoxazepine-3-acetate (0.25 g), ethyl iodide (0.06 ml), potassium carbonate (0.15 g) and N,N-dimethylformamide (200 ml) was stirred for 3 h. The mixture was diluted with water (50 ml) and extracted with ethyl acetate (100 ml). The extract was washed with 1N hydrochloric acid and aqueous sodium bicarbonate, dried over magnesium sulfate and concentrated in vacuo to give ethyl trans-7-chloro-5-(4-ethoxy-2-methoxyphenyl)-1-neopentyl-2-oxo-1,2,3,5-tetrahydro-4,1-benzoxazepine-3-acetate (0.24 g) as colorless crystals (mp=164°–166° C.).

Anal. Calcd. for $C_{27}H_{34}ClNO_6$ Calcd: C, 64.34; H, 6.80; N, 2.78 Found: C, 64.18; H, 6.70; N, 2.74.

(8) trans-5-(4-ethoxy-2-methoxyphenyl)-7-chloro-1-neopentyl-2-oxo-1,2,3,5-tetrahydro-4,1-benzoxazepine-3-acetic acid A mixture of ethyl trans-5-(4-ethoxy-2-methoxyphenyl)-7-chloro-1-neopentyl-2-oxo-1,2,3,5-tetrahydro-4,1-benzoxazepine-3-acetate (0.18 g), potassium carbonate (0.10 g), methanol (10 ml), tetrahydrofuran (10 ml) and water (5 ml) was refluxed for 1.5 h. The resulting mixture was concentrated in vacuo, acidified with 1N hydrochloric acid (50 ml) and extracted with ethyl acetate (50 ml). The extract was washed with water, dried over magnesium sulfate and concentrated in vacuo to give trans-5-(4-ethoxy-2-methoxyphenyl)-7-chloro-1-neopentyl-2-oxo-1,2,3,5-tetrahydro-4,1-benzoxazepine-3-acetic acid as colorless crystals (mp=230°–232° C.).

Anal. Calcd. for $C_{25}H_{30}ClNO_6$ Calcd: C, 63.09; H, 6.35; N, 2.94 Found: C, 62.92; H, 6.60; N, 3.01.

Example 177

(3R,5S)-7-chloro-5-(4-ethoxy-2-methoxyphenyl)-1-neopentyl-2-oxo-1,2,3,5-tetrahydro-4,1-benzoxazepine-3-acetic acid 7-chloro-5-(4-ethoxy-2-methoxyphenyl)-1-neopentyl-2-oxo-1,2,3,5-tetrahydro-4,1-benzoxazepine-3-acetic acid (2.2 g) was coupled with L-alanine tert-butyl ester in a similar manner to that described in example 169 to give N-[(3S,5R)-7-chloro-5-(4-ethoxy-2-methoxyphenyl)-1-neopentyl-2-oxo-1,2,3,5-tetrahydro-4,1-benzoxazepine-3-acetyl]-L-alanine tert-butyl ester (1.0 g) and N-[(3R,5S)-7-chloro-5-(4-ethoxy-2-methoxyphenyl)-1-neopentyl-2-oxo-1,2,3,5-tetrahydro-4,1-benzoxazepine-3-acetyl]-L-alanine tert-butyl ester (1.1 g).

N-[(3R,5S)-7-chloro-5-(4-ethoxy-2-methoxyphenyl)-1-neopentyl-2-oxo-1,2,3,5-tetrahydro-4,1-benzoxazepine-3-acetyl]-L-alanine tert-butyl ester (0.8 g) was converted to (3R,5S)-7-chloro-5-(4-ethoxy-2-methoxyphenyl)-1-neopentyl-2-oxo-1,2,3,5-tetrahydro-4,1-benzoxazepine-3-acetic acid (0.33 g) in a similar manner to that described in example 171 (2). colorless crystals (mp=162°–165° C.)

Anal. Calcd. for $C_{25}H_{30}ClNO_6$ Calcd: C, 63.09; H, 6.35; N, 2.94 Found: C, 62.92; H, 6.60; N, 3.01.

$[\alpha]_D^{23}$ –212.0° (c=0.94, MeOH)

Example 178 sodium (3R,5S)-7-chloro-5-(4-ethoxy-2-methoxyphenyl)-1-neopentyl-2-oxo-1,2,3,5-tetrahydro-4,1-benzoxazepine-3-acetate (3R,5S)-7-chloro-5-(4-ethoxy-2-methoxyphenyl)-1-neopentyl-2-oxo-1,2,3,5-tetrahydro-4,1-benzoxazepine-3-acetic acid (3.65 g) was converted to sodium (3R,5S)-7-chloro-5-(4-ethoxy-2-methoxyphenyl)-1-neopentyl-2-oxo-1,2,3,5-tetrahydro-4,1-benzoxazepine-3-acetate (3.54 g) in a similar manner to that described in example 172. colorless crystals (mp=230°–250° C., dec.)

Anal. Calcd. for $C_{25}H_{29}ClNO_6Na$ Calcd: C, 58.81; H, 6.00; N, 2.74 Found: C, 58.91; H, 6.24; N, 2.71.

$[\alpha]_D^{22}$ –218.8° (c=0.48, MeOH)

Squalene synthase inhibitory activity (in vitro)

| Example No. | Isomer form No. | rat enzyme IC$_{50}$ (μM) | human hepG2 enzyme IC$_{50}$ (μM) |
|---|---|---|---|
| 169 | I | 43%[1] | |
| 169 | II | 0.026 | 0.011 |
| 170 | I | 7.7 | |
| 170 | II | 0.017 | 0.011 |
| 171 | I | 15.8%[1] | |
| 171 | II | 0.022 | 0.0086 |
| 173 | | 0.067 | 0.020 |
| 177 | | 0.029 | 0.019 |
| 178 | | 0.041 | 0.022 |

[1] % Inhibition at $10^{-5}$ M.

TABLE 74

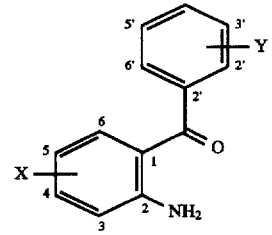

| | | m.p. | | Elemental Analysis (Found) | | |
|---|---|---|---|---|---|---|
| X | Y | (°C.) | Formula | C | H | N |
| 5-F | 2'-Cl | subjected to the next procedure without isolating | | | | |
| 5-MeO | 2'-Cl | oil | $^1$H-NMR(CDCl$_3$) δ: 3.59(3H, s), 5.88(2H, br), 6.51–7.52(7H, m) | | | |
| 5-Cl | 2',4'-Cl | 81–84 | $C_{13}H_8Cl_3NO$ | 51.95 (51.98 | 2.68 2.51 | 4.66 4.83) |
| 5-Cl | 2',4'-OMe | 102–103 | $C_{15}H_{14}ClNO_3$ | 61.76 (61.79 | 4.84 4.88 | 4.80 4.72) |
| 5-Cl | 2',6'-OMe | 172 | $C_{15}H_{14}ClNO_3$ | 61.76 (61.54 | 4.84 4.72 | 4.80 4.87) |

TABLE 75

| X | Y | m.p. (°C.) | Formula | C | H | N |
|---|---|---|---|---|---|---|
| 5-Cl | 2',5'-OMe | oil | | ¹H-NMR(CDCl₃) δ: 3.72(3H, s), 3.78(3H, s), 6.39(2H, br s), 6.64 (1H, d, J | | |
| 5-Cl | 2',4',5'-OMe | 188–189 | C₁₆H₁₆ClNO₄ | 59.73 (59.93 | 5.01 5.00 | 4.35 4.30) |
| 5-Cl | 2',3'-OCH₂O— | 119–120 | C₁₄H₁₀ClNO₃ | 60.99 (60.81 | 3.66 3.43 | 5.08 5.07) |
| 5-Cl | 3',4'-OCH₂O— | oil | | ¹H-NMR(CDCl₃) δ: 6.06(2H, s), 6.67(1H, d), 6.86(1H, d), 7.15–7.5(4H, m) | | |
| 4-Cl | 2'-Cl | 112–113 | C₁₃H₉Cl₂NO | 58.67 (58.47 | 3.41 3.45 | 5.26 5.16) |
| 3,5-Cl | 2'-OMe | 88–90 | C₁₄H₁₁Cl₂NO | 60.02 (59.96 | 3.96 3.85 | 5.00 4.96) |
| 5-Cl | 2',3'-OMe | 91–92 | C₁₅H₁₄ClNO₃ | 61.76 (61.59 | 4.84 4.87 | 4.80 4.79) |

TABLE 76

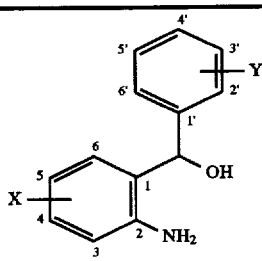

| X | Y | m.p. (°C.) | Formula | C | H | N |
|---|---|---|---|---|---|---|
| 4,5-(CH₂)₃— | 2'-Cl | oil | ¹H-NMR(CDCl₃) δ: 1.8–2.1(2H, m), 2.7–3.0(4H, m), 6.16(1H, s), 6.6–7.5(6H, m) | | | |
| 5-F | 2'-Cl | 77–79 | C₁₃H₁₁ClFNO | 62.04 (62.10 | 4.41 4.40 | 5.57 5.57) |
| 5-MeO | 2'-Cl | oil | ¹H-NMR(CDCl₃) δ: 3.67(3H, s), 6.23(1H, br s), 6.50–6.54(7H, m) | | | |
| 5-Cl | 2',4'-Cl | 104–106 | C₁₃H₁₀Cl₃NO +0.7H₂O | 49.54 (49.59 | 3.65 3.48 | 4.44 4.34) |
| 5-Cl | 2',4'-OMe | oil | ¹H-NMR(CDCl₃) δ: 3.81(3H, s), 3.85(3H, s), 5.94(1H, s), 6.4–6.7(3H, m), 6.95–7.1(3H, m) | | | |

TABLE 77

| X | Y | m.p. (°C.) | Formula | C | H | N |
|---|---|---|---|---|---|---|
| 5-Cl | 2',6'-OMe | 130–135 | C₁₅H₁₆ClNO₃ | 61.33 (61.26 | 5.49 5.46 | 4.77 4.71) |
| 5-Cl | 2',5'-OMe | 177–178 | C₁₅H₁₆ClNO₃ | 61.33 (61.22 | 5.49 5.54 | 4.77 4.72) |
| 5-Cl | 2',4',6'-OMe | 163–164 | C₁₆H₁₈ClNO₄ | 59.35 (59.57 | 5.60 5.63 | 4.33 4.39) |
| 5-Cl | 2',3'-OCH₂O— | 119–120 | C₁₄H₁₂ClNO₃ | 60.55 (60.49 | 4.36 4.20 | 5.04 5.10) |
| 5-Cl | 3',4'-OCH₂O— | 136–137 | C₁₄H₁₂ClNO₃ | 60.55 (60.41 | 4.36 4.48 | 5.04 4.96) |
| 4-Cl | 2'-Cl | oil | ¹H-NMR(CDCl₃) δ: 6.60(1H, s), 6.55–6.75(3H, m), 7.2–7.5(5H, m) | | | |
| 5-Cl | 2',3'-OMe | 124–126 | C₁₅H₁₆ClNO₃ | 61.33 (61.25 | 5.49 5.58 | 4.77 4.66) |
| 3,5-Cl | 2'-OMe | 84–86 | C₁₄H₁₃Cl₂NO₂ | 56.40 | 4.39 | 4.70 |

TABLE 77-continued

| X | Y | m.p. (°C.) | Formula | C | H | N |
|---|---|---|---|---|---|---|
| | | | | (56.06 | 4.35 | 4.59) |
| H | 2'-Cl | oil | | $^1$H-NMR(CDCl$_3$) δ: 5.30(1H, s), 6.17(1H, s), 6.5–7.6(7H, m) | | |

TABLE 78

| X | Y | m.p. (°C.) | Formula | C | H | N |
|---|---|---|---|---|---|---|
| 5-CH$_3$ | 2'-Cl | oil | | $^1$H-NMR(CDCl$_3$) δ: 2.17(3H, s), 6.16(1H, s), 6.6–7.6(7H, m) | | |
| 5-Cl | 2'-F | 100–101 | C$_{13}$H$_{11}$ClFNO | 62.03 | 4.41 | 5.57 |
| | | | | (61.86 | 4.62 | 5.51) |
| H | 2'-F | 106–107 | C$_{13}$H$_{12}$FNO | 71.87 | 5.57 | 6.45 |
| | | | | (71.76 | 5.59 | 6.36) |
| H | 2'-OMe | 105–106 | C$_{14}$H$_{15}$NO$_2$ | 73.34 | 6.59 | 6.11 |
| | | | | (73.11 | 6.63 | 6.19) |
| 5-Cl | 2'-CF$_3$ | 127–129 | C$_{14}$H$_{11}$ClF$_3$NO | 55.74 | 3.68 | 4.64 |
| | | | | (55.66 | 3.64 | 4.70) |
| 5-Cl | 2'-OMe | 81–82 | C$_{14}$H$_{14}$ClNO$_2$ | 63.76 | 5.35 | 5.31 |
| | | | | (63.83 | 5.56 | 5.32) |
| 5-Cl | 2'-Br | 87–88 | C$_{13}$H$_{11}$BrClNO | 49.95 | 3.55 | 4.48 |
| | | | | (50.03 | 3.71 | 4.44) |
| 5-Br | 2'-Cl | 97–99 | C$_{13}$H$_{11}$BrClNO | 49.95 | 3.55 | 4.48 |
| | | | | (49.87 | 3.76 | 4.37) |
| 5-Cl | 4'-Cl | 127–128 | C$_{13}$H$_{11}$Cl$_2$NO | 58.23 | 4.13 | 5.22 |
| | | | | (58.47 | 4.17 | 5.19) |

TABLE 79

| X | Y | m.p. (°C.) | Formula | C | H | N |
|---|---|---|---|---|---|---|
| H | 2'-Me | 110–111 | C$_{14}$H$_{15}$NO | 78.84 | 7.09 | 6.57 |
| 5-Cl | 3'-Cl | 136–138 | C$_{13}$H$_{11}$Cl$_2$NO | 58.23 | 4.13 | 5.22 |
| | | | | (58.36 | 4.23 | 5.14) |
| 5-CF$_3$ | H | 86–87 | C$_{14}$H$_{12}$F$_3$NO | 62.92 | 4.53 | 5.24 |
| | | | | (62.84 | 4.55 | 5.11) |
| 4-Cl | H | 107–109 | C$_{13}$H$_{12}$ClNO | 66.81 | 5.18 | 5.99 |
| | | | | (66.80 | 5.19 | 5.97) |

TABLE 80

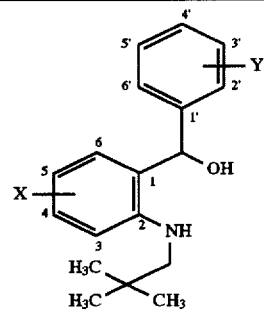

| X | Y | m.p. (°C.) | Formula | C | H | N |
|---|---|---|---|---|---|---|
| 5-Cl | 2',4'-OCH$_3$ | oil | C$_{20}$H$_{26}$ClNO$_3$ | $^1$H-NMR(CDCl$_3$) δ: 0.92 (9H, s, Bu$^t$), 2.82(2H, s), 2.9–3.3(1H, br), 3.81(3H, s), 3.86(3H, s), 4.6–5.0 (1H, br), 5.92(1H, s), 6.4–6.6(3H, m), 6.95–7.2(3H, m) | | |
| 5-Cl | 2', 6'-OCH$_3$ | oil | C$_2$H$_{26}$ClNO$_3$ | $^1$H-NMR(CDCl$_3$) δ: 1.06 (9H, s), 2.87(1H, d, J=11.4Hz), 2.96(1H, d, J=11.4Hz), 3.80(6H, s), 4.28, 5.61(each 1H, br), 6.26(1H, br), 6.53(1H, d, J=2.6Hz), 6.60(1H, d, J=8.6Hz), 6.66(2H, d, J=8.4Hz), 7.09(1H, dd, J=2.4, 8.6Hz), 7.31 (1H, t, J=8.4Hz) | | |
| 5-Cl | 2', 5'-OCH$_3$ | 126–128 | C$_2$H$_{26}$ClNO$_3$ | 66.02 (66.18 | 7.20 7.18 | 3.85 3.83) |

TABLE 81

| X | Y | m.p. (°C.) | Formula | Elemental Analysis (Found) C | H | N |
|---|---|---|---|---|---|---|
| 5-Cl | 2',4',6'-OCH$_3$ | 150–151 | C$_{21}$H$_{28}$ClNO$_4$ | 64.03 (64.19 | 7.16 7.00 | 3.56 3.48) |
| 5-Cl | 2',3'-OCH$_2$O— | | | subjected to the next procedure without isolating | | |
| 5-Cl | 3',4'-OCH$_2$O— | oil | C$_{19}$H$_{22}$ClNO$_3$ | $^1$H-NMR(CDCl$_3$) δ: 0.86(9H, s, Bu$^t$), 2.75 (2H, s), 5.67(1H, s), 5.95(2H, s), 6.5–7.3 (6H, m) | | |
| 4-Cl | 2'-Cl | oil | C$_{18}$H$_{21}$Cl$_2$NO | $^1$H-NMR(CDCl$_3$) δ: 0.94(9H, s, Bu$^t$), 2.84 (2H, s), 6.12(1H, s), 6.5–7.5(7H, m) | | |
| 3,5-Cl | 2'-OCH$_3$ | oil | C$_{19}$H$_{23}$Cl$_2$NO$_2$ | $^1$H-NMR(CDCl$_3$) δ: 0.98(9H, s, Bu$^t$), 2.75 (2H, s), 3.84(3H, s), 4.05(1H, br s), 6.28 (1H, s), 6.9–7.4(6H, m) | | |
| 5-Cl | 2'-OCH$_3$ | oil | C$_{19}$H$_{24}$ClNO$_2$ | $^1$H-NMR(CDCl$_3$) δ: 0.92(9H, s, Bu$^t$), 2.83 (2H, s), 3.1–3.5(1H, br), 3.89(3H, s), 4.6–5.0(1H, br), 5.99(1H, s), 6.59(1H, d, J=8.8Hz), 6.9–7.4(6H, m) | | |
| 5-Cl | 2'-Br | 99–100 | C$_{18}$H$_{21}$BrClNO | 56.49 (56.69 | 5.53 5.50 | 3.66 3.42) |
| 5-Br | 2'-Cl | 105–107 | C$_{18}$H$_{21}$BrClNO | 56.49 (56.48 | 5.53 5.50 | 3.66 3.59) |
| 5-Cl | 2',3'-OMe | 120–121 | C$_{20}$H$_{26}$ClNO$_3$ | 66.02 (65.74 | 7.20 7.01 | 3.85 3.71) |

TABLE 82

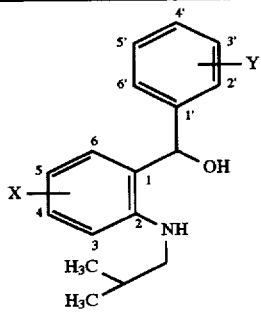

| X | Y | m.p. (°C.) | Formula | Elemental Analysis(Found) C | H | N |
|---|---|---|---|---|---|---|
| 5-F | 2'-Cl | 84–86 | C$_{17}$H$_{19}$ClFNO | 66.34 (66.21 | 6.22 6.22 | 4.55 4.50) |
| 5-OCH$_3$ | 2'-Cl | oil | C$_{18}$H$_{22}$ClNO$_2$ | $^1$H-NMR(CDCl$_3$) δ: 0.85, 0.87(each 3H, each d, J=6.6Hz), 1.80(1H, m), 2.86(2H, d, J=6.6Hz), 3.68(3H, s), 6.24(1H, s), 6.50–7.55(7H, m) | | |
| 5-Cl | 2',4'-Cl | 104–106 | C$_{17}$H$_{18}$Cl$_3$NO | 56.93 (56.96 | 5.06 4.85 | 3.90 3.66) |
| 5-Cl | 2'-CF$_3$ | 72–74 | C$_{18}$H$_{19}$ClF$_3$NO | 60.42 (59.96 | 5.35 5.37 | 3.91 3.83) |
| 5-Cl | 2'-OCH$_3$ | oil | C$_{18}$H$_{22}$ClNO$_2$ | $^1$H-NMR(CDCl$_3$) δ: 0.92 (6H, d, J=6.6H), 1.75–2.0(1H, m), 2.89(1H, d, J=6.8Hz), 3.1–3.4(1H, Br), 3.88(3H, s), 4.7–5.1(1H, br), 5.97(1H, s), 6.56 (1H, d, J=8.8Hz), 6.9–7.4(6H, m) | | |

TABLE 82-continued

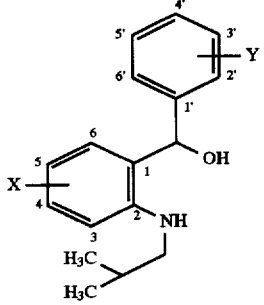

TABLE 83

| X | Y | m.p. (°C.) | Formula | C | H | N |
|---|---|---|---|---|---|---|
| 5-Cl | 2'-Br | 96–98 | $C_{17}H_{19}BrClNO$ | 55.38 (55.55 | 5.19 5.20 | 3.80 3.74) |
| 5-Br | 2'-Cl | oil | $C_{17}H_{19}BrClNO$ | $^1$H-NMR(CDCl$_3$) δ: 0.91(6H, d, J=6.6Hz), 1.7–2.0(1H, m), 2.89(2H, d, J=6.6Hz), 6.11(1H, s), 6.53(1H, d, J=8.6Hz), 7.05(1H, d, J=2.4Hz), 7.14–7.46(5H, m) | | |
| 5-Cl | 4'-Cl | oil | $C_{17}H_{19}Cl_2NO$ | $^1$H-NMR(CDCl$_3$) δ: 0.828(3H, d, J=6.8Hz), 0.834 (3H, d, J=6.8Hz), 1.64–1.86(1H, m), 2.2–2.8 (1H, br), 2.80(2H, d, J=6.8Hz), 4.2–4.7(1H, br), 5.73(1H, s), 6.54(1H, d, J=8.6Hz), 6.98(1H, d, J=2.4Hz), 7.14(1H, dd, J=8.6, 2.4Hz), 7.31(4H, s) | | |
| H | 2'-CH$_3$ | oil | $C_{18}H_{23}NO$ | $^1$H-NMR(CDCl$_3$) δ: 0.95(6H, d, J=6.6Hz), 1.8–2.0(1H, m), 2.21(3H, s), 2.94(2H, d, J=6.6Hz), 5.98(1H, s), 6.5–6.8(2H, m), 7.1–7.35(3H, m), 7.1–7.35(3H, m), 7.4–7.55(1H, m) | | |
| 5-Cl | 3'-Cl | 73–74 | $C_{17}H_{19}Cl_2NO$ | 62.97 (62.81 | 5.91 5.88 | 4.32 4.19) |
| 5-CF$_3$ | H | 60–62 | $C_{18}H_{20}F_3NO$ | 66.86 (66.89 | 6.23 6.27 | 4.33 4.22) |
| 15-Cl | H | 56–59 | $C_{17}H_{20}ClNO$ | 70.46 (70.45 | 6.96 7.11 | 4.83 4.90) |

TABLE 84

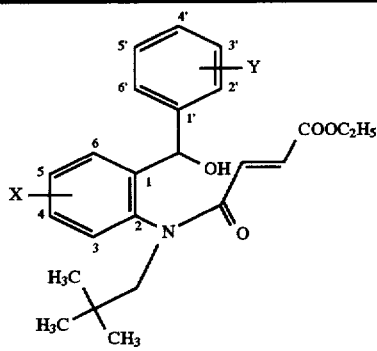

| X | Y | m.p. (°C.) | Formula | C H N |
|---|---|---|---|---|
| 5-Cl | 2',4'-OCH$_3$ | oil | $C_{26}H_{32}ClNO_6$ | $^1$H-NMR(CDCl$_3$) δ: 0.82 and 0.93(9H, each s, Bu$^t$), 1.22(3H, t, J=7.2Hz), 2.35–3.1(2H, m), 3.65–3.9(6H, m), 4.0–4.5(3H, m), 5.9–6.55(5H, m), 6.75–7.9(4H, m) |
| 5-Cl | 2',6'-OCH$_3$ | oil | $C_{26}H_{32}NO_6Cl$ | $^1$H-NMR(CDCl$_3$) δ: 0.90, 0.95(9H, each s, Bu$^t$), 1.19–1.30(3H, m), 2.88–3.10(1H, m), 3.72–3.82 (6H, m), 4.04–4.28(2H, m), 4.44–4.57(1H, m), 6.02–7.88(9H, m) |

TABLE 84-continued

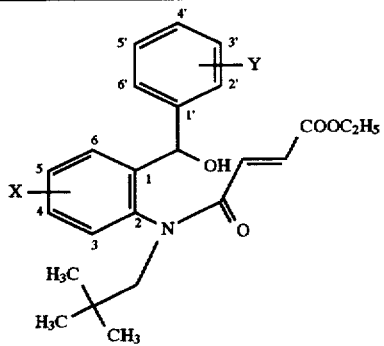

| X | Y | m.p. (°C.) | Formula | C | H | N |
|---|---|---|---|---|---|---|
| 5-Cl | 2',5'-OCH$_3$ | 140–142 | $C_{26}H_{32}ClNO_6$ | 63.73 (63.67 | 6.58 6.50 | 2.86 2.81) |
| 5-Cl | 2',4',6'-OCH$_3$ | oil | $C_{27}H_{34}ClNO_7$ | $^1$H-NMR(CDCl$_3$) δ: 0.90 and 0.94(9H, each s, Bu$^t$), 1.15–1.35(3H, m), 2.8–3.1(1H, m), 3.4–4.3(12H, m), 4.35–4.6(1H, m), 5.9–6.45(5H, m), 6.8–7.95 (3H, m) | | |

TABLE 85

| X | Y | m.p. (°C.) | Formula | C | H | N |
|---|---|---|---|---|---|---|
| 5-Cl | 2',3'-OCH$_2$O— | oil | $C_{25}H_{28}ClNO_6$ | $^1$H-NMR(CDCl$_3$) δ: 0.92 and 1.07(9H, each s, Bu$^t$), 1.18–1.33(3H, m), 2.85–3.04(1H, m), 4.05–4.34(2H, m), 4.46–4.54(1H, m), 5.87(2H, s), 6.05–7.89(9H, m) | | |
| 5-Cl | 3',4'-OCH$_2$O— | 125–126 | $C_{25}H_{28}ClNO_6$ | 63.36 | 5.95 | 2.96 |

TABLE 85-continued

| X | Y | m.p. (°C.) | Formula | C | H | N |
|---|---|---|---|---|---|---|
| | | | | (63.26 | 5.72 | 2.76) |
| 4-Cl | 2'-Cl | 152–153 | $C_{24}H_{27}Cl_2NO_4$ | 62.07 | 5.86 | 3.02 |
| | | | | (61.78 | 5.93 | 2.88) |
| 3,5-Cl | 2'-OCH$_3$ | 162–164 | $C_{25}H_{29}Cl_2NO_5$ | 60.73 | 5.91 | 2.83 |
| | | | | (60.84 | 5.89 | 2.70) |
| 5-Cl | 2'-OCH$_3$ | oil | $C_{25}H_{30}ClNO_5$ | \multicolumn{3}{l}{$^1$H-NMR(CDCl$_3$) δ: 0.84 and 0.93(9H, each s, Bu$^t$), 1.15–1.3(2H, m), 2.5–3.2(2H, m), 3.73 and 3.82(3H, each s), 4.0–4.25(2H, m), 4.25–4.6(1H, m), 6.0–6.5(3H, m), 6.7–7.85(7H, m)} |
| 5-Cl | 2'-Br | 168–169 | $C_{24}H_{27}BrClNO_4$ | 56.65 | 5.35 | 2.75 |
| | | | | (56.71 | 5.21 | 2.47) |
| 5-Br | 2'-Cl | 171–174 | $C_{24}H_{27}BrClNO_4$ | 56.65 | 5.35 | 2.75 |
| | | | | (56.71 | 5.21 | 2.47) |
| 5-Br | 2'-Cl | 171–174 | $C_{24}H_{27}BrClNO_4$ | 56.65 | 5.35 | 2.75 |
| | | | | (56.68 | 5.39 | 2.68) |
| 5-Cl | 2'-,3'-OCH$_3$ | 137–139 | $C_{26}H_{32}ClNO_6$ | 63.73 | 6.58 | 2.86 |
| | | | | (63.66 | 6.50 | 2.94) |

TABLE 86

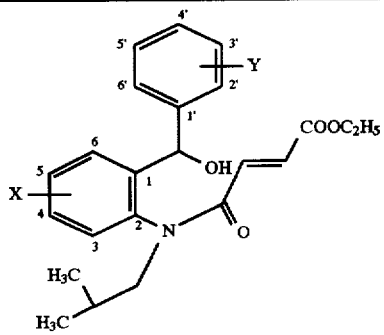

| X | Y | m.p. (°C.) | Formula | C | H | N |
|---|---|---|---|---|---|---|
| 5-F | 2'-Cl | 148–151 | $C_{23}H_{25}ClFNO_4$ | 63.67 (63.56 | 5.81 5.73 | 3.23 3.38) |
| 5-OCH$_3$ | 2'-Cl | oil | $C_{24}H_{28}NO_5Cl$ | \multicolumn{3}{l}{$^1$H-NMR(CDCl$_3$) δ: 0.73–1.25(total 9H, m), 1.78(1H, m), 2.35–3.10 (2H, m), 3.70, 3.75(3H, each s), 4.10–4.38 (4H, m), 5.89–7.73(10H, m)} |
| 5-Cl | 2',4'-Cl | 167– | $C_{23}H_{24}Cl_3NO_4$ | 56.98 | 4.99 | 2.89 |

TABLE 86-continued

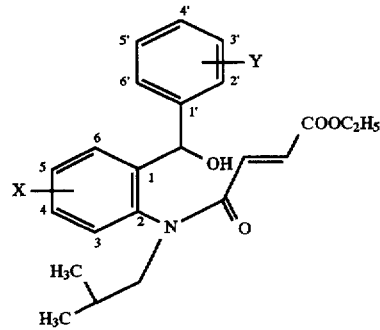

| X | Y | m.p. (°C.) | Formula | C | H | N |
|---|---|---|---|---|---|---|
| 5-Cl | 2'-CF$_3$ | 168 164–165 | $C_{24}H_{25}ClF_3NO_4$ | (56.85 59.57 (59.55 | 4.84 5.21 5.22 | 2.63) 2.89 2.83) |
| 5-Cl | 2'-OCH$_3$ | oil | $C_{24}H_{28}ClNO_5$ | \multicolumn{3}{l}{$^1$H-NMR(CDCl$_3$) δ: 0.7–1.15(6H, m), 1.15–3.76 and 3.80(3H, each s), 4.0–4.45(4H, m), 5.9–6.45(3H, m), 6.7–7.9 (7H, m)} |

TABLE 87

| X | Y | m.p. (°C.) | Formula | C | H | N |
|---|---|---|---|---|---|---|
| 5-Cl | 2'-Br | 158–160 | $C_{23}H_{25}BrClNO_4$ | 55.83 (55.89 | 5.09 5.10 | 2.83 2.89) |
| 5-Br | 2'-Cl | 157–159 | $C_{23}H_{25}BrClNO_4$ | 55.83 (55.42 | 5.09 5.18 | 2.83 2.65) |
| 5-Cl | 4'-Cl | amorphous | $C_{23}H_{25}Cl_2NO_4 + 0.2H_2O$ | 60.85 (60.85 | 5.64 5.62 | 3.09 3.00) |
| H | 2'-CH$_3$ | oil | $C_{24}H_{29}NO_4$ | \multicolumn{3}{l}{$^1$H-NMR(CDCl$_3$) δ: 0.7–1.1(6H, m), 1.21(3H, t, J=7.0Hz), 1.5–2.0(1H, m), 2.29(3H, s), 2.0–2.3 and 2.9–3.1(1H, each m), 3.9–4.5(3H, m), 5.9–6.4(2H, m), 6.6–6.9(1H, m), 6.95–7.9(8H, m)} |
| 5-Cl | 2'-Cl | 105–108 | $C_{23}H_{25}Cl_2NO_4$ | 61.34 | 5.60 | 3.11 |

TABLE 87-continued

| X | Y | m.p. (°C.) | Formula | Elemental Analysis (Found) | | |
|---|---|---|---|---|---|---|
| | | | | C | H | N |
| | | | | (61.37 | 5.53 | 3.08) |
| 5-CF$_3$ | H | amorphous solid | C$_{24}$H$_{26}$F$_3$NO$_4$ | 64.13 | 5.83 | 3.12 |
| | | | | (64.28 | 5.80 | 3.00) |
| 5-I | H | 110–113 | C$_{23}$H$_{26}$ClNO$_4$ | 66.42 | 6.30 | 3.37 |
| | | | | (66.05 | 6.29 | 3.35) |

TABLE 88

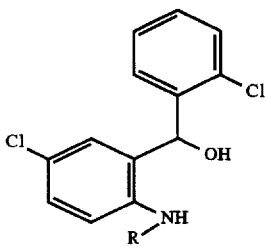

| R | m.p. (°C.) | Formula | Elemental Analysis (Found) | | |
|---|---|---|---|---|---|
| | | | C | H | N |
| O‖CCF$_2$CF$_3$ | 101–103 | C$_{10}$H$_{10}$Cl$_2$F$_5$NO$_2$ | 46.40 (46.28 | 2.43 2.42 | 3.38 3.47) |
| O‖C—△ | 115–116 | C$_{17}$H$_{15}$Cl$_2$NO$_2$ | 60.73 (60.61 | 4.50 4.72 | 4.17 4.03) |
| O‖CCH$_2$C(CH$_3$)$_3$ | 109–110 | C$_{19}$H$_{21}$Cl$_2$NO$_2$ | 62.30 (62.57 | 5.78 5.79 | 3.82 3.73) |
| O‖CCF$_3$ | 155–156 | C$_{15}$H$_{10}$Cl$_2$F$_3$NO$_2$ | 49.47 (49.22 | 2.77 2.86 | 3.85 3.71) |

Experimental Example 1
Assay Method of Squalene Synthetase Inhibitory Activity

The squalene synthetase inhibitory activity was assayed as follows with the enzyme solutions described in the subsequent Experimental Examples 2 and 3.

More specifically, an enzyme solution (protein content 0.8 ug) prepared in Experimental Example 1 or 2 was added to a solution (total volume 50 ul)) containing 5 uM [1-$^3$H] farnesyl pyrophosphate (specific activity 25 uCi/mole), 1 mM NADPH, 5 mM MgCl$_2$, 6 mM glutathione, a 100 mM buffer solution of potassium phosphate (pH 7.4) and a test drug (used as an aqueous solution or a DMSO solution), then the reaction was allowed to proceed at 37° C. for 45 minutes. To the reaction mixture was added 150 ul of a mixture of chloroform and methanol (1:2) to suspend the reaction, followed by adding 50 ul of chloroform and 50 ul of a 3N aqueous solution of sodium hydroxide. 50 ul of the chloroform layer (lower layer) containing the reaction mixture having squalene as the principal component and 3 ml of toluene-based liquid scintillator were mixed, and its radioactivity was determined by means of a liquid scintillation counter.

The squalene synthetase inhibitory activity was expressed in terms of the concentration inhibiting by 50% the radioactivity taken into the chloroform layer (IC$_{50}$, molar concentration (M)).

Experimental Example 2
Preparation of rat-derived enzyme

An SD male rat (6 week old) was killed by bleeding, and its liver was excised. About 10 g of the liver was washed with a physiological saline solution cooled with ice, which was then homogenized in 15 ml of an ice-cooled buffer solution [100 mM potassium phosphate (pH 7.4), 15 mM nicotinamide, 2 mM MgCl$_2$], followed by centrifugation for 20 minutes (4° C.) with 10000×g. The supernatant layer was separated and subjected to further centrifugation for 90 minutes (4° C.) with 105000×g. The sediment was then suspended in an ice-cooled 100 mM phosphate buffer solution (pH 7.4), which was again subjected to centrifugation for 90 minutes (4° C.) with 105000×g. The sediment thus obtained (microsome fraction) was suspended in an ice-cooled 100 mM potassium phosphate buffer (pH 7.4) (about 40 mg/ml protein concentration, determined with BCA protein assay kit of Pias Co., Ltd.). This suspension was used as the enzyme solution.

Experimental Example 3
Preparation of human-derived enzyme

Human hepatic carcinoma cells HepG2 (about 1×10$^9$ cells) obtained by incubation on a Dulbecco-modified Eagle's medium (37° C. in the presence of 5% CO$_2$) were suspended in 10 ml of an ice-cooled buffer solution [100 mM potassium phosphate buffer (pH 7.4), 30 mM nicotinamide and 2.5 mM MgCl$_2$]. The cells were crashed by means of ultrasonication (for 30 seconds, twice). From the sonicate thus obtained, the microsome fraction was obtained by the same procedure as in Experiment Example 1, which was suspended in an ice-cooled 100 mM potassium phosphate buffer (pH 7.4) (about 4 mg/ml protein concentration). This suspension was used as the enzyme solution. The results are shown in Table 74.

TABLE 74

| Compd. No. | | Rat Enzyme (10$^{-7}$M) | Man Enzyme (10$^{-7}$M) |
|---|---|---|---|
| Ref. Ex. | 5-1 | 83 | 68 |
| | -2 | 47 | 51 |
| | -3 | 40 | 38 |
| | -4 | 63 | 64 |
| | -7 | 5.4 | 7.1 |
| | -8 | 5.3 | — |
| | -12 | 2.3 | — |
| W. Ex. | 2-2 | 0.61 | 0.34 |
| | -4 | 0.72 | 0.24 |
| | 33-2 | 49 | 38 |
| | 35-1 | 72 | 53 |
| | -5 | 43 | 43 |
| | -6 | 34 | 33 |
| | -11 | 26 | 21 |
| | -12 | 40 | 35 |
| | -15 | 0.35 | 0.12 |
| | -19 | 0.28 | 0.30 |
| | -23 | 0.94 | 0.28 |

TABLE 74-continued

| Compd. No. | Rat Enzyme ($10^{-7}$M) | Man Enzyme ($10^{-7}$M) |
|---|---|---|
| 74-5 | 0.54 | 0.22 |
| -9 | 0.49 | 0.40 |
| -11 | 0.79 | 0.14 |
| -12 | 0.38 | 0.18 |
| 105 | 0.65 | 0.34 |
| 114 | 0.43 | 0.11 |
| 118(1) | 0.42 | 0.16 |
| 120 | 0.16 | 0.06 |
| 138 | 0.42 | 0.21 |
| 168 | 0.67 | 0.18 |
| 117 | >100 | — |

Experimental Example 4

Effects

The antifungal activities of the Compounds (I") were evaluated by the following method: a sheet of filter paper disc (manufactured by Toyo Seisakusho, 8 mm in diameter) soaked in a 1000 µg/ml solution of a compound (I") in methanol was placed on an agar plate, which was incubated at 28° C. for 2 days, and the diameter of the growth inhibition zone around the filter paper disc was measured. The following culture media were used:

A: yeast nitrogen base agar medium (pH 7.0)

B: peptone-yeast extract-glucose agar medium (pH 7.0)

The antifungal spectra of the compound (I") are shown in Table 90.

The below mentioned test fungi are deposited at the Institute for Fermentation, Osaka, Japan (IFO). Their accession numbers are shown in Table 90.

TABLE 90

Antifungal spectra

| Test fungi | Media | Inhibition zone diameter (mm) | | |
|---|---|---|---|---|
| | | Example 75-7 | Example 75-6 | Example 74-10 |
| *Candida albicans* IFO 0583 | A | 16 | 14 | 18 |
| *Aspergillus niger* IFO 4066 | A | 30 | 24 | 0 |
| *Cryptococcus neoformans* IFO 0410 | A | 19 | 13 | 14 |
| *Trichophyton rubrum* IFO 6467 | B | 16 | 13 | 20 |
| *Trichophyton mentagrophytes* IFO 7522 | B | 12 | 12 | 12 |
| *Microsporum gypseum* IFO 6076 | B | 13 | 12 | 13 |

Experimental Example 5

In vivo cholesterogenesis in the liver

Six-week-old, male Sprague-Dawley rats were given 5%-cholestylamine as a dietary admixture for 4 days. They were administered compound at a dose of 30 mg/kg as a suspension of 0.5%-methylcellulose solution and were intravenously given 2 uCi of [$^{14}$C]acetate 1 hour after the administration. One hour later, rats were sacrificed and livers were removed. Hepatic sterols were extracted with petroleum ether after saponification, and the radioactivity of digitonin-precipitable fraction was measured. Example 1-(4) inhibited the hepatic cholesterogenesis by 38% compared to the control group given only 5%-methylcellulose solution.

Formulation Examples

A squalene synthetase inhibiting agents containing, as its effective component, a 4,1-benzoxazepin-2-one derivative shown by the formula (I) of this invention or a salt thereof, in the case where it is used as a therapeutic agent of hypercholesteremia, can be formulated in accordance with, for example, the following prescriptions.

| 1. Capsules | |
|---|---|
| (1) Compound obtained in Example 28-19 | 10 mg |
| (2) Lactose | 96 mg |
| (3) Microcrystalline cellulose | 70 mg |
| (4) Magnesium stearate | 10 mg |
| One capsule | 180 mg |

(1), (2) and (3) and one half of (4) were blended and the the mixture was granulated, to which was added the balance of (4). The mixture was filled in a gelatin capsule.

| 2. Tablets | |
|---|---|
| (1) Compound obtained in Example 28-19 | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2) and (3) and two thirds of (4) and one half of (5) were blended and the mixture was granulated, to which were added the balance of (4) and (5). The mixture was subjected to compression-molding to provide tablets.

| 3. Injections | |
|---|---|
| (1) Sodium salt of the compound obtained in Example 28-19 | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

| 4. Capsules | |
|---|---|
| (1) Compound obtained in Example 1-4 | 10 mg |
| (2) Lactose | 90 mg |
| (3) Microcrystalline cellulose | 70 mg |
| (4) Magnesium stearate | 10 mg |
| One capsule | 180 mg |

(1), (2) and (3) and one half of (4) were blended and the the mixture was granulated, to which was added the balance of (4). The mixture was filled in a gelatin capsule.

| 5. Tablets | |
|---|---|
| (1) Compound obtained in Example 1-4 | 10 mg |
| (2) Lactose | 35 mg |
| (3) Corn starch | 150 mg |
| (4) Microcrystalline cellulose | 30 mg |

| 5. Tablets | |
|---|---|
| (5) Magnesium stearate | 5 mg |
| One tablet | 230 mg |

(1), (2) and (3) and two thirds of (4) and one half of (5) were blended and the mixture was granulated, to which were added the balance of (4) and (5). The mixture was subjected to compression-molding to provide tablets.

| 6. Injections | |
|---|---|
| (1) Sodium salt of the compound obtained in Example 1-4 | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

What is claimed is:

1. A compound of the formula:

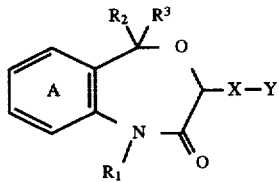

wherein $R_1$ is
(i) hydrogen,
(ii) a $C_{1-7}$ alkyl group, a $C_{2-6}$ alkenyl group, a $C_{2-6}$ alkynyl group,
(iii) a $C_{3-9}$ cycloalkyl group, a cycloalkenyl group selected from among 2-cyclopenten-1-yl, 3-cyclopenten-1-yl, 2-cyclohexen-1-yl, 3-cyclohexen-1-yl, 1-cyclobuten-1-yl and 1-cyclopenten-1-yl, a cycloalkadienyl group selected from among 2,4-cyclopentadien-1-yl, 2,4-cyclohexadien-1-yl, and 2,5-cyclohexadien-1-yl, or
(iv) an aryl group selected from among phenyl, naphthyl, anthryl, phenanthryl and acenaphthylenyl in which each of the group of (ii), (iii) and (iv) is unsubstituted or substituted with 1 to 5 substituent(s) selected from the group consisting of
(1) phenyl, naphthyl, anthyl, phenanthryl, acenaphthylenyl, $C_{3-7}$ cycloalkyl groups and $C_{3-6}$ cycloalkenyl groups each of which is unsubstituted or substituted with 1 to 2 substituent(s) selected from among $C_{1-3}$ alkoxy groups and $C_{1-3}$ alkyl groups,
(2) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, τ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo [1,2-b] pyridazinyl, pyrazolo [1,5-a]pyridyl, imidazo [1,2-a] pyridyl, imidazo [1,5-a] pyridyl, imidazo [1,2-b] pyridazinyl, imidazo [1,2-a] pyrimidinyl, 1,2,4-triazolo [4,3-a] pyridyl, 1,2,4-triazolo [4,3-b] pyridazinyl, oxiranyl, azetidinyl, oxetanyl, thiethanyl, pyrrolidinyl, tetrahydrofuryl, thioranyl, piperidyl, tetrahydropyranyl, morpholinyl, thiomorpholinyl or piperazinyl, each of said groups being unsubstituted or substituted with $C_{1-3}$ alkyl, (3) amino groups, hydroxyl groups and thiol groups each of which is unsubstituted or substituted with $C_{1-3}$ alkyl groups and (4) halogen atoms;

and having each of the groups of (iii) and (iv) may further have a $C_{1-3}$ alkyl group, and (5) $C_{1-6}$ acyl groups;

each of $R_2$ and $R_3$ is independently (i) hydrogen; (ii) a $C_{1-6}$ alkyl group unsubstituted or substituted with substituent(s) selected from among halogens and $C_{1-4}$ alkoxy groups; (iii) a phenyl group unsubstituted or substituted by 1 to 3 substituent(s) selected from among (1) halogen atoms, (2) $C_{1-4}$ alkyl groups unsubstituted or substituted with 1 to 3 halogen atoms, (3) $C_{1-4}$ alkoxy groups unsubstituted or substituted with 1 to 3 halogen atoms, (4) hydroxyl groups unsubstituted or substituted with a $C_{1-4}$ alkyl group, a $C_{3-6}$ cycloalkyl group, phenyl, 1-naphthyl, 2-naphthyl, benzyl or phenethyl, (5) nitro group and (6) cyano group in which the two adjoining substituents on the phenyl group may cooperate therewith to form a ring which is unsubstituted or substituted with a $C_{1-3}$ alkyl or (iv) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxaolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, τ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b] pyridazinyl, pyrazolo[1,5-a]pyridyl, imidazo[1,2-a] pyridiyl, imidazo[1,5-a]pyridyl, imidazo[1,2-b] pyridazinyl, imidazo[1,2-a]pyrimidinyl, 1,2,4-triazolo [4,3-a]pyridyl or 1,2,4-triazolo[4,3-b]pyridazinyl, each of said groups being unsubstituted or substituted with $C_{1-3}$ alkyl;

X is a bond or a divalent chain represented by the formula

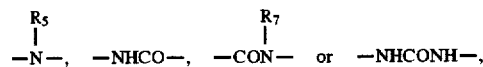

wherein m and n denote independently 0, 1, 2 or 3; E stands for a bond or oxygen atom, sulfur atom, sulfoxide, sulfone, $$\begin{array}{ccc} R_5 & & R_7 \\ | & & | \\ -N-, & -NHCO-, & -CON- \text{ or } -NHCONH-, \end{array}$$

wherein $R_6$ and $R_7$ independently stand for (i) hydrogen atom; (ii) a $C_{1-6}$ alkyl group unsubstituted or substituted with furyl, thienyl, pyridyl, pyrimidinyl, pyrazinyl, indolyl, imidazolyl, isoindolyl, an amino group unsubstituted or substituted with $C_{1-3}$ alkyl group(s), a hydroxyl group unsubstituted or substituted with a $C_{1-3}$ alkyl group, a thiol group unsubstituted or substituted with a $C_{1-3}$ alkyl group, a thiol group unsubstituted or substituted with a $C_{1-3}$ alkyl group, carboxyl group, methoxycarbonyl, ethoxycarbonyl, propoxycarbonyl, phenoxycarbonyl, 1-naphtoxycarbonyl or 2-naphtoxycarbonyl or a halogen atom; (iii) benzyl napthylmethyl, phenylethyl, phenylpropyl or phenylbutyl unsubstituted or substituted with substituent(s) selected from halogens, $C_{1-3}$ alkoxy groups, hydroxyl group, amino group, carboxyl group and sulfhydryl or (iv) a phenyl group unsubstituted or substituted with substituent(s) selected from halogen atoms and $C_{1-3}$ alkyl groups; $R_5$ stands for hydrogen atom, a $C_{1-4}$ alkyl, a $C_{7-15}$ aralkyl, a lower alkanoyl group, a lower alkenoyl group, a lower alkanesulfonyl group, benzoyl, p-toluoyl, 1-naphthoyl and 2-naphthoyl, phenylacetyl, phenylpropionyl, hydroatropoyl, phenylbuty cinnamoyl, atropoly, benzenesulfonyl or p-toluenesulfonyl;

Y is (i) (a) carboxyl group, (b) a lower alkoxy (thio) carbonyl group having optionally one or more substituent(s) selected from among
 (1) hydroxyl groups unsubstituted or substituted with a lower alkanoyl group, methoxycarbonyl, ethoxycarbonyl, propoxycarbonyl, isopropoxycarbonyl or cyclohexyloxycarbonyl,
 (2) $C_{1-4}$ alkoxy carbonyl groups,
 (3) carbamoyl groups unsubstituted or substituted with substituent(s) selected from among $C_{1-3}$ alkyl groups, $C_{3-6}$ cycloalkyl groups, phenyl group, benzyl group, carboxyl group, methoxycarbonyl, ethoxycarbonyl, and propoxycarbonyl,
 (4) phenyl and $C_{3-6}$ cycloalkyl groups, each of which is unsubstituted or substituted with substituent(s) selected from among $C_{1-3}$ alkyl groups and $C_{1-3}$ alkoxy groups,
 (5) $C_{1-3}$ alkenyl groups,
 (6) 5-membered heterocyclic groups having one to three oxygen atoms, which may have one or more substituent(s) selected from the group consisting of $C_{1-3}$ alkyl and oxo, or a fused ring formed by cooperating said 5-membered heterocyclic group with a benzene ring, or (c) phenoxy(thio)carbonyl, 1-naphtoxy(thio)carbonyl or benzyloxy(thio) carbonyl;
(ii) a hydroxyl group unsubstituted or substituted with (1) a $C_{1-4}$ alkyl group, (2) a $C_{3-6}$ cycloalkyl group, (3) a phenyl, 1-naphthyl, 2-naphthyl benzyl or phenethyl group each of which is unsubstituted or substituted with halogen atom(s) or carboxyl group(s) optionally esterified with $C_{1-4}$ alkyl;

(iii) an amino group, unsubstituted or substituted with (1) $C_{1-4}$ alkyl group(s), (2) $C_{3-6}$ cycloalkyl(s) or (3) phenyl, 1-naphthyl, 2-naphthyl, benzyl and phenethyl group(s) each of which is unsubstituted or substituted with substituent(s) selected from among halogen atoms and carboxyl groups optionally esterified with $C_{1-4}$ alkyl group in which the two substituents on the nitrogen atom may form, taken together with the nitrogen atom, a cyclic amino group;

(iv) a phenyl group unsubstituted or substituted with substituents selected from among (1) $C_{1-4}$ alkyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (2) $C_{1-4}$ alkoxy groups, (3) methoxycarbonyl, ethoxycarbonyl, propoxycarbonyl, isopropoxycarbonyl, butoxycarbonyl, tert-butoxycarbonyl and sec-butoxycarbonyl, (4) phenyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (5) amino groups unsubstituted or substituted with $C_{1-3}$ alkyl group(s) and (6) tetrazol-5-yl, 2,5-dihydro-5-oxo-1,2,4-oxadiazol-3-yl and 2,5-dihydro-5-oxo-1,2,4-thiadiazol-3-yl;

(v) a carbamoyl group unsubstituted or substituted with 1 to 2 substituent(s) selected from among
 (1) $C_{1-6}$ alkyl groups and $C_{3-6}$ cycloalkyl groups each of which is unsubstituted or substituted with 1 to 3 substituent(s) selected from among carboxyl groups optionally esterified the $C_{1-5}$ alkyl group, furyl, thienyl, indolyl, isoindolyl, pyrazinyl, pyridyl, pyrimidyl, imidazolyl, amino group, hydroxyl group and phenyl group,
 (2) aryl groups and aralkyl groups unsubstituted or substituted with substituent(s) selected from among halogen atoms and carboxyl groups optionally esterified with $C_{1-4}$ alkyl groups, in which the two substituents on the nitrogen atom may form a cyclic amino group taken together with the nitrogen atom; or (vi) tetrazol-5-yl or a group represented by the formula

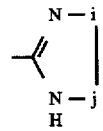

wherein i stands for —O— or —S—; j stands for

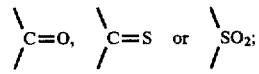

provided that, when X is methylene and $R_1$ is not an alkyl group having more than 4 carbon atoms, Y is neither carboxyl group nor alkoxycarbonyl group;

the ring A being optionally substituted by $C_{1-4}$ alkoxy or a halogen atom, or a pharmaceutically acceptable salt thereof.

2. The compound of claim 1, wherein $R_1$ is a lower $C_{1-7}$ alkyl group.

3. The compound of claim 1, wherein $R_1$ is a $C_{4-5}$ alkyl group.

4. The compound of claim 1, wherein each of $R_2$ and $R_3$ is independently (i) hydrogen; (ii) a $C_{1-6}$ alkyl group unsubstituted or substituted with substituent(s) selected from among halogens and $C_{1-4}$ alkoxy groups; (iii) a phenyl group unsubstituted or substituted by 1 to 3 substituent(s) selected from among (1) halogen atoms, (2) $C_{1-4}$ alkyl groups unsubstituted or substituted with 1 to 3 halogen atoms, (3) $C_{1-4}$ alkoxy groups unsubstituted or substituted with 1 to 3 halogen atoms, (4) hydroxyl groups unsubstituted or substituted with a $C_{1-4}$ alkyl group, a $C_{3-6}$ cycloalkyl group, phenyl, 1-naphthyl, 2-naphthyl, benzyl or phenethyl, (5) nitro group and (6) cyano group in which the two adjoining substituents on the phenyl group may cooperate therewith to form a ring which is unsubstituted or substituted with a $C_{1-3}$ alkyl or (iv) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxaolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, τ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl or 1,2,4-triazolo[4,3-b]pyridazinyl, each of said groups being unsubstituted or substituted with $C_{1-3}$ alkyl.

5. The compound of claim 1, wherein Y is a carboxyl group;

a lower alkoxy (thio) carbonyl group having optionally one or more substituent(s) selected from among (1) hydroxyl groups unsubstituted or substituted with a lower alkanoyl group, methoxycarbonyl, ethoxycarbonyl, propoxycarbonyl, isopropoxycarbonyl or cyclohexyloxycarbonyl, (2) $C_{1-4}$ alkoxy carbonyl groups, (3) carbamoyl groups unsubstituted or substituted with substituent(s) selected from among $C_{1-3}$ alkyl groups, $C_{3-6}$ cycloalkyl groups, phenyl group, benzyl group, carboxyl group, methoxycarbonyl, ethoxycarbonyl, and propoxycarbonyl, (4) phenyl and $C_{3-6}$ cycloalkyl groups each of which is unsubstituted or substituted with substituent(s) selected from among $C_{1-3}$ alkyl groups and $C_{1-3}$ alkoxy groups, (5) $C_{1-3}$ alkenyl groups, (6) 5-membered heterocyclic residue containing one to three of oxygen atom which may cooperate with a benzene ring to form a fused ring or more substituent (s) selected from among unsubstituted or substituted with $C_{1-3}$ alkyl groups and oxo; or phenoxy(thio)carbonyl, 1-naphtoxy(thio)carbonyl or benzyloxy(thio)carbonyl; or a phenyl group unsubstituted or substituted with substituents selected from among (1) $C_{1-4}$ alkyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (2) $C_{1-4}$ alkoxy groups, (3) methoxycarbonyl, ethoxycarbonyl, propoxycarbonyl, isopropoxycarbonyl, butoxycarbonyl, tert-butoxycarbonyl and sec-butoxycarbonyl, (4) phenyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (5) amino groups unsubstituted or substituted with $C_{1-3}$ alkyl group(s) and (6) tetrazol-5-yl, 2,5-dihydro-5-oxo-1,2,4-oxadiazol-3-yl and 2,5-dihydro-5-oxo-1,2,4-thiadiazol-3-yl.

6. A compound of claim 1, which is sodium (3R,5S)-7-chloro-5-(2,3-dimethoxyphenyl)-1-neopentyl-2-oxo-1,2,3,5-tetrahydro-4,1-benzoxazepine-3-acetate.

7. A compound according to claim 1, which is trans-7-chloro-5-(2,3-dimethoxyphenyl)-1-neopentyl-2-oxo-1,2,3,5-tetrahydro-4,1-benzoxazepine-3-acetic acid ethyl ester, trans-7-chloro-5-(2,3-dimethoxyphenyl)-1-neopentyl-2-oxo-1,2,3,5-tetrahydro-4,1-benzoxazepine-3-acetic acid or trans-7-chloro-5-(2-chlorophenyl)-1-neopentyl-2-oxo-1,2,3,5-tetrahydro-4,1-benzoxazepine-3-methylamine hydrochloride.

8. A compound of formula (I'):

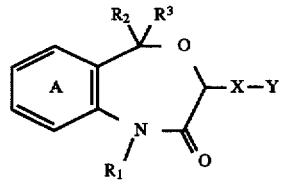

wherein $R_1$ is (i) hydrogen, (ii) a $C_{1-7}$ alkyl group, a $C_{2-6}$ alkenyl group, a $C_{2-6}$ alkynyl group, (iii) a $C_{3-9}$ cycloalkyl group, a cycloalkenyl group selected from among 2-cyclopenten-1-yl, 3-cyclopenten-1-yl, 2-cyclohexen-1-yl, 3-cyclohexen-1-yl, 1-cyclobuten-1-yl and 1-cyclopenten-1-yl, a cycloalkadienyl group selected from among 2,4-cyclopentadien-1-yl, 2,4-cyclohexadien-1-yl, and 2,5-cyclohexadien-1-yl, or (iv) an aryl group selected from among phenyl, naphthyl, anthryl, phenanthryl and acenaphythylenyl in which each of the (3) amino groups, hydroxyl groups and thiol groups each of which is unsubstituted or substituted with $C_{1-3}$ alkyl groups and (4) halogen atoms;

and having each of the groups of (iii) and (iv) may further have a $C_{1-3}$ alkyl group, and (5) $C_{1-6}$ acyl groups; each of $R_2$ and $R_3$ is independently (i) hydrogen; (ii) a $C_{1-6}$ alkyl group unsubstituted or substituted with substituent(s) selected from among halogens and $C_{1-4}$ alkoxy groups; (iii) a phenyl group unsubstituted or substituted by 1 to 3 substituent(s) selected from among (1) halogen atoms, (2) $C_{1-4}$ alkyl groups unsubstituted or substituted with 1 to 3 halogen atoms, (3) $C_{1-4}$ alkoxy groups unsubstituted or substituted with 1 to 3 halogen atoms, (4) hydroxyl groups unsubstituted or substituted with a $C_{1-4}$ alkyl group, a $C_{3-6}$ cycloalkyl group, phenyl, 1-naphthyl, 2-naphthyl, benzyl or phenethyl, (5) nitro group and (6) cyano group in which the two adjoining substituents on the phenyl group may cooperate therewith to form a ring which is unsubstituted or substituted with a $C_{1-3}$ alkyl or (iv) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, group of (ii), (iii) and (iv) is unsubstituted or substituted with 1 to 5 substituent(s) selected from the group consisting of (1) phenyl, naphthyl, anthyl, phenanthryl, acenaphthylenyl, $C_{3-7}$ cycloalkyl groups and $C_{3-6}$ cycloalkenyl groups each of which is unsubstituted or substituted with 1 to 2 substituent(s) selected from among $C_{1-3}$ alkoxy groups and $C_{1-3}$ alkyl groups, (2) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, τ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, oxiranyl, azetidinyl, oxetanyl, thiethanyl, pyrrolidinyl, tetrahydrofuryl, thioranyl, piperidyl, tetrahydropyranyl, morpholinyl, thiomorpholinyl or piperazinyl, each of said groups being unsubstituted or substituted with $C_{1-3}$ alkyl, β-carbolinyl, τ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl or 1,2,4-triazolo[4,3-b]pyridazinyl, each of said groups being unsubstituted or substituted with $C_{1-3}$ alkyl;

X is a bond or a divalent chain represented by the formula

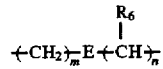

wherein m and n denote independently 0, 1, 2 or 3; E stands for a bond or oxygen atom, sulfur atom, sulfoxide, sulfone,

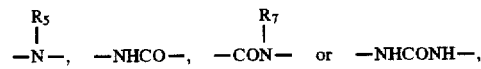

wherein $R_6$ and $R_7$ independently stand for (i) hydrogen atoms (ii) a $C_{1-6}$ alkyl group unsubstituted or substituted with furyl, thienyl, pyridyl, pyrimidinyl, pyrazinyl, indolyl, imidazolyl, isoindolyl, an amino group unsubstituted or substituted with $C_{1-3}$ alkyl group(s), a hydroxyl group unsubstituted or substituted with a $C_{1-3}$ alkyl group, a thiol group unsubstituted or substituted with a $C_{1-3}$ alkyl group, a thiol group unsubstituted or substituted with a $C_{1-3}$ alkyl group, carboxyl group, methoxycarbonyl, ethoxycarbonyl, propoxycarbonyl, phenoxycarbonyl, 1-naphtoxycarbonyl or 2-naphtoxycarbonyl or a halogen atom; (iii) benzyl napthylmethyl, phenylethyl, phenylpropyl or phenylbutyl unsubstituted or substituted with substituent(s) selected from halogens, $C_{1-3}$ alkoxy groups, hydroxyl group, amino group, carboxyl group and sulfhydryl or (iv) a phenyl group unsubstituted or substituted with substituent(s) selected from halogen atoms and $C_{1-3}$ alkyl groups; $R_5$ stand for hydrogen atom, a $C_{1-4}$ alkyl, a $C_{7-15}$ aralkyl, a lower alkanoyl group, a lower alkenoyl group, a lower alkanesulfonyl group, benzoyl, p-toluoyl, 1-naphthoyl and 2-naphthoyl, phenylacetyl, phenylpropionyl, hydroatropoyl, phenylbuty cinnamoyl, atropoly, benzenesulfonyl or p-toluenesulfonyl;

Y is (i) (a) carboxyl group, (b) a lower alkoxy (thio) carbonyl group having optionally one or more substituent(s) selected from among (1) hydroxyl groups unsubstituted or substituted with a lower alkanoyl group, methoxycarbonyl, ethoxycarbonyl, propoxycarbonyl, isopropoxycarbonyl or cyclohexyloxycarbonyl, (2) $C_{1-4}$ alkoxy carbonyl groups, (3) carbamoyl groups unsubstituted or substituted with substituent(s) selected from among $C_{1-3}$ alkyl groups, $C_{3-6}$ cycloalkyl groups, phenyl group, benzyl group, carboxyl group, methoxycarbonyl and ethoxycarbonyl, propoxycarbonyl, (4) phenyl and $C_{3-6}$ cycloalkyl groups each of which is unsubstituted or substituted with substituent(s) selected from among $C_{1-3}$ alkyl groups and $C_{1-3}$ alkoxy groups, (5) $C_{1-3}$ alkenyl groups, (6) 5-membered heterocyclic groups having one to three oxygen atoms, which may have one or more substituent(s) selected from the group consisting of $C_{1-3}$ alkyl and oxo, or a fused ring formed by cooperating said 5-membered heterocyclic group with a benzene ring, or (c) phenoxy(thio)carbonyl, 1-naphtoxy(thio)carbonyl or benzyloxy (thio) carbonyl;

(ii) a hydroxyl group unsubstituted or substituted with (1) a $C_{1-4}$ alkyl group, (2) a $C_{3-6}$ cycloalkyl group, (3) a phenyl, 1-naphthyl, 2-naphthyl benzyl or phenethyl group each of which is unsubstituted or substituted with halogen atom(s) or carboxyl group(s) optionally esterified with $C_{1-4}$ alkyl;

(iii) an amino group, unsubstituted or substituted with (1) $C_{1-4}$ alkyl group(s), (2) $C_{3-6}$ cycloalkyl(s) or (3) phenyl, 1-naphthyl, 2-naphthyl, benzyl and phenethyl group(s) each of which is unsubstituted or substituted with substituent(s) selected from among halogen atoms and carboxyl groups optionally esterified with $C_{1-4}$ alkyl group in which the two substituents on the nitrogen atom may form, taken together with the nitrogen atom, a cyclic amino group;

(iv) a phenyl group unsubstituted or substituted with substituents selected from among (1) $C_{1-4}$ alkyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (2) $C_{1-4}$ alkoxy groups, (3) methoxycarbonyl, ethoxycarbonyl, propoxycarbonyl, isopropoxycarbonyl, butoxycarbonyl, tert-butoxycarbonyl and sec-butoxycarbonyl, (4) phenyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (5) amino groups unsubstituted or substituted with $C_{1-3}$ alkyl group(s) and (6) tetrazol-5-yl, 2,5-dihydro-5-oxo-1,2,4-oxadiazol-3-yl and 2,5-dihydro-5-oxo-1,2,4-thiadiazol-3-yl;

(v) a carbamoyl group unsubstituted or substituted with 1 to 2 substituent(s) selected from among (1) $C_{1-6}$ alkyl groups and $C_{3-8}$ cycloalkyl groups each of which is unsubstituted or substituted with 1 to 3 substituent(s) selected from among carboxyl groups optionally esterified the $C_{1-5}$ alkyl group, furyl, thienyl, indolyl, isoindolyl, pyrazinyl, pyridyl, pyrimidyl, imidazolyl, amino group, hydroxyl group and phenyl group, (2) aryl groups and aralkyl groups unsubstituted or substituted with substituent(s) selected from among halogen atoms and carboxyl groups optionally esterified with $C_{1-4}$ alkyl groups, in which the two substituents on the nitrogen atom may form a cyclic amino group taken together with the nitrogen atom; or (vi) tetrazol-5-yl or a group represented by the formula

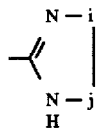

wherein i stands for —O— or —S—; j stands for

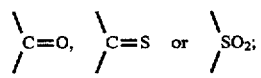

provided that, when X is methylene, Y is neither carboxyl group nor alkoxycarbonyl group; the ring A being optionally be substituted by $C_{1-4}$ alkoxy or a halogen atom, or a pharmaceutically acceptable salt thereof.

9. The compound of claim 8, wherein $R_1$ is a lower $C_{1-7}$ alkyl group.

10. The compound of claim 8, wherein each of $R_2$ and $R_3$ is independently (i) hydrogen; (ii) a $C_{1-6}$ alkyl group unsubstituted or substituted with substituent(s) selected from among halogens and $C_{1-4}$ alkoxy groups; (iii) a phenyl group unsubstituted or substituted by 1 to 3 substituent(s) selected from among (1) halogen atoms, (2) $C_{1-4}$ alkyl groups unsubstituted or substituted with 1 to 3 halogen atoms, (3) $C_{1-4}$ alkoxy groups unsubstituted or substituted with 1 to 3 halogen atoms, (4) hydroxyl groups unsubstituted or substituted with a $C_{1-4}$ alkyl group, a $C_{3-6}$ cycloalkyl group, phenyl, 1-naphthyl, 2-naphthyl, benzyl or phenethyl, (5) nitro group and (6) cyano group in which the two adjoining substituents on the phenyl group may cooperate therewith to form a ring which is unsubstituted or substituted with a $C_{1-3}$ alkyl or (iv) furyl, thienyl, pyrrolyl, oxazolyl, isoxazolyl, thiazolyl, isothiazolyl, imidazolyl, pyrazolyl,1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinlyl, phthalazinyl, naphthylidinyl, purinyl, pteridinyl, carbazolyl, α-carbolinyl, β-carbolinyl, τ-carbolinyl, acrydinyl, phenoxazinyl, phenothiazinly, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl or 1,2,4-triazolo[4,3-b]pyridazinyl, each of said groups being unsubstituted or substituted with $C_{1-3}$ alkyl.

11. The compound of claim 8, wherein Y is a carboxyl group;

a lower alkoxy (thio) carbonyl group having optionally one or more substituent(s) selected from among (1) hydroxyl groups unsubstituted or substituted with a lower alkanoyl group, methoxycarbonyl, ethoxycarbonyl, propoxycarbonyl, isopropoxycarbonyl or cyclohexyloxycarbonyl, (2) $C_{1-4}$ alkoxy carbonyl groups, (3) carbamoyl groups unsubstituted or substituted with substituent(s) selected from among $C_{1-3}$ alkyl groups, $C_{3-6}$ cycloalkyl groups, phenyl group, benzyl group, carboxyl group, methoxycarbonyl and ethoxycarbonyl, propoxycarbonyl, (4) phenyl and $C_{3-6}$ cycloalkyl groups each of which is unsubstituted or substituted with substituent(s)

selected from among $C_{1-3}$ alkyl groups and $C_{1-3}$ alkoxy groups,
(5) $C_{1-3}$ alkenyl groups,
(6) 5-membered heterocyclic groups having one to three oxygen atoms, which may have one or more substituent(s) selected from the group consisting of $C_{1-3}$ alkyl and oxo, or a fused ring formed by cooperating said 5-membered heterocyclic group with a benzene ring, or (c) phenoxy(thio)carbonyl, 1-naphtoxy(thio)carbonyl or benzyloxy(thio) carbonyl; or a phenyl group unsubstituted or substituted with substituents selected from among (1) $C_{1-4}$ alkyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (2) $C_{1-4}$ alkoxy groups, (3) methoxycarbonyl, ethoxycarbonyl, propoxycarbonyl, isopropoxycarbonyl, butoxycarbonyl, tert-butoxycarbonyl and sec-butoxycarbonyl, (4) phenyl groups unsubstituted or substituted with substituent(s) selected from carboxyl group, methoxycarbonyl, ethoxycarbonyl, propoxycarbonyl, isopropoxycarbonyl, butoxycarbonyl, tert-butoxycarbonyl and sec-butoxycarbonyl, (5) amino groups unsubstituted or substituted with $C_{1-3}$ alkyl group(s) and (6) tetrazol-5-yl, 2,5-dihydro-5-oxo-1,2,4-oxadiazol-3-yl and 2,5-dihydro-5-oxo-1,2,4-thiadiazol-3-yl.

* * * * *

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

| Column | Line | |
|---|---|---|
| 197 | 52 | delete "anthyl", and insert therefor --anthryl-- |
| 198 | 5 | delete "phenoxthinyl", and insert therefor --phenoxathiinyl-- |
| 198 | 53 | delete "1,2-benzoisoxaolyl", insert therefor --B-1,2-benzoisoxazolyl-- |
| 198 | 59 | delete "phenoxthinyl", and insert therefor --phenoxathiinyl-- |
| 199 | 26 | delete "benzyl napthylmethyl", and insert therefor --benzyl, naphthylmethyl-- |
| 199 | 37 | delete "phenylbuty", and insert therefor --phenylbutyryl-- |
| 199 | 37 | delete "atropoly", and insert therefor --atropoyl-- |
| 200 | 1 | delete "2-naphthyl", and insert therefor --2-naphthyl,-- |
| 201 | 32 | delete "1,2-benzoisoxaolyl", and insert therefor --B1,2-benzoisoxazolyl--. |

Signed and Sealed this

Sixth Day of June, 2000

Attest:

Q. TODD DICKINSON

*Attesting Officer*    *Director of Patents and Trademarks*

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

| Column | Line | |
|---|---|---|
| 201 | 38 | delete "phenoxthinyl", insert --phenoxathiinyl-- |
| 201 | 67 | delete "or more", and insert therefor --or may have one or more-- |
| 202 | 1 | delete "among unsubstituted or substituted", and insert therefor --among-- |
| 202 | 2 | delete "with $C_{1-3}$", and insert therefor --$C_{1-3}$-- |
| 203 | 34 | delete "anthyl", and insert therefor --anthryl-- |
| 203 | 54 | delete "phenoxthinyl", and insert therefor --phenoxathiinyl-- |
| 203 | 67 | delete "phenoxthinyl", and insert therefor --phenoxathiinyl-- |
| 204 | 34 | delete "benzyl napthylmethyl", and insert therefor --benzyl, naphthylmethyl-- |

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

Column    Line 204    45    delete "phenylbuty", and insert therefor --phenylbutyryl,--

204    45    delete "atropoly", and insert therefor --atropoyl--

205    9    delete "2-naphthyl", and insert therefor --2-naphthyl,--

206    44    delete "phenoxthinyl", and insert therefor --phenoxathiinyl--

Column 199, lines 21-22    Please delete the second occurrence of "a thiol group unsubstituted or substituted with a $C_{1-3}$ alkyl group,"

Column 204, lines 29-30    Please delete the second occurrence of "a thiol group unsubstituted or substituted with a $C_{1-3}$ alkyl group,"

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

Column 202, line 60 through Column 203, line 30 Please delete "(3) amino groups, hydroxyl groups and thiol groups each of which is unsubstitued or substitued with $C_{1-3}$ alkyl groups and (4) halogen atoms; and having each of the groups of (iii) and (iv) may further have a $C_{1-3}$ alkyl group, and (5) $C_{1-6}$ acyl groups; each of $R_2$ and $R_3$ is independently (i) hydrogen; (ii) a $C_{1-6}$ alkyl group unsubstituted or substituted with substituent(s) selected from among halogens and $C_{1-4}$ alkoxy groups; (iii) a phenyl group unsubstituted or substituted by 1 to 3 substituent(s) selected from among (1) halogen atoms, (2) $C_{1-4}$ alkyl groups unsubstituted or substituted with 1 to 3 halogen atoms, (3) $C_{1-4}$ alkoxy groups unsubstituted or substituted with 1 to 3 halogen atoms, (4) hydroxyl groups unsubstituted or substituted with a $C_{1-4}$ alkyl group, a $C_{3-6}$ cycloalkyl group, phenyl, 1-naphthyl, 2-naphthyl, benzyl or phenethyl, (5) nitro group and (60 cyano group in which the two adjoining substituents on the phenyl group may cooperate therewith to form a ring which is unsubstituted or substituted with a $C_{1-3}$ alkyl or (iv) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl,"

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

Column 202, line 60 through Column 203, line 30 and insert therefor, --group of (ii), (iii) and (iv) is unsubstituted or substituted with 1 to 5 substituent(s) selected from the group consisting of (1) phenyl, naphthyl, anthyl, phenanthryl, acenaphthylenyl, $C_{3-7}$ cycloalkyl groups and $C_{3-6}$ cycloalkenyl groups each of which is unsubstituted or substituted with 1 to 2 substituent(s) selected from among $C_{1-3}$ alkoxy groups and $C_{1-3}$ alkyl groups, (2) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, τ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, oxiranyl, azetidinyl, oxetanyl, thiethanyl, pyrrolidinyl, tetrahydrofuryl, thioranyl, piperidyl, tetrahydropyranyl, morpholinyl, thiomorpholinyl or piperazinyl, each of said groups being unsubstituted or substituted with $C_{1-3}$ alkyl,--

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

Column 203, lines 30 through 65  Please delete, "group of (ii), (iii) and (iv) is unsubstituted or substituted with 1 to 5 substituent(s) selected from the group consisting of (1) phenyl, naphthyl, anthyl, phenanthryl, acenaphthylenyl, $C_{3-7}$ cycloalkyl groups and $C_{3-6}$ cycloalkenyl groups each of which is unsubstituted or substituted with 1 to 2 substituent(s) selected from among $C_{1-3}$ alkoxy groups and $C_{1-3}$ alkyl groups, (2) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acrydinyl, phenoxazinyl, phenothiazinyl, phenazinyl, phenoxthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, oxiranyl, azetidinyl, oxetanyl, thiethanyl, pyrrolidinyl, tetrahydrofuryl, thioranyl, piperidyl, tetrahydropyranyl, morpholinyl, thiomorpholinyl or piperazinyl, each of said groups being unsubstituted or substituted with $C_{1-3}$ alkyl,"

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

and insert therefor, --(3) amino groups, hydroxyl groups and thiol groups each of which is unsubstitued or substitued with $C_{1-3}$ alkyl groups and (4) halogen atoms; and having each of the groups of (iii) and (iv) may further have a $C_{1-3}$ alkyl group, and (5) $C_{1-6}$ acyl groups; each of $R_2$ and $R_3$ is independently (i) hydrogen; (ii) a $C_{1-6}$ alkyl group unsubstituted or substituted with substituent(s) selected from among halogens and $C_{1-4}$ alkoxy groups; (iii) a phenyl group unsubstituted or substituted by 1 to 3 substituent(s) selected from among (1) halogen atoms, (2) $C_{1-4}$ alkyl groups unsubstituted or substituted with 1 to 3 halogen atoms, (3) $C_{1-4}$ alkoxy groups unsubstituted or substituted with 1 to 3 halogen atoms, (4) hydroxyl groups unsubstituted or substituted with a $C_{1-4}$ alkyl group, a $C_{3-6}$ cycloalkyl group, phenyl, 1-naphthyl, 2-naphthyl, benzyl or phenethyl, (5) nitro group and (60 cyano group in which the two adjoining substituents on the phenyl group may cooperate therewith to form a ring which is unsubstituted or substituted with a $C_{1-3}$ alkyl or (iv) furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl,--

UNITED STATES PATENT AND TRADEMARK OFFICE
CERTIFICATE OF CORRECTION

PATENT NO. : 5,726,306
DATED : March 10, 1998
INVENTOR(S) : Hidefumi YUKIMASA, et al.

It is certified that error appears in the above-identified patent and that said Letters Patent is hereby corrected as shown below:

Column 208, line 15, insert the following:

12. A pharmaceutical composition for inhibiting squalene synthetase which comprises a therapeutically effective amount of a compound of claim 1 or a pharmaceutically acceptable salt thereof, and a pharmaceutically acceptable carrier.

13. A pharmaceutical composition for inhibiting squalene synthetase which comprises a therapeutically effective amount of a compound of claim 8 or a pharmaceutically acceptable salt thereof, and a pharmaceutically acceptable carrier.

14. A method for inhibiting squalene synthetase in a mammal which comprises administering to said mammal a therapeutically effective amount of a compound of claim 1 or a pharmaceutically acceptable salt thereof.

15. The method according to claim 14, wherein $R_1$ is a $C_{1-7}$ alkyl group.

16. The method according to claim 14, wherein $R_2$ or $R_3$ is an optionally substituted phenyl group.

17. A method for inhibiting squalene synthetase in a mammal which comprises administering to said mammal a therapeutically effective amount of a compound of claim 5 or a pharmaceutically acceptable salt thereof.